United States Patent
Machacek et al.

(10) Patent No.: US 9,586,931 B2
(45) Date of Patent: Mar. 7, 2017

(54) TRIAZOLYL DERIVATIVES AS SYK INHIBITORS

(71) Applicants: Michelle R. Machacek, Brookline, MA (US); Eric T. Romeo, Allston, MA (US); Solomon D. Kattar, Arlington, MA (US); Matthew Christopher, Brookline, MA (US); Michael D. Altman, Needham, MA (US); Alan B. Northrup, Reading, MA (US); John Michael Ellis, Needham, MA (US); Brendan O'Boyle, Milpitas, CA (US); Anthony Donofrio, Cambridge, MA (US); Jonathan Grimm, Ashburn, VA (US); Michael H. Reutershan, Brookline, MA (US); Kaleen Konrad Childers, Medfield, MA (US); Ryan D. Otte, Natick, MA (US); Brandon Cash, Framingham, MA (US); Yves Ducharme, Brookline, MA (US); Andrew M. Haidle, Cambridge, MA (US); Kerrie Spencer, Woonsocket, RI (US); Dilrukshi Vitharana, Somerville, MA (US); Lingyun Wu, Shanghai (CN); Li Zhang, Shanghai (CN); Peng Zhang, Shanghai (CN); Christian Beaulieu, Laval (CA); Daniel Guay, Lachine (CA)

(72) Inventors: Michelle R. Machacek, Brookline, MA (US); Eric T. Romeo, Allston, MA (US); Solomon D. Kattar, Arlington, MA (US); Matthew Christopher, Brookline, MA (US); Michael D. Altman, Needham, MA (US); Alan B. Northrup, Reading, MA (US); John Michael Ellis, Needham, MA (US); Brendan O'Boyle, Milpitas, CA (US); Anthony Donofrio, Cambridge, MA (US); Jonathan Grimm, Ashburn, VA (US); Michael H. Reutershan, Brookline, MA (US); Kaleen Konrad Childers, Medfield, MA (US); Ryan D. Otte, Natick, MA (US); Brandon Cash, Framingham, MA (US); Yves Ducharme, Brookline, MA (US); Andrew M. Haidle, Cambridge, MA (US); Kerrie Spencer, Woonsocket, RI (US); Dilrukshi Vitharana, Somerville, MA (US); Lingyun Wu, Shanghai (CN); Li Zhang, Shanghai (CN); Peng Zhang, Shanghai (CN); Christian Beaulieu, Laval (CA); Daniel Guay, Lachine (CA)

(73) Assignees: Merck Sharp & Dohme Corp., Rahway, NJ (US); Merck Canada Inc., Kirkland, Quebec (CA)

(*) Notice: Subject to any disclaimer, the term of this patent is extended or adjusted under 35 U.S.C. 154(b) by 0 days.

(21) Appl. No.: 14/431,895

(22) PCT Filed: Sep. 24, 2013

(86) PCT No.: PCT/CN2013/001132
§ 371 (c)(1),
(2) Date: Mar. 27, 2015

(87) PCT Pub. No.: WO2014/048065
PCT Pub. Date: Apr. 3, 2014

(65) Prior Publication Data
US 2015/0239866 A1    Aug. 27, 2015

Related U.S. Application Data

(60) Provisional application No. 61/707,246, filed on Sep. 28, 2012.

(51) Int. Cl.
*A61K 9/10* (2006.01)
*C07D 401/14* (2006.01)
(Continued)

(52) U.S. Cl.
CPC ......... *C07D 401/14* (2013.01); *A61K 9/0019* (2013.01); *A61K 9/0073* (2013.01);
(Continued)

(58) Field of Classification Search
CPC .. A61K 9/4858; A61K 9/2027; A61K 9/0019; A61K 9/0075; A61K 9/0073;
(Continued)

(56) References Cited

U.S. PATENT DOCUMENTS 5,710,129 A    1/1998  Lynch et al.
6,248,790 B1   6/2001  Uckun et al.
(Continued)

FOREIGN PATENT DOCUMENTS

CN    201166734 A    4/2008
CN    102066340 A    5/2011
(Continued)

OTHER PUBLICATIONS

European Search Report of PCT/CN2013/001132 mailed Feb. 19, 2016.
(Continued)

*Primary Examiner* — Alexander R Pagano
*Assistant Examiner* — Ebenezer O Sackey
(74) *Attorney, Agent, or Firm* — Eric A. Meade; Anna L. Cocuzzo

(57) ABSTRACT

Provided are triazole derivatives of Formula I which are potent inhibitors of spleen tyrosine kinase and pharmaceutical composition. The triazole derivatives are useful in the treatment and prevention of diseases mediated by said (Continued)

enzyme, such as asthma, COPD, rheumatoid arthritis, and cancer.

15 Claims, No Drawings

(51) Int. Cl.
| | |
|---|---|
| C07D 405/14 | (2006.01) |
| C07D 409/14 | (2006.01) |
| C07D 417/14 | (2006.01) |
| C07D 498/04 | (2006.01) |
| C07D 413/14 | (2006.01) |
| C07D 239/42 | (2006.01) |
| A61K 9/00 | (2006.01) |
| A61K 9/20 | (2006.01) |
| A61K 9/48 | (2006.01) |
| C07D 403/12 | (2006.01) |
| C07D 405/12 | (2006.01) |
| C07D 409/12 | (2006.01) |
| C07D 471/04 | (2006.01) |

(52) U.S. Cl.
CPC .......... *A61K 9/0075* (2013.01); *A61K 9/2027* (2013.01); *A61K 9/4858* (2013.01); *C07D 239/42* (2013.01); *C07D 403/12* (2013.01); *C07D 405/12* (2013.01); *C07D 405/14* (2013.01); *C07D 409/12* (2013.01); *C07D 409/14* (2013.01); *C07D 413/14* (2013.01); *C07D 417/14* (2013.01); *C07D 471/04* (2013.01); *C07D 498/04* (2013.01); *A61K 9/10* (2013.01)

(58) Field of Classification Search
CPC ...... A61K 9/10; C07D 401/14; C07D 405/14; C07D 409/14; C07D 417/14; C07D 498/04; C07D 405/12; C07D 409/12; C07D 413/14; C07D 471/04; C07D 403/12; C07D 239/42
See application file for complete search history.

(56) References Cited

U.S. PATENT DOCUMENTS

| | | | |
|---|---|---|---|
| 6,432,963 | B1 | 8/2002 | Hisamichi et al. |
| 6,589,950 | B1 | 7/2003 | Collingwood et al. |
| 6,770,643 | B2 | 8/2004 | Cox et al. |
| 6,797,706 | B2 | 9/2004 | Hisamichi et al. |
| 6,897,208 | B2 | 5/2005 | Edwards et al. |
| 6,911,443 | B2 | 6/2005 | Yura et al. |
| 7,060,827 | B2 | 6/2006 | Singh et al. |
| 7,122,542 | B2 | 10/2006 | Singh et al. |
| 7,227,020 | B2 | 6/2007 | Cox et al. |
| 7,259,154 | B2 | 8/2007 | Cox et al. |
| 7,803,801 | B2 | 9/2010 | Kodama et al. |
| 8,138,339 | B2 | 3/2012 | Bauer et al. |
| 8,551,984 | B2 | 10/2013 | Altman et al. |
| 8,735,417 | B2 | 5/2014 | Altman et al. |
| 8,759,366 | B2 | 6/2014 | Childers et al. |
| 8,796,310 | B2 | 8/2014 | Romeo et al. |
| 8,987,456 | B2 | 3/2015 | Altman et al. |
| 9,006,444 | B2 | 4/2015 | Altman et al. |
| 9,120,785 | B2 | 9/2015 | Altman et al. |
| 2004/0029902 | A1 | 2/2004 | Singh et al. |
| 2004/0054179 | A1 | 3/2004 | Yura et al. |
| 2006/0135543 | A1 | 6/2006 | Singh et al. |
| 2006/0178407 | A1 | 8/2006 | Argade et al. |
| 2006/0211657 | A1 | 9/2006 | Singh et al. |
| 2006/0234483 | A1 | 10/2006 | Arak et al. |
| 2006/0247262 | A1 | 11/2006 | Baenteli et al. |
| 2007/0004626 | A1 | 1/2007 | Masuda et al. |
| 2007/0129362 | A1 | 6/2007 | Bhamidipati et al. |
| 2007/0197782 | A1 | 8/2007 | Clough et al. |
| 2013/0225548 | A1 | 8/2013 | Fujihara et al. |
| 2014/0148474 | A1 | 5/2014 | Altman et al. |
| 2014/0243336 | A1 | 8/2014 | Altman et al. |
| 2014/0249130 | A1 | 9/2014 | Deschenes et al. |
| 2015/0148327 | A1 | 5/2015 | Haidle et al. |
| 2015/0166486 | A1 | 6/2015 | Haidle et al. |
| 2015/0175575 | A1 | 6/2015 | Lim et al. |
| 2015/0191461 | A1 | 7/2015 | Machacek et al. |

FOREIGN PATENT DOCUMENTS

| | | |
|---|---|---|
| JP | 2004203748 | 12/2002 |
| WO | WO03057659 A1 | 7/2003 |
| WO | WO03078404 A1 | 9/2003 |
| WO | WO2004080463 A1 | 9/2004 |
| WO | WO2005013996 A2 | 2/2005 |
| WO | WO2005026158 A1 | 3/2005 |
| WO | WO2005033103 A1 | 4/2005 |
| WO | WO2006004865 A1 | 1/2006 |
| WO | WO2006028833 A1 | 3/2006 |
| WO | WO2006050480 A2 | 5/2006 |
| WO | WO2006068770 A1 | 6/2006 |
| WO | WO2006078846 A1 | 7/2006 |
| WO | WO2006093247 A1 | 9/2006 |
| WO | WO2006129100 A1 | 12/2006 |
| WO | WO2006133426 A2 | 12/2006 |
| WO | WO2006135915 A2 | 12/2006 |
| WO | WO2007009681 A1 | 1/2007 |
| WO | WO2007009773 A1 | 1/2007 |
| WO | WO2007028445 A1 | 3/2007 |
| WO | WO2007042298 A1 | 4/2007 |
| WO | WO2007042299 A1 | 4/2007 |
| WO | WO2007070872 A1 | 6/2007 |
| WO | WO2007085540 A1 | 8/2007 |
| WO | WO2007107469 A1 | 9/2007 |
| WO | WO2007120980 A2 | 10/2007 |
| WO | 2008/079933 A2 | 7/2008 |
| WO | WO2009031011 A2 | 3/2009 |
| WO | WO2009084695 A1 | 7/2009 |
| WO | WO2009097287 A1 | 8/2009 |
| WO | WO2009102468 A1 | 8/2009 |
| WO | WO2009131687 A2 | 10/2009 |
| WO | WO2009136995 A2 | 11/2009 |
| WO | WO2009145856 A1 | 12/2009 |
| WO | WO2010027500 A1 | 3/2010 |
| WO | WO2010068257 A1 | 6/2010 |
| WO | WO2010068258 A1 | 6/2010 |
| WO | WO2010129802 A1 | 11/2010 |
| WO | WO2011075515 A1 | 6/2011 |
| WO | WO2014031438 A2 | 2/2014 |

OTHER PUBLICATIONS

International Search Report and Written Opinion for PCT/CN2013/001132 mailed on Dec. 26, 2013.

TRIAZOLYL DERIVATIVES AS SYK INHIBITORS

CROSS REFERENCE TO RELATED APPLICATIONS

This application is a U.S. National Phase application under 35 U.S.C. §371 of PCT Application No. PCT/CN2013/001132, filed Sep. 24, 2013, which claims priority under 35 U.S.C. §119(e) from U.S. Provisional Application No. 61/707,246, filed Sep. 28, 2012.

BACKGROUND OF THE INVENTION

Spleen Tyrosine Kinase (Syk) is a protein tyrosine kinase which has been described as a key mediator of immunoreceptor signaling in a host of inflammatory cells including mast cells, B-cells, macrophages and neutrophils. These immunoreceptors, including Fc receptors and the B-cell receptor, are important for both allergic diseases and antibody-mediated autoimmune diseases and thus pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking $Fc_{epsilon}R1$ and or $Fc_{epsilon}R1$ receptors, and is positioned early in the signaling cascade. In mast cells, for example, the early sequence of $Fc_{epsilon}R1$ signaling following allergen cross-linking of receptor-IgE complexes involves first Lyn (a Src family tyrosine kinase) and then Syk Inhibitors of Syk activity would therefore be expected to inhibit all downstream signaling cascades thereby alleviating the immediate allergic response and adverse events initiated by the release of pro-inflammatory mediators and spasmogens (Wong et al 2004, Expert Opin. Investig. Drugs (2004) 13 (7) 743-762).

Recently, it has been shown that the Syk kinase inhibitor R112 (Rigel), dosed intranasally in a phase I/II study for the treatment of allergic rhinitis, gave a statistically significant decrease in PGD2, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B, Journal of Allergy and Clinical Immunology (2005), 115(4), 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterised by inflammation of articular joints leading to debilitating destruction of bone and cartilage. Recent clinical studies with Rituximab, which causes a reversible B cell depletion, (J. C. W. Edwards et al 2004, New Eng. J. Med. 350: 2572-2581) have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterised by a block in B cell development (M. Turner et al 1995 Nature 379: 298-302 and Cheng et al 1995, Nature 378: 303-306). These studies, along with studies on mature B cells deficient in Syk (Kurasaki et al 2000, Immunol. Rev. 176:19-29), demonstrate that Syk is required for the differentiation and activation of B cells. Hence, inhibition of Syk in RA patients is likely to block B cell function and thereby reduce Rheumatoid Factor production. In addition to the role of Syk in B cell function, and of further relevance to the treatment of RA, is the requirement for Syk activity in Fc receptor (FcR) signaling. FcR activation by immune complexes in RA has been suggested to contribute to the release of multiple pro-inflammatory mediators.

U.S. Pat. No. 7,803,801 discloses Syk inhibitors having the formula:

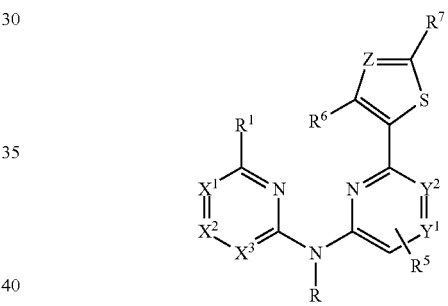

wherein the variables are as defined therein.

The present invention relates to novel compounds, which are inhibitors of Syk kinase activity. These compounds therefore have potential therapeutic benefit in the treatment of disorders associated with inappropriate Syk activity, in particular in the treatment and prevention of disease states mediated by Syk. Such disease states may include inflammatory, allergic and autoimmune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HIV and lupus.

SUMMARY OF THE INVENTION

The present invention provides novel compounds that are potent inhibitors of Syk as well as pharmaceutical compositions containing them. As Syk inhibitors compounds of the present invention are useful in the treatment and prevention of diseases and disorders mediated by the Syk protein; such diseases and disorders include, but are not limited to, asthma, COPD, rheumatoid arthritis, cancer and idiopathic thrombocytopenic purpura.

DETAILED DESCRIPTION OF THE INVENTION

The present invention provides compounds of Formula I:

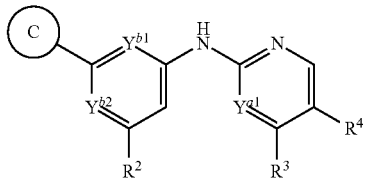

I or a pharmaceutically acceptable salt thereof, wherein:

C is:

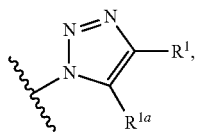
(1)

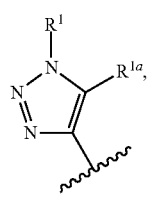
(2)

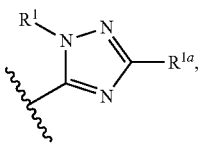
(3)

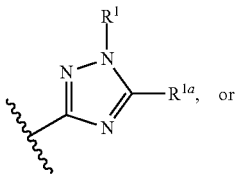
(4)

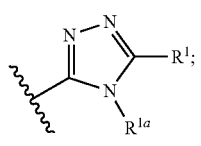
(5)

ring b is

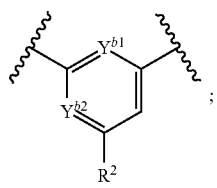

ring a is

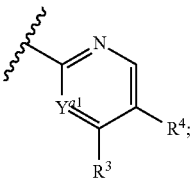

$Y^{a1}$ is independently CH or N;
$Y^{b1}$ and $Y^{b2}$ are independently CH or N, such that $Y^{a1}$ and $Y^{b1}$ are not both simultaneously N;
$R^{1a}$ is independently: H, halogen, or $C_1$-$C_3$-alkyl;
$R^1$ is
H;
halogen;
$Si(CH_3)_3$;
$C_1$-$C_6$-alkyl or $C_2$-$C_6$-alkenyl, optionally with one to four substituents selected from the group consisting of: CN; OH; oxo; $NH_2$; halogen; $CO_2R^c$; $CONH_2$; $C_1$-$C_3$-alkyl; $C_1$-$C_3$-haloalkyl; $C_1$-$C_3$-alkoxyl optionally substituted with OH or fluoro; aryl; Oaryl optionally substituted with halogen; or heterocyclyl;
$(CR^aR^b)_n CO_2R^c$;
$(CR^aR^b)_n CONR^dR^e$;
$(CHR^a)_n NHCONR^dR^e$;
$(CHR^a)_n OCONR^dR^e$;
$(CHR^a)_n CONHSO_2R^d$;
$(CHR^a)_n SO_2R^d$;
$(CHR^a)_n SO_2NR^dR^e$;
$(CR^aR^b)_n$-heterocyclyl;
$(CHR^a)_p$—C(O)-heterocyclyl;
$(CR^aR^b)_n$-carbocyclyl;
$(CR^aR^b)_n$-aryl;
$(CR^aR^b)_n$—O-carbocyclyl; or
$(CR^aR^b)_n$—O-aryl;

Heterocyclyl is a 4-, 5-, 6-, or 7-membered monocyclic ring or 8-, 9-, 10-, 11-membered bicyclic ring, or 13- or 14-membered tricyclic ring; the monocyclic, bicyclic or tricyclic ring can be saturated, unsaturated or aromatic, containing 1, 2, 3 or 4 heteroatoms selected from O, N. or S, the point of attachment of the heterocyclyl can be on the carbon or nitrogen and the heterocyclyl may optionally be substituted with one to four substituents selected from CN; OH; oxo; $NH_2$; halogen; $CO(CH_2)_m CH_3$, optionally substituted with one or two substituents selected from OH and $CO_2R^c$; $C_1$-$C_3$-alkyl; $C_2$-$C_4$-alkenyl; $C_1$-$C_3$-haloalkyl; $C_1$-$C_3$-alkoxyl optionally substituted with OH; aryl optionally substituted with one or two substituents selected from $C_1$-$C_3$-alkoxyl, halogen, or Oaryl; $CH_2$aryl; $OCH_2$aryl; Oaryl optionally substituted with one or two substituents selected from halogen; $(CR^aR^b)_n CO_2R^c$; $(CR^aR^b)_n CONR^dR^e$; $(CHR^a)_n NH CONR^dR^e$; $(CHR^a)_p$—C(O)-heterocyclyl; and furyl; or alternatively, 2 substituents which are geminally substituted on a common ring carbon atom of said heterocyclyl may together with the common ring carbon atom form a $C_3$-$C_6$ spirocyclic ring;

Carbocyclyl is a non-aromatic, saturated or partially unsaturated, 4-, 5-, 6-, or 7-membered monocyclic ring in which all ring atoms are carbon, and the ring being isolated or fused to one or two such rings or to a benzene ring; the carbocyclyl may optionally be substituted with one to four substituents selected from hydroxyl, amino, $C_1$-$C_3$-alkyl, $C_1$-$C_3$-alkoxyl, $(CR^aR^b)_nCO_2R^c$; $(CR^aR^b)_nCONR^dR^e$; and a Spiro-linked —$OCH_2CH_2O$—;

Aryl is a phenyl or napthalyl ring, the aryl may optionally be substituted with one to four substituents selected from halogen, hydroxyl, $C_1$-$C_3$-alkyl, $C_1$-$C_3$-alkoxyl, Oaryl, $(CR^aR^b)_nCO_2R^c$; and $(CR^aR^b)_nCONR^dR^e$;

$R^2$ is H, halogen, $C_1$-$C_3$-alkyl, $C_1$-$C_3$-haloalkyl, $C_3$-$C_7$-cycloalkyl, heterocyclyl, $NR^dR^e$, $CONR^dR^e$, $NHCONR^dR^e$, $CH_2OCH_3$; or $NO_2$;

$R^3$ is H or halogen, $C_1$-$C_4$-alkyl, $C_1$-$C_3$-fluoroalkyl, $C_1$-$C_3$-alkoxyl, optionally substituted with hydroxyl; $C_3$-$C_6$-cycloalkyl; O—$C_3$-$C_6$-cycloalkyl; O-tetrahydrofuranyl or pyridyl;

$R^4$ is H, halogen, or $C_1$-$C_3$-alkyl;

$R^a$ and $R^b$ are independently: H, OH, CN, $CO_2R^c$, $CONH_2$, $NH_2$, cyclopropyl, $C_1$-$C_3$-haloalkyl, or $C_1$-$C_3$-alkyl optionally substituted with hydroxyl;

$R^c$ is: H; $C_{1-4}$ alkyl; -M-$R^{CH}$; —$(CH_2)_{1-2}$—$R^f$; —$(CH_2)_2$—O—$(CH_2)_2$—$R^f$; —$(CH_2)_2$—$R^g$, —$CHR^hOCO_2R^i$, —$CHR^iR^h$, or —$(CHR^h)_sOC(O)R^i$;

$R^d$ and $R^e$ are independently: H, $C_1$-$C_3$-alkoxyl or $C_1$-$C_6$-alkyl, optionally substituted with one, two or three substituents CN; OH; oxo; $NH_2$; halogen; $CO_2R^c$; $CONH_2$; $C_1$-$C_3$-alkoxyl, $CO_2R^c$; aryl, carbocyclyl, or heterocyclyl; or cyclopropyl optionally substituted with phenyl;

$R^f$ is —$OC(O)R^{f1}$;

$R^{f1}$ is $C_{1-4}$alkyl; and $R^g$ is OH, $C_{1-4}$alkoxyl, $NH_2$, $NH(C_{1-4}$alkyl) or $N(C_{1-4}$alkyl)$_2$;

$R^h$ is H or $C_{1-4}$alkyl; and $R^i$ is $C_{1-4}$alkyl, $C_{3-6}$cycloalkyl, or phenyl; and, M is a bond or —$(CH_2)_{1-3}$—;

$R^{CH}$ is (a) aryl or carbocycle optionally substituted with 1-3 groups independently selected from halo, $C_{1-4}$alkyl, or $C_{1-4}$alkoxy; or (b) a 5- to 6-membered monocyclic heterocycle containing 1 or 2 heteroatoms independently selected from the group consisting of N and O, wherein said heterocycle of $R^{CH}$ is optionally substituted with 1 or 2 groups independently selected from the group consisting of oxo and $C_{1-3}$ alkyl;

m is 0, 1, or 2;

n is 0, 1, 2, 3 or 4;

p is 0 or 1; and s is 1 or 2.

In an embodiment of the compounds of Formula I, $R^1$ is
H;
halogen;
$Si(CH_3)_3$;
$C_1$-$C_6$-alkyl or $C_2$-$C_6$-alkenyl, optionally with one to four substituents selected from the group consisting of: CN; OH; oxo; $NH_2$; halogen; $CO_2R^c$; $CONH_2$; $C_1$-$C_3$-alkyl; $C_1$-$C_3$-haloalkyl; $C_1$-$C_3$-alkoxyl optionally substituted with OH; aryl; Oaryl optionally substituted with halogen; or heterocyclyl;
$(CR^aR^b)_nCO_2R^c$;
$(CR^aR^b)_nCONR^dR^e$;
$(CHR^a)_nNHCONR^dR^e$;
$(CHR^a)_nCONHSO_2R^d$;
$(CHR^a)_nSO_2R^d$;
$(CHR^a)_nSO_2NR^dR^e$;
$(CR^aR^b)_n$-heterocyclyl;
$(CHR^a)_p$—C(O)-heterocyclyl;
$(CR^aR^b)_n$-carbocyclyl;
$(CR^aR^b)_n$-aryl;
$(CR^aR^b)_n$—O-carbocyclyl; or
$(CR^aR^b)_n$—O-aryl;

said heterocyclyl is a 4-, 5-, 6-, or 7-membered monocyclic ring or 8-, 9-, 10-, 11-membered bicyclic ring, or 13- or 14-membered tricyclic ring; the monocyclic, bicyclic or tricyclic ring can be saturated, unsaturated or aromatic, containing 1, 2, 3 or 4 heteroatoms selected from O, N. or S, the point of attachment of the heterocyclyl can be on the carbon or nitrogen and the heterocyclyl may optionally be substituted with one to four substituents selected from CN; OH; oxo; $NH_2$; halogen; $CO(CH_2)_mCH_3$, optionally substituted with one or two substituents selected from OH and $CO_2R^c$; $C_1$-$C_3$-alkyl; $C_2$-$C_4$-alkenyl; $C_1$-$C_3$-haloalkyl; $C_1$-$C_3$-alkoxyl optionally substituted with OH; aryl optionally substituted with one or two substituents selected from $C_1$-$C_3$-alkoxyl, halogen, or Oaryl; $CH_2$aryl; $OCH_2$aryl; Oaryl optionally substituted with one or two substituents selected from halogen; $(CR^aR^b)_nCO_2R^c$; $(CR^aR^b)_nCONR^dR^e$; $(CHR^a)_nNHCONR^dR^e$; and $(CHR^a)_p$—C(O)-heterocyclyl; and said carbocyclyl is a non-aromatic, saturated or partially unsaturated, 4-, 5-, 6-, or 7-membered monocyclic ring in which all ring atoms are carbon, and the ring being isolated or fused to one or two such rings or to a benzene ring; the carbocyclyl may optionally be substituted with one to four substituents selected from hydroxyl, $C_1$-$C_3$-alkyl, $C_1$-$C_3$-alkoxyl, $(CR^aR^b)_nCO_2R^c$; $(CR^aR^b)_nCONR^dR^e$; and a Spiro-linked —$OCH_2CH_2O$—.

In an embodiment of the compounds of Formula I

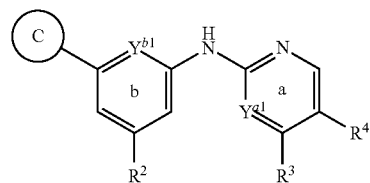

the rings a and b are defined as follows: a) $Y^{a1}$ is N; and $Y^{b1}$ is CH; and b) $Y^{b1}$ is N; and $Y^{a1}$ is CH; and all other substituents are as defined in the first embodiment.

An embodiment of the compounds of Formula I, wherein

is:

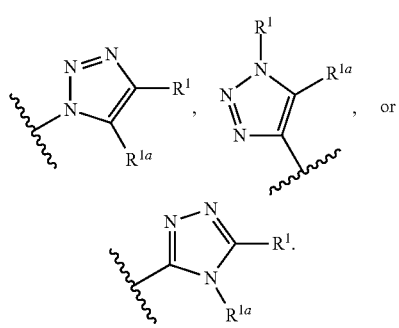

and all other substituents are as defined in the previous embodiments.

In one embodiment of the compounds of Formula Ia

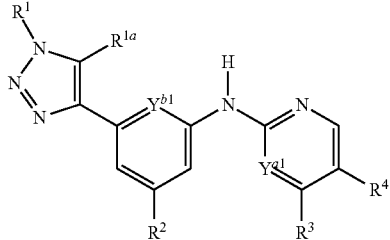

rings a and b are defined as: a) $Y^{a1}$ is N; and $Y^{b1}$ is CH; or b) $Y^{b1}$ is N; and $Y^{a1}$ is CH;
and all other substituents are as defined above.

In an embodiment of the compounds of Formula Ib

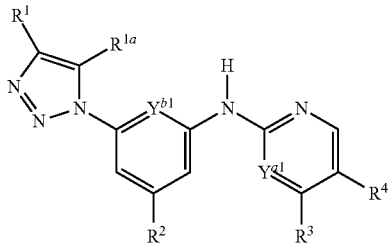

rings a and b are defined as: a) $Y^{a1}$ is N; and $Y^{b1}$ is CH; or b) $Y^{b1}$ and $Y^{a1}$ is CH;
and all other substituents are as defined above.

In an embodiment of the compounds of Formula Ic

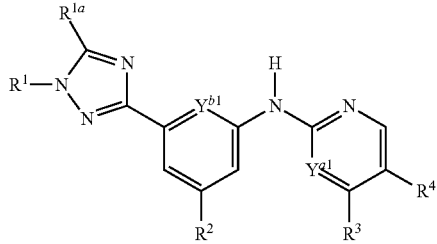

rings a and b are defined as: a) $Y^{a1}$ is N; and $Y^{b1}$ is CH; or b) $Y^{b1}$ are N; and $Y^{a1}$ is CH; and all other substituents are as defined above.

In an embodiment of the compounds of Formula Id

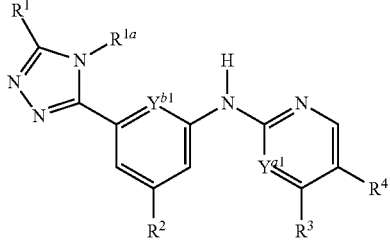

rings a and b are defined as: a) $Y^{a1}$ is N; and $Y^{b1}$ is CH; or b) $Y^{b1}$ is N; and $Y^{a1}$ is CH; and all other substituents are as defined above.

In an embodiment of the compounds of Formula Ie

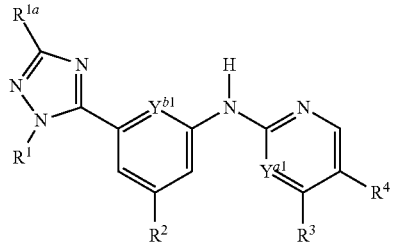

rings a and b are defined as: a) $Y^{a1}$ is N; and $Y^{b1}$ is CH; or b) $Y^{b1}$ is N; and $Y^{a1}$ is CH; and all other substituents are as defined above.

In any one of the above embodiments of the compounds of Formulae I, Ia, Ib, Ic, Id and Ie, $R^{1a}$ is independently H, $CH_3$, Cl, F, or $CF_3$. In a second embodiment of the compounds of Formula I, Ia, Ib, Ic, Id and Ie, $R^{1a}$ is H.

In any one of the above embodiments of the compounds of Formulae I, Ia, Ib, Ic, Id and Ie, or a pharmaceutically acceptable salt thereof, $R^2$ is H, $CH_3$ or $CH_2OMe$. In a second embodiment of the compounds of Formula I, Ia, Ib, Ic and Id, $R^2$ is $CH_3$.

In any one of the above embodiments of the compounds of Formulae I, Ia, Ib, Ic and Id, or a pharmaceutically acceptable salt thereof, $R^3$ is $CF_3$, $CHF_2$, $CHFCH_3$, F, $CH_3$, $CH_2CH_3$, c-propyl, c-butyl i-propyl, t-butyl, $CH(CH_3)OH$, $OCH_3$, $OCH_2CH_3$, $OCH(CH_3)_2$, $OCH_2CH_2OH$, or

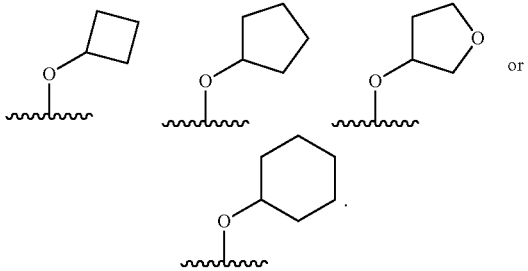

In a second embodiment of the compounds of Formulae I, Ia, Ib, Ic, Id and Ie, or a pharmaceutically acceptable salt thereof, $R^3$ is $CF_3$, $CHF_2$, $CH_3$, or c-propyl. In a third embodiment of the compounds of Formulae I, Ia, Ib, Ic, Id and Ie, $R^3$ is $CF_3$.

In any one of the above embodiments of the compounds of Formulae I, Ia, Ib, Ic and Id, or a pharmaceutically acceptable salt thereof, $R^4$ is H, Cl or F. In a second embodiment of the compounds of Formulae I, Ia, Ib, Ic and Id, $R^4$ is H.

In another embodiment of the compounds of Formulae I, Ia, Ib, Ic, Id and Ie or a pharmaceutically acceptable salt thereof, wherein: $R^{1a}$ is H, $R^2$ is H, or $CH_3$; $R^3$ is $CF_3$, $CHF_2$, $CH_3$, or c-propyl. $R^4$ is H, Cl or F; and all other substituents are as defined above.

In second embodiment of the compounds of Formulae I, Ia, Ib, Ic, Id and Ie or a pharmaceutically acceptable salt thereof, wherein: $R^1$ is H; $Si(CH)_3$, $C_1$-$C_6$-alkyl, optionally with one to four substituents selected from the group consisting of: CN, OH, oxo, $NH_2$, halogen, $CF_3$, $C_1$-$C_3$-alkyl, or $C_1$-$C_3$-alkoxyl; $(CR^aR^b)_nCO_2R^c$; $(CR^aR^b)_nCONR^dR^e$; $(CHR^a)_nSO_2R^d$; $(CR^aR^b)_n$-heterocyclyl; or $(CR^aR^b)_n$-carbocyclyl; and all other substituents are as defined above.

In third embodiment of the compounds of Formula I, Ia, Ib, Ic, Id and Ie or a pharmaceutically acceptable salt thereof, wherein: $R^1$ is H; $C_1$-$C_6$-alkyl, optionally with one to four substituents selected from the group consisting of: CN, OH, oxo, $NH_2$, halogen, $CF_3$, $CH_3$ or $OCH_3$; $(CR^aR^b)_n CO_2R$; $(CR^aR^b)_n CONH_2$; $(CR^aR^b)_n$-heterocyclyl; or $(CR^aR^b)_n$-carbocyclyl, wherein the heterocyclyl and carbocyclyl is optionally substituted with one to four substituents selected from the group consisting of: OH, $CONH_2$, oxo, $C_1$-$C_3$-alkyl, and $(CR^aR^b)_n CO_2R^c$; $R^a$ and $R^b$ are independently H, $CH_3$, or OH; n is 0, 1, 2, 3 or 4; $R^c$ is H, $C_{1-6}$alkyl, or —$CHR^hOCO_2R^i$; $R^h$ is H or $CH_3$; $R^i$ is ethyl or isopropyl; and all other substituents are as defined above.

In another embodiment are compounds of the Formula Ie as set forth above, wherein $R^1$ is $(CR^aR^b)_n$-heterocyclyl, wherein the heterocyclyl moiety of the $(CR^aR^b)_n$-heterocyclyl is pyrrolidine, oxazolidine, or piperidine, wherein the pyrrolidine, oxazolidine, or piperidine is unsubstituted or substituted or substituted with 1-4 substituents selected from the group consisting of oxo, hydroxyl, $C_{1-3}$ alkyl, $CO_2H$, and $CONH_2$. In a specific embodiment n is 0.

In another embodiment are compounds of the Formula Ie as set forth above, wherein $R^1$ is $(CR^aR^b)_n$-carbocyclyl, wherein the carbocyclyl moiety of the $(CR^aR^b)_n$-carbocyclyl is a $C_{4-8}$cycloalkyl, wherein the $C_{4-8}$cycloalkyl is unsubstituted or substituted or substituted with 1-4 substituents selected from the group consisting of hydroxyl, $C_{1-3}$ alkyl, $CO_2H$, and $CONH_2$. In a specific embodiment n is 0.

In another embodiment of the compounds of Formula I or a pharmaceutically acceptable salt thereof are compounds having the formula If

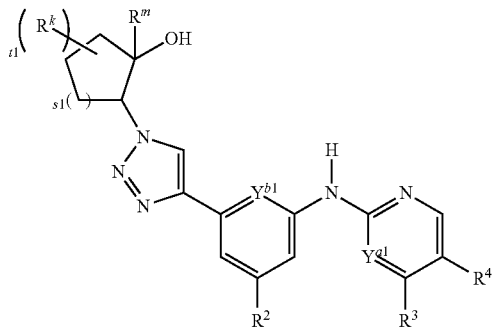

wherein
(i) $Y^{a1}$ is N and $Y^{b1}$ is CH or
(ii) $Y^{a1}$ is CH and $Y^{b1}$ is N;
each $R^k$ is independently $C_{1-3}$alkyl or OH;
$R^m$ is H or $C_1$-$C_3$-alkyl;
$R^2$ is H or methyl;
$R^3$ is H, methyl, isopropyl, $C_1$-$C_3$-fluoroalkyl, cyclopropyl, or methoxy;
$R^4$ is H or fluoro;
s1 is 1, 2, or 3; and
t1 is 0, 1, or 2.

In another embodiment are compounds having the formula If or a pharmaceutically acceptable salt thereof, wherein
the group

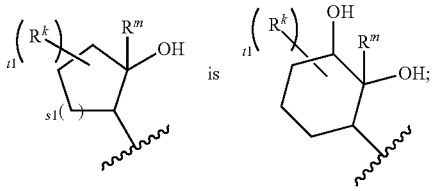

$R^2$ is methyl;
t1 is 0 or 1; and
$R^2$, $R^3$, $R^k$ and $R^m$ are as set forth above.

In one embodiment of the compounds of Formula If or a pharmaceutically acceptable salt thereof, wherein $Y^{a1}$ is N and $Y^{b1}$ is CH.

In another embodiment of the compounds of Formula If or a pharmaceutically acceptable salt thereof, wherein $Y^{a1}$ is CH and $Y^{b1}$ is N.

In another embodiment of the compounds of Formula I or a pharmaceutically acceptable salt thereof are compounds having the formula Ig

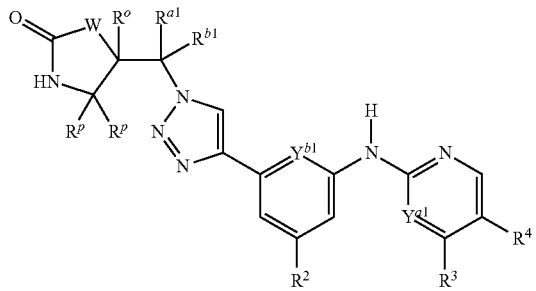

wherein
(i) $Y^{a1}$ is N and $Y^{b1}$ is CH; or
(ii) $Y^{a1}$ is CH and $Y^{b1}$ is N;
W is O or $CH_2$;
$R^{a1}$ and $R^{b1}$ are independently H or $C_1$-$C_3$-alkyl;
$R^o$ is H, OH, or $C_1$-$C_3$-alkyl;
each $R^p$ is independently H or $C_{1-3}$alkyl; or both $R^p$ together with the carbon atom to which they are attached form a $C_3$-$C_6$-spirocycle;
$R^2$ is H or methyl;
$R^3$ is H, methyl, isopropyl, $C_{1-3}$fluoroalkyl, cyclopropyl, or methoxy; and
$R^4$ is H or fluoro.

In another embodiment are compounds having the formula Ig or a pharmaceutically acceptable salt thereof, wherein W is O.

In another embodiment are compounds having the formula Ig or a pharmaceutically acceptable salt thereof, wherein W is $CH_2$.

In another embodiment are compounds having the formula Ig or a pharmaceutically acceptable salt thereof, wherein
$Y^{a1}$ is N and $Y^{b1}$ is CH;
W is O;
$R^{a1}$ and $R^{b1}$ are independently H or $C_1$-$C_3$-alkyl;
$R^o$ is H or methyl;
each $R^p$ is independently H or methyl; or both $R^p$ together with the carbon atom to which they are attached form a spirocyclopropane;
$R^2$ is methyl;
$R^3$ is H, methyl, or $C_{1-3}$fluoroalkyl; and
$R^4$ is H or fluoro.

In another embodiment are compounds having the formula Ig or a pharmaceutically acceptable salt thereof, wherein
$Y^{a1}$ is CH and $Y^{b1}$ is N;
W is O;
$R^{a1}$ and $R^{b1}$ are independently H or $C_1$-$C_3$-alkyl;
$R^o$ is H or methyl;
each $R^p$ is independently H or methyl; or both $R^p$ together with the carbon atom to which they are attached form a spirocyclopropane;
$R^2$ is methyl;
$R^3$ is H, methyl, or $C_{1-3}$fluoroalkyl; and
$R^4$ is H or fluoro.

In another embodiment of the compounds of Formula I or a pharmaceutically acceptable salt thereof are compounds having the formula Ih

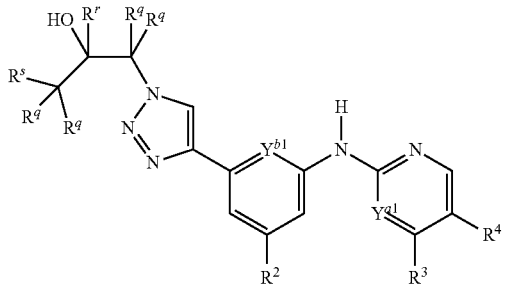

wherein
(i) $Y^{a1}$ is N and $Y^{b1}$ is CH or
(ii) $Y^{a1}$ is CH and $Y^{b1}$ is N;
each $R^q$ is independently H, $C_{1-3}$alkyl, or $C_{1-3}$fluoroalkyl;
Rr is H or $C_1$-$C_3$-alkyl;
$R^s$ is hydroxyl or CN;
$R^2$ is H or methyl;
$R^3$ is H, methyl, isopropyl, $C_{1-3}$fluoroalkyl, cyclopropyl, or methoxy; and
$R^4$ is H or fluoro.

In another embodiment are compounds having the formula Ih or a pharmaceutically acceptable salt thereof, wherein
$Y^{a1}$ is N and $Y^{b1}$ is CH;
each $R^q$ is independently H or Me;
$R^r$ is H or Me;
$R^s$ is hydroxyl;
$R^2$ is methyl;
$R^3$ is H, methyl, or $C_{1-3}$fluoroalkyl; and
$R^4$ is H or fluoro.

In another embodiment are compounds having the formula Ih or a pharmaceutically acceptable salt thereof, wherein
$Y^{a1}$ is CH and $Y^{b1}$ is N;
each $R^q$ is independently H or Me;
$R^r$ is H or Me;
$R^s$ is hydroxyl;
$R^2$ is methyl;
$R^3$ is H, methyl, or $C_{1-3}$fluoroalkyl; and
$R^4$ is H or fluoro.

Representative compounds of the present invention are as follows, where each named compound is intended to encompass its individual isomers, mixtures thereof (including racemates and diastereomeric mixtures), as well as pharmaceutically acceptable salts thereof:

methyl N-{(2S)-2-[4-(4-methyl-6-{[4-(trifluoromethyl)pyridin-2-yl]amino}pyridin-2-yl)-1H-1,2,3-triazol-1-yl]propanoyl}glycinate trifluoroacetate;

N-(1,1-dioxidotetrahydrothiophen-3-yl)-2-[4-(4-methyl-6-{[4-(trifluoromethyl)pyridin-2-yl]amino}pyridin-2-yl)-1H-1,2,3-triazol-1-yl]propanamide;

3-[4-(4-methyl-6-{[4-(trifluoromethyl)pyridin-2-yl]amino}pyridin-2-yl)-1H-1,2,3-triazol-1-yl]propanamide;

2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxamide;

2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxamide;

2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxamide;

4-[4-(3-methyl-5-{[4-(trifluoromethyl)pyrimidin-2-yl]amino}phenyl)-1H-1,2,3-triazol-1-yl]cyclohexanecarboxamide;

2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxamide;

4-{2-hydroxy-1-[4-(4-methyl-6-{[4-(trifluoromethyl)pyridin-2-yl]amino}pyridin-2-yl)-1H-1,2,3-triazol-1-yl]ethyl}benzamide;

4-{1-hydroxy-2-[4-(4-methyl-6-{[4-(trifluoromethyl)pyridin-2-yl]amino}pyridin-2-yl)-1H-1,2,3-triazol-1-yl]ethyl}benzamide;

4-[4-(4-methyl-6-{[4-(trifluoromethyl)pyridin-2-yl]amino}pyridin-2-yl)-1H-1,2,3-triazol-1-yl]-1,2,3,4-tetrahydronaphthalene-1-carboxamide;

2-hydroxy-2-methyl-3-[4-(4-methyl-6-{[4-(trifluoromethyl)pyridin-2-yl]amino}pyridin-2-yl)-1H-1,2,3-triazol-1-yl]propanamide;

(2S)-2-hydroxy-3-[4-(4-methyl-6-{[4-(trifluoromethyl)pyridin-2-yl]amino}pyridin-2-yl)-1H-1,2,3-triazol-1-yl]propanamide;

(2R)-2-hydroxy-3-[4-(4-methyl-6-{[4-(trifluoromethyl)pyridin-2-yl]amino}pyridin-2-yl)-1H-1,2,3-triazol-1-yl]propanamide;

4-[4-(4-methyl-6-{[4-(trifluoromethyl)pyridin-2-yl]amino}pyridin-2-yl)-1H-1,2,3-triazol-1-yl]benzamide;

4-{1-[4-(4-methyl-6-{[4-(trifluoromethyl)pyridin-2-yl]amino}pyridin-2-yl)-1H-1,2,3-triazol-1-yl]ethyl}benzamide;

2-(4-fluorophenyl)-2-[4-(4-methyl-6-{[4-(trifluoromethyl)pyridin-2-yl]amino}pyridin-2-yl)-1H-1,2,3-triazol-1-yl]acetamide;

2-[4-(4-methyl-6-{[4-(trifluoromethyl)pyridin-2-yl]amino}pyridin-2-yl)-1H-1,2,3-triazol-1-yl]-2-phenylacetamide;

1-{(2R)-2-[4-(4-methyl-6-{[4-(trifluoromethyl)pyridin-2-yl]amino}pyridin-2-yl)-1H-1,2,3-triazol-1-yl]propanoyl}prolinamide;

1-{(2S)-2-[4-(4-methyl-6-{[4-(trifluoromethyl)pyridin-2-yl]amino}pyridin-2-yl)-1H-1,2,3-triazol-1-yl]propanoyl}prolinamide;

(2R)—N-(2-amino-2-oxoethyl)-2-[4-(4-methyl-6-{[4-(trifluoromethyl)pyridin-2-yl]amino}pyridin-2-yl)-1H-1,2,3-triazol-1-yl]propanamide;

(2S)—N-(2-amino-2-oxoethyl)-2-[4-(4-methyl-6-{[4-(trifluoromethyl)pyridin-2-yl]amino}pyridin-2-yl)-1H-1,2,3-triazol-1-yl]propanamide;

(2R)-2-[4-(4-methyl-6-{[4-(trifluoromethyl)pyridin-2-yl]amino}pyridin-2-yl)-1H-1,2,3-triazol-1-yl]propanamide;

(2S)-2-[4-(4-methyl-6-{[4-(trifluoromethyl)pyridin-2-yl]amino}pyridin-2-yl)-1H-1,2,3-triazol-1-yl]propanamide;

2-[4-(4-methyl-6-{[4-(trifluoromethyl)pyridin-2-yl]amino}pyridin-2-yl)-1H-1,2,3-triazol-1-yl]propanamide;

(2E)-4-[4-(4-methyl-6-{[4-(trifluoromethyl)pyridin-2-yl]amino}pyridin-2-yl)-1H-1,2,3-triazol-1-yl]but-2-enamide;

N-[(1R)-1-benzyl-2-hydroxyethyl]-2-[4-(4-methyl-6-{[4-(trifluoromethyl)pyridin-2-yl]amino}pyridin-2-yl)-1H-1,2,3-triazol-1-yl]propanamide;

6-{1-[2-(3,4-dihydroisoquinolin-2(1H)-yl)-1-methyl-2-oxoethyl]-1H-1,2,3-triazol-4-yl}-4-methyl-N-[4-(trifluoromethyl)pyridin-2-yl]pyridin-2-amine;

N-[2-(1H-indol-3-yl)ethyl]-2-[4-(4-methyl-6-{[4-(trifluoromethyl)pyridin-2-yl]amino}pyridin-2-yl)-1H-1,2,3-triazol-1-yl]propanamide;

N-{2-[5-(benzyloxy)-1H-indol-3-yl]ethyl}-2-[4-(4-methyl-6-{[4-(trifluoromethyl)pyridin-2-yl]amino}pyridin-2-yl)-1H-1,2,3-triazol-1-yl]propanamide;

4-methyl-6-{1-[1-methyl-2-oxo-2-(1,3,4,9-tetrahydro-2H-beta-carbolin-2-yl)ethyl]-1H-1,2,3-triazol-4-yl}-N-[4-(trifluoromethyl)pyridin-2-yl]pyridin-2-amine;

2-[4-(4-methyl-6-{[4-(trifluoromethyl)pyridin-2-yl]amino}pyridin-2-yl)-1H-1,2,3-triazol-1-yl]-N-(2-naphthalen-2-ylethyl)propanamide;

N-(2,1,3-benzothiadiazol-4-ylmethyl)-2-[4-(4-methyl-6-{[4-(trifluoromethyl)pyridin-2-yl]amino}pyridin-2-yl)-1H-1,2,3-triazol-1-yl]propanamide;

6-{1-[2-(6,7-dimethoxy-3-methyl-3,4-dihydroisoquinolin-2(1H)-yl)-1-methyl-2-oxoethyl]-1H-1,2,3-triazol-4-yl}-4-methyl-N-[4-(trifluoromethyl)pyridin-2-yl]pyridin-2-amine;

N-{1-[1-(2-fluorophenyl)-1H-pyrazol-4-yl]ethyl}-2-[4-(4-methyl-6-{[4-(trifluoromethyl)pyridin-2-yl]amino}pyridin-2-yl)-1H-1,2,3-triazol-1-yl]propanamide;

2-[4-(4-methyl-6-{[4-(trifluoromethyl)pyridin-2-yl]amino}pyridin-2-yl)-1H-1,2,3-triazol-1-yl]-N-[2-(3-phenoxyphenyl)ethyl]propanamide;

N-[(5-furan-2-ylisoxazol-3-yl)methyl]-2-[4-(4-methyl-6-{[4-(trifluoromethyl)pyridin-2-yl]amino}pyridin-2-yl)-1H-1,2,3-triazol-1-yl]propanamide;

N-[2-(2,5-dimethoxyphenyl)-2-hydroxy-1-methylethyl]-2-[4-(4-methyl-6-{[4-(trifluoromethyl)pyridin-2-yl]amino}pyridin-2-yl)-1H-1,2,3-triazol-1-yl]propanamide;

6-(1-{2-[3-(4-fluorophenyl)-6,7-dihydroisoxazolo[4,5-c]pyridin-5(4H)-yl]-1-methyl-2-oxoethyl}-1H-1,2,3-triazol-4-yl)-4-methyl-N-[4-(trifluoromethyl)pyridin-2-yl]pyridin-2-amine;

2-[4-(4-methyl-6-{[4-(trifluoromethyl)pyridin-2-yl]amino}pyridin-2-yl)-1H-1,2,3-triazol-1-yl]-N-[(1S,2R)-2-phenylcyclopropyl]propanamide;

6-{1-[2-(6-chloro-1,3,4,5-tetrahydro-2H-pyrido[4,3-b]indol-2-yl)-1-methyl-2-oxoethyl]-1H-1,2,3-triazol-4-yl}-4-methyl-N-[4-(trifluoromethyl)pyridin-2-yl]pyridin-2-amine;

2-[4-(4-methyl-6-{[4-(trifluoromethyl)pyridin-2-yl]amino}pyridin-2-yl)-1H-1,2,3-triazol-1-yl]-N-[2-(2-phenoxyphenyl)ethyl]propanamide;

N-[(7-fluoro-2-oxo-1,2-dihydroquinolin-3-yl)methyl]-2-[4-(4-methyl-6-{[4-(trifluoromethyl)pyridin-2-yl]amino}pyridin-2-yl)-1H-1,2,3-triazol-1-yl]propanamide;

2-[4-(4-methyl-6-{[4-(trifluoromethyl)pyridin-2-yl]amino}pyridin-2-yl)-1H-1,2,3-triazol-1-yl]-N-(2-naphthalen-1-ylethyl)propanamide;

6-(1-{2-[2-(4-methoxyphenyl)thiomorpholin-4-yl]-1-methyl-2-oxoethyl}-1H-1,2,3-triazol-4-yl)-4-methyl-N-[4-(trifluoromethyl)pyridin-2-yl]pyridin-2-amine;

2-[4-(4-methyl-6-{[4-(trifluoromethyl)pyridin-2-yl]amino}pyridin-2-yl)-1H-1,2,3-triazol-1-yl]-N-[2-(4-phenoxyphenyl)ethyl]propanamide;

N-[(5-methyl-3-phenylisoxazol-4-yl)methyl]-2-[4-(4-methyl-6-{[4-(trifluoromethyl)pyridin-2-yl]amino}pyridin-2-yl)-1H-1,2,3-triazol-1-yl]propanamide;

6-{1-[2-(6-methoxy-1,3,4,9-tetrahydro-2H-beta-carbolin-2-yl)-1-methyl-2-oxoethyl]-1H-1,2,3-triazol-4-yl}-4-methyl-N-1.[4-(trifluoromethyl)pyridin-2-yl]pyridin-2-amine;

N-{[4-(4-fluorophenyl)tetrahydro-2H-pyran-4-yl]methyl}-2-[4-(4-methyl-6-{[4-(trifluoromethyl)pyridin-2-yl]amino}pyridin-2-yl)-1H-1,2,3-triazol-1-yl]propanamide;

6-{1-[2-(4-benzyl-3-phenylpiperazin-1-yl)-1-methyl-2-oxoethyl]-1H-1,2,3-triazol-4-yl}-4-methyl-N-[4-(trifluoromethyl)pyridin-2-yl]pyridin-2-amine;

N-[2-(1-methyl-1H-indol-3-yl)ethyl]-2-[4-(4-methyl-6-{[4-(trifluoromethyl)pyridin-2-yl]amino}pyridin-2-yl)-1H-1,2,3-triazol-1-yl]propanamide;

2-[4-(4-methyl-6-{[4-(trifluoromethyl)pyridin-2-yl]amino}pyridin-2-yl)-1H-1,2,3-triazol-1-yl]-N-{2-morpholin-4-yl-2-[4-(trifluoromethyl)phenyl]ethyl}propanamide;

4-methyl-6-{1-[1-methyl-2-oxo-2-(3-pyridin-4-ylpyrrolidin-1-yl)ethyl]-1H-1,2,3-triazol-4-yl}-N-[4-(trifluoromethyl)pyridin-2-yl]pyridin-2-amine;

3-{2-[4-(4-methyl-6-{[4-(trifluoromethyl)pyridin-2-yl]amino}pyridin-2-yl)-1H-1,2,3-triazol-1-yl]propanoyl}-1-phenyl-2,3,4,5-tetrahydro-1H-3-benzazepine-7,8-diol;

methyl 1-{(2R)-2-[4-(4-methyl-6-{[4-(trifluoromethyl)pyridin-2-yl]amino}pyridin-2-yl)-1H-1,2,3-triazol-1-yl]propanoyl}prolinate;

methyl 1-{(2S)-2-[4-(4-methyl-6-{[4-(trifluoromethyl)pyridin-2-yl]amino}pyridin-2-yl)-1H-1,2,3-triazol-1-yl]propanoyl}prolinate;

methyl N-{(2R)-2-[4-(4-methyl-6-{[4-(trifluoromethyl)pyridin-2-yl]amino}pyridin-2-yl)-1H-1,2,3-triazol-1-yl]propanoyl}glycinate;

(1S,4R)-4-hydroxy-2,2-dimethyl-4-[1-(3-methyl-5-{[4-(trifluoromethyl)pyrimidin-2-yl]amino}phenyl)-1H-1,2,3-triazol-4-yl]cyclohexanecarboxamide;

4-(1-(4-(3-((4-ethylpyridin-2-yl)amino)-5-methylphenyl)-1H-1,2,3-triazol-1-yl)ethyl)benzoic acid;

4-[1-(4-{6-[(4-fluoropyridin-2-yl)amino]-4-methylpyridin-2-yl}-1H-1,2,3-triazol-1-yl)ethyl]benzoic acid;

4-{1-[4-(6-{[4-(1-hydroxyethyl)pyridin-2-yl]amino}-4-methylpyridin-2-yl)-1H-1,2,3-triazol-1-yl]ethyl}benzoic acid;

4-{1-[4-(6-{[4-(2-hydroxyethoxyl)pyridin-2-yl]amino}-4-methylpyridin-2-yl)-1H-1,2,3-triazol-1-yl]ethyl}benzoic acid;

4-{1-[4-(4-methyl-6-{[4-(tetrahydrofuran-3-yloxy)pyridin-2-yl]amino}pyridin-2-yl)-1H-1,2,3-triazol-1-yl]ethyl}benzoic acid;

4-{1-[4-(6-{[4-(cyclohexyloxy)pyridin-2-yl]amino}-4-methylpyridin-2-yl)-1H-1,2,3-triazol-1-yl]ethyl}benzoic acid;

4-{1-[4-(6-{[4-(cyclopentyloxy)pyridin-2-yl]amino}-4-methylpyridin-2-yl)-1H-1,2,3-triazol-1-yl]ethyl}benzoic acid;

4-{1-[4-(6-{[4-(cyclobutyloxy)pyridin-2-yl]amino}-4-methylpyridin-2-yl)-1H-1,2,3-triazol-1-yl]ethyl}benzoic acid;

4-[1-(4-{6-[(4-ethoxypyridin-2-yl)amino]-4-methylpyridin-2-yl}-1H-1,2,3-triazol-1-yl)ethyl]benzoic acid;

4-[1-(4-{6-[(4-cyclobutylpyridin-2-yl)amino]-4-methylpyridin-2-yl}-1H-1,2,3-triazol-1-yl)ethyl]benzoic acid;

4-[1-(4-{6-[(4-cyclopropylpyridin-2-yl)amino]-4-methylpyridin-2-yl}-1H-1,2,3-triazol-1-yl)ethyl]benzoic acid;

4-[1-(4-{6-[(4-tert-butylpyridin-2-yl)amino]-4-methylpyridin-2-yl}-1H-1,2,3-triazol-1-yl)ethyl]benzoic acid;

4-{1-[4-(4-methyl-6-{[4-(1-methylethyl)pyridin-2-yl]amino}pyridin-2-yl)-1H-1,2,3-triazol-1-yl]ethyl}benzoic acid;

N-[3-methyl-5-(1H-1,2,4-triazol-3-yl)phenyl]-4-(trifluoromethyl)pyrimidin-2-amine;

(2S)-3-[5-(3-methyl-5-{[4-(trifluoromethyl)pyrimidin-2-yl]amino}phenyl)-1H-1,2,4-triazol-1-yl]propane-1,2-diol;

4-hydroxy-2,2-dimethyl-4-{[4-(4-methyl-6-{[4-(trifluoromethyl)pyridin-2-yl]amino}pyridin-2-yl)-1H-1,2,3-triazol-1-yl]methyl}cyclohexanecarboxylic acid;

4-hydroxy-2,2-dimethyl-4-{[4-(3-methyl-5-{[4-(trifluoromethyl)pyrimidin-2-yl]amino}phenyl)-1H-1,2,3-triazol-1-yl]methyl}cyclohexanecarboxylic acid;

4-hydroxy-2,2-dimethyl-4-{[4-(3-methyl-5-{[4-(trifluoromethyl)pyrimidin-2-yl]amino}phenyl)-1H-1,2,3-triazol-1-yl]methyl}cyclohexanecarboxylic acid;

4-hydroxy-2,2-dimethyl-4-{[4-(3-methyl-5-{[4-(trifluoromethyl)pyrimidin-2-yl]amino}phenyl)-1H-1,2,3-triazol-1-yl]methyl}cyclohexanecarboxylic acid;

4-hydroxy-2,2-dimethyl-4-{[4-(4-methyl-6-{[4-(trifluoromethyl)pyridin-2-yl]amino}pyridin-2-yl)-1H-1,2,3-triazol-1-yl]methyl}cyclohexanecarboxylic acid;

2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylic acid;

2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylic acid;

2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylic acid;

2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylic acid;

(4-fluorophenyl)[4-(4-methyl-6-{[4-(trifluoromethyl)pyridin-2-yl]amino}pyridin-2-yl)-1H-1,2,3-triazol-1-yl]acetic acid;

[4-(4-methyl-6-{[4-(trifluoromethyl)pyridin-2-yl]amino}pyridin-2-yl)-1H-1,2,3-triazol-1-yl](phenyl)acetic acid;

1-{(2R)-2-[4-(4-methyl-6-{[4-(trifluoromethyl)pyridin-2-yl]amino}pyridin-2-yl)-1H-1,2,3-triazol-1-yl]propanoyl}proline;

1-{(2S)-2-[4-(4-methyl-6-{[4-(trifluoromethyl)pyridin-2-yl]amino}pyridin-2-yl)-1H-1,2,3-triazol-1-yl]propanoyl}proline;

N-{(2R)-2-[4-(4-methyl-6-{[4-(trifluoromethyl)pyridin-2-yl]amino}pyridin-2-yl)-1H-1,2,3-triazol-1-yl]propanoyl}glycine;

N-{(2S)-2-[4-(4-methyl-6-{[4-(trifluoromethyl)pyridin-2-yl]amino}pyridin-2-yl)-1H-1,2,3-triazol-1-yl]propanoyl}glycine;

4-[4-(3-methyl-5-{[4-(trifluoromethyl)pyrimidin-2-yl]amino}phenyl)-1H-1,2,3-triazol-1-yl]cyclohexanecarboxylic acid;

4-{2-hydroxy-1-[4-(4-methyl-6-{[4-(trifluoromethyl)pyridin-2-yl]amino}pyridin-2-yl)-1H-1,2,3-triazol-1-yl]ethyl}benzoic acid;

4-{1-hydroxy-2-[4-(4-methyl-6-{[4-(trifluoromethyl)pyridin-2-yl]amino}pyridin-2-yl)-1H-1,2,3-triazol-1-yl]ethyl}benzoic acid;

4-[4-(4-methyl-6-{[4-(trifluoromethyl)pyridin-2-yl]amino}pyridin-2-yl)-1H-1,2,3-triazol-1-yl]-1,2,3,4-tetrahydronaphthalene-1-carboxylic acid;

4-hydroxy-2,2-dimethyl-4-((4-(3-methyl-5-((4-(trifluoromethyl)-pyrimidin-2-yl)amino)phenyl)-1H-1,2,3-triazol-1-yl)methyl)cyclohexanecarboxylic acid;

3-hydroxy-4-[4-(4-methyl-6-{[4-(trifluoromethyl)pyridin-2-yl]amino}pyridin-2-yl)-1H-1,2,3-triazol-1-yl]pentanenitrile;

3-hydroxy-4-[4-(4-methyl-6-{[4-(trifluoromethyl)pyridin-2-yl]amino}pyridin-2-yl)-1H-1,2,3-triazol-1-yl]pentanenitrile;

4-[4-(3-methyl-5-{[4-(trifluoromethyl)pyrimidin-2-yl]amino}phenyl)-1H-1,2,3-triazol-1-yl]tetrahydrofuran-3-ol;

4-[4-(3-methyl-5-{[4-(trifluoromethyl)pyrimidin-2-yl]amino}phenyl)-1H-1,2,3-triazol-1-yl]tetrahydrofuran-3-ol;

3-hydroxy-4-[4-(3-methyl-5-{[4-(trifluoromethyl)pyrimidin-2-yl]amino}phenyl)-1H-1,2,3-triazol-1-yl]pentanenitrile;

3-hydroxy-4-[4-(3-methyl-5-{[4-(trifluoromethyl)pyrimidin-2-yl]amino}phenyl)-1H-1,2,3-triazol-1-yl]pentanenitrile;

4-[4-(3-methyl-5-{[4-(trifluoromethyl)pyrimidin-2-yl]amino}phenyl)-1H-1,2,3-triazol-1-yl]tetrahydrofuran-3-ol;

3-hydroxy-4-[4-(3-methyl-5-{[4-(trifluoromethyl)pyrimidin-2-yl]amino}phenyl)-1H-1,2,3-triazol-1-yl]pentanenitrile;

3-hydroxy-4-[4-(4-methyl-6-{[4-(trifluoromethyl)pyridin-2-yl]amino}pyridin-2-yl)-1H-1,2,3-triazol-1-yl]pentanenitrile;

methyl 4-hydroxy-2,2-dimethyl-4-{[4-(3-methyl-5-{[4-(trifluoromethyl)pyrimidin-2-yl]amino}phenyl)-1H-1,2,3-triazol-1-yl]methyl}cyclohexanecarboxylate;

methyl 4-hydroxy-2,2-dimethyl-4-{[4-(4-methyl-6-{[4-(trifluoromethyl)pyridin-2-yl]amino}pyridin-2-yl)-1H-1,2,3-triazol-1-yl]methyl}cyclohexanecarboxylate;

4-{[4-(4-methyl-6-{[4-(trifluoromethyl)pyridin-2-yl]amino}pyridin-2-yl)-1H-1,2,3-triazol-1-yl]methyl}tetrahydro-2H-pyran-4-ol;

4-{[4-(3-methyl-5-{[4-(trifluoromethyl)pyrimidin-2-yl]amino}phenyl)-1H-1,2,3-triazol-1-yl]methyl}tetrahydro-2H-pyran-4-ol;

4-[4-(4-methyl-6-{[4-(trifluoromethyl)pyridin-2-yl]amino}pyridin-2-yl)-1H-1,2,3-triazol-1-yl]pyrrolidin-3-ol;

methyl 4-{2-hydroxy-1-[4-(4-methyl-6-{[4-(trifluoromethyl)pyridin-2-yl]amino}pyridin-2-yl)-1H-1,2,3-triazol-1-yl]ethyl}benzoate;

methyl 4-{1-hydroxy-2-[4-(4-methyl-6-{[4-(trifluoromethyl)pyridin-2-yl]amino}pyridin-2-yl)-1H-1,2,3-triazol-1-yl]ethyl}benzoate;

2-hydroxy-2-methyl-3-[4-(4-methyl-6-{[4-(trifluoromethyl)pyridin-2-yl]amino}pyridin-2-yl)-1H-1,2,3-triazol-1-yl]propanoic acid;

(2S)-2-hydroxy-3-[4-(4-methyl-6-{[4-(trifluoromethyl)pyridin-2-yl]amino}pyridin-2-yl)-1H-1,2,3-triazol-1-yl]propanoic acid;

(2R)-2-hydroxy-3-[4-(4-methyl-6-{[4-(trifluoromethyl)pyridin-2-yl]amino}pyridin-2-yl)-1H-1,2,3-triazol-1-yl]propanoic acid;

(2R)-2-hydroxy-3-[3-(3-methyl-5-{[4-(trifluoromethyl)pyrimidin-2-yl]amino}phenyl)-1H-1,2,4-triazol-1-yl]propanoic acid;

2-(4-(3-Methyl-5((4-(trifluoromethyl)pyrimidin-2-yl)amino)phenyl)-1H-1,2,3-triazol-1-yl)ethanol;

(4-{[4-(3-methyl-5-{[4-(trifluoromethyl)pyrimidin-2-yl]amino}phenyl)-1H-1,2,3-triazol-1-yl]methyl}phenyl)acetic acid;

(5R)-5-{[4-(4-methyl-6-{[4-(trifluoromethyl)pyridin-2-yl]amino}pyridin-2-yl)-1H-1,2,3-triazol-1-yl]methyl}pyrrolidin-2-one;

4-methyl-6-[1-(tetrahydro-2H-pyran-2-ylmethyl)-1H-1,2,3-triazol-4-yl]-N-[4-(trifluoromethyl)pyridin-2-yl]pyridin-2-amine;

1-[4-(4-methyl-6-{[4-(trifluoromethyl)pyridin-2-yl]amino}pyridin-2-yl)-1H-1,2,3-triazol-1-yl]butan-2-ol;

4-{2-[4-(4-methyl-6-{[4-(trifluoromethyl)pyridin-2-yl]amino}pyridin-2-yl)-1H-1,2,3-triazol-1-yl]ethyl}benzoic acid;

(2S)-3-[4-(4-methyl-6-{[4-(trifluoromethyl)pyridin-2-yl]amino}pyridin-2-yl)-1H-1,2,3-triazol-1-yl]propane-1,2-diol;

(2S)-3-(3-{[4-(2-hydroxyethoxyl)pyrimidin-2-yl]amino}-5-methylphenyl)-1H-1,2,3-triazol-1-yl]propane-1,2-diol;

3-[4-(4-methyl-6-{[4-(trifluoromethyl)pyridin-2-yl]amino}pyridin-2-yl)-1H-1,2,3-triazol-1-yl]propanoic acid;

methyl 3-[4-(4-methyl-6-{[4-(trifluoromethyl)pyridin-2-yl]amino}pyridin-2-yl)-1H-1,2,3-triazol-1-yl]propanoate;

3-{[4-(4-methyl-6-{[4-(trifluoromethyl)pyridin-2-yl]amino}pyridin-2-yl)-1H-1,2,3-triazol-1-yl]methyl}tetrahydrofuran-3-ol;

3-{[4-(4-methyl-6-{[4-(trifluoromethyl)pyridin-2-yl]amino}pyridin-2-yl)-1H-1,2,3-triazol-1-yl]methyl}tetrahydrofuran-3-ol;

3-{[4-(4-methyl-6-{[4-(trifluoromethyl)pyridin-2-yl]amino}pyridin-2-yl)-1H-1,2,3-triazol-1-yl]methyl}tetrahydrofuran-3-ol;

(3R)-3-hydroxy-4-(4-{4-methyl-6-[(4-methylpyridin-2-yl)amino]pyridin-2-yl}-1H-1,2,3-triazol-1-yl)butanenitrile;

(2R)-2-methyl-3-(4-{4-methyl-6-[(4-methylpyridin-2-yl)amino]pyridin-2-yl}-1H-1,2,3-triazol-1-yl)propan-1-ol;

(2S)-2-methyl-3-(4-{4-methyl-6-[(4-methylpyridin-2-yl)amino]pyridin-2-yl}-1H-1,2,3-triazol-1-yl)propan-1-ol;

1,1,1-trifluoro-3-(4-{4-methyl-6-[(4-methylpyridin-2-yl)amino]pyridin-2-yl}-1H-1,2,3-triazol-1-yl)propan-2-ol;

2-(4-{4-methyl-6-[(4-methylpyridin-2-yl)amino]pyridin-2-yl}-1H-1,2,3-triazol-1-yl)ethanol;

(2R)-3-[4-(4-methyl-6-{[4-(trifluoromethyl)pyridin-2-yl]amino}pyridin-2-yl)-1H-1,2,3-triazol-1-yl]propane-1,2-diol;

methyl 2-[4-(4-methyl-6-{[4-(trifluoromethyl)pyridin-2-yl]amino}pyridin-2-yl)-1H-1,2,3-triazol-1-yl]propanoate;

4-{[4-(3-methyl-5-{[4-(trifluoromethyl)pyrimidin-2-yl]amino}phenyl)-1H-1,2,3-triazol-1-yl]methyl}benzoic acid;

4-[4-(4-methyl-6-{[4-(trifluoromethyl)pyridin-2-yl]amino}pyridin-2-yl)-1H-1,2,3-triazol-1-yl]pyrrolidin-3-ol;

(2S)-3-{4-[3-(methoxymethyl)-5-{[4-(trifluoromethyl)pyrimidin-2-yl]amino}phenyl]-1H-1,2,3-triazol-1-yl}propane-1,2-diol;

(2S)-3-[4-(3-methyl-5-{[4-(trifluoromethyl)pyrimidin-2-yl]amino}phenyl)-1H-1,2,3-triazol-1-yl]propane-1,2-diol;

methyl 4-[4-(4-methyl-6-{[4-(trifluoromethyl)pyridin-2-yl]amino}pyridin-2-yl)-1H-1,2,3-triazol-1-yl]-1,2,3,4-tetrahydronaphthalene-1-carboxylate;

methyl (4-fluorophenyl)[4-(4-methyl-6-{[4-(trifluoromethyl)pyridin-2-yl]amino}pyridin-2-yl)-1H-1,2,3-triazol-1-yl]acetate;

ethyl 2-[4-(4-methyl-6-{[4-(trifluoromethyl)pyridin-2-yl]amino}pyridin-2-yl)-1H-1,2,3-triazol-1-yl]pentanoate;

ethyl 2-[4-(4-methyl-6-{[4-(trifluoromethyl)pyridin-2-yl]amino}pyridin-2-yl)-1H-1,2,3-triazol-1-yl]butanoate;

(2R)-2-[4-(4-methyl-6-{[4-(trifluoromethyl)pyridin-2-yl]amino}pyridin-2-yl)-1H-1,2,3-triazol-1-yl]propanoic acid;

(2S)-2-[4-(4-methyl-6-{[4-(trifluoromethyl)pyridin-2-yl]amino}pyridin-2-yl)-1H-1,2,3-triazol-1-yl]propanoic acid;

4-methyl-6-{1-[(2E)-pent-2-en-1-yl]-1H-1,2,3-triazol-4-yl}-N-[4-(trifluoromethyl)pyridin-2-yl]pyridin-2-amine;

6-{1-[(2E)-4-(2-chlorophenoxy)but-2-en-1-yl]-1H-1,2,3-triazol-4-yl}-4-methyl-N-[4-(trifluoromethyl)pyridin-2-yl]pyridin-2-amine;

4-methyl-6-{1-[(2E)-3-pyridin-4-ylprop-2-en-1-yl]-1H-1,2,3-triazol-4-yl}-N-[4-(trifluoromethyl)pyridin-2-yl]pyridin-2-amine;

ethyl (2E)-4-[4-(4-methyl-6-{[4-(trifluoromethyl)pyridin-2-yl]amino}pyridin-2-yl)-1H-1,2,3-triazol-1-yl]but-2-enoate;

4-methyl-6-{1-[(2E)-3-phenylprop-2-en-1-yl]-1H-1,2,3-triazol-4-yl}-N-[4-(trifluoromethyl)pyridin-2-yl]pyridin-2-amine;

6-(1-cyclohex-2-en-1-yl-1H-1,2,3-triazol-4-yl)-4-methyl-N-[4-(trifluoromethyl)pyridin-2-yl]pyridin-2-amine;

4-methyl-6-[1-(3-methylbut-2-en-1-yl)-1H-1,2,3-triazol-4-yl]-N-[4-(trifluoromethyl)pyridin-2-yl]pyridin-2-amine;

6-{1-[(2E)-but-2-en-1-yl]-1H-1,2,3-triazol-4-yl}-4-methyl-N-[4-(trifluoromethyl)pyridin-2-yl]pyridin-2-amine;

2-hydroxy-3-[4-(4-methyl-6-{[4-(trifluoromethyl)pyridin-2-yl]amino}pyridin-2-yl)-1H-1,2,3-triazol-1-yl]propanoic acid;

4-methyl-6-[1-(2-methylprop-2-en-1-yl)-1H-1,2,3-triazol-4-yl]-N-[4-(trifluoromethyl)pyridin-2-yl]pyridin-2-amine;

4-{1-[4-(4-methyl-6-{[4-(trifluoromethyl)pyridin-2-yl]amino}pyridin-2-yl)-1H-1,2,3-triazol-1-yl]ethyl}benzoic acid;

4-{[4-(4-methyl-6-{[4-(trifluoromethyl)pyridin-2-yl]amino}pyridin-2-yl)-1H-1,2,3-triazol-1-yl]methyl}benzoic acid;

2-[4-(4-methyl-6-{[4-(trifluoromethyl)pyridin-2-yl]amino}pyridin-2-yl)-1H-1,2,3-triazol-1-yl]propanoic acid;

(3R)-3-hydroxy-4-[4-(4-methyl-6-{[4-(trifluoromethyl)pyridin-2-yl]amino}pyridin-2-yl)-1H-1,2,3-triazol-1-yl]butanenitrile;

(2E)-4-[4-(4-methyl-6-{[4-(trifluoromethyl)pyridin-2-yl]amino}pyridin-2-yl)-1H-1,2,3-triazol-1-yl]but-2-enoic acid;

4-[4-(4-methyl-6-{[4-(trifluoromethyl)pyridin-2-yl]amino}pyridin-2-yl)-1H-1,2,3-triazol-1-yl]cyclohexanecarboxylic acid;

N-[3-(1-{2-[trans-3,5-dimethylmorpholin-4-yl]-2-oxoethyl}-1H-1,2,3-triazol-4-yl)-5-methylphenyl]-4-(trifluoromethyl)pyrimidin-2-amine;

N-{3-[1-(3-aminopropyl)-1H-1,2,3-triazol-4-yl]-5-methylphenyl}-4-(trifluoromethyl)pyrimidin-2-amine;

2-{2-[4-(3-methyl-5-{[4-(trifluoromethyl)pyrimidin-2-yl]amino}phenyl)-1H-1,2,3-triazol-1-yl]ethoxy}ethanol;

N-{3-methyl-5-[1-(oxetan-2-ylmethyl)-1H-1,2,3-triazol-4-yl]phenyl}-4-(trifluoromethyl)pyrimidin-2-amine;

N-{3-methyl-5-[1-(3-morpholin-4-ylpropyl)-1H-1,2,3-triazol-4-yl]phenyl}-4-(trifluoromethyl)pyrimidin-2-amine;

1-fluoro-3-[4-(3-methyl-5-{[4-(trifluoromethyl)pyrimidin-2-yl]amino}phenyl)-1H-1,2,3-triazol-1-yl]propan-2-ol;

1-methoxy-3-[4-(3-methyl-5-{[4-(trifluoromethyl)pyrimidin-2-yl]amino}phenyl)-1H-1,2,3-triazol-1-yl]propan-2-ol;

1,1,1-trifluoro-3-[4-(3-methyl-5-{[4-(trifluoromethyl)pyrimidin-2-yl]amino}phenyl)-1H-1,2,3-triazol-1-yl]propan-2-ol;

2-methyl-1-[4-(3-methyl-5-{[4-(trifluoromethyl)pyrimidin-2-yl]amino}phenyl)-1H-1,2,3-triazol-1-yl]propan-2-ol;
1-{2-[4-(3-methyl-5-{[4-(trifluoromethyl)pyrimidin-2-yl]amino}phenyl)-1H-1,2,3-triazol-1-yl]ethyl}urea;
2-[4-(3-methyl-5-{[4-(trifluoromethyl)pyrimidin-2-yl]amino}phenyl)-1H-1,2,3-triazol-1-yl]cyclohexanol;
[4-(3-methyl-5-{[4-(trifluoromethyl)pyrimidin-2-yl]amino}phenyl)-1H-1,2,3-triazol-1-yl]acetic acid;
N-(3-{1-[2-(4-acetylpiperazin-1-yl)-2-oxoethyl]-1H-1,2,3-triazol-4-yl}-5-methylphenyl)-4-(trifluoromethyl)pyrimidin-2-amine;
3-[4-(3-methyl-5-{[4-(trifluoromethyl)pyrimidin-2-yl]amino}phenyl)-1H-1,2,3-triazol-1-yl]propanoic acid;
2-hydroxy-3-[4-(3-methyl-5-{[4-(trifluoromethyl)pyrimidin-2-yl]amino}phenyl)-1H-1,2,3-triazol-1-yl]propanoic acid;
N-(3-methyl-5-{1-[2-(methylsulfonyl)ethyl]-1H-1,2,3-triazol-4-yl}phenyl)-4-(trifluoromethyl)pyrimidin-2-amine;
4-[4-(3-methyl-5-{[4-(trifluoromethyl)pyrimidin-2-yl]amino}phenyl)-1H-1,2,3-triazol-1-yl]tetrahydrothiophene-3-ol 1,1-dioxide;
2-[4-(3-methyl-5-{[4-(trifluoromethyl)pyrimidin-2-yl]amino}phenyl)-1H-1,2,3-triazol-1-yl]propanoic acid;
N-[3-(1-{2-[(cis)-3,5-dimethylmorpholin-4-yl]-2-oxoethyl}-1H-1,2,3-triazol-4-yl)-5-methylphenyl]-4-(trifluoromethyl)pyrimidin-2-amine;
N-(3-{1-[2-(3,3-dimethylmorpholin-4-yl)-2-oxoethyl]-1H-1,2,3-triazol-4-yl}-5-methylphenyl)-4-(trifluoromethyl)pyrimidin-2-amine;
N-(2-methoxy-1,1-dimethylethyl)-2-[4-(3-methyl-5-{[4-(trifluoromethyl)pyrimidin-2-yl]amino}phenyl)-1H-1,2,3-triazol-1-yl]acetamide;
N-(3-{1-[2-(4,4-dimethyl-1,3-oxazolidin-3-yl)-2-oxoethyl]-1H-1,2,3-triazol-4-yl}-5-methylphenyl)-4-(trifluoromethyl)pyrimidin-2-amine;
N-(3-methyl-5-{1-[(5-methyl-1,2,4-oxadiazol-3-yl)methyl]-1H-1,2,3-triazol-4-yl}phenyl)-4-(trifluoromethyl)pyrimidin-2-amine;
N-tert-butyl-2-[4-(3-methyl-5-{[4-(trifluoromethyl)pyrimidin-2-yl]amino}phenyl)-1H-1,2,3-triazol-1-yl]acetamide;
1-{3-[4-(3-methyl-5-{[4-(trifluoromethyl)pyrimidin-2-yl]amino}phenyl)-1H-1,2,3-triazol-1-yl]propyl}imidazolidin-2-one;
(2S)-2-methyl-3-[4-(3-methyl-5-{[4-(trifluoromethyl)pyrimidin-2-yl]amino}phenyl)-1H-1,2,3-triazol-1-yl]propan-1-ol;
(2R)-2-methyl-3-[4-(3-methyl-5-{[4-(trifluoromethyl)pyrimidin-2-yl]amino}phenyl)-1H-1,2,3-triazol-1-yl]propan-1-ol;
N-{3-[1-(2-aminoethyl)-1H-1,2,3-triazol-4-yl]-5-methylphenyl}-4-(trifluoromethyl)pyrimidin-2-amine;
3-[4-(3-methyl-5-{[4-(trifluoromethyl)pyrimidin-2-yl]amino}phenyl)-1H-1,2,3-triazol-1-yl]propanamide;
3-[4-(3-methyl-5-{[4-(trifluoromethyl)pyrimidin-2-yl]amino}phenyl)-1H-1,2,3-triazol-1-yl]propane-1,2-diol;
3-[4-(3-methyl-5-{[4-(trifluoromethyl)pyrimidin-2-yl]amino}phenyl)-1H-1,2,3-triazol-1-yl]propan-1-ol;
[4-(3-methyl-5-{[4-(trifluoromethyl)pyrimidin-2-yl]amino}phenyl)-1H-1,2,3-triazol-1-yl]acetonitrile;
2-[4-(3-methyl-5-{[4-(trifluoromethyl)pyrimidin-2-yl]amino}phenyl)-1H-1,2,3-triazol-1-yl]acetamide;
1-{[4-(4-methyl-6-{[4-(trifluoromethyl)pyridin-2-yl]amino}pyridin-2-yl)-1H-1,2,3-triazol-1-yl]acetyl}piperidine-4-carboxylic acid;
(2R)-2-methyl-3-[4-(4-methyl-6-{[4-(trifluoromethyl)pyridin-2-yl]amino}pyridin-2-yl)-1H-1,2,3-triazol-1-yl]propan-1-ol;
(2S)-2-methyl-3-[4-(4-methyl-6-{[4-(trifluoromethyl)pyridin-2-yl]amino}pyridin-2-yl)-1H-1,2,3-triazol-1-yl]propan-1-ol;
1,1,1-trifluoro-3-[4-(4-methyl-6-{[4-(trifluoromethyl)pyridin-2-yl]amino}pyridin-2-yl)-1H-1,2,3-triazol-1-yl]propan-2-ol;
5-{[4-(4-methyl-6-{[4-(trifluoromethyl)pyridin-2-yl]amino}pyridin-2-yl)-1H-1,2,3-triazol-1-yl]methyl}-1,3-oxazolidin-2-one;
methyl 2-methyl-4-[4-(4-methyl-6-{[4-(trifluoromethyl)pyridin-2-yl]amino}pyridin-2-yl)-1H-1,2,3-triazol-1-yl]butanoate;
methyl (2S)-2-methyl-3-[4-(4-methyl-6-{[4-(trifluoromethyl)pyridin-2-yl]amino}pyridin-2-yl)-1H-1,2,3-triazol-1-yl]propanoate;
4-methyl-6-[1-(2-oxo-2-pyrrolidin-1-ylethyl)-1H-1,2,3-triazol-4-yl]-N-[4-(trifluoromethyl)pyridin-2-yl]pyridin-2-amine;
[4-(4-methyl-6-{[4-(trifluoromethyl)pyridin-2-yl]amino}pyridin-2-yl)-1H-1,2,3-triazol-1-yl]acetic acid;
2-[4-(4-methyl-6-{[4-(trifluoromethyl)pyridin-2-yl]amino}pyridin-2-yl)-1H-1,2,3-triazol-1-yl]cyclohexanol;
4-[4-(4-methyl-6-{[4-(trifluoromethyl)pyridin-2-yl]amino}pyridin-2-yl)-1H-1,2,3-triazol-1-yl]tetrahydrothiophene-3-ol 1,1-dioxide;
2-[4-(4-methyl-6-{[4-(trifluoromethyl)pyridin-2-yl]amino}pyridin-2-yl)-1H-1,2,3-triazol-1-yl]ethanol;
[4-(4-methyl-6-{[4-(trifluoromethyl)pyridin-2-yl]amino}pyridin-2-yl)-1H-1,2,3-triazol-1-yl]acetonitrile;
1-fluoro-3-[4-(4-methyl-6-{[4-(trifluoromethyl)pyridin-2-yl]amino}pyridin-2-yl)-1H-1,2,3-triazol-1-yl]propan-2-ol;
3-[4-(4-methyl-6-{[4-(trifluoromethyl)pyridin-2-yl]amino}pyridin-2-yl)-1H-1,2,3-triazol-1-yl]propan-1-ol;
3-[4-(4-methyl-6-{[4-(trifluoromethyl)pyridin-2-yl]amino}pyridin-2-yl)-1H-1,2,3-triazol-1-yl]propane-1,2-diol;
4-methyl-6-{1-[2-(methylsulfonyl)ethyl]-1H-1,2,3-triazol-4-yl}-N-[4-(trifluoromethyl)-pyridin-2-yl]pyridin-2-amine;
2-methyl-1-[4-(4-methyl-6-{[4-(trifluoromethyl)pyridin-2-yl]amino}pyridin-2-yl)-1H-1,2,3-triazol-1-yl]propan-2-ol;
(3R)-3-hydroxy-4-[4-(3-methyl-5-{[4-(trifluoromethyl)pyrimidin-2-yl]amino}phenyl)-1H-1,2,3-triazol-1-yl]butanenitrile;
methyl 4-[4-(3-methyl-5-{[4-(trifluoromethyl)pyrimidin-2-yl]amino}phenyl)-1H-1,2,3-triazol-1-yl]cyclohexanecarboxylate;
ethyl [4-(4-methyl-6-{[4-(trifluoromethyl)pyridin-2-yl]amino}pyridin-2-yl)-1H-1,2,3-triazol-1-yl]acetate;
4-methyl-6-(1H-1,2,3-triazol-4-yl)-N-[4-(trifluoromethyl)pyridin-2-yl]pyridin-2-amine;
6-(1-(3-chloropyridin-2-yl)-1H-1,2,3-triazol-4-yl)-4-methyl-N-(4-(trifluoromethyl)-pyridin-2-yl)pyridin-2-amine;
6-[1-(5-bromopyridin-2-yl)-1H-1,2,3-triazol-4-yl]-4-methyl-N-[4-(trifluoromethyl)pyridin-2-yl]pyridin-2-amine;
4-(4-(4-methyl-6-((4-(trifluoromethyl)pyridin-2-yl)amino)pyridin-2-yl)-1H-1,2,3-triazol-1-yl)benzoic acid;
methyl 1-[4-(4-methyl-6-{[4-(trifluoromethyl)pyridin-2-yl]amino}pyridin-2-yl)-1H-1,2,3-triazol-1-yl]cyclopropanecarboxylate;
ethyl 1-[4-(4-methyl-6-{[4-(trifluoromethyl)-pyridin-2-yl]amino}-pyridin-2-yl)-1H-1,2,3-triazol-1-yl]cyclobutanecarboxylate;

(R or S) 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylic acid;

6-(1-cyclohept-2-en-1-yl-1H-1,2,3-triazol-4-yl)-4-methyl-N-[4-(trifluoromethyl)-pyridin-2-yl]pyridin-2-amine;

methyl 2,2-dimethyl-4-[4-(4-methyl-6-{[4-(trifluoromethyl)pyridin-2-yl]amino}pyridin-2-yl)-1H-1,2,3-triazol-1-yl]cyclohexane-carboxylate tert-butyl 4-[4-(3-methyl-5-{[4-(trifluoromethyl)-pyrimidin-2-yl]amino}-phenyl)-1H-1,2,3-triazol-1-yl]cyclohexane-carboxylate;

4-{(1R)-1-[4-(4-methyl-6-{[4-(trifluoromethyl)-pyridin-2-yl]amino}pyridin-2-yl)-1H-1,2,3-triazol-1-yl]ethyl}benzoic acid;

6-[1-(cyclohex-1-en-1-ylmethyl)-1H-1,2,3-triazol-4-yl]-4-methyl-N-[4-(trifluoromethyl)pyridin-2-yl]pyridin-2-amine;

4-{(1S)-1-[4-(4-methyl-6-{[4-(trifluoromethyl)pyridin-2-yl]amino}pyridin-2-yl)-1H-1,2,3-triazol-1-yl]ethyl}benzoic acid;

3-(4-(4-methyl-6-((4-(trifluoromethyl)pyridin-2-yl)amino)pyridin-2-yl)-1H-1,2,3-triazol-1-yl)-1-phenylpropane-1,2-diol;

3-[4-(4-methyl-6-{[4-(trifluoromethyl)pyridin-2-yl]amino}pyridin-2-yl)-1H-1,2,3-triazol-1-yl]cycloheptane-1,2-diol;

3-[4-(4-methyl-6-{[4-(trifluoromethyl)pyridin-2-yl]amino}pyridin-2-yl)-1H-1,2,3-triazol-1-yl]cycloheptane-1,2-diol;

3-[4-(4-methyl-6-{[4-(trifluoromethyl)pyridin-2-yl]amino}pyridin-2-yl)-1H-1,2,3-triazol-1-yl]cycloheptane-1,2-diol;

3-[4-(4-methyl-6-{[4-(trifluoromethyl)pyridin-2-yl]amino}pyridin-2-yl)-1H-1,2,3-triazol-1-yl]cycloheptane-1,2-diol;

3-[4-(4-methyl-6-{[4-(trifluoromethyl)pyridin-2-yl]amino}pyridin-2-yl)-1H-1,2,3-triazol-1-yl]cycloheptane-1,2-diol;

1,4,5-trideoxy-1-[4-(4-methyl-6-{[4-(trifluoromethyl)pyridin-2-yl]amino}pyridin-2-yl)-1H-1,2,3-triazol-1-yl]pentitol;

1-(2-chlorophenoxy)-4-[4-(4-methyl-6-{[4-(trifluoromethyl)pyridin-2-yl]amino}pyridin-2-yl)-1H-1,2,3-triazol-1-yl]butane-2,3-diol;

ethyl 2,3-dihydroxy-4-[4-(4-methyl-6-{[4-(trifluoromethyl)pyridin-2-yl]amino}pyridin-2-yl)-1H-1,2,3-triazol-1-yl]butanoate;

1-{[4-(4-methyl-6-{[4-(trifluoromethyl)pyridin-2-yl]amino}pyridin-2-yl)-1H-1,2,3-triazol-1-yl]methyl}cyclohexane-1,2-diol;

3-[4-(4-methyl-6-{[4-(trifluoromethyl)pyridin-2-yl]amino}pyridin-2-yl)-1H-1,2,3-triazol-1-yl]cyclohexane-1,2-diol;

3-methyl-1-[4-(4-methyl-6-{[4-(trifluoromethyl)pyridin-2-yl]amino}pyridin-2-yl)-1H-1,2,3-triazol-1-yl]butane-2,3-diol;

1-[4-(4-methyl-6-{[4-(trifluoromethyl)pyridin-2-yl]amino}pyridin-2-yl)-1H-1,2,3-triazol-1-yl]butane-2,3-diol;

2-methyl-3-[4-(4-methyl-6-{[4-(trifluoromethyl)pyridin-2-yl]amino}pyridin-2-yl)-1H-1,2,3-triazol-1-yl]propane-1,2-diol;

2-methyl-3-[4-(4-methyl-6-{[4-(trifluoromethyl)pyridin-2-yl]amino}pyridin-2-yl)-1H-1,2,3-triazol-1-yl]propane-1,2-diol;

2-methyl-3-[4-(4-methyl-6-{[4-(trifluoromethyl)pyridin-2-yl]amino}pyridin-2-yl)-1H-1,2,3-triazol-1-yl]propane-1,2-diol;

5-[4-(4-Methyl-6-{[4-(trifluoromethyl)pyridin-2-yl]amino}pyridin-2-yl)-1H-1,2,3-triazol-1-yl]azepan-2-one;

5-[4-(4-methyl-6-{[4-(trifluoromethyl)pyridin-2-yl]amino}pyridin-2-yl)-1H-1,2,3-triazol-1-yl]azepan-2-one;

5-[4-(4-methyl-6-{[4-(trifluoromethyl)pyridin-2-yl]amino}pyridin-2-yl)-1H-1,2,3-triazol-1-yl]azepan-2-one;

5-hydroxy-5-[1-(3-methyl-5-{[4-(trifluoromethyl)pyrimidin-2-yl]amino}phenyl)-1H-1,2,3-triazol-4-yl]azepan-2-one;

((R)-3-hydroxy-4-(4-(4-methyl-6-((4-(trifluoromethyl)pyridin-2-yl)amino)pyridin-2-yl)-1H-1,2,3-triazol-1-yl)butanamide;

(+/−)-2-hydroxy-1-((3R,4R)-3-hydroxy-4-(4-(4-methyl-6-((4-(trifluoromethyl)pyridin-2-yl)amino)pyridin-2-yl)-1H-1,2,3-triazol-1-yl)pyrrolidin-1-yl)ethanone;

1-[2-hydroxypropanoyl]-4-[4-(4-methyl-6-{[4-(trifluoromethyl)pyridin-2-yl]amino}pyridin-2-yl)-1H-1,2,3-triazol-1-yl]pyrrolidin-3-ol;

1-[2-hydroxypropanoyl]-4-[4-(4-methyl-6-{[4-(trifluoromethyl)pyridin-2-yl]amino}pyridin-2-yl)-1H-1,2,3-triazol-1-yl]pyrrolidin-3-ol;

1-[2-hydroxypropanoyl]-4-[4-(4-methyl-6-{[4-(trifluoromethyl)pyridin-2-yl]amino}pyridin-2-yl)-1H-1,2,3-triazol-1-yl]pyrrolidin-3-ol;

4-{-3-hydroxy-4-[4-(4-methyl-6-{[4-(trifluoromethyl)pyridin-2-yl]amino}pyridin-2-yl)-1H-1,2,3-triazol-1-yl]pyrrolidin-1-yl}-4-oxobutanamide;

{1-[4-(4-methyl-6-{[4-(trifluoromethyl)pyridin-2-yl]amino}pyridin-2-yl)-1H-1,2,3-triazol-1-yl]cyclobutyl}methanol;

2-(4-fluorophenyl)-2-[4-(4-methyl-6-{[4-(trifluoromethyl)pyridin-2-yl]amino}pyridin-2-yl)-1H-1,2,3-triazol-1-yl]ethanol;

2-[4-(4-methyl-6-{[4-(trifluoromethyl)pyridin-2-yl]amino}pyridin-2-yl)-1H-1,2,3-triazol-1-yl]-2-phenylethanol;

2-[4-(4-methyl-6-{[4-(trifluoromethyl)pyridin-2-yl]amino}pyridin-2-yl)-1H-1,2,3-triazol-1-yl]butan-1-ol;

4-[4-(4-methyl-6-{[4-(trifluoromethyl)pyridin-2-yl]amino}pyridin-2-yl)-1H-1,2,3-triazol-1-yl]butane-1,2,3-triol 2-Hydroxy-3-(4-(4-methyl-6-((4-(trifluoromethyl)pyridin-2-yl)amino)pyridin-2-yl)-1H-1,2,3-triazol-1-yl)propanoic acid 8-[1-(3-Methyl-5-{[4-(trifluoromethyl)pyrimidin-2-yl]amino}phenyl)-1H-1,2,3-triazol-4-yl]-1,4-dioxaspiro[4.5]decan-8-ol 4-hydroxy-2,2-dimethyl-4-[1-(3-methyl-5-{[4-(trifluoromethyl)pyrimidin-2-yl]amino}phenyl)-1H-1,2,3-triazol-4-yl]cyclohexanecarboxylic acid;

(4-hydroxy-2,2-dimethyl-4-[1-(3-methyl-5-{[4-(trifluoromethyl)pyrimidin-2-yl]amino}phenyl)-1H-1,2,3-triazol-4-yl]cyclohexanecarboxylic acid;

trans-4-hydroxy-4-[1-(3-methyl-5-{[4-(trifluoromethyl)pyrimidin-2-yl]amino}phenyl)-1H-1,2,3-triazol-4-yl]cyclohexanecarboxylic acid;

cis-4-hydroxy-4-[1-(3-methyl-5-{[4-(trifluoromethyl)pyrimidin-2-yl]amino}phenyl)-1H-1,2,3-triazol-4-yl]cyclohexanecarboxylic acid;

tert-butyl trans-4-hydroxy-4-[1-(3-methyl-5-{[4-(trifluoromethyl)pyrimidin-2-yl]amino}phenyl)-1H-1,2,3-triazol-4-yl]cyclohexanecarboxylate;

tert-butyl cis-4-hydroxy-4-[1-(3-methyl-5-{[4-(trifluoromethyl)pyrimidin-2-yl]amino}phenyl)-1H-1,2,3-triazol-4-yl]cyclohexanecarboxylate;
3-[1-(3-methyl-5-{[4-(trifluoromethyl)pyrimidin-2-yl]amino}phenyl)-1H-1,2,3-triazol-4-yl]propane-1,2-diol;
8-[1-(3-methyl-5-{[4-(trifluoromethyl)pyrimidin-2-yl]amino}phenyl)-1H-1,2,3-triazol-4-yl]-1,4-dioxaspiro[4.5]decan-8-ol;
4-hydroxy-2,2-dimethyl-4-[1-(3-methyl-5-{[4-(trifluoromethyl)pyrimidin-2-yl]amino}phenyl)-1H-1,2,3-triazol-4-yl]cyclohexanecarboxylic acid;
methyl (1S,4R)-4-hydroxy-2,2-dimethyl-4-[1-(3-methyl-5-{[4-(trifluoromethyl)pyrimidin-2-yl]amino}phenyl)-1H-1,2,3-triazol-4-yl]cyclohexanecarboxylate;
N-[3-methyl-5-(1H-1,2,3-triazol-1-yl)phenyl]-4-(trifluoromethyl)pyrimidin-2-amine;
N-{3-methyl-5-[4-(trimethylsilyl)-1H-1,2,3-triazol-1-yl]phenyl}-4-(trifluoromethyl)pyrimidin-2-amine;
2,2-dimethyl-3-[1-(3-methyl-5-{[4-(trifluoromethyl)pyrimidin-2-yl]amino}phenyl)-1H-1,2,3-triazol-4-yl]propanoic acid;
3-[1-(3-methyl-5-{[4-(trifluoromethyl)pyrimidin-2-yl]amino}phenyl)-1H-1,2,3-triazol-4-yl]propanoic acid;
ethyl 2,2-dimethyl-3-[1-(3-methyl-5-{[4-(trifluoromethyl)pyrimidin-2-yl]amino}phenyl)-1H-1,2,3-triazol-4-yl]propanoate;
trans-1-[1-(3-methyl-5-{[4-(trifluoromethyl)pyrimidin-2-yl]amino}phenyl)-1H-1,2,3-triazol-4-yl]cyclohexane-1,4-diol;
cis-1-[1-(3-methyl-5-{[4-(trifluoromethyl)pyrimidin-2-yl]amino}phenyl)-1H-1,2,3-triazol-4-yl]cyclohexane-1,4-diol;
6-(4,5-dimethyl-4H-1,2,4-triazol-3-yl)-4-methyl-N-[4-(trifluoromethyl)pyridin-2-yl]pyridin-2-amine;
4-methyl-6-(4H-1,2,4-triazol-3-yl)-N-[4-(trifluoromethyl)pyridin-2-yl]pyridin-2-amine;
4-methyl-6-(4-methyl-4H-1,2,4-triazol-3-yl)-N-[4-(trifluoromethyl)pyridin-2-yl]pyridin-2-amine;
cis-3-(4-(3-methyl-5-((4-(trifluoromethyl)pyrimidin-2-yl)amino)phenyl)-1H-1,2,3-triazol-1-yl)cyclohexanol;
2-[4-(4-methyl-6-{[4-(trifluoromethyl)pyridin-2-yl]amino}pyridin-2-yl)-1H-1,2,3-triazol-1-yl]propan-1-ol;
(+/−)-(3S,4R)-4-(4-(4-methyl-6-((4-(trifluoromethyl)pyridin-2-yl)amino)pyridin-2-yl)-1H-1,2,3-triazol-1-yl)pyrrolidin-3-ol;
3-(5-(3-methyl-5-((4-(trifluoromethyl)pyrimidin-2-yl)amino)phenyl)-4H-1,2,4-triazol-3-yl)propanoic acid;
1-amino-3-[4-(4-methyl-6-{[4-(trifluoromethyl)pyridin-2-yl]amino}pyridin-2-yl)-1H-1,2,3-triazol-1-yl]propan-2-ol;
1-methoxy-3-[4-(4-methyl-6-{[4-(trifluoromethyl)pyridin-2-yl]amino}pyridin-2-yl)-1H-1,2,3-triazol-1-yl]propan-2-ol;
3-methyl-1-[4-(4-methyl-6-{[4-(trifluoromethyl)pyridin-2-yl]amino}pyridin-2-yl)-1H-1,2,3-triazol-1-yl]butan-2-ol;
3,3-dimethyl-1-[4-(4-methyl-6-{[4-(trifluoromethyl)pyridin-2-yl]amino}pyridin-2-yl)-1H-1,2,3-triazol-1-yl]butan-2-ol;
trans-3-hydroxy-3-{[4-(4-methyl-6-{[4-(trifluoromethyl)pyridin-2-yl]amino}pyridin-2-yl)-1H-1,2,3-triazol-1-yl]methyl}cyclobutanecarbonitrile;
1-{[4-(4-methyl-6-{[4-(trifluoromethyl)pyridin-2-yl]amino}pyridin-2-yl)-1H-1,2,3-triazol-1-yl]methyl}cyclobutanol;
1-[4-(4-methyl-6-{[4-(trifluoromethyl)pyridin-2-yl]amino}pyridin-2-yl)-1H-1,2,3-triazol-1-yl]-3-(1H-pyrazol-1-yl)propan-2-ol;
4-{[4-(4-methyl-6-{[4-(trifluoromethyl)pyridin-2-yl]amino}pyridin-2-yl)-1H-1,2,3-triazol-1-yl]methyl}tetrahydro-2H-thiopyran-4-ol 1,1-dioxide;
1-{2-hydroxy-3-[4-(4-methyl-6-{[4-(trifluoromethyl)pyridin-2-yl]amino}pyridin-2-yl)-1H-1,2,3-triazol-1-yl]propyl}pyrrolidin-2-one;
3-{[4-(4-methyl-6-{[4-(trifluoromethyl)pyridin-2-yl]amino}pyridin-2-yl)-1H-1,2,3-triazol-1-yl]methyl}pentan-3-ol;
1-[4-(4-methyl-6-{[4-(trifluoromethyl)pyridin-2-yl]amino}pyridin-2-yl)-1H-1,2,3-triazol-1-yl]-3-(2,2,2-trifluoroethoxy)propan-2-ol;
3-{2-hydroxy-3-[4-(4-methyl-6-{[4-(trifluoromethyl)pyridin-2-yl]amino}pyridin-2-yl)-1H-1,2,3-triazol-1-yl]propyl}-1,3-oxazolidin-2-one;
(2-[4-(3-{[4-(difluoromethyl)pyrimidin-2-yl]amino}-5-methylphenyl)-1H-1,2,3-triazol-1-yl]cyclohexanol;
5-{[4-(4-methyl-6-{[4-(trifluoromethyl)pyridin-2-yl]amino}pyridin-2-yl)-1H-1,2,3-triazol-1-yl]methyl}-1,3-oxazolidin-2-one;
4-methyl-6-{1-[(2-methyl-1H-imidazol-5-yl)methyl]-1H-1,2,3-triazol-4-yl}-N-[4-(trifluoromethyl)pyridin-2-yl]pyridin-2-amine;
4-methyl-6-{1-[2-(1H-pyrazol-4-yl)ethyl]-1H-1,2,3-triazol-4-yl}-N-[4-(trifluoromethyl)pyridin-2-yl]pyridin-2-amine;
4-methyl-6-{1-[(4-methyl-1H-imidazol-5-yl)methyl]-1H-1,2,3-triazol-4-yl}-N-[4-(trifluoromethyl)pyridin-2-yl]pyridin-2-amine;
1-[4-(4-methyl-6-{[4-(trifluoromethyl)pyridin-2-yl]amino}pyridin-2-yl)-1H-1,2,3-triazol-1-yl]methanesulfonamide;
6-[1-(1H-imidazol-4-ylmethyl)-1H-1,2,3-triazol-4-yl]-4-methyl-N-[4-(trifluoromethyl)pyridin-2-yl]pyridin-2-amine;
4-methyl-6-[1-(1H-tetrazol-5-ylmethyl)-1H-1,2,3-triazol-4-yl]-N-[4-(trifluoromethyl)pyridin-2-yl]pyridin-2-amine;
2-[4-(4-methyl-6-{[4-(trifluoromethyl)pyridin-2-yl]amino}pyridin-2-yl)-1H-1,2,3-triazol-1-yl]ethyl carbamate;
4-methyl-6-[1-(1H-pyrazol-3-ylmethyl)-1H-1,2,3-triazol-4-yl]-N-[4-(trifluoromethyl)pyridin-2-yl]pyridin-2-amine;
6-{1-[(1-aminocyclopropyl)methyl]-1H-1,2,3-triazol-4-yl}-4-methyl-N-[4-(trifluoromethyl)pyridin-2-yl]pyridin-2-amine;
5-(1-(4-(3-((4-(difluoromethyl)pyrimidin-2-yl)amino)-5-methylphenyl)-1H-1,2,3-triazol-1-yl)ethyl)oxazolidin-2-one;
5-((4-(3-((4-(difluoromethyl)pyrimidin-2-yl)amino)-5-methylphenyl)-1H-1,2,3-triazol-1-yl)methyl)oxazolidin-2-one;
5-((4-(3-((4-(difluoromethyl)pyrimidin-2-yl)amino)-5-methylphenyl)-1H-1,2,3-triazol-1-yl)methyl)-4-methyloxazolidin-2-one;
5-((4-(6-((4-(difluoromethyl)pyrimidin-2-yl)amino)-4-methylpyridin-2-yl)-1H-1,2,3-triazol-1-yl)methyl)-5-methyloxazolidin-2-one;
5-(1-(4-(6-((4-(difluoromethyl)pyrimidin-2-yl)amino)-4-methylpyridin-2-yl)-1H-1,2,3-triazol-1-yl)ethyl)oxazolidin-2-one;
5-(1-(4-(6-((4-(difluoromethyl)pyrimidin-2-yl)amino)-4-methylpyridin-2-yl)-1H-1,2,3-triazol-1-yl)ethyl)oxazolidin-2-one;
5-((4-(6-((4-(difluoromethyl)pyrimidin-2-yl)amino)-4-methylpyridin-2-yl)-1H-1,2,3-triazol-1-yl)methyl)oxazolidin-2-one;

5-((4-(4-(6-((4-(difluoromethyl)pyridin-2-yl)amino)-4-methylpyridin-2-yl)-1H-1,2,3-triazol-1-yl)methyl)-4-methyloxazolidin-2-one;

5-((4-(3-((4-(difluoromethyl)pyrimidin-2-yl)amino)-5-methylphenyl)-1H-1,2,3-triazol-1-yl)methyl)pyridin-2(3H)-one;

7-((4-(3-((4-(difluoromethyl)pyrimidin-2-yl)amino)-5-methylphenyl)-1H-1,2,3-triazol-1-yl)methyl)-6-oxa-4-azaspiro[2.4]heptan-5-one;

2-[4-(3-{[4-(difluoromethyl)pyrimidin-2-yl]amino}-5-methylphenyl)-1H-1,2,3-triazol-1-yl]-1-methylcyclohexanol;

2-(4-{3-methyl-5-[(4-methylpyrimidin-2-yl)amino]phenyl}-1H-1,2,3-triazol-1-yl)cyclohexanol;

2-[4-(6-{[4-(difluoromethyl)pyridin-2-yl]amino}-4-methylpyridin-2-yl)-1H-1,2,3-triazol-1-yl]cyclohexanol;

2-[4-(3-{[4-(difluoromethyl)-5-fluoropyrimidin-2-yl]amino}-5-methylphenyl)-1H-1,2,3-triazol-1-yl]-1-methylcyclohexanol;

1-methyl-2-(4-{3-methyl-5-[(4-methylpyrimidin-2-yl)amino]phenyl}-1H-1,2,3-triazol-1-yl)cyclohexanol;

2-[4-(3-{[4-(difluoromethyl)-5-fluoropyrimidin-2-yl]amino}-5-methylphenyl)-1H-1,2,3-triazol-1-yl]cyclohexanol 5-{[4-(3-{[4-(difluoromethyl)pyrimidin-2-yl]amino}-5-methylphenyl)-1H-1,2,3-triazol-1-yl]methyl}-5-methyl-1,3-oxazolidin-2-one;

7-{[4-(3-{[4-(difluoromethyl)-5-fluoropyrimidin-2-yl]amino}-5-methylphenyl)-1H-1,2,3-triazol-1-yl]methyl}-6-oxa-4-azaspiro[2.4]heptan-5-one;

5-{[4-(3-{[4-(difluoromethyl)-5-fluoropyrimidin-2-yl]amino}-5-methylphenyl)-1H-1,2,3-triazol-1-yl]methyl}-1,3-oxazolidin-2-one;

5-{[4-(3-{[4-(difluoromethyl)-5-fluoropyrimidin-2-yl]amino}-5-methylphenyl)-1H-1,2,3-triazol-1-yl]methyl}-4-methyl-1,3-oxazolidin-2-one;

5-{[4-(3-{[4-(difluoromethyl)pyrimidin-2-yl]amino}-5-methylphenyl)-1H-1,2,3-triazol-1-yl]methyl}-4-methyl-1,3-oxazolidin-2-one;

2-methyl-3-(4-(3-methyl-5-((4-methylpyrimidin-2-yl)amino)phenyl)-1H-1,2,3-triazol-1-yl)propane-1,2-diol;

2-methyl-3-[4-(3-methyl-5-{[4-(trifluoromethyl)pyrimidin-2-yl]amino}phenyl)-1H-1,2,3-triazol-1-yl]propane-1,2-diol;

2-methyl-3-[4-(3-{[4-(trifluoromethyl)pyrimidin-2-yl]amino}phenyl)-1H-1,2,3-triazol-1-yl]propane-1,2-diol;

3-[4-(3-{[4-(difluoromethyl)pyrimidin-2-yl]amino}-5-methylphenyl)-1H-1,2,3-triazol-1-yl]-2-methylpropane-1,2-diol;

1-[4-(6-{[4-(difluoromethyl)pyridin-2-yl]amino}-4-methylpyridin-2-yl)-1H-1,2,3-triazol-1-yl]-2,3-dimethylbutane-2,3-diol;

1-(4-{6-[(5-chloro-4-methylpyridin-2-yl)amino]-4-methylpyridin-2-yl}-1H-1,2,3-triazol-1-yl)-2,3-dimethylbutane-2,3-diol;

1-(4-{3-[(5-chloro-4-methylpyrimidin-2-yl)amino]-5-methylphenyl}-1H-1,2,3-triazol-1-yl)-2,3-dimethylbutane-2,3-diol;

1-(4-{3-[(4-methoxypyrimidin-2-yl)amino]-5-methylphenyl}-1H-1,2,3-triazol-1-yl)-2,3-dimethylbutane-2,3-diol;

2,3-dimethyl-1-[4-(3-methyl-5-{[4-(1-methylethoxy)pyrimidin-2-yl]amino}phenyl)-1H-1,2,3-triazol-1-yl]butane-2,3-diol;

1-(4-{3-[(4-cyclopropylpyrimidin-2-yl)amino]-5-methylphenyl}-1H-1,2,3-triazol-1-yl)-2,3-dimethylbutane-2,3-diol;

1-[4-(3-{[4-(difluoromethyl)-5-fluoropyrimidin-2-yl]amino}-5-methylphenyl)-1H-1,2,3-triazol-1-yl]-2,3-dimethylbutane-2,3-diol;

1-(4-{3-[(5-chloro-4-methoxypyrimidin-2-yl)amino]-5-methylphenyl}-1H-1,2,3-triazol-1-yl)-2,3-dimethylbutane-2,3-diol;

1-[4-(6-{[4-(1-fluoroethyl)pyridin-2-yl]amino}-4-methylpyridin-2-yl)-1H-1,2,3-triazol-1-yl]-2,3-dimethylbutane-2,3-diol;

1-[4-(3-{[4-(difluoromethyl)pyrimidin-2-yl]amino}-5-methylphenyl)-1H-1,2,3-triazol-1-yl]-2,3-dimethylbutane-2,3-diol;

2,3-dimethyl-1-[4-(3-methyl-5-{[(4-(trifluoromethyl)pyrimidin-2-yl]amino}phenyl)-1H-1,2,3-triazol-1-yl]butane-2,3-diol;

1-(4-{3-[(5-fluoro-4-methoxypyrimidin-2-yl)amino]-5-methylphenyl}-1H-1,2,3-triazol-1-yl)-2,3-dimethylbutane-2,3-diol;

2,3-dimethyl-1-(4-{3-methyl-5-[(4-methylpyrimidin-2-yl)amino]phenyl}-1H-1,2,3-triazol-1-yl)butane-2,3-diol;

1-(4-{6-[(5-fluoro-4-methylpyridin-2-yl)amino]-4-methylpyridin-2-yl}-1H-1,2,3-triazol-1-yl)-2,3-dimethylbutane-2,3-diol;

3-(4-(6-((4-(difluoromethyl)pyridin-2-yl)amino)-4-methylpyridin-2-yl)-1H-1,2,3-triazol-1-yl)cyclohexane-1,2-diol;

3-(4-(6-((4-(difluoromethyl)pyridin-2-yl)amino)-4-methylpyridin-2-yl)-1H-1,2,3-triazol-1-yl)-2-methylpropane-1,2-diol;

4-(difluoromethyl)-N-(3-methyl-5-(1-(morpholin-2-ylmethyl)-1H-1,2,3-triazol-4-yl)phenyl) pyrimidin-2-amine;

4-(4-(6-((4-(difluoromethyl)pyridin-2-yl)amino)-4-methylpyridin-2-yl)-1H-1,2,3-triazol-1-yl)-3-hydroxy-3-methylbutanenitrile;

4-((4-(6-((4-(difluoromethyl)pyridin-2-yl)amino)-4-methylpyridin-2-yl)-1H-1,2,3-triazol-1-yl)methyl)pyrrolidin-2-one;

3-(4-(3-((4-(difluoromethyl)pyrimidin-2-yl)amino)-5-methylphenyl)-1H-1,2,3-triazol-1-yl)cyclohexane-1,2-diol;

N-(4-(difluoromethyl)pyridin-2-yl)-4-methyl-6-(1-(morpholin-2-ylmethyl)-1H-1,2,3-triazol-4-yl)pyridin-2-amine;

4-(4-(3-((4-(difluoromethyl)pyrimidin-2-yl)amino)-5-methylphenyl)-1H-1,2,3-triazol-1-yl)-3-hydroxy-3-methylbutanenitrile;

4-((4-(3-((4-(difluoromethyl)pyrimidin-2-yl)amino)-5-methylphenyl)-1H-1,2,3-triazol-1-yl)methyl)pyrrolidin-2-one;

6-[4-(3-{[4-(difluoromethyl)pyrimidin-2-yl]amino}-5-methylphenyl)-1H-1,2,3-triazol-1-yl]-1-methylcyclohexane-1,2-diol;

3-(4-(3-((4-(difluoromethyl)pyrimidin-2-yl)amino)-5-methylphenyl)-1H-1,2,3-triazol-1-yl)-2-methylbutane-1,2-diol;

3-[4-(6-{[4-(difluoromethyl)pyridin-2-yl]amino}-4-methylpyridin-2-yl)-1H-1,2,3-triazol-1-yl]-2-methylbutane-1,2-diol;

4-((4-(3-((4-(difluoromethyl)pyrimidin-2-yl)amino)-5-methylphenyl)-1H-1,2,3-triazol-1-yl)methyl)-4-hydroxypyrrolidin-2-one;

5-((4-(3-((4-(difluoromethyl)-5-fluoropyrimidin-2-yl)amino)-5-methylphenyl)-1H-1,2,3-triazol-1-yl)methyl)pyridin-2-ol; and 5-((4-(3-((4-(difluoromethyl)pyrimidin-2-yl)amino)-5-methylphenyl)-1H-1,2,3-triazol-1-yl)methyl)pyridin-2(3H)-one.

In another embodiment, the compounds of Formula I (including pharmaceutically acceptable salts thereof) are selected from the following compounds:

2-methyl-3-[4-(4-methyl-6-{[4-(trifluoromethyl)pyridin-2-yl]amino}pyridin-2-yl)-1H-1,2,3-triazol-1-yl]propane-1,2-diol;

(3R)-3-hydroxy-4-[4-(4-methyl-6-{[4-(trifluoromethyl)pyridin-2-yl]amino}pyridin-2-yl)-1H-1,2,3-triazol-1-yl]butanenitrile;

3-[4-(4-methyl-6-{[4-(trifluoromethyl)pyridin-2-yl]amino}pyridin-2-yl)-1H-1,2,3-triazol-1-yl]propane-1,2-diol;

1-fluoro-3-[4-(4-methyl-6-{[4-(trifluoromethyl)pyridin-2-yl]amino}pyridin-2-yl)-1H-1,2,3-triazol-1-yl]propan-2-ol;

3-[4-(4-methyl-6-{[4-(trifluoromethyl)pyridin-2-yl]amino}pyridin-2-yl)-1H-1,2,3-triazol-1-yl]cyclohexane-1,2-diol;

5-{[4-(4-methyl-6-{[4-(trifluoromethyl)pyridin-2-yl]amino}pyridin-2-yl)-1H-1,2,3-triazol-1-yl]methyl}-1,3-oxazolidin-2-one;

3-hydroxy-4-[4-(4-methyl-6-{[4-(trifluoromethyl)pyridin-2-yl]amino}pyridin-2-yl)-1H-1,2,3-triazol-1-yl]pentanenitrile;

(2S)-3-[4-(4-methyl-6-{[4-(trifluoromethyl)pyridin-2-yl]amino}pyridin-2-yl)-1H-1,2,3-triazol-1-yl]propane-1,2-diol;

3-{[4-(4-methyl-6-{[4-(trifluoromethyl)pyridin-2-yl]amino}pyridin-2-yl)-1H-1,2,3-triazol-1-yl]methyl}tetrahydrofuran-3-ol;

1-[4-(4-methyl-6-{[4-(trifluoromethyl)pyridin-2-yl]amino}pyridin-2-yl)-1H-1,2,3-triazol-1-yl]butane-2,3-diol;

(3R)-3-hydroxy-4-[4-(4-methyl-6-{[4-(trifluoromethyl)pyridin-2-yl]amino}pyridin-2-yl)-1H-1,2,3-triazol-1-yl]butanamide;

2-[4-(4-methyl-6-{[4-(trifluoromethyl)pyridin-2-yl]amino}pyridin-2-yl)-1H-1,2,3-triazol-1-yl]ethanol;

2-methyl-1-[4-(4-methyl-6-{[4-(trifluoromethyl)pyridin-2-yl]amino}pyridin-2-yl)-1H-1,2,3-triazol-1-yl]propan-2-ol;

(2R)-2-[4-(4-methyl-6-{[4-(trifluoromethyl)pyridin-2-yl]amino}pyridin-2-yl)-1H-1,2,3-triazol-1-yl]propanamide;

4-[4-(3-methyl-5-{[4-(trifluoromethyl)pyrimidin-2-yl]amino}phenyl)-1H-1,2,3-triazol-1-yl]cyclohexanecarboxamide;

2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxamide;

3-[4-(4-methyl-6-{[4-(trifluoromethyl)pyridin-2-yl]amino}pyridin-2-yl)-1H-1,2,3-triazol-1-yl]cycloheptane-1,2-diol;

4-hydroxy-2,2-dimethyl-4-[1-(3-methyl-5-{[4-(trifluoromethyl)pyrimidin-2-yl]amino}phenyl)-1H-1,2,3-triazol-4-yl]cyclohexanecarboxamide;

4-{[4-(4-methyl-6-{[4-(trifluoromethyl)pyridin-2-yl]amino}pyridin-2-yl)-1H-1,2,3-triazol-1-yl]methyl}tetrahydro-2H-pyran-4-ol; and 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylic acid.

In another embodiment, the compounds of Formula I (including pharmaceutically acceptable salts thereof) are selected from the following compounds:

(1R,2R)-(2-[4-(3-{[4-(difluoromethyl)pyrimidin-2-yl]amino}-5-methylphenyl)-1H-1,2,3-triazol-1-yl]cyclohexanol;

(1S,2S)-2-[4-(3-{[4-(difluoromethyl)pyrimidin-2-yl]amino}-5-methylphenyl)-1H-1,2,3-triazol-1-yl]cyclohexanol;

(5R)-5-{[4-(4-methyl-6-{[4-(trifluoromethyl)pyridin-2-yl]amino}pyridin-2-yl)-1H-1,2,3-triazol-1-yl]methyl}-1,3-oxazolidin-2-one;

(5S)-5-{[4-(4-methyl-6-{[4-(trifluoromethyl)pyridin-2-yl]amino}pyridin-2-yl)-1H-1,2,3-triazol-1-yl]methyl}-1,3-oxazolidin-2-one;

(5R)-5-((4-(3-((4-(difluoromethyl)pyrimidin-2-yl)amino)-5-methylphenyl)-1H-1,2,3-triazol-1-yl)methyl)oxazolidin-2-one;

(5S)-5-((4-(3-((4-(difluoromethyl)pyrimidin-2-yl)amino)-5-methylphenyl)-1H-1,2,3-triazol-1-yl)methyl)oxazolidin-2-one;

(5R)-5-((4-(6-((4-(difluoromethyl)pyrimidin-2-yl)amino)-4-methylpyridin-2-yl)-1H-1,2,3-triazol-1-yl)methyl)-5-methyloxazolidin-2-one;

(5S)-5-((4-(6-((4-(difluoromethyl)pyrimidin-2-yl)amino)-4-methylpyridin-2-yl)-1H-1,2,3-triazol-1-yl)methyl)-5-methyloxazolidin-2-one (5R)-5-((4-(6-((4-(difluoromethyl)pyrimidin-2-yl)amino)-4-methylpyridin-2-yl)-1H-1,2,3-triazol-1-yl)methyl)oxazolidin-2-one;

(5S)-5-((4-(6-((4-(difluoromethyl)pyrimidin-2-yl)amino)-4-methylpyridin-2-yl)-1H-1,2,3-triazol-1-yl)methyl)oxazolidin-2-one;

(R)-7-((4-(3-((4-(difluoromethyl)pyrimidin-2-yl)amino)-5-methylphenyl)-1H-1,2,3-triazol-1-yl)methyl)-6-oxa-4-azaspiro[2.4]heptan-5-one;

(S)-7-((4-(3-((4-(difluoromethyl)pyrimidin-2-yl)amino)-5-methylphenyl)-1H-1,2,3-triazol-1-yl)methyl)-6-oxa-4-azaspiro[2.4]heptan-5-one;

(1R,2R)-2-[4-(3-{[4-(difluoromethyl)pyrimidin-2-yl]amino}-5-methylphenyl)-1H-1,2,3-triazol-1-yl]-1-methylcyclohexanol;

(1S,2S)-2-[4-(3-{[4-(difluoromethyl)pyrimidin-2-yl]amino}-5-methylphenyl)-1H-1,2,3-triazol-1-yl]-1-methylcyclohexanol;

(1R,2R)-2-(4-{3-methyl-5-[(4-methylpyrimidin-2-yl)amino]phenyl}-1H-1,2,3-triazol-1-yl)cyclohexanol;

(1S,2S)-2-(4-{3-methyl-5-[(4-methylpyrimidin-2-yl)amino]phenyl}-1H-1,2,3-triazol-1-yl)cyclohexanol;

(1R,2R)-2-[4-(6-{[4-(difluoromethyl)pyridin-2-yl]amino}-4-methylpyridin-2-yl)-1H-1,2,3-triazol-1-yl]cyclohexanol;

(1S,2S)-2-[4-(6-{[4-(difluoromethyl)pyridin-2-yl]amino}-4-methylpyridin-2-yl)-1H-1,2,3-triazol-1-yl]cyclohexanol;

(1R,2R)-2-[4-(3-{[4-(difluoromethyl)-5-fluoropyrimidin-2-yl]amino}-5-methylphenyl)-1H-1,2,3-triazol-1-yl]-1-methylcyclohexanol;

(1S,2S)-2-[4-(3-{[4-(difluoromethyl)-5-fluoropyrimidin-2-yl]amino}-5-methylphenyl)-1H-1,2,3-triazol-1-yl]-1-methylcyclohexanol;

(1R,2R)-1-methyl-2-(4-{3-methyl-5-[(4-methylpyrimidin-2-yl)amino]phenyl}-1H-1,2,3-triazol-1-yl)cyclohexanol;

(1S,2S)-1-methyl-2-(4-{3-methyl-5-[(4-methylpyrimidin-2-yl)amino]phenyl}-1H-1,2,3-triazol-1-yl)cyclohexanol;

(1R,2R)-2-[4-(3-{[4-(difluoromethyl)-5-fluoropyrimidin-2-yl]amino}-5-methylphenyl)-1H-1,2,3-triazol-1-yl]cyclohexanol;

(1S,2S)-2-[4-(3-{[4-(difluoromethyl)-5-fluoropyrimidin-2-yl]amino}-5-methylphenyl)-1H-1,2,3-triazol-1-yl]cyclohexanol;

(5R)-5-{[4-(3-{[4-(difluoromethyl)pyrimidin-2-yl]amino}-5-methylphenyl)-1H-1,2,3-triazol-1-yl]methyl}-5-methyl-1,3-oxazolidin-2-one;

(5S)-5-{[4-(3-{[4-(difluoromethyl)pyrimidin-2-yl]amino}-5-methylphenyl)-1H-1,2,3-triazol-1-yl]methyl}-5-methyl-1,3-oxazolidin-2-one;

(R)-7-{[4-(3-{[4-(difluoromethyl)-5-fluoropyrimidin-2-yl]amino}-5-methylphenyl)-1H-1,2,3-triazol-1-yl]methyl}-6-oxa-4-azaspiro[2.4]heptan-5-one;

(S)-7-{[4-(3-{[4-(difluoromethyl)-5-fluoropyrimidin-2-yl]amino}-5-methylphenyl)-1H-1,2,3-triazol-1-yl]methyl}-6-oxa-4-azaspiro[2.4]heptan-5-one;

(5R)-5-{[4-(3-{[4-(difluoromethyl)-5-fluoropyrimidin-2-yl]amino}-5-methylphenyl)-1H-1,2,3-triazol-1-yl]methyl}-1,3-oxazolidin-2-one;

(5S)-5-{[4-(3-{[4-(difluoromethyl)-5-fluoropyrimidin-2-yl]amino}-5-methylphenyl)-1H-1,2,3-triazol-1-yl]methyl}-1,3-oxazolidin-2-one;

(4R,5R)-5-{[4-(3-{[4-(difluoromethyl)-5-fluoropyrimidin-2-yl]amino}-5-methylphenyl)-1H-1,2,3-triazol-1-yl]methyl}-4-methyl-1,3-oxazolidin-2-one;

(4S,5S)-5-{[4-(3-{[4-(difluoromethyl)-5-fluoropyrimidin-2-yl]amino}-5-methylphenyl)-1H-1,2,3-triazol-1-yl]methyl}-4-methyl-1,3-oxazolidin-2-one;

(4R,5S)-5-{[4-(3-{[4-(difluoromethyl)-5-fluoropyrimidin-2-yl]amino}-5-methylphenyl)-1H-1,2,3-triazol-1-yl]methyl}-4-methyl-1,3-oxazolidin-2-one;

(4S,5R)-5-{[4-(3-{[4-(difluoromethyl)-5-fluoropyrimidin-2-yl]amino}-5-methylphenyl)-1H-1,2,3-triazol-1-yl]methyl}-4-methyl-1,3-oxazolidin-2-one;

(4R,5R)-5-{[4-(3-{[4-(difluoromethyl)pyrimidin-2-yl]amino}-5-methylphenyl)-1H-1,2,3-triazol-1-yl]methyl}-4-methyl-1,3-oxazolidin-2-one;

(4S,5S)-5-{[4-(3-{[4-(difluoromethyl)pyrimidin-2-yl]amino}-5-methylphenyl)-1H-1,2,3-triazol-1-yl]methyl}-4-methyl-1,3-oxazolidin-2-one;

(4R,5S)-5-{[4-(6-{[4-(difluoromethyl)pyridin-2-yl]amino}-4-methylpyridin-2-yl)-1H-1,2,3-triazol-1-yl]methyl}-4-methyl-1,3-oxazolidin-2-one;

(4S,5R)-5-{[4-(6-{[4-(difluoromethyl)pyridin-2-yl]amino}-4-methylpyridin-2-yl)-1H-1,2,3-triazol-1-yl]methyl}-4-methyl-1,3-oxazolidin-2-one;

(2R)-2-methyl-3-(4-(3-methyl-5-((4-methylpyrimidin-2-yl)amino)phenyl)-1H-1,2,3-triazol-1-yl)propane-1,2-diol;

(2S)-2-methyl-3-(4-(3-methyl-5-((4-methylpyrimidin-2-yl)amino)phenyl)-1H-1,2,3-triazol-1-yl)propane-1,2-diol;

(2R)-2-methyl-3-[4-(3-methyl-5-{[4-(trifluoromethyl)pyrimidin-2-yl]amino}phenyl)-1H-1,2,3-triazol-1-yl]propane-1,2-diol;

(2S)-2-methyl-3-[4-(3-methyl-5-{[4-(trifluoromethyl)pyrimidin-2-yl]amino}phenyl)-1H-1,2,3-triazol-1-yl]propane-1,2-diol;

(2R)-2-methyl-3-[4-(3-{[4-(trifluoromethyl)pyrimidin-2-yl]amino}phenyl)-1H-1,2,3-triazol-1-yl]propane-1,2-diol;

(2S)-2-methyl-3-[4-(3-{[4-(trifluoromethyl)pyrimidin-2-yl]amino}phenyl)-1H-1,2,3-triazol-1-yl]propane-1,2-diol;

(2R)-3-[4-(3-{[4-(difluoromethyl)pyrimidin-2-yl]amino}-5-methylphenyl)-1H-1,2,3-triazol-1-yl]-2-methylpropane-1,2-diol;

(2S)-3-[4-(3-{[4-(difluoromethyl)pyrimidin-2-yl]amino}-5-methylphenyl)-1H-1,2,3-triazol-1-yl]-2-methylpropane-1,2-diol;

(R)-1-[4-(6-{[4-(difluoromethyl)pyridin-2-yl]amino}-4-methylpyridin-2-yl)-1H-1,2,3-triazol-1-yl]-2,3-dimethylbutane-2,3-diol;

(S)-1-[4-(6-{[4-(difluoromethyl)pyridin-2-yl]amino}-4-methylpyridin-2-yl)-1H-1,2,3-triazol-1-yl]-2,3-dimethylbutane-2,3-diol;

(R)-1-(4-{6-[(5-chloro-4-methylpyridin-2-yl)amino]-4-methylpyridin-2-yl}-1H-1,2,3-triazol-1-yl)-2,3-dimethylbutane-2,3-diol;

(S)-1-(4-{6-[(5-chloro-4-methylpyridin-2-yl)amino]-4-methylpyridin-2-yl}-1H-1,2,3-triazol-1-yl)-2,3-dimethylbutane-2,3-diol;

(R)-1-(4-{3-[(5-chloro-4-methylpyrimidin-2-yl)amino]-5-methylphenyl}-1H-1,2,3-triazol-1-yl)-2,3-dimethylbutane-2,3-diol;

(S)-1-(4-{3-[(5-chloro-4-methylpyrimidin-2-yl)amino]-5-methylphenyl}-1H-1,2,3-triazol-1-yl)-2,3-dimethylbutane-2,3-diol;

(R)-1-(4-{3-[(4-methoxypyrimidin-2-yl)amino]-5-methylphenyl}-1H-1,2,3-triazol-1-yl)-2,3-dimethylbutane-2,3-diol;

(S)-1-(4-{3-[(4-methoxypyrimidin-2-yl)amino]-5-methylphenyl}-1H-1,2,3-triazol-1-yl)-2,3-dimethylbutane-2,3-diol;

(R)-2,3-dimethyl-1-[4-(3-methyl-5-{[4-(1-methylethoxyl)pyrimidin-2-yl]amino}phenyl)-1H-1,2,3-triazol-1-yl]butane-2,3-diol;

(S)-2,3-dimethyl-1-[4-(3-methyl-5-{[4-(1-methylethoxyl)pyrimidin-2-yl]amino}phenyl)-1H-1,2,3-triazol-1-yl]butane-2,3-diol;

(R)-1-(4-{3-[(4-cyclopropylpyrimidin-2-yl)amino]-5-methylphenyl}-1H-1,2,3-triazol-1-yl)-2,3-dimethylbutane-2,3-diol;

(S)-1-(4-{3-[(4-cyclopropylpyrimidin-2-yl)amino]-5-methylphenyl}-1H-1,2,3-triazol-1-yl)-2,3-dimethylbutane-2,3-diol;

(R)-1-[4-(3-{[4-(difluoromethyl)-5-fluoropyrimidin-2-yl]amino}-5-methylphenyl)-1H-1,2,3-triazol-1-yl]-2,3-dimethylbutane-2,3-diol;

(S)-1-[4-(3-{[4-(difluoromethyl)-5-fluoropyrimidin-2-yl]amino}-5-methylphenyl)-1H-1,2,3-triazol-1-yl]-2,3-dimethylbutane-2,3-diol;

(R)-1-(4-{3-[(5-chloro-4-methoxypyrimidin-2-yl)amino]-5-methylphenyl}-1H-1,2,3-triazol-1-yl)-2,3-dimethylbutane-2,3-diol;

(S)-1-(4-{3-[(5-chloro-4-methoxypyrimidin-2-yl)amino]-5-methylphenyl}-1H-1,2,3-triazol-1-yl)-2,3-dimethylbutane-2,3-diol;

(R)-1-[4-(6-{[4-(1-fluoroethyl)pyridin-2-yl]amino}-4-methylpyridin-2-yl)-1H-1,2,3-triazol-1-yl]-2,3-dimethylbutane-2,3-diol;

(S)-1-[4-(6-{[4-(1-fluoroethyl)pyridin-2-yl]amino}-4-methylpyridin-2-yl)-1H-1,2,3-triazol-1-yl]-2,3-dimethylbutane-2,3-diol;

(R)-1-[4-(3-{[4-(difluoromethyl)pyrimidin-2-yl]amino}-5-methylphenyl)-1H-1,2,3-triazol-1-yl]-2,3-dimethylbutane-2,3-diol;

(S)-1-[4-(3-{[4-(difluoromethyl)pyrimidin-2-yl]amino}-5-methylphenyl)-1H-1,2,3-triazol-1-yl]-2,3-dimethylbutane-2,3-diol;

2,3-dimethyl-1-[4-(3-methyl-5-{[4-(trifluoromethyl)pyrimidin-2-yl]amino}phenyl)-1H-1,2,3-triazol-1-yl]butane-2,3-diol;

2,3-dimethyl-1-[4-(3-methyl-5-{[4-(trifluoromethyl)pyrimidin-2-yl]amino}phenyl)-1H-1,2,3-triazol-1-yl]butane-2,3-diol;

(R)-1-(4-{3-[(5-fluoro-4-methoxypyrimidin-2-yl)amino]-5-methylphenyl}-1H-1,2,3-triazol-1-yl)-2,3-dimethylbutane-2,3-diol;

(S)-1-(4-{3-[(5-fluoro-4-methoxypyrimidin-2-yl)amino]-5-methylphenyl}-1H-1,2,3-triazol-1-yl)-2,3-dimethylbutane-2,3-diol;
(R)-2,3-dimethyl-1-(4-{3-methyl-5-[(4-methylpyrimidin-2-yl)amino]phenyl}-1H-1,2,3-triazol-1-yl)butane-2,3-diol;
(S)-2,3-dimethyl-1-(4-{3-methyl-5-[(4-methylpyrimidin-2-yl)amino]phenyl}-1H-1,2,3-triazol-1-yl)butane-2,3-diol;
(R)-1-(4-{6-[(5-fluoro-4-methylpyridin-2-yl)amino]-4-methylpyridin-2-yl}-1H-1,2,3-triazol-1-yl)-2,3-dimethylbutane-2,3-diol;
(S)-1-(4-{6-[(5-fluoro-4-methylpyridin-2-yl)amino]-4-methylpyridin-2-yl}-1H-1,2,3-triazol-1-yl)-2,3-dimethylbutane-2,3-diol;
(R)-3-(4-(6-((4-(Difluoromethyl)pyridin-2-yl)amino)-4-methylpyridin-2-yl)-1H-1,2,3-triazol-1-yl)cyclohexane-1,2-diol;
(S)-3-(4-(6-((4-(difluoromethyl)pyridin-2-yl)amino)-4-methylpyridin-2-yl)-1H-1,2,3-triazol-1-yl)cyclohexane-1,2-diol;
(R)-3-(4-(6-((4-(difluoromethyl)pyridin-2-yl)amino)-4-methylpyridin-2-yl)-1H-1,2,3-triazol-1-yl)-2-methylpropane-1,2-diol;
(S)-3-(4-(6-((4-(difluoromethyl)pyridin-2-yl)amino)-4-methylpyridin-2-yl)-1H-1,2,3-triazol-1-yl)-2-methylpropane-1,2-diol;
(R)-4-(difluoromethyl)-N-(3-methyl-5-(1-(morpholin-2-ylmethyl)-1H-1,2,3-triazol-4-yl)phenyl) pyrimidin-2-amine;
(S)-4-(difluoromethyl)-N-(3-methyl-5-(1-(morpholin-2-ylmethyl)-1H-1,2,3-triazol-4-yl)phenyl) pyrimidin-2-amine;
(3R)-4-(4-(6-((4-(difluoromethyl)pyridin-2-yl)amino)-4-methylpyridin-2-yl)-1H-1,2,3-triazol-1-yl)-3-hydroxy-3-methylbutanenitrile;
(3S)-4-(4-(6-((4-(difluoromethyl)pyridin-2-yl)amino)-4-methylpyridin-2-yl)-1H-1,2,3-triazol-1-yl)-3-hydroxy-3-methylbutanenitrile;
(4R)-4-((4-(6-((4-(difluoromethyl)pyridin-2-yl)amino)-4-methylpyridin-2-yl)-1H-1,2,3-triazol-1-yl)methyl)pyrrolidin-2-one;
(4S)-((4-(6-((4-(difluoromethyl)pyridin-2-yl)amino)-4-methylpyridin-2-yl)-1H-1,2,3-triazol-1-yl)methyl)pyrrolidin-2-one;
3-(4-(3-((4-(difluoromethyl)pyrimidin-2-yl)amino)-5-methylphenyl)-1H-1,2,3-triazol-1-yl)cyclohexane-1,2(cis)-diol;
(2R)—N-(4-(difluoromethyl)pyridin-2-yl)-4-methyl-6-(1-(morpholin-2-ylmethyl)-1H-1,2,3-triazol-4-yl)pyridin-2-amine;
(2S)—N-(4-(difluoromethyl)pyridin-2-yl)-4-methyl-6-(1-(morpholin-2-ylmethyl)-1H-1,2,3-triazol-4-yl)pyridin-2-amine;
(3R)-4-(4-(3-((4-(difluoromethyl)pyrimidin-2-yl)amino)-5-methylphenyl)-1H-1,2,3-triazol-1-yl)-3-hydroxy-3-methylbutanenitrile;
(3S)-4-(4-(3-((4-(difluoromethyl)pyrimidin-2-yl)amino)-5-methylphenyl)-1H-1,2,3-triazol-1-yl)-3-hydroxy-3-methylbutanenitrile;
(4R)-4-((4-(3-((4-(difluoromethyl)pyrimidin-2-yl)amino)-5-methylphenyl)-1H-1,2,3-triazol-1-yl)methyl)pyrrolidin-2-one;
(4S)-4-((4-(3-((4-(difluoromethyl)pyrimidin-2-yl)amino)-5-methylphenyl)-1H-1,2,3-triazol-1-yl)methyl)pyrrolidin-2-one;
(2R,3R)-3-(4-(3-((4-(difluoromethyl)pyrimidin-2-yl)amino)-5-methylphenyl)-1H-1,2,3-triazol-1-yl)-2-methylbutane-1,2-diol;
(2R,3S)-3-(4-(3-((4-(difluoromethyl)pyrimidin-2-yl)amino)-5-methylphenyl)-1H-1,2,3-triazol-1-yl)-2-methylbutane-1,2-diol;
(2S,3R)-3-(4-(3-((4-(difluoromethyl)pyrimidin-2-yl)amino)-5-methylphenyl)-1H-1,2,3-triazol-1-yl)-2-methylbutane-1,2-diol;
(2S,3S)-3-(4-(3-((4-(difluoromethyl)pyrimidin-2-yl)amino)-5-methylphenyl)-1H-1,2,3-triazol-1-yl)-2-methylbutane-1,2-diol;
(2R,3R)-3-[4-(6-{[4-(difluoromethyl)pyridin-2-yl]amino}-4-methylpyridin-2-yl)-1H-1,2,3-triazol-1-yl]-2-methylbutane-1,2-diol;
(2R,3S)-3-[4-(6-{[4-(difluoromethyl)pyridin-2-yl]amino}-4-methylpyridin-2-yl)-1H-1,2,3-triazol-1-yl]-2-methylbutane-1,2-diol;
(2S,3R)-3-[4-(6-{[4-(difluoromethyl)pyridin-2-yl]amino}-4-methylpyridin-2-yl)-1H-1,2,3-triazol-1-yl]-2-methylbutane-1,2-diol;
(2S,3S)-3-[4-(6-{[4-(difluoromethyl)pyridin-2-yl]amino}-4-methylpyridin-2-yl)-1H-1,2,3-triazol-1-yl]-2-methylbutane-1,2-diol;
(4R)-4-((4-(3-((4-(difluoromethyl)pyrimidin-2-yl)amino)-5-methylphenyl)-1H-1,2,3-triazol-1-yl)methyl)-4-hydroxypyrrolidin-2-one; and
(4S)-((4-((4-(3-((4-(difluoromethyl)pyrimidin-2-yl)amino)-5-methylphenyl)-1H-1,2,3-triazol-1-yl)methyl)-4-hydroxypyrrolidin-2-one.

In the application various terms are as defined below, unless otherwise specified:

"Alkyl" refers to a straight- or branched-chain hydrocarbon radical having the specified number of carbon atoms. Examples of "alkyl" include, but are not limited to, methyl, ethyl, n-propyl, isopropyl, n-butyl, isobutyl, t-butyl, n-pentyl, isopentyl, and the like.

Aryl is a 6-membered monocyclic or 10-membered bicyclic aromatic carbon ring, the aryl may optionally be substituted with one to four substituents selected from hydroxyl, $C_1$-$C_3$-alkyl, $C_1$-$C_3$-alkoxyl, $(CR^aR^b)_nCO_2R^c$; and $(CR^aR^b)_nCONR^dR^e$. Examples or aryl are benzene or naphthalene.

"Carbocyclyl" refers to a 4-, 5-, 6-, 7- or 8-membered monocyclic ring or 8-, 9-, 10-membered bicyclic ring, or 13- or 14-membered tricyclic ring, in which all ring atoms are carbon, at least one ring is saturated or partially unsaturated (non-aromatic) and that ring being isolated or fused (including ortho-fused, spiro-fused and bridged) to one or two such rings or to a benzene ring. In the case of a polycyclic carbocyclyl the attachment point may be on any ring; the carbocyclyl may optionally be substituted with one to four substituents selected from hydroxyl, $C_1$-$C_3$-alkyl, $C_1$-$C_3$-alkoxyl, $(CR^aR^b)_nCO_2R^c$; $(CR^aR^b)_nCONR^dR^e$; and a spiro-linked —OCH$_2$CH$_2$O—. Examples of carbocycles include, but are not limited to, cyclopropyl, cyclobutyl, cyclopentyl, cyclohexyl, cyclohexenyl, cycloheptyl, cycloheptenyl, bicyclo[3.3.0]octane, indane, bicyclo[3.3.1]nonane, decalin, tetrahydronaphthalene, spiro[3.3]heptane, bicyclo[3.1.0]hexane, adamantane, tricyclo[2.2.1.0$^{2,6}$]heptane, dispiro[2.1.2.3]decane.

"Cycloalkyl" refers to a saturated ring containing the specified number of ring carbon atoms, and no heteroatom. In a like manner the term "$C_{3-6}$ cycloalkyl" refers to a saturated ring having from 3 to 6 ring carbon atoms. Exemplary "cycloalkyl" groups useful in the present invention include, but are not limited to, cyclopropyl, cyclobutyl, cyclopentyl and cyclohexyl. The carbocyclyl may be optionally be substituted with one or more substituents selected from oxo, halo, hydroxyl, $C_1$-$C_3$-alkyl, $C_2$-$C_6$-alkenyl, $C_1$-$C_3$-alkoxyl, $(CR^aR^b)_nCO_2R^c$; $(CR^aR^b)_nCONR^dR^e$; $(CHR^a)_nNHCONR^dR^e$.

"Halogen" or "halo" refers to fluorine, chlorine, bromine, or iodine.

"Haloalkyl" refers to an alkyl group as defined above in which one and up to all hydrogen atoms are replaced by a halogen; halogen is as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo. Examples of "haloalkyl" include, but are not limited to, fluoromethyl, difluoromethyl, trifluoromethyl, 1-fluoroethyl, 2-fluoroethyl, 2,2-difluoroethyl, 2,2,2-trifluoroethyl, and perfluoro-n-propyl.

"Hydroxyalkyl" refers to an alkyl group as defined above in which one hydrogen on each carbon atom may be replaced by a hydroxy group. Examples of "hydroxyalkyl" include, but are not limited to, hydroxymethyl, hydroxyethyl, propane-1,2-diol.

"Heterocyclyl" refers to a 4-, 5-, 6-, or 7-membered monocyclic ring or 8-, 9-, 10-membered bicyclic ring, or 13- or 14-membered tricyclic ring, saturated, unsaturated or aromatic, containing 1, 2, 3 or 4 heteroatoms selected from O, N. or S, the heterocyclyl may optionally be substituted with one to four substituents selected from oxo, halo, hydroxyl, $C_1$-$C_3$-alkyl, $C_2$-$C_6$-alkenyl, $C_1$-$C_3$-alkoxyl, $(CR^aR^b)_nCO_2R^c$; $(CR^aR^b)_nCONR^dR^e$; $(CHR^a)_nNH$ $CONR^dR^e$; $(CHR^a)_p$—C(O)-heterocyclyl; and heterocycles having a N-atom may by the point of attachment. Representative heterocycles are: azetidinyl, pyrrolidinyl, pyrrolyl, tetrahydrofuran, imidazolyl, imidazolinyl, 1,3-oxazolidinyl, 1,2-oxazolidinyl, isoxazolyl, 1,2,4-oxadiazolyl, 1,3,4-oxadiazolyl, tetrahydropyranyl, piperidinyl, piperazinyl, morpholinyl, pyrimidinyl, pyrrolopyrazine, pyrrolopyridine, and indolyl.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

As used herein, the term "optionally" means that the subsequently described event(s) may or may not occur, and includes both event(s), which occur, and events that do not Occur.

As used herein, the term "substituted with one or more groups" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

Each variable is independently defined each time it occurs within the generic structural formula definitions. For example, when an alkyl is indicated as substituted (or optionally substituted) with more than one substituent, each substituent is independently selected at each occurrence, and each substituent can be the same or different from the other(s).

The term "Syk inhibitor", is used to mean a compound which inhibits the Syk enzyme.

The term "Syk mediated disease" or a "disorder or disease or condition mediated by inappropriate Syk activity" is used to mean any disease state mediated or modulated by Syk kinase mechanisms. Such disease states may include inflammatory, allergic and autoimmune diseases, for example, asthma, chronic obstructive pulmonary disease (COPD), adult respiratory distress syndrome (ARDs), ulcerative colitis, Crohns disease, bronchitis, dermatitis, allergic rhinitis, psoriasis, scleroderma, urticaria, rheumatoid arthritis, multiple sclerosis, cancer, HIV and lupus, in particular, asthma, chronic obstructive pulmonary disease (COPD), adult respiratory distress syndrome (ARDs), allergic rhinitis and rheumatoid arthritis.

As used herein, "a compound of the invention" means a compound of Formula I or a salt, solvate or physiologically functional derivative thereof.

As used herein, the term "solvate" refers to a complex of variable stoichiometry formed by a solute (in this invention, a compound of Formula I, or a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents include water, ethanol and acetic acid. Most preferably the solvent is water.

As used herein, the term "physiologically functional derivative" refers to a compound (e.g., a drug precursor) that is transformed in vivo to yield a compound of Formula I or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds of Formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by chromatography employing columns with a chiral stationary phase. Also, some of the compounds of Formula I may be atropisomers (e.g., substituted biaryls) and are considered as part of this invention.

It is also noted that the compounds of Formula I may form tautomers. It is understood that all tautomers and mixtures of tautomers of the compounds of the present invention are included within the scope of the compounds of the present invention. Some of the compounds described herein contain olefinic double bonds, and unless specified otherwise, are meant to include both E and Z geometric isomers.

Whilst the embodiments for each variable have generally been listed above separately for each variable, this invention also includes those compounds in which several or each embodiment in Formula I is selected from each of the embodiments listed above. Therefore, this invention is intended to include all combinations of embodiments for each variable.

The compounds of the present invention may be in the form of and/or may be administered as a pharmaceutically acceptable salt. For a review on suitable salts see Berge et al, J. Pharm. Sci. 1977, 66, 1-19. Typically, the salts of the present invention are pharmaceutically acceptable salts. Salts encompassed within the term "pharmaceutically acceptable salts" refer to non-toxic salts of the compounds of this invention. Suitable pharmaceutically acceptable salts can include acid or base additions salts.

A pharmaceutically acceptable acid addition salt can be formed by reaction of a compound of Formula I with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated, for example, by crystallisation and filtration. A pharmaceutically acceptable acid addition salt of a compound of Formula I can comprise or be, for example, a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

A pharmaceutically acceptable base salt can be formed by reaction of a compound of Formula I with a suitable inorganic or organic base. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethyl-piperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Other, non-pharmaceutically acceptable, salts, e.g., oxalates or trifluoroacetates, may also be used, for example, in the isolation of compounds of the invention, and are included within the scope of this invention.

The invention includes within its scope all possible stoichiometric and non-stoichiometric forms of the compounds of Formula I.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates The compounds of Formula I and salts, solvates and physiologically functional derivatives thereof are believed to be inhibitors of Syk activity, and thus be potentially useful in the treatment of diseases and conditions associated with inappropriate Syk activity.

Compound of Formula I or its pharmaceutically acceptable salts and pharmaceutical compositions can be used to treat or prevent a variety of conditions or diseases mediated by Spleen tyrosine kinase (Syk). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g., precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors) myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, including cystic fibrosis, vascular spasms, migraine, reperfusion injury, and post-myocardial infarction.

The invention thus provides compounds of Formula I and salts, solvates and physiologically functional derivatives thereof for use in therapy, and particularly in the treatment of diseases and conditions mediated by inappropriate Syk activity. The inappropriate Syk activity referred to herein is any Syk activity that deviates from the normal Syk activity expected in a particular mammalian subject. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a mammal suffering from a disorder mediated by Syk activity, which comprises administering to said mammal an effective amount of a compound of Formula I or a pharmaceutically acceptable salt, solvate, or a physiologically functional derivative thereof.

In a further embodiment, the present invention provides for the use of a compound of Formula I, or a pharmaceutically acceptable salt or solvate thereof, or a physiologically functional derivative thereof, in the preparation of a medicament for the treatment of a disorder mediated by Syk activity.

In a further embodiment said disorder mediated by Syk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Syk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

While it is possible that, for use in therapy, a compound of Formula I, as well as salts, solvates and physiological functional derivatives thereof, may be administered as the raw chemical, it is possible to present the active ingredient as a pharmaceutical composition. Accordingly, the invention further provides a pharmaceutical composition, which comprises a compound of Formula I and salts, solvates and physiological functional derivatives thereof, and one or more pharmaceutically acceptable carriers, diluents, or excipients. The compounds of the Formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula I, or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 µg to 3 g, preferably 1 mg to 700 mg, more preferably 5 mg to 100 mg of a compound of the Formula I, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, or parenteral (including intravenous and intramuscular) route. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula I, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula I and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula I is in a particle-size-reduced form, and more preferably the size-reduced form is obtained or obtainable by micronisation. The preferable particle size of the size-reduced (e.g., micronised) compound or salt or solvate is defined by a D50 value of about 0.5 to about 10 microns (for example as measured using laser diffraction).

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition.

Such a composition can comprise a powder base such as lactose, glucose, trehalose, mannitol or starch, the compound of Formula I or salt or solvate thereof (preferably in particle-size-reduced form, e.g., in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula I or salt thereof. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler® (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of Formula I or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The following are examples of representative pharmaceutical dosage forms for the compounds of this invention:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Inhalation Aerosol | Per dose |
|---|---|
| Compound of Formula I | 100 mcg |
| Oleic Acid | 5 mcg |
| Ethanol | 1 mg |
| HFA 227 (1,1,1,2,3,3,3-heptafluoropropane) | 75 mg |

| Dry Powder Inhalation Aerosol | Per dose |
|---|---|
| Compound of Formula I | 100 mcg |
| Lactose | 12.5 mg |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of Formula I for the treatment of diseases or conditions associated with inappropriate Syk activity, will generally be in the range of 5 μg to 100 mg/kg body weight of recipient (mammal) per day and more usually in the range of 5 μg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula I per se.

Compounds of the present invention, and their salts and solvates, and physiologically functional derivatives thereof, may be employed alone or in combination with other therapeutic agents for the treatment of diseases and conditions associated with inappropriate Syk activity. Combination therapies according to the present invention thus comprise the administration of at least one compound of Formula I or a pharmaceutically acceptable salt or solvate thereof, or a physiologically functional derivative thereof, and the use of at least one other pharmaceutically active agent. The compound(s) of Formula I and the other pharmaceutically active agent(s) may be administered together or separately and, when administered separately this may occur simultaneously or sequentially in any order. The amounts of the compound(s) of Formula I and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of Formula I may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2) such as tofacitinib (Pfizer), baricitinib (Incyte), VX-509 (Vertex), ASP-015K (Astellas), GLPG0634 (Galapagos), SB-1578 (SBIO), and AC-430 (Ambit Biosciences); p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for so-called "triple combination" therapy, comprising a compound of Formula I or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of Formula I or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol fumarate), or a pharmaceutically acceptable salt thereof (e.g., salmeterol xinafoate) and fluticasone propionate.

For the treatment of cancer a compound of Formula I may be combined with one or more of an anticancer agent. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such as antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycylamino]-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl)methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxyl)phenoxy)propoxy)-2-ethylchromane-2-carboxylic acid (disclosed in U.S. Ser. No. 60/235,708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AG014699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refers to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of Formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin;

bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Syk inhibition may be determined using the following assay protocol:
Biological Assay Homogeneous Time-Resolved Fluorescence (HTRF) assay for the recombinant human Syk enzyme: A recombinant GST-hSyk fusion protein was used to measure potency of compounds to inhibit human Syk activity. The recombinant human GST-Syk (Carna Biosciences #08-176) (5 pM final concentration) was incubated with various concentrations of the inhibitor diluted in DMSO (0.1% final concentration) for 10 minutes at room temperature in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for Syk was added with magnesium (5 mM final concentration) and ATP (25 µM final concentration). Final volume of the reaction was 10 µL. Phosphorylation of the peptide was allowed to proceed for 45 minutes at room temperature. To quench the reaction and detect the phosphorylated product, 2 nM of a Europium-anti-phosphotyrosine antibody (Perkin Elmer #AD0161) and 70 nM SA-APC (Perkin-Elmer #CR130-100) were added together in 15 mM Tris pH 7.5, 40 mM EDTA, 0.01% tween 20. Final volume of the quenching solution was 10 µL. The resulting HTRF signal was measured after 30 minutes on an EnVision (Perkin-Elmer) reader using a time-resolved fluorescence protocol. $IC_{50}$ was determined following 10-dose titration (10 µM to 0.508 nM) and four parameter logistic curve fitting using the Merck Assay Data Analyzer. $IC_{50}$ values (in nM) are provided for the following compounds:

| Ex. | rhSYK Activity $IC_{50}$ |
|---|---|
| 1.1 | 76.3 |
| 1.2 | 42.8 |
| 1.3 | 3.8 |
| 1.4 | 3.8 |
| 1.5 | 8.0 |
| 1.6 | 26.6 |
| 1.7 | 15.3 |
| 1.8 | 5.8 |
| 1.9 | 2.9 |
| 1.10 | 6.3 |
| 1.11 | 20.3 |
| 1.12 | 4.9 |
| 1.13 | 3.4 |
| 1.14 | 9.1 |
| 1.15 | 15.4 |
| 1.16 | 13.3 |
| 1.17 | 4.4 |
| 1.18 | 11.8 |
| 1.19 | 123 |
| 1.20 | 87.2 |
| 1.21 | 23.1 |
| 1.22 | 22.8 |
| 1.23 | 6.8 |
| 1.24 | 14.2 |
| 1.25 | 8.8 |
| 1.26 | 1109 |
| 1.27 | 101.9 |
| 1.28 | 644.7 |
| 1.29 | 124 |
| 1.30 | 1624 |
| 1.31 | 319.8 |
| 1.32 | 357.3 |
| 1.33 | 325.4 |
| 1.34 | 2704 |
| 1.35 | 170.8 |
| 1.36 | 1456 |
| 1.37 | 33.9 |
| 1.38 | 634.7 |
| 1.39 | 367.3 |
| 1.40 | 118.4 |
| 1.41 | 131.1 |
| 1.42 | 911.9 |
| 1.43 | 64.2 |
| 1.44 | 626.4 |
| 1.45 | 172.1 |
| 1.46 | 1399 |
| 1.47 | 345.2 |
| 1.48 | 257.3 |
| 1.49 | 404.2 |
| 1.50 | 569.7 |
| 1.51 | 186.3 |
| 1.52 | 434.9 |
| 1.53 | 34.7 |
| 1.54 | 134.3 |

| Ex. | rhSYK Activity IC$_{50}$ |
|---|---|
| 1.55 | 449.5 |
| 1.56 | 423.4 |
| 1.57 | 92.8 |
| 1.58 | 29.7 |
| 2.1 | 11.2 |
| 2.2 | 8.88 |
| 2.3 | 21.1 |
| 2.4 | 28.1 |
| 2.5 | 132.4 |
| 2.6 | 26.6 |
| 2.7 | 16.7 |
| 2.8 | 5048 |
| 2.9 | 58.7 |
| 2.10 | 3.7 |
| 2.11 | 6.4 |
| 2.12 | 5.5 |
| 2.13 | 8.40 |
| 2.14 | 280.6 |
| 2.15 | 3149 |
| 3.1 | 60.7 |
| 3.2 | 46.8 |
| 3.3 | 54.3 |
| 3.4 | 81.4 |
| 3.5 | 70.4 |
| 3.6 | 3.5 |
| 3.7 | 3.7 |
| 3.8 | 9.8 |
| 3.9 | 3.0 |
| 3.10 | 3.9 |
| 3.11 | 5.1 |
| 3.12 | 104.7 |
| 3.13 | 95.0 |
| 3.14 | 9.6 |
| 3.15 | 8.9 |
| 3.16 | 33.3 |
| 3.17 | 0.1 |
| 3.18 | 1.9 |
| 3.19 | 16.0 |
| 4.1 | 81.4 |
| 4.2 | 12.8 |
| 4.3 | 4.6 |
| 4.4 | 26.1 |
| 4.5 | 61.2 |
| 4.6 | 45.5 |
| 4.7 | 15.8 |
| 4.8 | 35.1 |
| 4.9 | 25.2 |
| 4.10 | 5.7 |
| 4.11 | 144.7 |
| 4.12 | 144.9 |
| 4.13 | 25.6 |
| 4.14 | 48.1 |
| 4.15 | 32.9 |
| 4.16 | 40.3 |
| 4.17 | 26.6 |
| 4.18 | 26.6 |
| 4.19 | 14.9 |
| 4.20 | 17.0 |
| 4.21 | 68.6 |
| 4.22 | 3.0 |
| 4.23 | 5.4 |
| 4.24 | 8.3 |
| 4.25 | 12.1 |
| 4.26 | 0.7 |
| 4.27 | 2.0 |
| 4.28 | 6.6 |
| 4.29 | 8.2 |
| 4.30 | 26.6 |
| 4.31 | 8.1 |
| 4.32 | 4.8 |
| 4.33 | 14.9 |
| 4.34 | 4.1 |
| 4.35 | 11.0 |
| 5.1 | 14.9 |
| 5.2 | 4.4 |
| 5.3 | 128.7 |
| 5.4 | 63.5 |
| 5.5 | 15.8 |
| 5.10 | 40.4 |
| 5.6 | 2.2 |
| 5.7 | 7.3, 3.4 |
| 5.8 | 62.0 |
| 5.9 | 38.1 |
| 5.11 | 21.8 |
| 5.12 | 11.2 |
| 5.13 | 11.7 |
| 5.14 | 23.4 |
| 5.15 | 239.9 |
| 5.16 | 235.3 |
| 5.17 | 128.4 |
| 5.18 | 153.6 |
| 5.19 | 4.0 |
| 5.20 | 24.1 |
| 5.21 | 3.3 |
| 5.22 | 19.8 |
| 5.23 | 64.7 |
| 5.24 | 24.6 |
| 5.25 | 524.7 |
| 5.26 | 62.9 |
| 5.27 | 145.8 |
| 5.28 | 76.5 |
| 5.29 | 166.5 |
| 5.30 | 39.8 |
| 5.31 | 48.6 |
| 5.32 | 751.9 |
| 5.33 | 58.5 |
| 5.34 | 171.3 |
| 5.35 | 299.7 |
| 5.36 | 52.0 |
| 5.37 | 30.2 |
| 5.38 | 17.8 |
| 5.39 | 44.9 |
| 5.40 | 28.9 |
| 5.41 | 1.1 |
| 5.42 | 3.3 |
| 5.43 | 35.2, 17.0 |
| 5.44 | 4.1, 3.18 |
| 5.45 | 8.3 |
| 5.46 | 4.9 |
| 5.47 | 80.2 |
| 5.48 | 32.9 |
| 5.49 | 78.8 |
| 5.50 | 504 |
| 5.51 | 177.3 |
| 5.52 | 16.4 |
| 5.53 | 58.6 |
| 5.54 | 29.4 |
| 5.55 | 23.5 |
| 5.56 | 76.8 |
| 5.57 | 17 |
| 5.58 | 61.3 |
| 5.59 | 69.8 |
| 5.60 | 41.8 |
| 5.61 | 29.4 |
| 5.62 | 46.4 |
| 5.63 | 24.1 |
| 5.64 | 41.4 |
| 5.65 | 122.3 |
| 5.66 | 151.5 |
| 5.67 | 296.2 |
| 5.68 | 113.9 |
| 5.69 | 57.2 |
| 5.70 | 183.4 |
| 5.71 | 151.9 |
| 5.72 | 38.1 |
| 5.73 | 39.2 |
| 5.74 | 187 |
| 5.75 | 31.6 |
| 5.76 | 32.4 |
| 5.77 | 50.7 |
| 5.78 | 84.1 |
| 5.79 | 73.8, 81.8 |
| 5.80 | 24.5 |
| 5.81 | 6.9 |

| Ex. | rhSYK Activity IC$_{50}$ |
|---|---|
| 5.82 | 7.9 |
| 5.83 | 4.4 |
| 5.84 | 2.1 |
| 5.85 | 80.0 |
| 5.86 | 66.4 |
| 5.87 | 81.2 |
| 5.88 | 52.9 |
| 5.89 | 4.0 |
| 5.90 | 11.5 |
| 5.91 | 8.3 |
| 5.92 | 22.0 |
| 5.93 | 6.0 |
| 5.94 | 474.1 |
| 5.95 | 7.9 |
| 5.96 | 47.1 |
| 5.97 | 15.0 |
| 5.98 | 20.0 |
| 5.99 | 429.9 |
| 5.100 | 27.7 |
| 5.101 | 25.2 |
| 5.102 | 1.1 |
| 5.103 | 1.9 |
| 5.104 | 3.2 |
| 5.105 | 2.1 |
| 5.106 | 1.6 |
| 5.107 | 5.1 |
| 5.108 | 2.5 |
| 5.109 | 12.6 |
| 5.110 | 6.2 |
| 5.111 | 2.2 |
| 5.112 | 17.0 |
| 6.1 | 41.0 |
| 6.2 | 1126 |
| 7.1 | 11.1 |
| 7.2 | 3.3 |
| 7.3 | 5.5 |
| 7.4 | 1.8 |
| 7.5 | 7.1 |
| 7.6 | 10.2 |
| 7.7 | 9.9 |
| 7.8 | 1.9 |
| 7.9 | 8.4 |
| 7.10 | 1.7 |
| 7.11 | 1.4 |
| 7.12 | 2.0 |
| 7.13 | 2.0 |
| 7.14 | 1.6 |
| 7.15 | 4.3 |
| 7.16 | 2.3 |
| 7.17 | 1.1 |
| 7.18 | 11.7 |
| 7.19 | 16.2 |
| 7.20 | 15.4 |
| 7.21 | 69.5 |
| 7.22 | 56.0 |
| 7.23 | 3.9 |
| 7.24 | 1.2 |
| 7.25 | 38.2 |
| 7.26 | 13.1 |
| 7.27 | 90.4 |
| 7.28 | 77.6 |
| 7.29 | 14.3 |
| 7.30 | 9.9 |
| 7.31 | 8.0 |
| 7.32 | 5.0 |
| 7.33 | 11.1 |
| 7.34 | 9.9 |
| 7.35 | 7.6 |
| 7.36 | 16.2 |
| 7.37 | 15.9 |
| 7.38 | 33.1 |
| 7.39 | 12.3 |
| 7.40 | 25.7 |
| 7.41 | 12.8 |
| 7.42 | 10.7 |
| 7.43 | 3.8 |
| 7.44 | 18.0 |
| 8.1 | 14.9 |
| 8.2 | 71.8 |
| 9.1 | 3.7 |
| 9.2 | 54 |
| 9.3 | 313.5 |
| 9.4 | 7217 |
| 9.5 | 8.1 |
| 9.6 | 78.8 |
| 9.7 | 3.3 |
| 10.1 | 8.8 |
| 10.2 | 17.7 |
| 10.3 | 1.0 |
| 10.4 | 3.3 |
| 10.5 | 2.6 |
| 10.6 | 4.7 |
| 10.7 | 30.4 |
| 10.8 | 63.3 |
| 10.9 | 33.1 |
| 10.10 | 19.6 |
| 10.11 | 3.3 |
| 10.12 | 23.3 |
| 10.13 | 18.8 |
| 10.14 | 9.1 |
| 10.15 | 7.2 |
| 10.16 | 6.1 |
| 11.1 | 21.2 |
| 11.2 | 23.8 |
| 11.3 | 118.4 |
| 11.4 | 161.2 |
| 12.1 | 14.8 |
| 13.1 | 4.2 |
| 13.2 | 23.6 |
| 13.3 | 10.5 |
| 13.4 | 15.0 |
| 13.5 | 15.0 |
| 13.6 | 3.2 |
| 13.7 | 3.7 |
| 13.8 | 7.1 |
| 13.9 | 2.9 |
| 14 | 44.9 |
| 15 | 94.7 |
| 15.1 | 6.5 |
| 15.2 | 14.5 |
| 15.3 | 231.5 |
| 15.4 | 12.5 |
| 15.5 | 2393 |
| 15.6 | 849.8 |
| 15.7 | 53.1 |
| 15.8 | 94.7 |
| 15.9 | 8.1 |
| 15.10 | 178.8 |
| 15.11 | 102.2 |
| 15.12 | 283.6 |
| 15.13 | 88.0 |
| 15.14 | 79.6 |
| 15.15 | 254.9 |
| 15.16 | 117.1 |
| 15.17 | 30.0 |
| 16.1 | 650 |
| 16.2 | 327.7 |
| 16.3 | 389 |
| 17.1 | 55.4 |
| 18.1 | 2.2 |
| 19.1 | 32.3 |
| 20.1 | 7.7 |
| 21.1 | 6.2 |
| 21.2 | 2.0 |
| 21.3 | 7.0 |
| 21.4 | 10.3 |
| 21.5 | 47.0 |

-continued

| Ex. | rhSYK Activity IC$_{50}$ |
|---|---|
| 21.6 | 44.6 |
| 21.7 | 7.2 |
| 21.8 | 13.1 |
| 21.9 | 13.5 |
| 21.10 | 20.1 |
| 21.11 | 182.4 |
| 21.12 | 28.3 |
| 21.13 | 39.6 |
| 21.14 | 7.4 |
| 21.15 | 47.5 |
| 21.16 | 50.6 |
| 21.17 | 23.1 |
| 21.18 | 38.5 |
| 21.19 | 29.3 |
| 21.20 | 108.7 |
| 21.21 | 191.3 |
| 21.22 | 85.8 |
| 21.23 | 27.9 |
| 21.24 | 31.9 |
| 21.25 | 13.6 |
| 21.26 | 12.7 |
| 21.27 | 41.5 |
| 21.28 | 13.2 |
| 21.29 | 85.6 |
| 21.30 | 88.5 |
| 21.31 | 21.1 |
| 21.32 | 22.2 |
| 21.33 | 66.3 |
| 21.34 | 18.2 |
| 21.35 | 83.9 |
| 21.36 | 8.1 |
| 21.37 | 1.9 |
| 21.38 | 3.7 |
| 21.39 | 1.8 |
| 21.40 | 5.9 |
| 22.1 | 14.3 |
| 22.2 | 1.7 |
| 23.1 | 7.3 |
| 23.2 | 9.0 |
| 24.1 | 12.3 |
| 24.2 | 8.6 |
| 25.1 | 9.5 |
| 25.2 | 7.3 |
| 26.1 | 5.7 |
| 26.2 | 3.3 |
| 27.1 | 19.7 |
| 27.2 | 21.1 |
| 28.1 | 8.4 |
| 28.2 | 5.4 |
| 29.1 | 19.7 |
| 29.2 | 30.7 |
| 29.3 | 10.5 |
| 29.4 | 6.6 |
| 29.5 | 22.6 |
| 29.6 | 10.3 |
| 29.7 | 11.6 |
| 30.1 | 12.4 |
| 30.2 | 6.3 |
| 30.3 | 8.0 |
| 30.4 | 11.4 |
| 30.5 | 2.7 |
| 30.6 | 6.5 |
| 30.7 | 1.4 |
| 30.8 | 1.2 |
| 31.1 | 7.3 |
| 31.2 | 4.7 |
| 32 | 6.8 |
| 33 | 3.7 |

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Examples.

Compounds of general Formula I may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of Formula I. Those skilled in the art will recognize if a stereocenter exists in compounds of Formula I. Accordingly, the present invention includes all possible stereoisomers and includes not only mixtures of stereoisomers (such as racemic compounds) but the individual stereoisomers as well. When a compound is desired as a single enantiomer, it may be obtained by stereospecific or stereoselective synthesis or by resolution of the final product or any convenient intermediate. Resolution of the final product, an intermediate, or a starting material may be affected by any suitable method known in the art. See, for example, Stereochemistry of Organic Compounds by E. L. Eliel, S. H. Wilen, and L. N. Mander (Wiley-Interscience, 1994).

The following abbreviations are used in the schemes and examples: Ac=Acetyl; ACN=Acetontrile; AcOH=Acetic acid; Bn=benzyl; Boc (t-Boc)=t-butyloxycarbonyl; BOP=(Benzotriazol-1-yloxy)tris(dimethylamino)phosphonium hexafluorophosphate; DAST=(Diethylamino)sulfur trifluoride; dba=dibenzylideneacetone; DBU=1,8-Diazabicyclo[5.4.0]undec-7-ene; DCE=1,2-dichloroethane; DCM=Dichloromethane; Dibal/Dibal-H=Diisobutylaluminum hydride; DIPEA/DIEA=Diisopropylethylamine; DMA=N,N-Dimethylaniline; DMAP=N,N-dimethylaminopyridine; DME=1,2-dimethoxyethane; DMF=Dimethyl formamide; DMSO=Dimethylsulfoxide; Dppf=1,1'-Bis(diphenylphosphino)ferrocene; EDC=N-(3-Dimethylaminopropyl)-N'-ethylcarbodiimide; EtOAc=Ethyl acetate; HATU=N,N,N',N'-Tetramethyl-O-(7-azabenzotriazol-1-yl)uronium hexafluorophosphate; HMDS=Hexamethyldisilazane; HOBT=1-Hydroxybenzotriazole; HPLC=High Pressure Liquid Chromatography IPA=Isopropyl alcohol; LDA=Lithium diisopropylamide; M=Molar; mCPBA=Meta-chloroperoxybenzoic acid; Ms=Methanesulfonyl (mesyl); MTBE=Methyl t-butyl ether; NBS=N-bromosuccinimide; Ph=phenyl; NMR=Nuclear Magnetic Resonance; SiDMT=Si-Dimercaptotriazole; TBAF=t-butylammonium fluoride; TBDMS/TBS=t-butyl dimethylsilyl; TFA=Trifluoroacetic acid/trifluroacetate; THF=Tetrahydrofuran; TLC=Thin-layer chromatography; TMS=Trimethylsilyl; Ts=Toluenesulfonyl (tosyl); TSA=p-toluenesulfonic acid. Abbreviations for alkyl/cycloalkyl groups: Me=methyl, Et=ethyl, nPr=n-propyl, iPr=isopropyl, nBu=n-butyl, t-Bu=tertiary butyl, cPr=cyclopropyl, cBu=cyclobutyl, cPen=cyclopentyl, cHex=cyclohexyl, cHept=cycloheptyl.

SCHEME 1
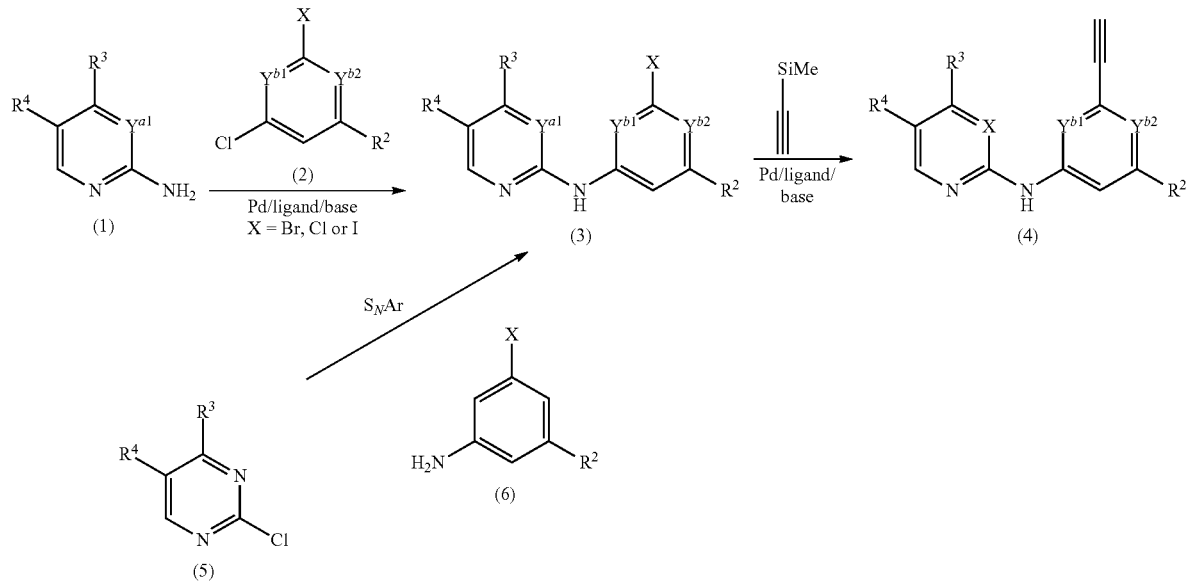
Reaction of substituted-aryl amines 1 with aryl chlorides 2 in the presence of Pd catalyst affords compound 3. Compounds of formula 3 may also be obtained by reacting chloropyrimidines 5 with anilines 6. reaction of 3 with trimethylsilylacetylene in the presence of Pd catalyst affords acetylene 4.
SCHEME 2
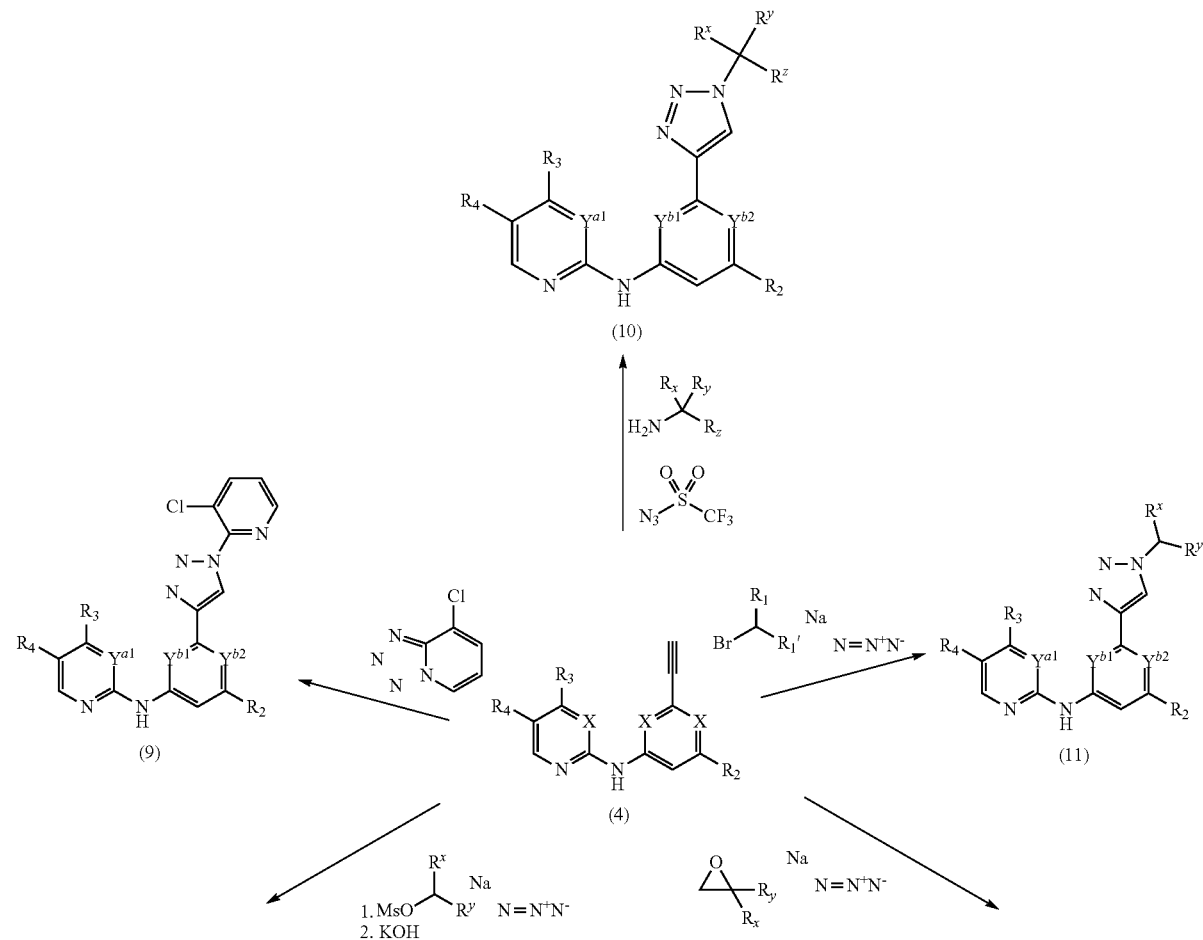

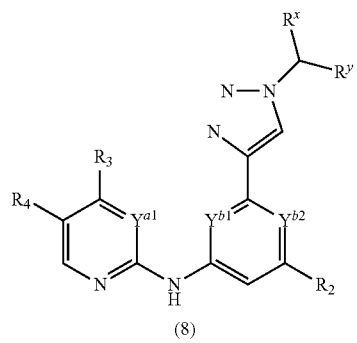

(8)

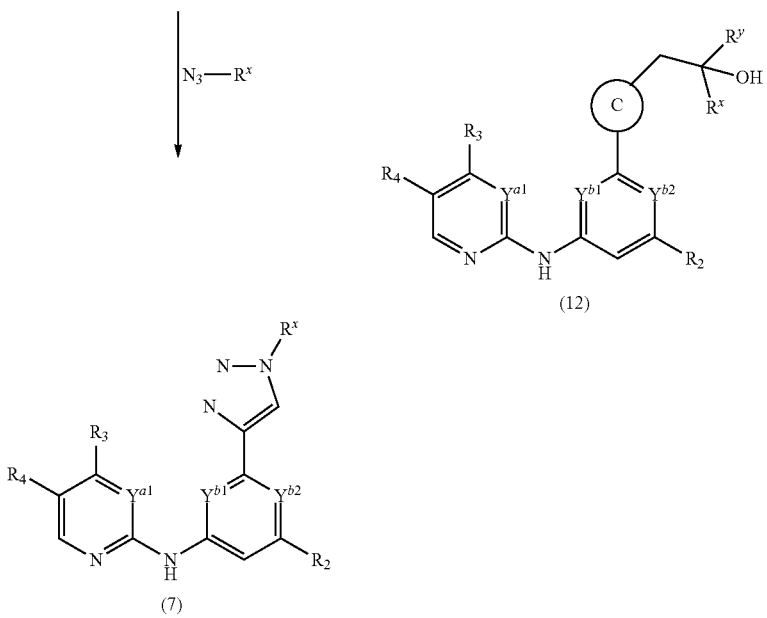

(7)

Acetylene 4 can be reacted in a variety of manners. Compounds of formula 7 can be prepared via click chemistry of 4 with an azide. Mesylate or halide displacement with sodium azide followed by click chemistry affords compounds 8 or 11, respectively. Alternatively, click chemistry with a tetrazole affords compounds 9. Reaction of acetylene 4 with azides prepared in situ, by reaction of an amine with triflic azide, yields compound 10 while reaction of 4 with epoxides in the presence of sodium azide affords compounds 12.

SCHEME 3

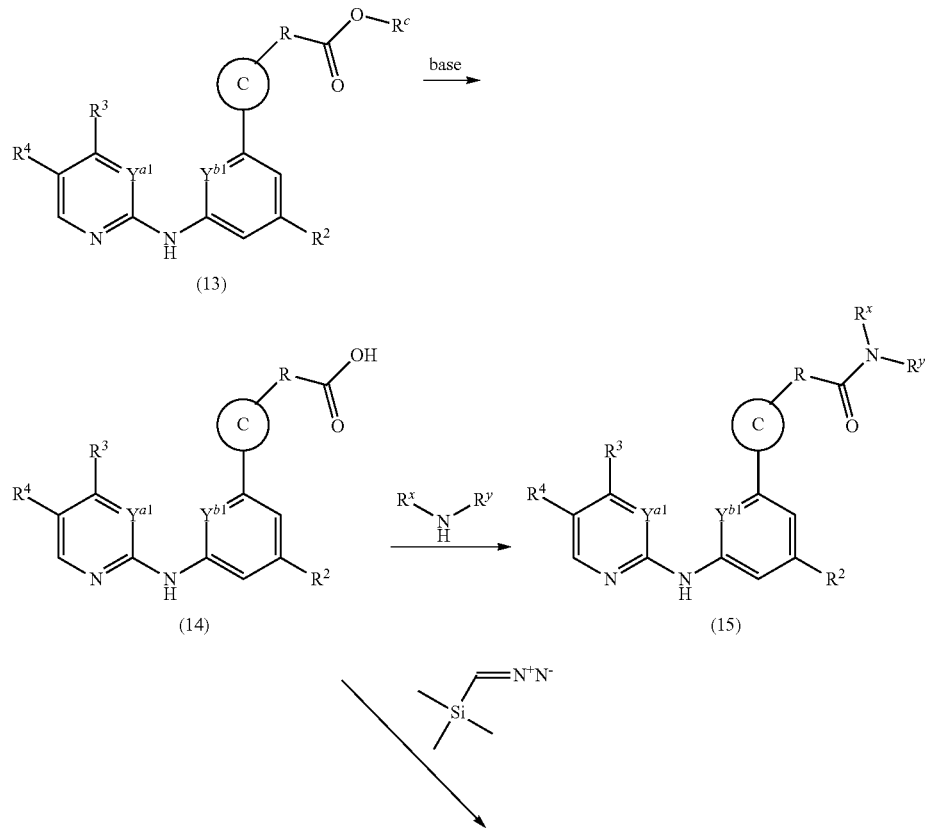

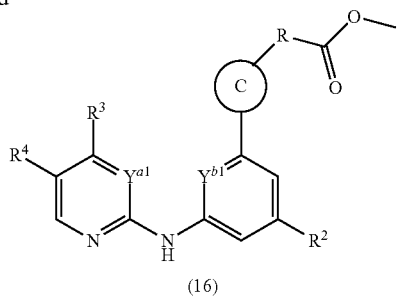
(16)
Hydrolysis of esters 13 affords carboxylic acid 14 which can be directly converted to the amide 15 by coupling with amines. Alternatively, esterification by reaction with diazomethane affords methyl esters 16.
SCHEME 4
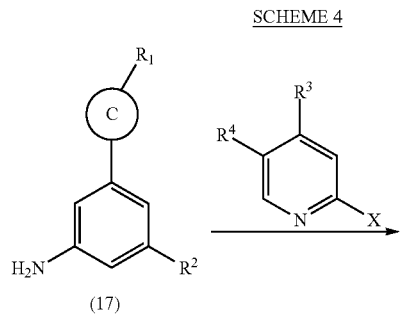
(17)
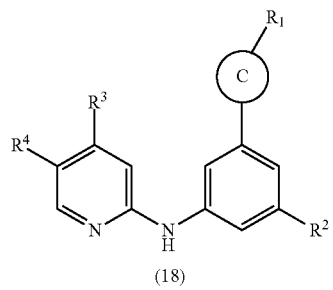
(18)
Anilines 17 reacted with halo-pyridines affords compound 18.
SCHEME 5
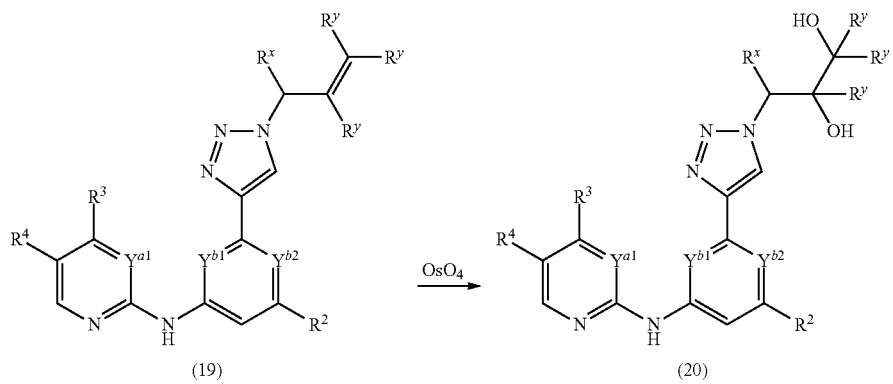
(19)    (20)
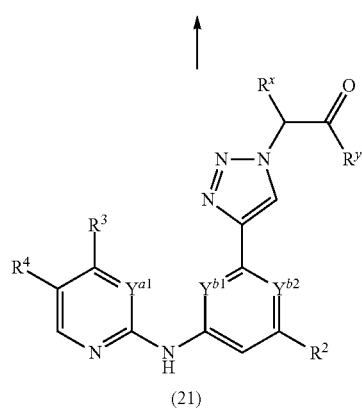
(21)

Dihydroxylation of the olefin 19 leads to diol 20. Olefin 19 can be prepared from ketone 21 along with other methods described in Scheme 2.
SCHEME 6
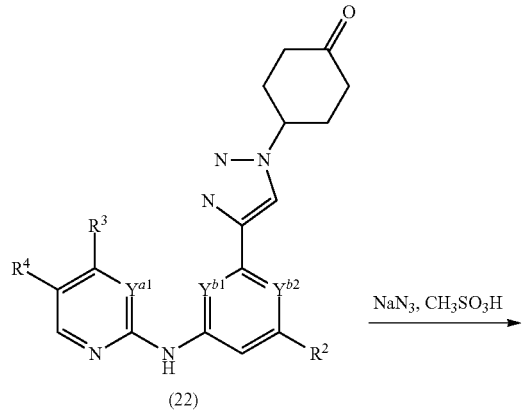
(22)
NaN₃, CH₃SO₃H →
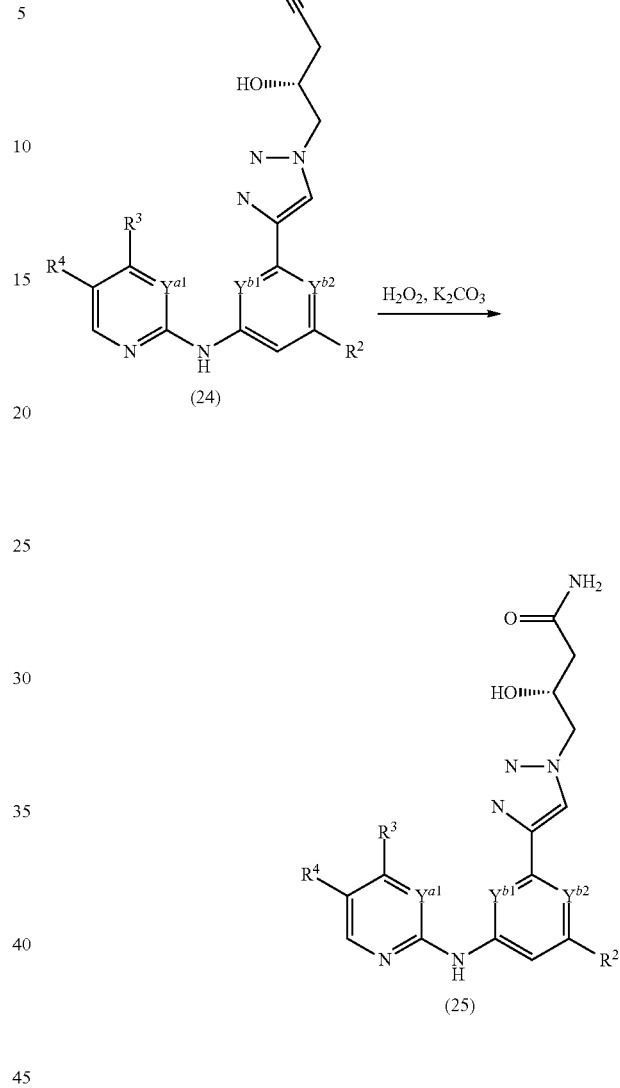
SCHEME 7
(24)
H₂O₂, K₂CO₃ →
(25)
(23)
Compounds 23 are prepared by azido-Schmidt reaction of 22.
Compounds 25 are be prepared by reduction of nitrile with hydrogen peroxide.
SCHEME 8
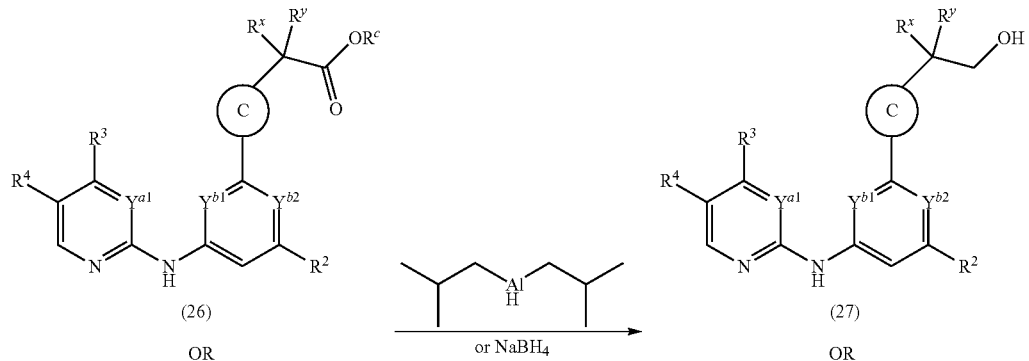
(26)
OR
or NaBH₄ →
(27)
OR -continued
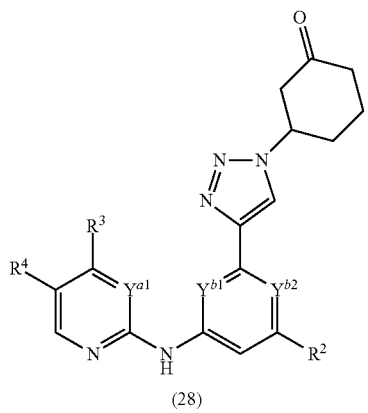
(28)
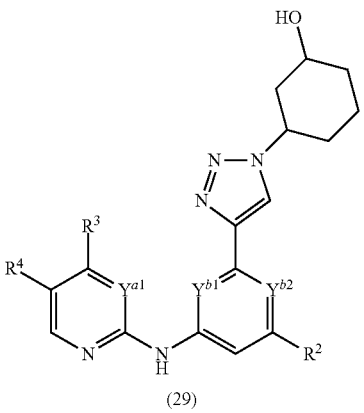
(29)
Alcohols 27 and 29 are prepared by reduction from the corresponding ketones, 26 or 28.
SCHEME 9
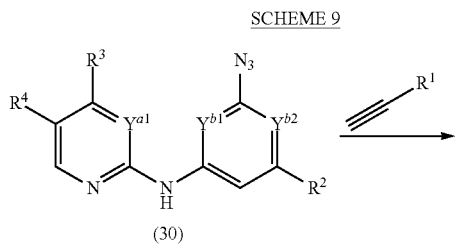
(30)
-continued
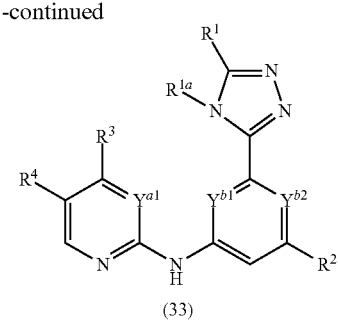
(33)
Compounds of formula 33 are prepared by reaction of formamides with acyl hydrazides 32.
SCHEME 11
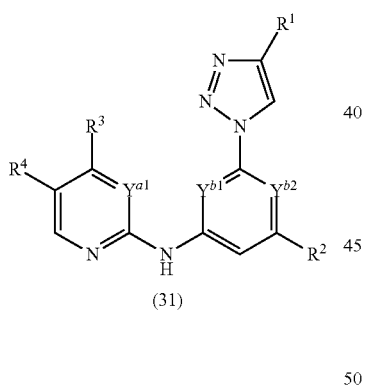
(31)
Click chemistry with aryl azides 30 affords substituted triazoles 31.
SCHEME 10
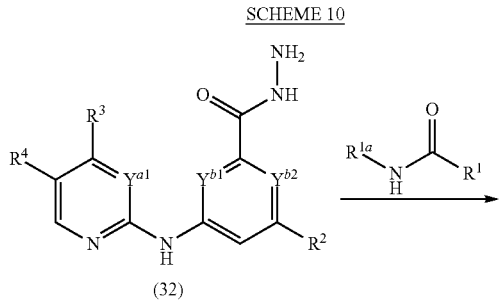
(32)
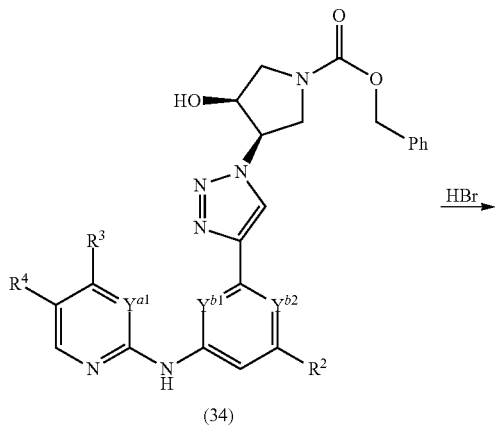
(34)
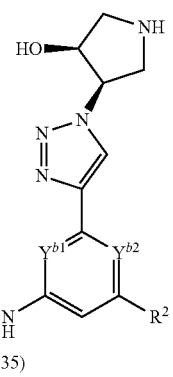
(35)
Acid deprotection of 34 affords compounds 35.

SCHEME 12
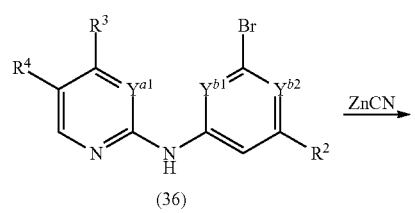
(36)
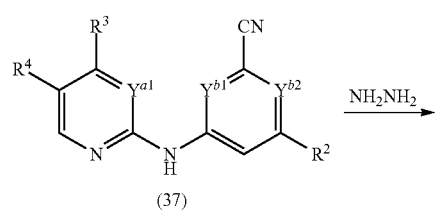
(37)
(38)
(39)
Reaction of bromide 36 with zinc cyanide affords nitrile 37. Condensation of 37 with hydrazide, followed by further condensation with 4-methoxy-4-oxobutanoic acid affords 39.
SCHEME 13
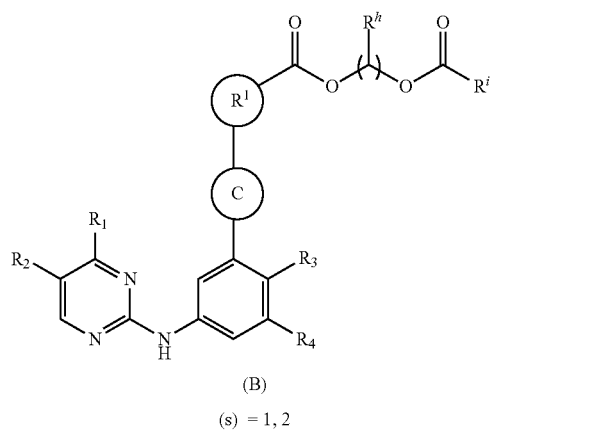
(B)
(s) = 1, 2
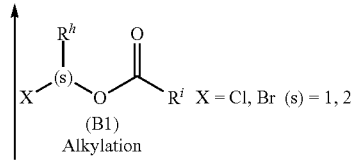
(B1)
Alkylation

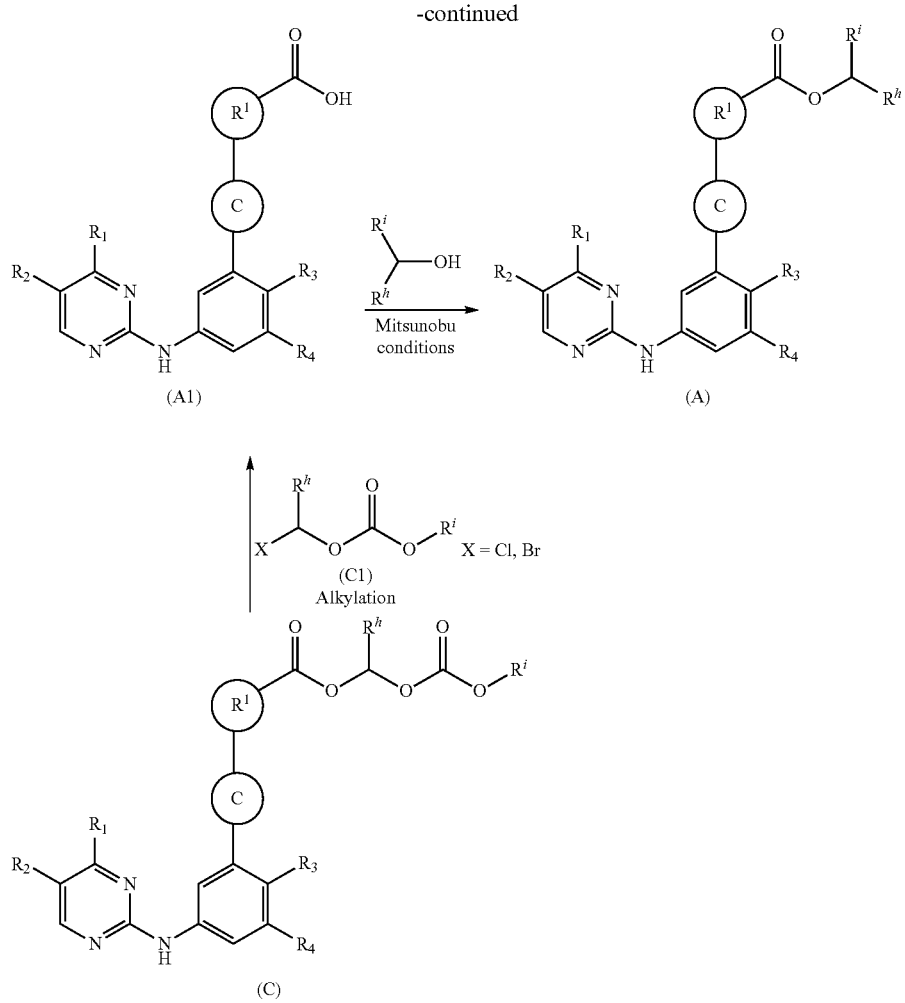

As shown in Scheme 13, compounds of structural subtype (A) are prepared from the trans-cyclohexane carboxylic acid (A1) by a Mitsunobu reaction with various primary and secondary alcohols. Compounds of structural subtype (B) are prepared by the alkylation of the trans-cyclohexane carboxylic acid (A1) by alkyl halides of formula (B1). Compounds of structural subtype (C) are prepared by the alkylation of the trans-cyclohexane carboxylic acid (A1) by alkyl halides of formula (C1).

SCHEME 14

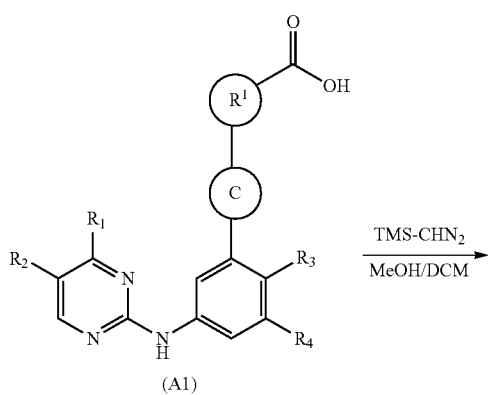

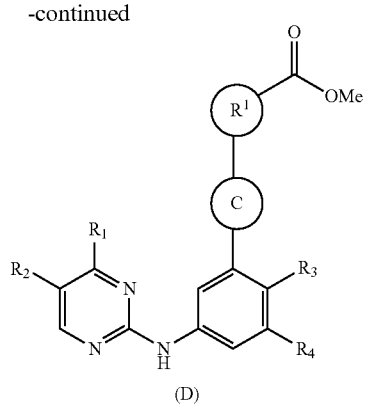

As shown in Scheme 14, compounds of structural subtype (D) are prepared by the reaction of (A1) with trimethylsilyldiazomethane and methanol.

The suitability of the compounds of Formula I as prodrugs of Syk inhibitors can be tested as described below.

Hydrolysis Assay

Analysis of Hydrolysis of Prodrug to Parent Species

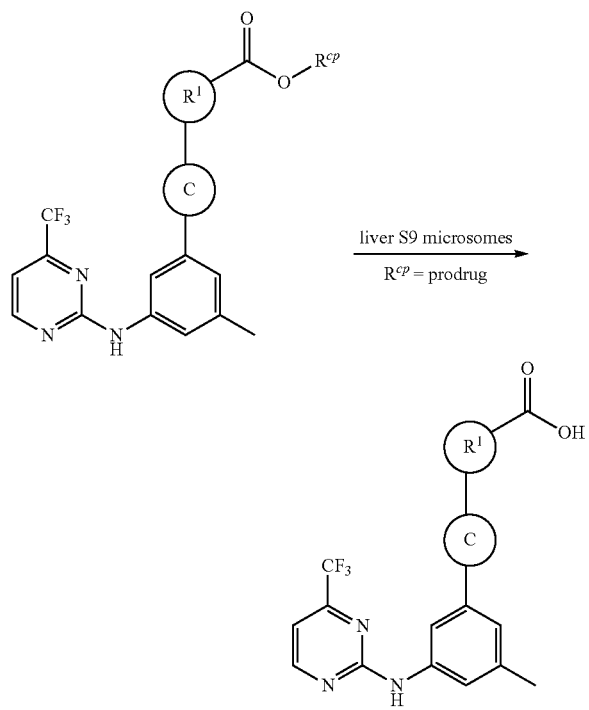

The stability of prodrugs is investigated in human liver S9 microsomes. Incubations of prodrugs (10 μM) with liver S9 (1 mg protein/mL) are carried out at 37° C. in a phosphate buffer, pH 7.4, containing 1 mM NADPH. Control incubations contain BSA (1.1 mg/mL) instead of liver S9 microsomes. Aliquots are removed at 0, 5, 15, 30, 60 and 120 min, treat with 4 volumes of acetonitrile containing 2% formic acid and an internal standard, and centrifuge. The supernatants are analyzed by LC-MS/MS for prodrug disappearance and appearance of active drug. The half-life of the prodrug is calculated from the % prodrug remaining at different time points calculated from on the peak area ratio relative to t=0. The amount of active drug generated at the different time points is determined using a standard curve.

PREPARATIVE EXAMPLES

Preparative Example 1.1

N-(3-Bromo-5-methylphenyl)-4-(trifluoromethyl)pyrimidin-2-amine

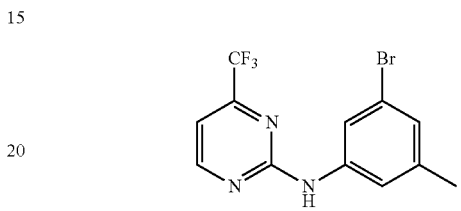

A solution of 3-bromo-5-methylaniline (162.5 g, 874 mmol) in dioxane (2 L) was prepared, and 2-chloro-4-(trifluoromethyl)pyrimidine (182 g, 995 mmol) and methanesulfonic acid (97.5 g, 1.02 mol) were added sequentially. The resulting solution was heated to reflux overnight. The resulting mixture was cooled and concentrated under reduced pressure. The residue was diluted with water (2 L), then adjusted to pH 7-8 with aqueous sodium bicarbonate solution, followed by extraction with EtOAc (2×2 L) The organic layers were combined, washed with water (2×2 L), dried over anhydrous sodium sulfate and concentrated under reduced pressure to afford N-(3-bromo-5-methylphenyl)-4-(trifluoromethyl)pyrimidin-2-amine (200 g, 602 mmol) as a light yellow solid. MS ESI [M+3]$^+$ 334.0. $^1$H NMR (400 MHz, CDCl$_3$): δ 8.68 (d, J=4.9 Hz, 1H), 7.79 (s, 1H), 7.30 (s, 2H), 7.10-7.06 (m, 2H), 2.36 (s, 3H).

The intermediates in the following table were prepared according to the method described for Preparative Example 1.1. $^1$H NMR data is provided when [M+H]$^+$ was not available.

| Prep. Ex. | Structure | Chemical Name | [M + H]$^+$ Calc'd | [M + H]$^+$ Observed |
|---|---|---|---|---|
| 1.2 | 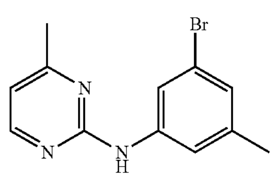 [SMILES: Cc1cc(Br)cc(Nc2nccc(C)n2)c1] | N-(3-bromo-5-methylphenyl)-4-methylpyrimidin-2-amine | 278, 280 | 278, 280 |
| 1.3 | 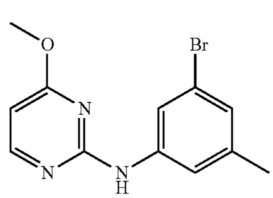 [SMILES: COc1ccnc(Nc2cc(C)cc(Br)c2)n1] | N-(3-bromo-5-methylphenyl)-4-methoxypyrimidin-2-amine | 294, 296 | 294, 296 |

| Prep. Ex. | Structure | Chemical Name | [M + H]+ Calc'd | [M + H]+ Observed |
|---|---|---|---|---|
| 1.4 | 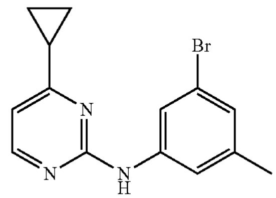 [SMILES: Cc1cc(Br)cc(Nc2nccc(C3CC3)n2)c1] | N-(3-bromo-5-methylphenyl)-4-cyclopropylpyrimidin-2-amine | 304, 306 | 304, 306 |
| 1.5 | 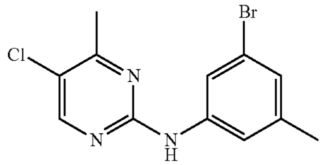 [SMILES: Cc1cc(Br)cc(Nc2ncc(Cl)c(C)n2)c1] | N-(3-bromo-5-methylphenyl)-5-chloro-4-methylpyrimidin-2-amine | 312, 214 | 312, 314 |
| 1.6 | 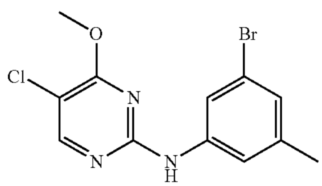 [SMILES: COc1nc(Nc2cc(C)cc(Br)c2)ncc1Cl] | N-(3-bromo-5-methylphenyl)-5-chloro-4-methoxypyrimidin-2-amine | 328 | 1H NMR (600 MHz, DMSO-d6) δ 9.81 (s, 1H), 8.28 (s, 1H), 7.84 (s, 1H), 7.46 (s, 1H), 6.93 (s, 1H), 3.97 (s, 3H), 2.22 (s, 3H). |
| 1.7 | 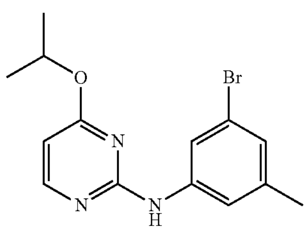 [SMILES: Cc1cc(Br)cc(Nc2nccc(OC(C)C)n2)c1] | N-(3-bromo-5-methylphenyl)-4-isopropoxypyrimidin-2-amine | 322, 324 | 322, 324 |
| 1.8 | 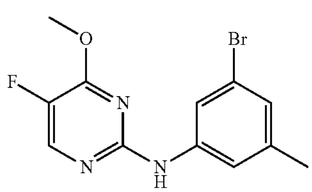 [SMILES: COc1nc(Nc2cc(C)cc(Br)c2)ncc1F] | N-(3-bromo-5-methylphenyl)-5-fluoro-4-methoxypyrimidin-2-amine | 312, 314 | 312, 314 |
| 20.2 | 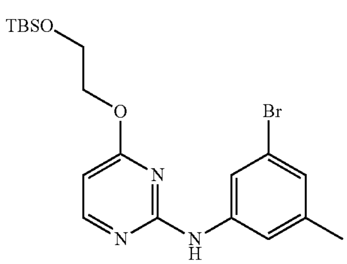 [SMILES: Cc1cc(Br)cc(Nc2nccc(OCCO[Si](C)(C)C(C)(C)C)n2)c1] | N-(3-bromo-5-methylphenyl)-4-(2-{[tert-butyl(dimethyl)silyl]oxy}ethoxy)pyrimidin-2-amine-methane (1:2) | 438, 440 | 438, 440 |

Preparative Example 2.1

N-(3-Ethynyl-5-methylphenyl)-4-(trifluoromethyl-thyrimidin-2-amine

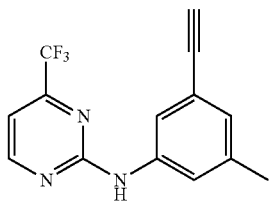 [SMILES: C#Cc1cc(C)cc(Nc2nccc(C(F)(F)F)n2)c1]

Step 1:

N-(3-Bromo-5-methylphenyl)-4-(trifluoromethyl)pyrimidin-2-amine (14.7 g, 44.2 mmol) was added to a round bottom flask along with Pd(OAc)$_2$ (0.744 g, 3.31 mmol), and tri-o-tolylphosphine (2.02 g, 6.63 mmol) suspended in N$_2$ sparged acetonitrile (0.3 M). Trimethylsilylacetylene (10.9 g, 110 mmol) and diisopropylamine (13.4 g, 133 mmol) were then added. The reaction flask was evacuated and backfilled with N$_2$ (3×) and was placed into a 75° C. oil bath for 3 hours. After cooling to ambient temperature the reaction was diluted with MTBE (100 mL) and water (50 mL). The aqueous and organic layers were separated and washed with saturated sodium bicarbonate (2×50 mL) and brine (50 mL). The organic phase was concentrated under reduced pressure. The residue was purified by column chromatography on silica gel (0 to 15% EtOAc/hexanes) to afford N-{3-methyl-5-[(trimethylsilyl)ethynyl]phenyl}-4-(trifluoromethyl)pyrimidin-2-amine.

Step 2:

Potassium carbonate (3.0 g, 21.6 mmol) was added to a suspension of N-{3-methyl-5-[(trimethylsilyl)ethynyl]phenyl}-4-(trifluoromethyl)pyrimidin-2-amine (7.55 g, 21.6 mmol) in methanol (0.27M). The reaction was allowed to stir for 3 hours and was then filtered and concentrated under reduced pressure. The reaction residue was diluted with water and extracted with ethyl acetate (2×). The organic layers were separated, combined and concentrated under reduced pressure. The residue was purified by column chromatography on silica gel (0 to 20% EtOAc/hexanes) to afford N-(3-ethynyl-5-methylphenyl)-4-(trifluoromethyl)pyrimidin-2-amine. MS ESI calc'd. for $C_{14}H_{10}F_3N_3$ [M+H]$^+$ 278. found 278.

The intermediates in the following table were prepared according to the method described for Preparative Example 2.1. Preparative Examples 2.17-2.20 only utilized step 1 from Example 2.1.

| Prep. Ex. | Structure | Chemical Name | Calc'd [M + H]$^+$ | [M + H]$^+$ Observed |
|---|---|---|---|---|
| 2.2 | 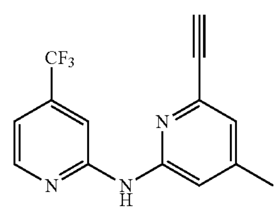 [SMILES: C#Cc1cc(C)cc(Nc2cc(C(F)(F)F)ccn2)n1] | 6-ethynyl-4-methyl-N-[4-(trifluoromethyl)-pyridin-2-yl]pyridin-2-amine | 278 | 278 |
| 2.3 | 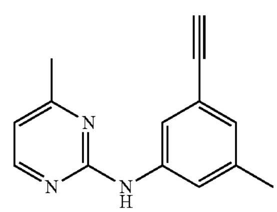 [SMILES: C#Cc1cc(C)cc(Nc2nccc(C)n2)c1] | N-(3-ethynyl-5-methylphenyl)-4-methylpyrimidin-2-amine | 224 | 224 |
| 2.4 | 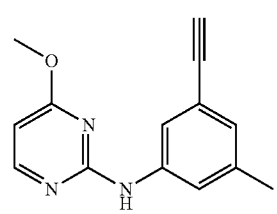 [SMILES: C#Cc1cc(C)cc(Nc2nccc(OC)n2)c1] | N-(3-ethynyl-5-methylphenyl)-4-methoxypyrimidin-2-amine | 240 | 240 |
| 2.5 | 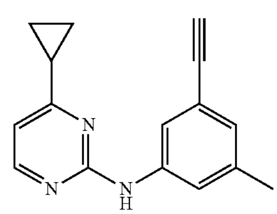 [SMILES: C#Cc1cc(C)cc(Nc2nccc(C3CC3)n2)c1] | 4-cyclopropyl-N-(3-ethynyl-5-methylphenyl)pyrimidin-2-amine | 250 | 250 |

-continued

| Prep. Ex. | Structure | Chemical Name | Calc'd [M + H]+ | [M + H]+ Observed |
|---|---|---|---|---|
| 2.6 | 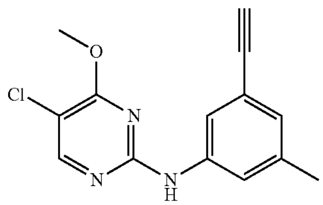 [SMILES: C#Cc1cc(C)cc(Nc2ncc(Cl)c(OC)n2)c1] | 5-chloro-N-(3-ethynyl-5-methylphenyl)-4-methoxypyrimidin-2-amine | 274 | 274 |
| 2.7 | 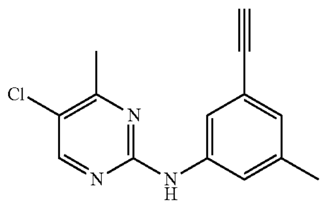 [SMILES: C#Cc1cc(C)cc(Nc2ncc(Cl)c(C)n2)c1] | 5-chloro-N-(3-ethynyl-5-methylphenyl)-4-methylpyrimidin-2-amine | 258 | 258 |
| 2.8 | 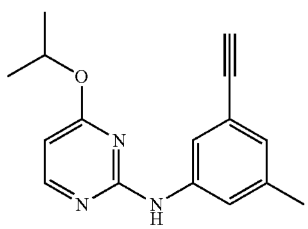 [SMILES: C#Cc1cc(C)cc(Nc2nccc(OC(C)C)n2)c1] | N-(3-ethynyl-5-methylphenyl)-4-isopropoxypyrimidin-2-amine | 268 | 268 |
| 2.9 | 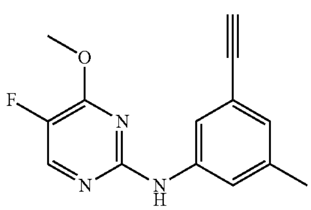 [SMILES: C#Cc1cc(C)cc(Nc2ncc(F)c(OC)n2)c1] | N-(3-ethynyl-5-methylphenyl)-5-fluoro-4-methoxypyrimidin-2-amine | 258 | 258 |
| 2.10 | 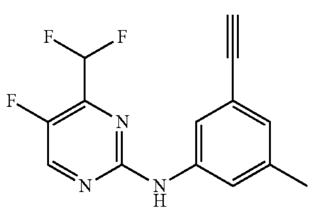 [SMILES: C#Cc1cc(C)cc(Nc2ncc(F)c(C(F)F)n2)c1] | 4-(difluoromethyl)-N-(3-ethynyl-5-methylphenyl)-5-fluoropyrimidin-2-amine | 278 | 278 |
| 2.11 | 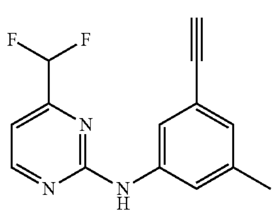 [SMILES: C#Cc1cc(C)cc(Nc2nccc(C(F)F)n2)c1] | 4-(difluoromethyl)-N-(3-ethynyl-5-methylphenyl)pyrimidin-2-amine | 260 | 260 |
| 2.12 | 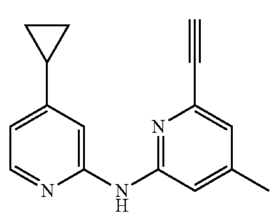 [SMILES: C#Cc1cc(C)cc(Nc2cc(C3CC3)ccn2)n1] | N-(4-cyclopropylpyridin-2-yl)-6-ethynyl-4-methylpyridin-2-amine | 250 | 250 |

-continued

| Prep. Ex. | Structure | Chemical Name | Calc'd [M + H]+ | [M + H]+ Observed |
|---|---|---|---|---|
| 2.13 | 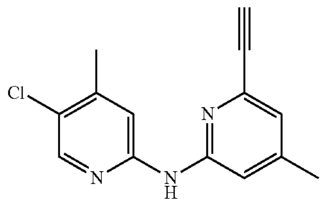 [SMILES: C#Cc1cc(C)cc(Nc2cc(C)c(Cl)cn2)n1] | 5-chloro-N-(6-ethynyl-4-methylpyridin-2-yl)-4-methylpyridin-2-amine | 258 | 258 |
| 2.14 | 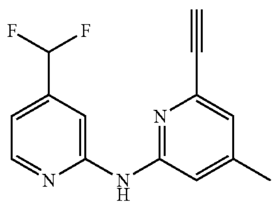 [SMILES: C#Cc1cc(C)cc(Nc2cc(C(F)F)ccn2)n1] | N-(4-(difluoromethyl)pyridin-2-yl)-6-ethynyl-4-methylpyridin-2-amine | 260 | 260 |
| 2.15 | 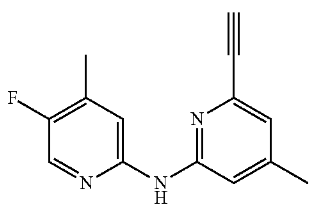 [SMILES: C#Cc1cc(C)cc(Nc2cc(C)c(F)cn2)n1] | 6-ethynyl-N-(5-fluoro-4-methylpyridin-2-yl)-4-methylpyridin-2-amine | 242 | 242 |
| 2.16 | 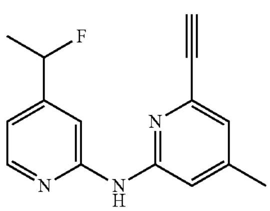 [SMILES: C#Cc1cc(C)cc(Nc2cc(C(C)F)ccn2)n1] | 5-ethynyl-N-(4-(1-fluoroethyl)pyridin-2-yl)-4-methylpyridin-2-amine | 256 | 256 |
| 2.17 | 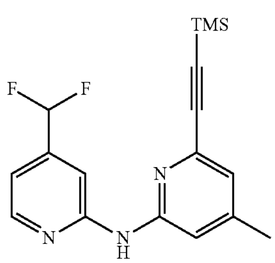 [SMILES: Cc1cc(C#C[Si](C)(C)C)nc(Nc2cc(C(F)F)ccn2)c1] | N-(4-(difluoromethyl)pyridin-2-yl)-4-methyl-6-((trimethylsilyl)ethynyl)-pyridine-2-amine | 332 | 332 |
| 2.18 | 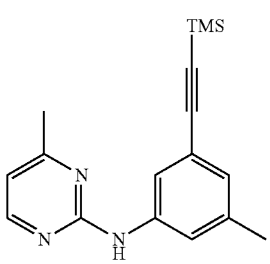 [SMILES: Cc1cc(C#C[Si](C)(C)C)cc(Nc2nccc(C)n2)c1] | 4-methyl-N-(3-methyl-5-((trimethylsilyl)ethynyl)phenyl)pyrimidin-2-amine | 296 | 296 |

-continued

| Prep. Ex. | Structure | Chemical Name | Calc'd [M + H]+ | [M + H]+ Observed |
|---|---|---|---|---|
| 2.19 | 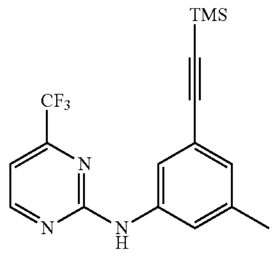 [SMILES: Cc1cc(C#C[Si](C)(C)C)cc(Nc2nccc(C(F)(F)F)n2)c1] | N-(3-methyl-5-((trimethylsilyl)ethynyl)phenyl)-4-(trifluoromethyl)pyrimidin-2-amine | 336 | 336 |
| 2.20 | 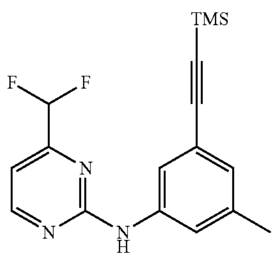 [SMILES: Cc1cc(C#C[Si](C)(C)C)cc(Nc2nccc(C(F)F)n2)c1] | 4-(difluoromethyl)-N-(3-methyl-5-((trimethylsilyl)ethynyl)phenyl)pyrimidin-2-amine | 332 | 332 |

Preparative Example 3

N-(3-Bromophenyl)-4-(trifluoromethyl)pyrimidin-2-amine

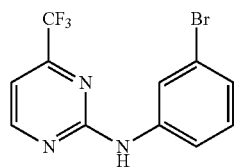 [SMILES: FC(F)(F)c1ccnc(Nc2cccc(Br)c2)n1]

A solution of 3-bromoaniline (250 g, 1.46 mol) in dioxane (2.5 L) was prepared, and 2-chloro-4-(trifluoromethyl)pyrimidine (267 g, 1.47 mol) and methanesulfonic acid (155 g, 1.61 mol) were added sequentially. The resulting solution was heated to 100° C. overnight. The resulting mixture was cooled and concentrated under reduced pressure. The residue was adjusted to pH 7-8 with aqueous sodium bicarbonate solution. The solid was filtered, and the filtrate was extracted with EtOAc (4×500 mL) The organic layers were combined, washed with water (2×2 L), dried over anhydrous sodium sulfate and concentrated under reduced pressure to afford N-(3-bromophenyl)-4-(trifluoromethyl)pyrimidin-2-amine as a light yellow solid. MS APCI [M+3]+ m/z 319. $^1$H NMR (500 MHz, CDCl$_3$) δ 8.68 (d, J=4.9 Hz, 1H), 7.95 (s, 1H), 0.53-7.50 (m, 1H), 7.44 (br s, 1H), 7.22 (m, 2H), 7.08 (d, T=4.9 Hz, 1H).

Preparative Example 4.1

6-Bromo-4-methyl-N-[4-(trifluoromethyl)pyridine-2-yl]pyridine-2-amine

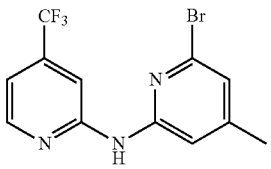 [SMILES: Cc1cc(Br)nc(Nc2cc(C(F)(F)F)ccn2)c1]

Sodium tert-butoxide (5.87 g, 61.1 mmol) and 1,1'-bis(di-tert-butylphsophino)ferrocene palladium dichloride (0.91 g, 1.4 mmol) were added to a solution of 2,6-dibromo-4-methyl pyridine (13.9 g, 55.5 mmol) and 2-amino-4-trifluoromethyl pyridine (9.0 g, 55.5 mmol) in nitrogen sparged dioxane (180 mL). The slurry was evacuated and refilled with nitrogen. The mixture was stirred at 25° C. for 15 minutes and then heated to 75° C. for 12 hours. The reaction mixture was cooled to 25° C., water (20 mL) was added, and the mixture was extracted with EtOAc (2×200 mL). The combined extracts were dried over anhydrous sodium sulfate, filtered, concentrated under reduced pressure. The residue was purified by column chromatography on silica gel to afford 6-bromo-4-methyl-N-[4-(trifluoromethyl)pyridine-2-yl]pyridine-2-amine as a white solid. MS ESI calc'd. for C$_{12}$H$_{10}$BrF$_3$N$_3$ [M+H]+ 332 and 334. found 332 and 334. $^1$H NMR (600 MHz, DMSO-d$_6$) δ 10.40 (s, 1H), 8.46 (d, T=6.0 Hz, 1H), 7.90 (s, 1H), 7.60 (s, 1H), 7.18 (d, J=6.0 Hz, 1H), 7.00 (s, 1H), 2.25 (s, 3H).

The intermediates in the following table were prepared according to the method described for Preparative Example 4.1. $^1$H NMR data is provided when [M+H]+ was not available.

| Prep. Ex. | Structure | Chemical Name | Calc'd [M + H]+ | [M + H]+ Observed |
|---|---|---|---|---|
| 4.2 | 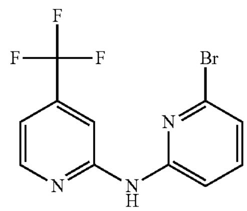 [SMILES: FC(F)(F)c1ccnc(Nc2cccc(Br)n2)c1] | N-(6-bromopyridin-2-yl)-4-(trifluoromethyl)-pyridin-2-amine | 318 | 318 |
| 4.3 | 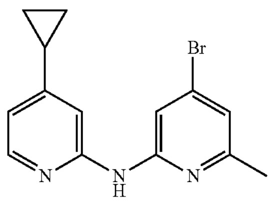 [SMILES: Cc1cc(Br)cc(Nc2cc(C3CC3)ccn2)n1] | 6-bromo-N-(4-cyclopropylpyridin-2-yl)-4-methylpyridin-2-amine | 304, 306 | 304, 306 |
| 4.4 | 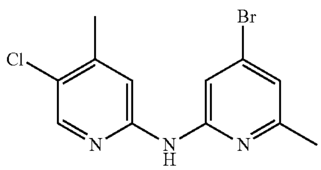 [SMILES: Cc1cc(Br)cc(Nc2cc(C)c(Cl)cn2)n1] | N-(6-bromo-4-methyl-pyridin-2-yl)-5-chloro-4-methylpyridin-2-amine | 312 | $^1$H NMR (600 MHz, DMSO-$d^6$) δ 10.01 (s, 1H), 8.18 (s, 1H), 7.63 (s, 1H), 7.40 (s, 1H), 6.94 (s, 1H), 2.26 (s, 3H), 2.23 (s, 3H). |
| 4.5 | 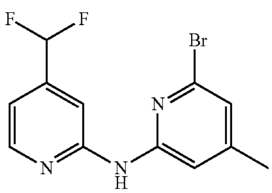 [SMILES: Cc1cc(Br)nc(Nc2cc(C(F)F)ccn2)c1] | 6-bromo-N-(4-(difluoromethyl)pyridin-2-yl)-4-methylpyridin-2-amine | 314, 316 | 314, 316 |
| 4.6 | 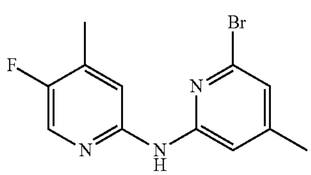 [SMILES: Cc1cc(Br)nc(Nc2cc(C)c(F)cn2)c1] | 6-bromo-N-(5-fluoro-4-methylpyridin-2-yl)-4-methylpyridin-2-amine | 296, 298 | 296, 298 |

Preparative Example 5

2-Chloro-6-methyl-N-[4-(trifluoromethyl)pyridin-2-yl]pyrimidin-4-amine

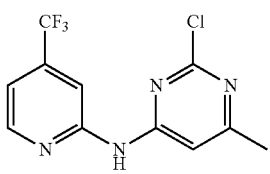 [SMILES: Cc1cc(Nc2cc(C(F)(F)F)ccn2)nc(Cl)n1]

Nitrogen was bubbled through a solution of 4-(trifluoromethyl)pyridin-2-amine (10.96 g, 67.6 mmol), 2,4-dichloro-6-methylpyrimidine (11.02 g, 67.6 mmol) in dioxane (198 mL) for 10 minutes. Sodium tert-butoxide (6.50 g, 67.6 mmol) and 1,1' bis(di-t-butylphosphino ferrocene) (3.21 g, 6.76 mmol) were added, followed by Pd$_2$(dba)$_3$ (3.10 g, 3.38 mmol) and the solution was evacuated and then purged with nitrogen. After heating to reflux for 3 hours, the reaction mixture was cooled to room temperature and EtOAc (1 L) was added. The organic layer was washed with saturated sodium bicarbonate, water and brine, then dried over anhydrous sodium sulfate, filtered and concentrated under reduced pressure. The residue was purified by column chromatography on silica gel (EtOAc/hexanes) to afford 2-chloro-6-methyl-N-[4-(trifluoromethyl)pyridin-2-yl]pyrimidin-4-amine as a yellow solid. MS ESI calcd. for C$_{11}$H$_{18}$ClF$_3$N$_4$ [M+H]$^+$ 289. found 289.

Preparative Example 6

N-(3-Azido-5-methylphenyl)-4-(trifluoromethyl)pyrimidin-2-amine

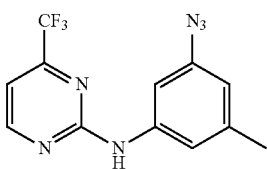 [SMILES: Cc1cc(N=[N+]=[N-])cc(Nc2nccc(C(F)(F)F)n2)c1]

Step 1:

N-(3-Bromo-5-methylphenyl)-4-(trifluoromethyl)pyrimidin-2-amine (200 mg, 0.60 mmol), copper(I) iodide (5.73 mg, 0.030 mmol), sodium iodide (181 mg, 1.20 mmol), dimethylethylenediamine (12 μl, 0.12 mmol) and dioxane (1.2 mL) were added to a vial. The vial was sealed, evacuated, purged with Argon and stirred at 110° C. heat overnight. The reaction mixture was diluted with EtOAc and the organics were washed with saturated sodium bicarbonate, then brine, dried over anhydrous sodium sulfate, filtered and concentrated under reduced pressure. The residue was purified by column chromatography on silica (5 to 80% EtOAc/Hexanes) to afford N-(3-iodo-5-methylphenyl)-4-(trifluoromethyl)pyrimidin-2-amine. MS ESI calcd. for $C_{12}H_{10}F_3IN_3$ [M+H]$^+$ 379. found 379.

Step 2:

N-(3-Iodo-5-methylphenyl)-4-(trifluoromethyl)pyrimidin-2-amine (2.44 g, 6.44 mmol), copper(I) iodide (0.25 g, 1.29 mmol), sodium azide (0.84 g, 12.9 mmol), and sodium ascorbate (0.13 g, 0.64 mmol) were combined in a 5 mL microwave vial. The vial was sealed, evacuated and purged with nitrogen. Racemic-trans-N,N'-dimethylcyclohexane-1,2-diamine (0.30 ml, 1.93 mmol), DMSO (20 mL), and water (4.0 mL) were added, and the reaction was stirred at room temperature for 2 hours. The reaction mixture was diluted with water and extracted with EtOAc (2×). The combined organics were washed with brine, dried over anhydrous magnesium sulfate, and concentrated under reduced pressure. The residue was purified by column chromatography on silica gel (0 to 30% EtOAc/hexanes) to afford N-(3-azido-5-methylphenyl)-4-(trifluoromethyl)pyrimidin-2-amine as an off-white solid. MS ESI calcd. for $C_{12}H_{10}F_3N_6$ [M+H]$^+$ 295. found 295. $^1$H NMR (500 MHz, DMSO-d$_6$) δ 10.31 (s, 1H), 8.83 (d, T=4.8, 1H), 7.58 (s, 1H), 7.32-7.26 (m, 2H), 6.58 (s, 1H), 2.26 (s, 3H).

Preparative Example 7 tert-Butyl 4-ethynyl-4-hydroxycyclohexanecarboxylate (anti)

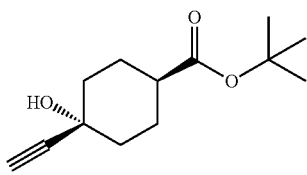 [SMILES: C#C[C@]1(O)CC[C@H](C(=O)OC(C)(C)C)CC1]

Step 1:

n-Butyl lithium (5.30 mL, 13.24 mmol) was added to a solution of trimethylsilylacetylene (2.12 mL, 15.1 mmol) in THF (20 mL) cooled to −78° C. under nitrogen. In a separate flask, under nitrogen, tert-butyl 4-oxocyclohexanecarboxylate (2.50 g, 12.61 mmol) was dissolved in THF (30 mL) and cooled to −78° C. After stirring for 20 min at −78° C., the lithium acetylide solution was transferred drop wise by cannula to the cold solution of the ketone. Upon completion of the addition, the reaction was stirred at −78° C. for 2 hours. Saturated ammonium chloride was then added and the mixture was allowed to warm to room temperature. The mixture was extracted with ethyl acetate (2×) and the combined organic layers were washed with brine, dried over anhydrous magnesium sulfate, filtered and concentrated under reduced pressure. The residue was purified by column chromatography on silica gel (0 to 40% diethyl ether/hexanes). Mixed fractions were combined and re-purified by the same method to afford -tert-butyl 4-hydroxy-4-((trimethylsilyl)ethynyl)cyclohexanecarboxylate as a white solid. $^1$H NMR (500 MHz, CDCl$_3$) δ 2.14 (1H, tt, J=11.70, 3.85 Hz), 2.01 (2H, d, J=12.48 Hz), 1.94 (2H, dd, J=13.97, 4.18 Hz), 1.73 (2H, qd, J=12.72, 3.10 Hz), 1.53 (2H, td, J=12.69, 3.56 Hz), 1.44 (9H, s), 0.17 (9H, s). NMR analysis of later stage intermediates confirmed that the first spot by TLC was the syn diastereomer, and that the second spot by TLC was the anti diastereomer.

Step 2:

Potassium carbonate (2.37 g, 17.1 mmol) was added to a solution of tert-butyl 4-hydroxy-4-((trimethylsilyl)ethynyl)cyclohexanecarboxylate (2.03 g, 6.85 mmol) in THF (14 mL)/MeOH (14 mL). The reaction mixture was vigorously stirred at room temperature for 2 hours then, diluted with water and extracted with EtOAc (2×). The combined organic layers were washed with brine, dried over anhydrous magnesium sulfate, filtered and concentrated under reduced pressure. The residue was purified by column chromatography on silica gel (0 to 50% diethyl ether/hexanes) to afford tert-butyl 4-ethynyl-4-hydroxycyclohexanecarboxylate (anti) as a colorless solid. $^1$H NMR (500 MHz, CDCl$_3$) δ 2.52 (s, 1H), 2.17 (tt, J=3.8, 11.6, 1H), 2.04 (d, J=12.5, 2H), 1.96 (dd, J=3.8, 14.3, 2H), 1.75 (ddd, J=3.3, 13.9, 16.3, 2H), 1.56 (td, J=3.6, 12.7, 2H), 1.44 (s, 9H). NMR analysis of a later stage intermediate confirmed the anti stereochemistry.

Preparative Example 8

Methyl 4-ethynyl-4-hydroxy-2,2-dimethylcyclohexanecarboxylate (syn)

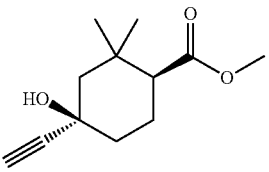

Step 1:

n-Butyl lithium (4.34 mL, 10.86 mmol) was added to a solution of trimethylsilylacetylene (1.83 mL, 13.0 mmol) in THF (20 mL) cooled to −78° C. under nitrogen. In a separate flask, under nitrogen, methyl 2,2-dimethyl-4-oxocyclohexanecarboxylate (2.00 g, 10.86 mmol) was dissolved in THF (30 mL) and cooled to −78° C. After stirring for 20 min at −78° C., the lithium acetylide solution was transferred drop wise by cannula to the cold solution of the ketone. Upon completion of the addition, the reaction was stirred at −78° C. for 2 h. Saturated ammonium chloride was then added and the mixture was allowed to warm to room temperature. The mixture was extracted with ethyl acetate (2×) and the combined organic layers were washed with brine, dried over anhydrous magnesium sulfate, filtered and concentrated under reduced pressure. The residue was purified by column chromatography on silica gel (0 to 25% diethyl ether/hexanes) to afford methyl 4-hydroxy-2,2-dimethyl-4-((trimethylsilyl)ethynyl)cyclohexane-carboxylate as a colorless gum. $^1$H NMR (500 MHz, CDCl$_3$) δ 3.66 (s, 3H), 2.22 (dd, J=3.1, 10.6, 1H), 2.05 (m, 2H), 1.86 (d, J=14.3, 1H), 1.69 (m, 4H), 1.06 (d, J=9.8, 6H), 0.15 (s, J=1.3, 9H). NMR analysis of a later stage intermediate confirmed the syn stereochemistry.

Step 2:

Potassium carbonate (1.77 g, 12.8 mmol) was added to a solution of (1S,4R)-methyl 4-hydroxy-2,2-dimethyl-4-((trimethylsilyl)ethynyl)cyclohexanecarboxylate (1.45 g, 5.12 mmol) in THF (12 mL)/MeOH (12 mL). The reaction mixture was vigorously stirred at room temperature for 2 hours then diluted with water and extracted with EtOAc (2×). The combined organic layers were washed with brine, dried over anhydrous magnesium sulfate, filtered and concentrated under reduced pressure. The residue was purified by column chromatography on silica gel (0 to 50% diethyl ether/hexanes) to afford methyl 4-ethynyl-4-hydroxy-2,2-dimethylcyclohexanecarboxylate (syn) as a colorless oil. $^1$H NMR (500 MHz, CDCl$_3$) δ 3.66 (s, 3H), 2.45 (s, 1H), 2.23 (m, 1H), 2.05 (m, 2H), 1.87 (dd, J=2.0, 14.3, 1H), 1.70 (m, 4H), 1.09 (d, J=3.1, 3H), 1.05 (s, 3H). NMR analysis of a later stage intermediate confirmed the syn stereochemistry.

Preparative Example 9 tert-Butyl 4-ethynyl-4-hydroxycyclohexanecarboxylate (syn)

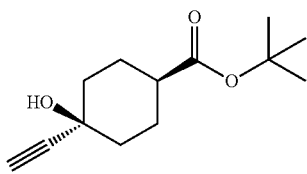 [SMILES: C#C[C@]1(O)CC[C@@H](C(=O)OC(C)(C)C)CC1]

Potassium carbonate (956 mg, 6.91 mmol) was added to a solution of tert-butyl 4-hydroxy-4-((trimethylsilyl)ethynyl)cyclohexanecarboxylate (820 mg, 2.77 mmol) dissolved in THF (6 mL)/MeOH (6 mL). The reaction mixture was vigorously stirred at room temperature for 2 hours then diluted with water and extracted with EtOAc (2×). The combined organic layers were washed with brine, dried over anhydrous magnesium sulfate, filtered and concentrated under reduced pressure. The residue was purified by column chromatography on silica gel (0 to 50% diethyl ether/hexanes) to afford (1S,4S)-tert-butyl 4-ethynyl-4-hydroxycyclohexanecarboxylate as a colorless oil. $^1$H NMR (500 MHz, CDCl$_3$) δ 2.45 (s, 1H), 2.27 (td, J=4.2, 8.7, 1H), 1.89 (m, 5H), 1.77 (m, 6H), 1.44 (s, 11H). NMR analysis of a later stage intermediate confirmed the syn stereochemistry.

Preparative Example 10

1-((tert-Butyldimethylsilyl)oxy)-5-(trimethylsilyl)pent-4-yn-2-ol (racemic)

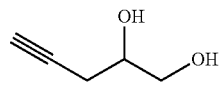

Step 1:

n-Butyl lithium (9.6 mL 23.9 mmol) was added to a solution of trimethylsilylacetylene (4.5 mL, 31.9 mmol) in THF (50 mL) cooled to −78° C. The reaction mixture was stirred for 30 minutes at −78° C., then boron trifluoride etherate (3.0 ml, 23.9 mmol) was added. The reaction mixture was stirred an additional 10 minutes at −78° C. tert-Butyldimethylsilyl glycidyl ether (3.00 g, 15.93 mmol) in THF (10 mL) was added. The reaction mixture was stirred for 2 hours at −78° C. and then diluted, at −78° C., with saturated ammonium chloride. The mixture was warmed to room temperature, diluted with water, and extracted with EtOAc (2×). The combined organic layers were washed with brine, dried over anhydrous magnesium sulfate, filtered and concentrated under reduced pressure. The residue was purified by column chromatography on silica gel (0 to 20% EtOAc/hexanes) to afford 1-((tert-butyldimethylsilyl)oxy)-5-(trimethylsilyl)pent-4-yn-2-ol as a pale yellow oil. $^1$H NMR (500 MHz, CDCl$_3$) δ 3.78 (dd, J=5.7, 11.4, 1H), 3.72 (dd, J=4.1, 10.0, 1H), 3.63 (dd, J=5.6, 10.0, 1H), 2.46 (qd, J=6.5, 16.8, 3H), 0.92-0.89 (s, 9H), 0.17-0.12 (m, 9H), 0.08 (d, J=6.7, 6H).

Step 2:

TBAF (29.2 mL, 29.2 mmol) was added to a solution of 1-((tert-butyldimethylsilyl)oxy)-5-(trimethylsilyl)pent-4-yn-2-ol (4.19 g, 14.62 mmol) in THF (40 mL). The reaction mixture was stirred at room temperature for 1 hour then, diluted with water and extracted with EtOAc (2×). The combined organic layers were washed with brine, dried over anhydrous magnesium sulfate, filtered and concentrated under reduced pressure. The residue was purified by column chromatography on silica gel (25 to 100% EtOAc/hexanes) to afford pent-4-yne-1,2-diol (racemic) as a colorless liquid. $^1$H NMR (500 MHz, CDCl$_3$) δ 3.88 (qd, J=3.3, 6.5, 1H), 3.73 (dd, J=3.2, 11.4, 1H), 3.58 (dd, J=6.7, 11.4, 1H), 3.18 (s, 3H), 2.50-2.33 (m, 2H), 2.06 (t, J=2.7, 1H).

Preparative Examples 11 and 12

4-((tert-Butyldimethylsilyl)oxy)-1-ethynylcyclohexanol (syn) and 4-((tert-butyldimethylsilyl)oxy)-1-ethynylcyclohexanol (anti)

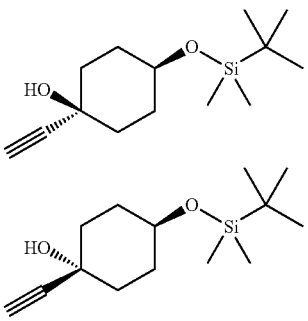

4-(tert-Butyldimethylsiloxy)cyclohexanone (2.00 g, 8.76 mmol) was taken up in THF (30 mL) and cooled to −78° C. Ethynylmagnesium bromide (26.3 mL, 13.1 mmol) was added over 5 minutes. After 10 minutes of stirring at −78° C., the reaction was allowed to warm to room temperature then diluted with saturated ammonium chloride and extracted with EtOAc (2×). The combined organic layers were washed with brine, dried over anhydrous magnesium sulfate, filtered and concentrated under reduced pressure. The residue was purified by column chromatography on silica gel (0 to 30% diethyl ether/hexanes). Mixed fractions were concentrated under reduced pressured and re-purified by the same method to afford 4-((tert-butyldimethylsilyl)oxy)-1-ethynylcyclohexanol (syn, faster-eluting diastereomer) as a colorless solid and 4-((tert-butyldimethylsilyl)oxy)-1-ethynylcyclohexanol (anti, slower-eluting spot) as a colorless solid.

Preparative Example 13

8-Ethynyl-1,4-dioxaspiro[4.5]decan-8-ol

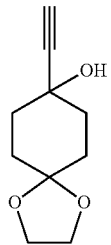

Step 1:

A solution of trimethylsilylacetylene (1.1 ml, 7.7 mmol) in THF (12.8 ml) was cooled to −78° C. under nitrogen, and n-butyllithlium (4.0 ml, 1.6 M in hexanes, 6.4 mmol) was added. In a separate flask, 1,4-dioxaspiro[4.5]decan-8-one (1 g, 6.4 mmol) was dissolved in THF (12.81 ml) and cooled to −78° C. After stirring the lithium acetylide solution for 20 min at −78° C., it was cannula transferred, drop wise, to the cold solution of 1,4-dioxaspiro[4.5]decan-8-one. Upon completion of the addition, the reaction was stirred at −78° C. for 2 hours. Saturated aqueous ammonium chloride was then added, and the mixture was allowed to warm to room temperature. The mixture was extracted with EtOAc (3×). The combined organic layers were dried over magnesium sulfate, filtered, and concentrated under reduced pressure. The residue was purified by column chromatography on silica gel (0 to 50% ethyl acetate/hexanes) to afford 8-[(trimethylsilyl)ethynyl]-1,4-dioxaspiro[4.5]decan-8-ol as a colorless oil.

Step 2:

8-[(Trimethylsilyl)ethynyl]-1,4-dioxaspiro[4.5]decan-8-ol (1.33 g, 5.23 mmol) was taken up in methanol (34.9 ml) and potassium carbonate (2.17 g, 15.7 mmol) was added. The slurry was stirred at room temperature for two hours. The mixture was then concentrated under reduced pressure. The resulting residue was taken up in ethyl acetate and saturated aqueous ammonium chloride. The layers were separated and the aqueous layer was extracted once more with ethyl acetate. The combined organics were dried over magnesium sulfate, filtered, and concentrated under reduced pressure. The residue was purified by column chromatography on silica gel (0 to 60% EtOAc/hexanes) to afford 8-ethynyl-1,4-dioxaspiro[4.5]decan-8-ol as a colorless oil. $^1$H NMR (500 MHz, DMSO-d$_6$) δ 5.40 (s, 1H), 3.82 (s, 4H), 3.27 (s, 1H), 1.76-1.69 (m, 4H), 1.66-1.62 (m, 2H), 1.58-1.53 (m, 2H).

Preparative Example 14

N-[3-Methyl-5-(1H-1,2,4-triazol-3-yl)phenyl]-4-(trifluoromethyl)pyrimidin-2-amine

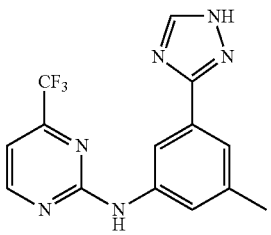 [SMILES: Cc1cc(Nc2nccc(C(F)(F)F)n2)cc(-c2nc[nH]n2)c1]

Triethylsilane (0.05 mL, 0.31 mmol) and TFA (0.05 mL, 0.65 mmol) were added to a solution of N-[3-methyl-5-(1-trityl-1H-1,2,4-triazol-3-yl)phenyl]-4-(trifluoromethyl)pyrimidin-2-amine (60 mg, 0.11 mmol) in dichloromethane and the reaction mixture was stirred for 3 hours and then concentrated under reduced pressure. The residue was triturated with diethyl ether to afford a white solid. The ether solution was concentrated under reduced pressure and purified by reverse phase HPLC (20% to 80% ACN/water with 0.1% TFA) to afford N-[3-methyl-5-(1H-1,2,4-triazol-3-yl)phenyl]-4-(trifluoromethyl)pyrimidin-2-amine as the TFA salt. MS ESI calcd. for $C_{14}H_{12}F_3N_6$. [M+H]$^1$321. found 321. $^1$H NMR (500 MHz, DMSO-d$_6$) δ 10.26 (s, 1H), 8.82 (d, J=4.9, 1H), 8.25 (s, 1H), 7.60 (s, 1H), 7.50 (s, 1H), 7.26 (d, T=4.8, 1H), 2.34 (s, 3H).

Preparative Example 15

(3-Methyl-5-{[4-(trifluoromethyl)pyrimidin-2-yl]amino}phenyl)boronic acid

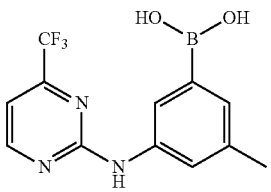 [SMILES: Cc1cc(Nc2nccc(C(F)(F)F)n2)cc(B(O)O)c1]

Ammonium acetate (305 mg, 3.96 mmol) and sodium periodate (846 mg, 3.96 mmol) were added to a suspension of N-[3-methyl-5-(4,4,5,5-tetramethyl-1,3,2-dioxaborolan-2-yl)phenyl]-4-(trifluoromethyl)pyrimidin-2-amine (500 mg, 1.319 mmol) in water (5.5 mL) and acetone (5.5 ml). The suspension was stirred for 19 hours then filtered in vacuo and concentrated under reduced pressure. The filtrate was purified by column chromatography on silica gel (EtOAc) to afford (3-methyl-5-{[4-(trifluoromethyl)pyrimidin-2-yl]amino}phenyl)boronic acid. MS ESI calcd. for $C_{12}H_{12}BF_3N_3O_2$ [M+H]$^+$ 298. found 298. $^1$H NMR (500 MHz, DMSO-d$_6$) δ 10.00 (s, 1H), 8.75 (d, J=4.8, 1H), 7.91 (s, 2H), 7.76 (s, 1H), 7.57 (s, 1H), 7.27 (s, 1H), 7.18 (d, T=4.9, 1H), 2.30 (d, T=37.9, 3H).

Preparative Example 16

4-Methyl-6-{[4-(trifluoromethyl)pyridin-2-yl]amino}pyridine-2-carbohydrazide hydrochloride

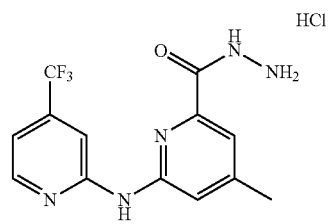 [SMILES: Cl ; Cc1cc(Nc2cc(C(F)(F)F)ccn2)nc(C(=O)NN)c1]

Step 1:

nBuLi (2.35 mL, 3.76 mmol) was added drop wise to a solution of 6-bromo-4-methyl-N-[4-(trifluoromethyl)pyridin-2-yl]pyridin-2-amine (500 mg, 1.51 mmol) in toluene (8.5 mL) under argon cooled to −78° C. The reaction mixture was warmed to 0° C., stirred for 30 minutes then warmed to room temperature. Finely crushed dry ice (~50 g) and toluene (5 mL) were added slowly to the reaction and the mixture was stirred until all CO$_2$ evaporated. The reaction mixture was warmed to room temperature, acidified with HCl, the organics were washed with brine, dried over anhydrous sodium sulfate, filtered and concentrated under reduced pressure to afford 4-methyl-6-{[4-(trifluoromethyl)pyridin-2-yl]amino}pyridine-2-carboxylic acid. MS ESI calcd. for $C_{13}H_{10}F_3N_3O_2$ [M+H]$^+$ 298. found 298.

Step 2:

Oxalyl chloride (185 μl, 2.12 mmol) was added to a solution of 4-methyl-6-{[4-(trifluoromethyl)pyridin-2-yl]amino}pyridine-2-carboxylic acid (286 mg, 0.962 mmol) in dichloromethane (6.4 mL), followed by DMF (2 drops). The reaction mixture was stirred for 30 minutes at room temperature were gas evolution occurred. DIPEA (841 μl, 4.82 mmol) was added followed by tert-butyl carbazate (150 mg, 1.14 mmol) in dichloromethane (0.2 mL). The reaction mixture was acidified with 1M HCl and diluted with ethyl acetate. The organics were washed with saturated sodium bicarbonate, then brine, dried over anhydrous sodium sulfate, filtered and concentrated under reduced pressure. The residue was purified by column chromatography on silica (10 to 100% EtOAc/hexane) to afford tert-butyl 2-[(4-methyl-6-{[4-(trifluoromethyl)pyridin-2-yl]amino}pyridin-2-yl)carbonyl]hydrazinecarboxylate. MS ESI calcd. for $C_{18}H_{20}F_3N_5O_3$ [M+H]$^+$ 412. found 412.

Step 3:

HCl (4M in dioxane, 3.0 mL, 12.0 mmol) was added to tert-butyl 2-[(4-methyl-6-{[4-(trifluoromethyl)pyridin-2-yl]amino}pyridin-2-yl)carbonyl]hydrazinecarboxylate (550 mg, 1.337 mmol) in ethyl acetate (8.9 mL). The mixture was stirred at room temperature where white solids crashed out. The solids were filtered in vacuo and dried to afford 4-methyl-6-{[4-(trifluoromethyl)pyridin-2-yl]amino}pyridine-2-carbohydrazide hydrochloride as a white solid. MS ESI calcd. for $C_{13}H_{12}F_3N_5O \cdot ClH$ [M+H]$^+$ 312. found 312. $^1$H NMR (500 MHz, DMSO-d$_6$) δ 10.27 (s, 1H), 8.49 (d, J=4.8, 1H), 8.15 (s, 1H), 7.69 (s, 1H), 7.46 (s, 1H), 7.22 (d, J=6.0, 1H), 2.38 (s, 3H).

Preparative Example 17

N-[3-Methyl-5-(4,4,5,5-tetramethyl-1,3,2-dioxaborolan-2-yl)phenyl]-4-(trifluoromethyl)pyrimidin-2-amine

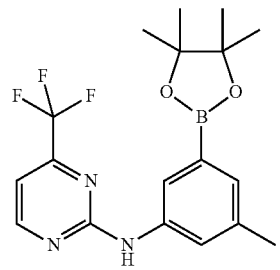 [SMILES: Cc1cc(Nc2nccc(C(F)(F)F)n2)cc(B2OC(C)(C)C(C)(C)O2)c1]

Preparative Example 17 was prepared according to the procedures described in PCT Publication No. WO 2011/075515.

Preparative Example 18

Methyl 4-{1-[4-(6-amino-4-methylpyridin-2-yl)-1H-1,2,3-triazol-1-yl]ethyl}benzoate (racemic)

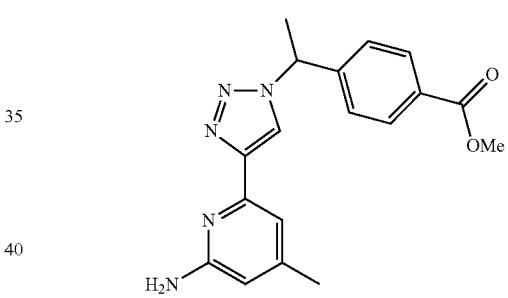

Step 1:

2,6-dibromo-4-methylpyridine (300 mg, 1.20 mmol), tert-butyl carbamate (168 mg, 1.44 mmol), sodium tert-butoxide (138 mg, 1.44 mmol) and 1,1'-bis(di-tert-butylphosphino)ferrocene palladium dichloride (39.0 mg, 0.06 mmol) were dissolved in nitrogen sparged 2-MeTHF. The system was evacuated and purged with nitrogen (3×) then placed into 70° C. oil bath. After 3 hours, the temperature was increased to 80° C. for 4 hours. The reaction mixture was diluted with EtOAc and brine. The product was extracted with EtOAc, washed with brine, dried and concentrated under reduced pressure to afford crude tert-butyl {4-methyl-6-[(trimethylsilyl)ethynyl]pyridin-2-yl}carbamate. Copper (I) iodide (0.13 g, 0.7 mmol) and bis(triphenylphosphine)palladium (II) dichloride (0.24 g, 0.35 mmol) were added to the crude product and then dissolved in nitrogen sparged dimethylacetamide. The system was evacuated and purged with nitrogen (3×). Triethylamine (1.5 mL, 10.45 mmol) and trimethylsilylactylene (1.5 mL, 10.45 mmol) were added and the solution was stirred at room temperature overnight. The reaction mixture was diluted with EtOAc (25 mL) and brine. The product was extracted with EtOAc (25 mL), washed with brine, dried and concentrated under reduced pressure. The residue was purified by column chromatography on silica gel (5% EtOAc). The fractions were concentrated under reduced pressure, suspended in hexanes, filtered in vacuo and dried to afford tert-butyl {4-methyl-6-[(trimethylsilyl)ethynyl]pyridin-2-yl}carbamate. MS ESI calcd. for $C_{16}H_{25}N_2O_2Si$ [M+H]$^+$ 305. found 305.

Step 2:
Potassium carbonate (2.04 g, 14.8 mmol) and methanol (2.0 ml, 49.3 mmol) were added to a solution of tert-butyl {4-methyl-6-[(trimethylsilyl)ethynyl]pyridin-2-yl}carbamate (1.5 g, 4.9 mmol) in dichloromethane (4.9 ml) at room temperature. The reaction mixture was stirred overnight, then diluted with dichloromethane and filtered through celite. Hydrogen chloride in ether (12.3 mL, 24.6 mmol) was added to the filtrate, and the resulting mixture was stirred at room temperature overnight. The reaction was directly concentrated under reduced pressure. The residue was washed with aqueous sodium bicarbonate and the product was extracted with methylene chloride (3×). The combined organic fractions were washed with brine, dried over anhydrous sodium sulfate and concentrated under reduced pressure. The residue purified by column chromatography on silica (0 to 100% EtOAc/hexanes) to afford 6-ethynyl-4-methylpyridin-2-amine as a light yellow oil. MS ESI calcd. for $C_8H_9N_2$ [M+H]$^+$ 338. found 338.

Step 3:
Sodium azide (295 mg, 4.54 mmol) was added to a solution of methyl 4-(1-bromoethyl)benzoate (809 mg, 3.33 mmol) in t-butanol (3.0 mL) and water (3.0 mL) under argon, and the resulting mixture was stirred at 65° C. overnight. 6-ethynyl-4-methylpyridin-2-amine (400 mg, 3.03 mmol), copper(II) sulfate pentahydrate (76 mg, 0.303 mmol), and sodium ascorbate (240 mg, 1.211 mmol) were added and the mixture was stirred at 65° C. for 4 hours. The reaction mixture was quenched with water and product was extracted with EtOAc (3×). The combined organic fractions were combined, dried over anhydrous magnesium sulfate, and concentrated under reduced pressure. The residue was purified by column chromatography on silica (0 to 15% methanol/dichloromethane) to afford methyl 4-{1-[4-(6-amino-4-methylpyridin-2-yl)-1H-1,2,3-triazol-1-yl]ethyl}benzoate (racemic) as a brown oil. MS ESI calcd. for $C_{18}H_{20}N_5O_2$ [M+H]$^+$ 338. found 338. $^1$H NMR (500 MHz, DMSO-d$_6$) δ 7.94 (d, J=8.3, 2H), 7.47 (d, J=8.3, 2H), 7.03 (s, 1H), 6.23 (s, 1H), 6.09 (q, J=6.9, 1H), 5.88-5.77 (m, 2H), 5.74 (s, 1H), 3.82 (s, 3H), 2.18 (s, 3H), 2.01-1.86 (m, 3H).

Preparative Example 19

Racemic methyl 4-bromo-1,2,3,4-tetrahydronaphthalene-1-carboxylate

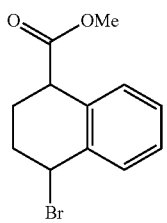

Step 1:
4-Oxo-1,2,3,4-tetrahydronaphthalene-1-carboxylic acid (3.50 g, 18.4 mmol) in THF (18.4 ml) was added to a dry flask and the solution was purged and then evacuated with argon. Sodium borohydride (1.74 g, 46.0 mmol) was added in one portion and the mixture was stirred at room temperature overnight. The reaction was diluted with aqueous HCl and the mixture was extracted with EtOAc (3×). The organic layer was dried over anhydrous magnesium sulfate and concentrated under reduced pressure. The resulting oily solid was taken-up in methanol/dichloromethane (1:1, 20 ml). Trimethylsilyldiazomethane (18.4 ml, 36.8 mmol) was added drop wise until the solution turned bright yellow and then the mixture was concentrated under reduced pressure. The residue was purified by column chromatography on silica gel (0 to 100% EtOAc/hexanes) to afford methyl 4-hydroxy-1,2,3,4-tetrahydronaphthalene-1-carboxylate as a yellow oil.

Step 2:
Methyl 4-hydroxy-1,2,3,4-tetrahydronaphthalene-1-carboxylate (3.68 g, 17.84 mmol) was taken-up in dichloromethane (17.8 ml) and the solution was purged and then evacuated with argon. Phosphorus tribromide (3.4 ml, 36 mmol) was added, and the resulting mixture was allowed to stir at room temperature over the weekend. The reaction was diluted with aqueous sodium bicarbonate and product was extracted with dichloromethane (3×). The organic layer was dried over anhydrous sodium sulfate and concentrated under reduced pressure. The residue was purified by column chromatography on silica gel (0 to 100% EtOAc/hexanes) to afford racemic methyl 4-bromo-1,2,3,4-tetrahydronaphthalene-1-carboxylate as a light yellow oil.

Preparative Example 20

4-(2-{[tert-Butyl(dimethyl)silyl]oxy}ethoxyl-N-(3-ethynyl-5-methylphenyl)pyrimidin-2-amine

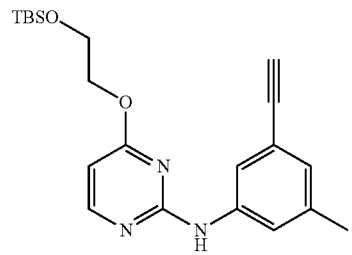 [SMILES: C#Cc1cc(C)cc(Nc2nccc(OCCO[Si](C)(C)C(C)(C)C)n2)c1]

Step 1:
A sealed tube was charged with N-(3-bromo-5-methylphenyl)-4-(2-{[tert-butyl(dimethyl)silyl]oxy}ethoxy)pyrimidin-2-amine (300 mg, 0.68 mmol), bis(triphenylphosphine)palladium(II) chloride (48.0 mg, 0.07 mmol), and copper(I) iodide (26.1 mg, 0.14 mmol). The tube was evacuated and backfilled with argon (3×). Fully degassed DMF (2.3 mL) was added, followed immediately by the addition of DIPEA (360 μl, 2.05 mmol) and trimethylsilylacetylene (290 μl, 2.05 mmol). The tube was sealed and heated to 90° C. for 16 hours. The mixture was then cooled to room temperature, diluted with EtOAc, and washed with water/brine (1:1). The organic layer was dried over anhydrous magnesium sulfate, filtered, and concentrated under reduced pressure. The residue was purified by column chromatography on silica gel (0 to 20% EtOAc/hexanes) to afford 4-(2-{[tert-butyl(dimethyl)silyl]oxy}ethoxy)-N-{3-methyl-5-[(trimethylsilyl)ethynyl]phenyl}pyrimidin-2-amine as a tan oil. $^1$H NMR (500 MHz, DMSO-d$_6$) δ 9.54 (s, 1H), 8.21 (d, J=5.7, 1H), 7.72 (s, 1H), 7.52 (s, 1H), 6.84

(s, 1H),), 6.27 (d, J=5.7, 1H), 4.45-4.33 (m, 2H), 4.00-3.90 (m, 2H), 2.23 (s, 3H), 0.82 (s, 9H), 0.20 (s, 9H), 0.01 (s, 6H).

Step 2:

4-(2-{[tert-Butyl(dimethyl)silyl]oxy}ethoxy)-N-{3-methyl-5-[(trimethylsilyl)ethynyl]phenyl}pyrimidin-2-amine (250 mg, 0.549 mmol) was taken up in MeOH (3.66 mL) and potassium carbonate (227 mg, 1.64 mmol) was added. The slurry was stirred at room temperature for 2 hours. The mixture was concentrated under reduced pressure and the residue was taken up in EtOAc and saturated aqueous ammonium chloride. The layers were separated and the aqueous layer was extracted once more with EtOAc. The combined organics were dried over anhydrous magnesium sulfate, filtered, and concentrated under reduced pressure. The residue was purified by column chromatography on silica gel (0 to 30% ethyl acetate/hexanes) to afford 4-(2-{[tert-Butyl(dimethyl)silyl]oxy}ethoxy)-N-(3-ethynyl-5-methylphenyl)pyrimidin-2-amine as a tan solid. $^1$H NMR (500 MHz, DMSO-d$_6$) δ 9.55 (s, 1H), 8.21 (d, J=5.7, 1H), 7.69 (s, 1H), 7.60 (s, 1H), 6.85 (s, 1H),), 6.27 (d, J=5.7, 1H), 4.40-4.36 (m, 2H), 4.05 (s, 1H), 3.94-3.89 (m, 2H), 2.24 (s, 3H), 0.87 (s, 9H), 0.02 (s, 6H).

Preparative Example 21

3-(Chloromethyl)tetrahydrofuran-3-ol (racemic)

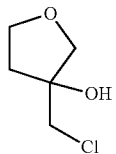

Step 1:

3-chloro-2-(chloromethyl)prop-1-ene (0.84 ml, 8.00 mmol) and paraformaldehyde (1.44 g, 48.0 mmol) were dissolved in 1,2-dichloroethane (10 mL) followed by addition of sulfuric acid (80% in water, 0.59 ml, 8.80 mmol). The reaction stirred at 90° C. for 3 hours. The crude reaction mixture was diluted with ethyl acetate and washed with water and NaOH. The organic layer was dried over anhydrous sodium sulfate, filtered, and concentrated under reduced pressure. The residue was purified by column chromatography on silica gel (2 to 20% EtOAc/isohexane) to afford 4,4-bis(chloromethyl)-1,3-dioxane (613 mg, 3.31 mmol) as a colorless liquid. $^1$H NMR (500 MHz, CDCl$_3$) δ 4.89 (s, 2H), 3.91 (t, J=5.1 Hz, 2H), 3.84 (d, J=11.8 Hz, 2H), 3.71 (d, J=11.7 Hz, 2H), 1.90 (t, J=5.1 Hz, 2H).

Step 2:

In a pressure sealed vial, 4,4-bis(chloromethyl)-1,3-dioxane (613.2 mg, 3.31 mmol) was dissolved in sulfuric acid (3% in water, 1.18 mL, 0.66 mmol) and heated to 150° C. for 3 hours. The crude reaction mixture was extracted with IPA/CHCl$_3$ (3:1, 3×). The combined organic layers were dried over anhydrous sodium sulfate, filtered, silica gel was added, and concentrated under reduced pressure. The residue was purified by column chromatography (10 to 80% EtOAc/isohexane) to afford 3-(chloromethyl)tetrahydrofuran-3-ol (236 mg, 1.73 mmol) as a colorless liquid. $^1$H NMR (500 MHz, CDCl$_3$) δ 4.04-4.00 (m, 1H), 3.95-3.87 (m, 1H), 3.77 (d, J=9.7 Hz, 1H), 3.70 (d, J=9.8 Hz, 1H), 3.74-3.68 (m, 2H), 2.42 (s, 1H), 2.06-1.96 (m, 2H).

Preparative Example 22.1

Methyl 5,5-dimethyl-1-oxaspiro[2.5]octane-6-carboxylate (syn)

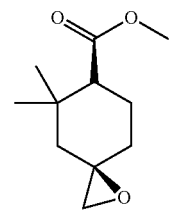

Step 1:

Trimethylsulfoxonium iodide (1.20 g, 5.43 mmol) was dissolved in DMSO (10 mL) and cooled to 0° C. Sodium hydride (0.26 g, 6.51 mmol) was added and the reaction mixture warmed to room temperature and stirred for 3 hours. The reaction mixture was cooled to 0° C. and methyl 2,2-dimethyl-4-oxocyclohexanecarboxylate (1.0 g, 5.4 mmol) was added, then warmed to room temperature and stirred overnight. The crude reaction mixture was diluted with ether and washed with water. The product was extracted with ether and the combined organic layers were washed with brine, dried over anhydrous sodium sulfate, filtered, silica gel was added, and concentrated under reduced pressure. The residue was purified by column chromatography on silica gel (5 to 40% EtOAc/isohexane) to afford methyl 5,5-dimethyl-1-oxaspiro[2.5]octane-6-carboxylate (syn) as a yellow liquid. $^1$H NMR (500 MHz, CDCl$_3$) δ 3.66 (s, 3H), 2.50-2.49 (m, 2H), 2.06-2.04 (m, 2H), 1.76-1.75 (m, 2H), 1.67-1.66 (m, 1H), 1.47-1.45 (m, 1H), 1.27-1.25 (m, 1H), 1.07 (s, 3H), 1.00 (s, 3H).

The intermediates in the following table were prepared according to the method described for Preparative Example 22.1.

| Prep. Ex. | Structure | Chemical Name | $^1$H NMR |
|---|---|---|---|
| 22.2 | 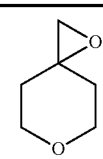 | 1,6-dioxaspiro [2.5]octane | $^1$H NMR (500 MHz, CDCl$_3$) δ 3.89-3.77 (m, 4H), 2.69 (s, 2H), 1.87-1.74 (m, 2H), 1.56-150 (m, 2H |

Preparative Example 23

1,6-Dioxaspiro[2.5]octane was prepared using the same procedure described for (3R and S,6R and S)-methyl 5,5-dimethyl-1-oxaspiro[2.5]octane-6-carboxylate (Intermediate 1.29).).

Preparative Example 24

Cyclohept-2-en-1-yl methanesulfonate (racemic)

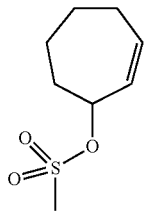

Step 1:
Dibal-H (13.0 ml, 1.0M in hexanes) was added drop wise to a cooled (−78° C.) solution of cyclohept-2-en-1-one (1.0 g, 9.1 mmol) in DCM (36.3 ml). The mixture was stirred for 1.5 hours. Methanol (2.5 mL) was added and the reaction was allowed to warm to room temperature. Saturated aqueous sodium potassium tartrate (100 ml) and ethyl acetate (100 ml) were added and the mixture was vigorously stirred until the emulsion broke (overnight). The layers were then separated and the aqueous layer was extracted with dichloromethane (3×). The combined organics were dried over anhydrous magnesium sulfate, filtered, and concentrated under reduced pressure. The residue was purified by column chromatography on silica gel (0 to 50% ethyl acetate/hexanes) to afford cyclohept-2-en-1-ol as a colorless oil.

Step 2:
Cyclohept-2-en-1-ol (840 mg, 7.49 mmol) was taken up in dichloromethane (30 ml) under argon and cooled to 0° C. Triethylamine (2.09 ml, 14.98 mmol) and methanesulfonyl chloride (1.17 ml, 14.98 mmol) were sequentially added, and the mixture was left to stir for 3 hours. The reaction was quenched with aqueous sodium bicarbonate and extracted with dichloromethane (3×). The organic fractions were combined, dried over anhydrous magnesium sulfate, and concentrated under reduced pressure to afford cyclohept-2-en-1-yl methanesulfonate (racemic) as a colorless oil. $^1$H NMR (500 MHz, DMSO-$d_6$) δ 5.86-5.78 (m, 2H), 4.90-4.87 (m, 1H), 2.25 (s, 3H), 2.15-2.12 (m, 2H), 1.98-1.93 (m, 2H), 1.92-1.84 (m, 1H), 1.73-1.64 (m, 1H), 1.63-1.55 (m, 1H), 1.52-1.47 (m, 1H).

Preparative Example 25

1,4-Dioxaspiro[4.5]dec-8-yl methanesulfonate

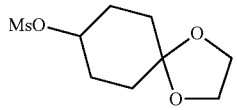

Step 1:
Sodium borohydride (182 mg, 4.80 mmol) was added to a 0° C. solution of 1,4-dioxaspiro[4.5]decan-8-one (500 mg, 3.20 mmol) in ethanol (12.8 ml). The mixture was stirred at 0° C. for 5 hours. HCl (1M aqueous) was then added drop wise until gas evolution ceased and the resulting mixture was extracted with dichloromethane (2×). The combined organic fractions were dried over anhydrous magnesium sulfate, filtered, and concentrated under reduced pressure. The residue was purified by column chromatography on silica gel (0 to 100% ethyl acetate/hexanes) to afford 1,4-dioxaspiro[4.5]decan-8-ol as a colorless oil.

Step 2:
1,4-Dioxaspiro[4.5]decan-8-ol (503 mg, 3.18 mmol) was taken up in dichloromethane (12.7 ml) under argon and cooled to 0° C. Triethylamine (1.1 ml, 7.95 mmol) and methanesulfonyl chloride (0.5 ml, 6.36 mmol) were sequentially added, and the mixture was left to stir for 4 hours. The reaction was diluted with aqueous sodium bicarbonate and extracted with dichloromethane (3×). The organic fractions were combined, dried over anhydrous magnesium sulfate, and concentrated under reduced pressure to afford 1,4-dioxaspiro[4.5]dec-8-yl methanesulfonate as an orange oil.
$^1$H NMR (500 MHz, DMSO-$d_6$) δ 4.77 (m, 1H), 3.86-3.82 (m, 4H), 3.16 (s, 3H), 1.90-1.84 (m, 2H), 1.81-1.74 (m, 2H), 1.69-1.64 (m, 2H), 1.60-1.55 (m, 2H).

Preparative Example 26

Methyl 2,2-dimethyl-4-oxocyclohexanecarboxylate (racemic)

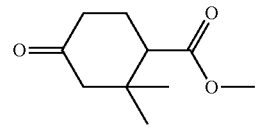

Step 1:
Piperidine (10 g, 117.44 mmol) was added to a mixture of methyl 3-oxobutanoate (232 g, 2.00 mol) and paraformaldehyde (30.0 g, 999.0 mmol). The resulting solution was stirred for 2 hours at 0° C. The solution was heated to 60° C. for 2 hours then extracted with diethyl ether (3×). The organic layers were combined and dried over anhydrous sodium sulfate, filtered and concentrated under reduced pressure to afford crude dimethyl 2-methyl-6-oxocyclohex-1-ene-1,3-dicarboxylate as a brown oil. MS ESI [M+H]$^+$ 227. found 227.

Step 2:
Dimethyl 2-methyl-6-oxocyclohex-1-ene-1,3-dicarboxylate (150 g, 663.0 mmol) in methanol (150 mL) was added drop wise over 30 minutes to a solution of sodium methanolate (90 g, 1.67 mol) in methanol (300 mL). The resulting solution was heated to 80° C. for 30 minutes and the mixture was concentrated under reduced pressure. The reaction mixture was then diluted by the addition of H$_2$O/ice (120 mL), then further diluted with acetic acid (130 mL). The resulting solution was extracted with diethyl ether (3×), and the organic layers were combined and dried over anhydrous sodium sulfate, filtered and concentrated under reduced pressure. The residue was purified by distillation under reduced pressure (5 mm Hg, 110~120° C.) to afford methyl 2-methyl-4-oxocyclohex-2-enecarboxylate as a yellow oil. MS ESI [M+H]+ 169. found 169.

Step 3:
Methyllithium (1.6 M in diethyl ether, 800 mL, 1.28 mol) was added drop wise at −40° C. over 3 hours to a solution of copper iodide (121.8 g, 639.54 mmol) in diethyl ether (800 mL). A solution of methyl 2-methyl-4-oxocyclohex-2-enecarboxylate (53.8 g, 320 mmol) in diethyl ether (400 mL) was added at −40° C. over 2 minutes. The resulting solution was stirred 5 hours at −20° C. The reaction mixture was diluted via the addition of saturated aqueous ammonium chloride (2.5 L), and then extracted with EtOAc (3×2 L). The combined organic extracts were dried over anhydrous sodium sulfate, filtered, and concentrated under reduced pressure. The residue was purified column chromatography on silica (1:20 EtOAc/petroleum ether) to afford methyl 2,2-dimethyl-4-oxo-cyclohexanecarboxylate as a yellow oil. MS ESI [M+H]+ 185. found 185. $^1$H NMR (600 MHz, CDCl$_3$) δ 3.49 (s, 3H), 2.43-2.40 (m, 1H), 2.35-2.29 (m, 1H), 2.21-2.17 (m, 1H), 2.11-2.04 (m, 1H), 2.00-1.96 (m, 1H), 1.91-1.85 (m, 1H), 0.85 (s, 3H), 0.77 (s, 3H).

Preparative Example 27

Methyl 4-{(1S)-1-[(methylsulfonyl)oxy]ethyl}benzoate

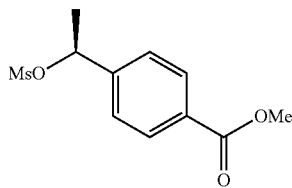 [SMILES: COC(=O)c1ccc([C@H](C)OS(C)(=O)=O)cc1]

Methyl 4-{(1S)-1-[(methylsulfonyl)oxy]ethyl}benzoate was prepared according to the procedure outlined in Scheme 20 in PCT Publication No. WO 2009/005646.

Preparative Example 28

2-Chloro-1-cis-3,5-dimethylmorpholin-4-yl]ethanone

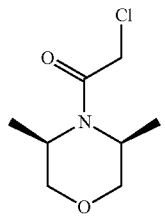

Step 1:
Platinum dioxide (800 mg) was added to a solution of dl-2-amino-1-propanol (100 g) and hydroxyacetone (115 g) in methanol (1100 mL). The reaction mixture was hydrogenated at 60 psi for 20 hours, after which time, the catalyst was filtered off and the solvent removed under reduce pressure to give crude 2,2'-iminodipropan-1-ol.
Step 2:
Crude 2,2'-iminodipropan-1-ol (260 g) was added in one portion at 0° C. to concentrated sulphuric acid (800 mL) at 0° C. The reaction mixture was heated to 160° C. for 8 hours with stirring. Aqueous potassium hydroxide solution was added to the cooled mixture, the pH was adjusted to 7~8 and the mixture was then filtrated. The filtrate and NaOH (310 g) was added to di-tert-butyl-dicarbonate (355 g) in one portion at room temperature. The mixture was stirred overnight, and then poured into water and extracted with ether. The combined organic layers were dried and concentrated under reduced pressure. The residue was purified by column chromatography on silica gel (1:30, ethyl acetate/petroleum ether) to afford cis-tert-butyl-3,5-dimethylmorpholine-4-carboxylate and trans-tert-butyl-3,5-dimethylmorpholine-4-carboxylate.
Step 3:
cis-tert-Butyl-3,5-dimethylmorpholine-4-carboxylate was dissolved in methanol (500 mL) and HCl (8N in methanol, 500 mL), and stirred at 0° C. for 10 minutes. The mixture was allowed to warm to room temperature with stirring for 6 hours. The mixture was concentrated under reduced pressure to afford of the cis-3,5-dimethylmorpholine as the hydrochloride salt.
Step 4:
cis-3,5-Dimethylmorpholine hydrochloride salt (19 g) was dissolved in DCM (200 mL) and cooled to 0° C. Aqueous sodium bicaronate (32 g in 70 mL of water) was added and allowed to stir at room temperature. Subsequently of 2-chloroacetyl chloride (25 g) in DCM was added drop wise and the mixture was stirred at 0° C. for 30 minutes then, warmed to room temperature and continuously stirred for 5 hours. The reaction mixture was diluted with water and extracted with DCM. The organic layer was separated and washed with water (2×), dried over anhydrous sodium sulfate and concentrated under reduced pressure. The residue was purified by crystallization in ether to give 2-chloro-1-cis-3,5-dimethylmorpholin-4-yl]ethanone.

Preparative Example 29

2-Chloro-1-(3,3-dimethylmorpholin-4-yl)ethanone

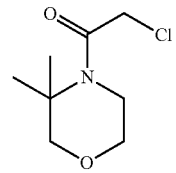

Step 1:
2-Amino-2-methyl-1-propanol (200 g) in water (400 mL) was cooled by an ice water bath. Propylene oxide (100 mL) was added drop wise with vigorous stirring, and the mixture was then reacted for 1 hour at 0-10° C. Subsequently, water and 2-amino-2-methyl-1-propanol were distilled off, and the remaining residue was further distilled to afford 2-[(2-hydroxyethyl)amino]-2-methylpropan-1-ol.
Step 2:
2-[(2-Hydroxyethyl)amino]-2-methylpropan-1-ol (120 g) was slowly added to sulfuric acid (98%, 100 mL) in a water-ice bath. The mixture was then heated to 180° C. for 9 hours, cooled, and basified with sodium hydroxide solution. The solution was taken up in dichloromethane, dried, and concentrated under reduced pressure. The residue was dissolved in dichloromethane (500 mL) and saturated sodium bicarbonate solution (300 mL). 2-Chloroacetyl chloride (50 mL) was added drop wise, and the mixture was the stirred for 1.5 hours at room temperature. The solution was extracted with dichloromethane, the organic layer was dried and concentrated under reduced pressure. The residue was purified by column chromatography on silica gel to afford 2-chloro-1-(3,3-dimethylmorpholin-4-yl)ethanone. $^1$H NMR (300 Hz, CDCl$_3$) δ 3.99 (2H, s), 3.76-3.78 (2H, m), 3.41-3.44 (2H, m), 3.36 (2H, s), 1.40 (6H, s).

Preparative Example 30

2-Chloro-N-(1-methoxy-2-methylpropan-2-yl)acetamide

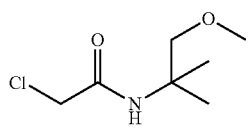

Step 1:

Et$_3$N (140 mL) and 2-methyl-2-aminopropan-1-ol (100 mL) were dissolved in dry THF (1.5 L) and the mixture was cooled to 0° C. (Boc)$_2$O (230 g) was added and the cooling bath was removed. After stirring for 90 minutes at room temperature, the solvent was removed by vacuum distillation. Water was added to the residue, and the mixture was extracted with EtOAc. The organic layer was recrystallized from EtOAc/petroleum ether to afford tert-butyl (1-hydroxy-2-methylpropan-2-yl)carbamate as a white solid.

Step 2:

KOH (250 g) was added in a single portion to a 0° C. cooled solution of tert-butyl (1-hydroxy-2-methylpropan-2-yl)carbamate (200 g) in THF (1000 mL) and water (500 mL) and the cold bath was then removed. The mixture was stirred for 15 minutes at room temperature, then Me$_2$SO$_4$ (133.5 g) was added via additional funnel drop wise over 45 minutes. The reaction mixture was stirred for 4 hours at room temperature, excess KOH was filtered off and the liquor was poured into a mixture of EtOAc and saturated aqueous ammonium chloride. The layers were separated and the combined organic layers were dried over anhydrous sodium sulfate, filtered and concentrated under reduced pressure to afford of tert-butyl (1-methoxy-2-methylpropan-2-yl)carbamate Step 3:

tert-Butyl (1-methoxy-2-methylpropan-2-yl)carbamate (170 g) was added to a saturated solution of MeOH. HCl at 5° C. and the mixture was stirred for 16 hours at room temperature. The solvent was then distilled off and the crude product was purified by reduced pressure distillation to afford 1-methoxy-2-methylpropan-2-amine.

Step 4:

1-Methoxy-2-methylpropan-2-amine was dissolved in the mixture of THF and water (1000 mL:500 mL) and cooled to room temperature. NaOH (160 g) was added and the mixture was stirred for 15 min at 0° C. ClCH$_2$COCl (65 mL) was added drop wise to the reaction mixture at below 20° C. and the reaction mixture was then stirred at room temperature for 30 minutes. Saturated ammonium chloride solution was added, the layers was separated and the organic layer was concentrated under reduced pressure. The residue was washed with hexanes (3×) to afford 2-chloro-N-(1-methoxy-2-methylpropan-2-yl)acetamide as a white crystalline solid.

$^1$H NMR (300 MHz, CDCl$_3$) δ 1.37 (s, 6H), 3.36 (s, 2H), 3.38 (s, 3H), 3.39 (s, 2H), 6.6 (bs, 1H).

Preparative Example 31

2-Chloro-1-(4,4-dimethyl-1,3-oxazolidin-3-yl)ethanone

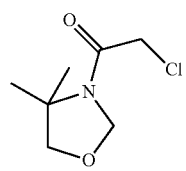

Aqueous formaldehyde (37%, 300 mL) was added to a solution of 2-amino-2-methylpropan-1-ol (100 g) in toluene (500 mL). The mixture was heated to 70-75° C. and stirred for 3 hours. Water was removed by azeoptrope with toluene, cooled and concentrated under reduced pressure. The residue was dissolved in a mixture of DCM/saturated sodium bicarbonate (800 mL/600 mL) and chloroacetyl chloride (95 g) was added drop wise at room temperature. The mixture was then stirred for 1.5 hours followed by extraction with dichloromethane, dried over anhydrous sodium sulfate, concentrated under reduced pressure. The residue was purified by column chromatography on silica gel (10/1 petroleum ether/EtOAc) to afford 2-chloro-1-(4,4-dimethyl-1,3-oxazolidin-3-yl)ethanone as white solid. $^1$H-NMR (300 MHz, CDCl$_3$) δ 5.04 (s, 2H), 3.85 (s, 2H), 3.76 (s, 2H), 1.49 (s, 6H).

Preparative Example 32

3-(Chloromethyl)-5-methyl-1,2,4-oxadiazole

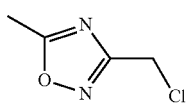

Step 1:

Sodium ethoxide (21% in ethanol, 360 mL) was added drop wise to a suspension of NH$_2$OHHCl (66.72 g) at 0° C. and the reaction mixture was stirred for 10 minutes. Cyanic chloride (71.58 g) was added drop wise and the reaction mixture was warmed to room temperature over 1 hour. The mixture was filtered and concentrated under reduced pressure to afford 2-chloro-N-hydroxyethanimidamide.

Step 2:

2-Chloro-N-hydroxyethanimidamide (0.2 g) was added to Ac$_2$O (132.6 g) and the mixture was stirred for 2 hours at 125° C. The reaction mixture was neutralized using sodium carbonate and extracted with EtOAc (2 L). The organic layer was dried over anhydrous sodium sulfate, filtered, and then concentrated under reduced pressure to afford 3-(chloromethyl)-5-methyl-1,2,4-oxadiazole. $^1$H NMR (300 MHz, CDCl$_3$) δ 2.62 (s, 3H), 4.58 (s, 2H).

Preparative Example 33

2-Chloro-4-(difluoromethyl)pyrimidine

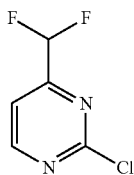

Step 1:

2,2-difluoroacetic anhydride and DMAP in DCM were cooled to −20° C. and ethyl vinyl ether was added drop wise at such a rate that the internal temperature did not exceed −10° C. When complete the reaction mixture was stirred over night while slowly warming it to room temperature. Water and DCM were added and the layers were cut. The organic layer was washed sequentially with aqueous saturated sodium bicarbonate then brine. The aqueous layers were sequentially back extracted with a second portion of DCM and the combined organics were dried with anhydrous magnesium sulfate, filtered and concentrated under reduced pressure. The residue was then taken up in EtOH, urea was added followed by concentrated hydrochloric acid. The resulting mixture stirred for 18 h then concentrated under reduced pressure. Ethanol was added and again concentrated under reduced pressure. This was repeated then repeated with EtOAc (2×). The resulting residue was diluted with EtOAc stirred for 1 h then filtered and washed with EtOAc/Hexanes (1:1) to afford 4-(difluoromethyl)pyrimidin-2-ol as a brown solid.

Step 2:

4-(difluoromethyl)pyrimidin-2-ol was diluted with phosphorus oxychloride (80 mL) then heated at 85° C. for 3 hours with periodic venting of the reaction mixture. The mixture was cooled to rt, diluted with DCM (500 mL) and poured into water (~1 L) cooled in an ice bath at such a rate the exotherm was maintained at 30° C. The mixture was transferred to a reparatory funnel and the layers were separated. The aqueous layer was extracted with DCM (2×500 mL) and the organics were combined and dried with anhydrous magnesium sulfate, filtered and concentrated under reduced pressure to afford 2-chloro-4-(difluoromethyl) as a light yellow oil. MS ESI calcd. for $C_5H_4ClF_2N_2$ $[M+H]^+$ 165. found 165. $^1H$ NMR δ ppm DMSO-$d_6$): 8.18 (1H, d, J=6.25 Hz), 6.63 (1H, t, J=54.22 Hz). 6.57 (2H, d, J=6.26 Hz).

Preparative Example 34

2-Chloro-4-(difluoromethyl)-5-fluoropyrimidine

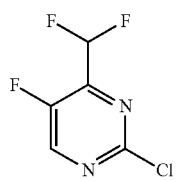 [SMILES: Fc1cnc(Cl)nc1C(F)F]

Step 1:

2,4-Dichloro-5-fluoropyrimidine (111 g, 661.47 mmol, 1.00 equiv., 99.5%), potassium trifluoro(vinyl)borate (98 g, 716.72 mmol, 1.08 equiv., 98%), TEA (67 g, 98%), 1-propanol (1100 mL), PdCl$_2$(dppf).CH$_2$Cl$_2$ (27 g, 33.06 mmol, 0.05 equiv) were added into five 2000-mL pressure tank reactors which purged and maintained with an inert atmosphere of nitrogen. The resulting solution was stirred overnight at 105° C. The reaction mixture of five batches was combined and then cooled to room temperature with a water bath. The solid was filtered out. The filtrate was concentrated under reduced vacuum. The residue was applied onto a silica gel column and eluted with ethyl acetate/petroleum ether (1:20) to afford 2-chloro-4-ethenyl-5-fluoropyrimidin as a highly volatile yellow oil.

Step 2:

A solution of OsO$_4$ in water (0.015 g/ml, 265 mL) was added into a 10-L 4-necked round-bottom flask with 2-chloro-4-ethenyl-5-fluoropyrimidine (303 g, 1.24 mol, 1.00 equiv, 65%), tetrahydrofuran (2400 mL) and water (1600 mL). This was followed by the addition of NaIO$_4$ (424 g, 1.94 mol, 1.56 equiv, 98%), in portions at 0-10° C. The resulting solution was stirred for 60 min at 0-10° C. in a water/ice bath. The resulting solution was diluted with water (4 L), then extracted with ethyl acetate (5×1000 mL). The organic layers were combined, dried over anhydrous sodium sulfate and concentrated under reduced pressure. The residue was applied onto a silica gel column and eluted with ethyl acetate/petroleum ether (1:5) to afford (2-chloro-5-fluoropyrimidin-4-yl)methanediol as a white solid and (2-chloro-5-fluoropyrimidin-4-yl)methanediol as a yellow oil.

Step 3:

(2-Chloro-5-fluoropyrimidin-4-yl)methanediol (80 g, 426 mmol, 1.00 equiv, 95%), dichloromethane (1300 mL), ethyl acetate (7.3 mL) were added to a 3-L 4-necked round-bottom flask purged and maintained with an inert atmosphere of nitrogen. This was followed by the addition of DAST (86.7 g, 537.87 mmol, 1.26 equiv) drop wise with stirring at 15-25° C. The resulting solution was stirred overnight at 25° C. The reaction was then quenched by the addition of saturated aqueous ammonium chloride (1500 mL). The resulting solution was extracted with dichloromethane (2×1000 mL). The organic layers were combined, dried over anhydrous magnesium sulfate and concentrated under reduced pressure. The crude product was purified by distillation under reduced pressure (20 mmHg) and the fraction was collected at 80-85° C. to afford 2-chloro-4-(difluoromethyl)-5-fluoropyrimidine as brown oil. MS ESI calcd. for $C_5HClF_3N_2$ $[M+H]^+$ 182. found 182. $^1H$ NMR (300 MHz, CDCl$_3$) δ 8.68 (1H, m), 6.99-6.49 (1H, m).

Preparative Example 35.1

N-(3-Bromo-5-methylphenyl)-4-(difluoromethyl)-5-fluoropyrimidin-2-amine

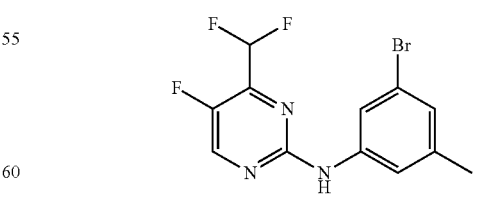

2-Chloro-4-(difluoromethyl)-5-fluoropyrimidine (30 g, 162 mmol, 1.00 equiv) p-TsOH (37 g, 215 mmol, 1.33 equiv), 1,4-dioxane (600 mL), 3-bromo-5-methylaniline (46 g, 247 mmol, 1.53 equiv) were added into a 1000-mL pressure tank reactor purged and maintained with an inert atmosphere of nitrogen. The resulting solution was stirred for 72 h at 105° C. The reaction mixture was cooled to room temperature. The solid was filtered out and the filtrate was concentrated under reduced pressure. The residue was applied onto a silica gel and purified column chromatography on silica (1:20 ethyl acetate/petroleum ether) to afford N-(3-bromo-5-methylphenyl)-4-(difluoromethyl)-5-fluoropyrimidin-2-amine as a yellow solid. MS ESI calc'd. for $C_{12}H_{10}BrF_3N_3$ $[M+H]^+$ 332/334. found 332/334. $^1$H NMR (400 MHz, CDCl$_3$): δ 8.45 (1H, s), 7.73 (1H, s), 7.21 (1H, s), 7.18 (1H, s), 7.05 (1H, s), 6.63 (1H, t, J=53.37 Hz), 2.34 (3H, s).

The intermediate in the following table was prepared according to the method described for Preparative Example 36.1.

| Prep. Ex. | Structure | Chemical Name | Calc'd $[M + H]^+$ | $[M + H]^+$ Observed |
|---|---|---|---|---|
| 35.2 | 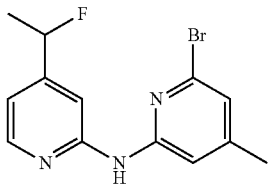 [SMILES: Cc1cc(Br)nc(Nc2cc(C(C)F)ccn2)c1] | N-(3-bromo-5-methylphenyl)-4-(difluoromethyl)pyrimidin-2-amine | 314, 316 | 314, 316 |

Preparative Example 36

6-Bromo-N-[4-(1-fluoroethyl)pyridin-2-yl]-4-methylpyridin-2-amine

Step 1:
2-Chloropyridine-4-carbonitrile (250 g, 1.80 mol, 1.00 equiv) and ether (3750 mL) were combined in a 10000-mL 4-necked round-bottom flask purged and maintained with an inert atmosphere of nitrogen. A solution of MeMgI in ether (1200 mL) was added drop wise with stirring at 0° C. in 30 min. The resulting solution was stirred for 6 h at room temperature and then poured into water/ice/6N hydrogen chloride (3000 mL) and stirred for 10 min. The organic phase was separated and the aqueous phase was extracted with ether (3×2000 mL). The combined organic layer was washed with brine (2×2000 mL), dried over anhydrous sodium sulfate and concentrated under vacuum. The residue was purified by column chromatography on silica gel (1:20 ethyl acetate/petroleum ether) to afford 1-(2-chloropyridin-4-yl)ethan-1-one as a light yellow solid.

Step 2:
1-(2-Chloropyridin-4-yl)ethan-1-one (110 g, 707 mmol, 1.00 equiv) and methanol (1500 mL) were added to a 3000-mL 4-necked round-bottom flask purged and maintained with an inert atmosphere of nitrogen. NaBH$_4$ (26.4 g, 698 mmol, 1.00 equiv) was added in portions at 0° C. The reaction mixture was stirred overnight at room temperature. The reaction was then quenched by the addition of water (1000 mL). The resulting mixture was concentrated under vacuum and extracted with dichloromethane (3×2000 mL). The combined organic layer was washed with brine (2×2000 mL), dried over anhydrous sodium sulfate and concentrated under vacuum. The residue was purified by column chromatography on silica gel (1:5 ethyl acetate/petroleum ether) to afford 1-(2-chloropyridin-4-yl)ethan-1-ol as colorless oil.

Step 3:
1-(2-Chloropyridin-4-yl)ethan-1-ol (115 g, 729 mmol, 1.00 equiv) and dichloromethane (3300 mL) were added to a 5000-mL 4-necked round-bottom flask purged and maintained with an inert atmosphere of nitrogen. DAST (144 g, 893 mmol, 1.25 equiv) was added drop wise with stirring at –78° C. in 30 min. The resulting solution was stirred overnight at room temperature. The reaction was then slowly quenched by the addition of water (1000 mL). The resulting solution was extracted with dichloromethane (3×1000 mL). The combined organic layer was washed with brine (3×1000 mL), dried over anhydrous sodium sulfate and concentrated under vacuum. The residue was purified by column chromatography on silica gel column (1:10 ethyl acetate/petroleum ether) to afford 2-chloro-4-(1-fluoroethyl)pyridine as light yellow oil.

Step 4:
2-Chloro-4-(1-fluoroethyl)pyridine (70 g, 439 mmol, 1.00 equiv), NaI (661 g, 4.41 mol, 10.00 equiv), ACN (700 mL) and acetyl chloride (56 g, 713 mmol, 1.60 equiv) were combined in a 2000-mL 4-necked round-bottom flask. The resulting solution was stirred overnight at 80° C. in an oil bath and then cooled to r.t, diluted with ice aqueous saturated sodium carbonate (500 mL) and extracted with dichloromethane (3×500 mL). The combined organic layer was washed with NaS$_2$O$_3$ (10%, 3×300 mL) and the aqueous phase was extracted with dichloromethane (2×200 mL). The combined organic layer was washed with brine (2×500 mL), dried over anhydrous sodium sulfate and concentrated under vacuum. The residue was purified by column chromatography on silica gel column (1:10 ethyl acetate/petroleum ether) to afford 4-(1-fluoroethyl)-2-iodopyridine as yellow oil.

Step 5:
4-(1-Fluoroethyl)-2-iodopyridine (90 g, 359 mmol, 1.05 equiv), 6-bromo-4-methylpyridin-2-amine (63.7 g, 341 mmol, 1.00 equiv), toluene (900 mL), t-BuOK (57.6 g, 1.50 equiv), BINAP (10.8 g, 17.3 mmol, 0.05 equiv) and Pd$_2$(dba)$_3$ (15.7 g, 17.1 mmol, 0.05 equiv) were combined into a 2000-mL 4-necked round-bottom flask purged and maintained with an inert atmosphere of nitrogen. The reaction mixture was stirred overnight at 90° C. in an oil bath and then cooled to r.t, diluted with DCM (500 mL). The solid was filtered out, washed with DCM and the filtrate was concentrated under vacuum. The residue was purified by column chromatography on silica gel column (1:15 ethyl acetate/petroleum ether) to afford 6-bromo-N-[4-(1-fluoroethyl)pyridin-2-yl]-4-methylpyridin-2-amine as a light yellow solid. ESI calc'd for $C_{13}H_{14}BrFN_3$ $[M+H]^+$ 309. found 309. $^1$H NMR (CD$_3$OD, 400 MHz, ppm): δ 8.23-8.22 (m, 1H), 7.66 (s, 1H), 7.45 (s, 1H), 6.934-6.91 (m, 2H), 5.72-5.51 (m, 1H), 2.32 (s, 3H), 1.68-1.61 (m, 3H).

Preparative Example 37

5-(1-azidoethyl)oxazolidin-2-one

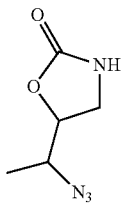

A solution of 5-(1-iodoethyl)oxazolidin-2-one (100 mg, 0.41 mmol) and sodium azide (81 mg, 1.24 mmol) in DMF (1 mL) was heated to 80° C. for 6 hours. After cooling to room temperature, water (50 mL) was added and the mixture was extracted with EtOAc (50 mL×3), dried over anhydrous sodium sulfate, filtered, and concentrated under reduced pressure to give crude 5-(1-azidoethyl)oxazolidin-2-one as yellow oil.

Preparative Example 38

5-(azidomethyl)oxazolidin-2-one

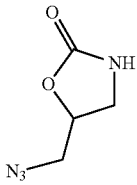

A mixture of 5-(chloromethyl)oxazolidin-2-one (500 mg, 3.70 mmol) and sodium azide (480 mg, 7.40 mmol) in DMF (5 mL) was stirred at 80° C. under N$_2$ for 12 hours. The mixture was diluted with H$_2$O (20 mL) and extracted with ethyl acetate (50 mL×3). The combined organic layers were washed with brine (50 mL), dried over anhydrous sodium sulfate, filtered, and concentrated under reduced pressure to give 5-(azidomethyl)oxazolidin-2-one which was used without further purification. MS ESI calc'd. for C$_4$H$_7$N$_4$O$_2$ [M+H]$^+$ 143. found 143.

Preparative Example 39

5-(azidomethyl)-4-methyloxazolidin-2-one

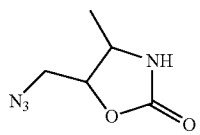

Step 1:
DIEA (16.0 mL, 90.0 mmol) and isobutyl carbonochloridate (10.4 mL, 79.4 mmol) were added to a solution of 2-((tert-butoxycarbonyl)amino)propanoic acid (10.0 g, 52.9 mmol) in THF (115 mL) at 0° C. The mixture was stirred at 0° C. for 4 hours. The mixture was then diluted with acetonitrile (73 mL) until the heterogeneous mixture turned clear. TMS-diazomethane (2.0 M in hexane, 53.0 mL, 106 mmol) was then added slowly to the mixture at 0° C. The mixture was stirred at 0° C. for 3 hours and was then allowed to warm to room temperature and stirred overnight. The mixture was concentrated under reduced pressure and the residue was purified by column chromatography on silica (petroleum ether/ethyl acetate) to afford tert-butyl (4-diazo-3-oxobutan-2-yl)carbamate as colorless oil. MS ESI calcd. for C$_9$H$_{16}$N$_3$O$_3$ [M+H]$^+$ 214. found 214.
Step 2:
Hydrochloric acid (3.91 mL, 46.9 mmol) was added to a mixture of tert-butyl (4-diazo-3-oxobutan-2-yl)carbamate (2.00 g, 9.40 mmol) in diethyl ether (20 mL) at 0° C. The mixture was stirred vigorously for 20 minutes and then warmed to room temperature and stirred vigorously until the mixture went from yellow to clear. The mixture was washed with saturated sodium bicarbonate (20 mL), dried over anhydrous sodium sulfate, filtered, and concentrated under reduced pressure. The crude tert-butyl (4-chloro-3-oxobutan-2-yl)carbamate was used in the next step without further purification. $^1$H NMR (400 MHz, CDCl$_3$) δ 5.08 (s, 1H), 4.57-4.52 (m, 1H), 4.28 (s, 2H), 1.45 (s, 9H), 1.38 (d, J=8.8 Hz, 3H).
Step 3:
Sodium borohydride (603 mg, 15.9 mmol) was added to a mixture of tert-butyl (4-chloro-3-oxobutan-2-yl)carbamate (880 mg, 3.97 mmol) in methanol (10 mL) at 0° C. and the mixture was stirred for 1 hour. A few drops of acetic acid were added to quench the reaction and then the reaction was concentrated under reduced pressure. The residue was taken up in EtOAc (200 mL), washed with water (20 mL), dried over anhydrous sodium sulfate, filtered, and concentrated under reduced pressure. The product was purified by column chromatography on silica (petroleum ether/ethyl acetate) to give tert-butyl(4-chloro-3-hydroxybutan-2-yl) carbamate as a colorless oil. $^1$H NMR (300 MHz, CDCl$_3$) δ 4.72 (s, 1H), 3.90-3.70 (m, 2H), 3.61-3.51 (m, 2H), 2.93 (s, 1H), 1.46 (s, 9H), 1.19 (d, J=8.8 Hz, 3H).
Step 4:
Sodium azide (0.97 g, 14.9 mmol) and sodium iodide (1.12 g, 7.50 mmol) were added to a solution of tert-butyl (4-chloro-3-hydroxybutan-2-yl)carbamate (1.67 g, 7.50 mmol) in DMSO (17 mL). The mixture was stirred at 100° C. for 5 hours. The mixture was poured into water (50 mL) and extracted with EtOAc (50 mL×3). The combined organic layers were dried over anhydrous sodium sulfate, filtered, and concentrated under reduced pressure. The residue was purified by column chromatography on silica (petroleum ether/ethyl acetate) to give tert-butyl (4-azido-3-hydroxybutan-2-yl)carbamate as yellow oil. MS ESI calcd. for C$_9$H$_{19}$N$_4$O$_3$ [M+H]$^+$ 231. found 231.
Step 5:
NaH (2.78 g, 69.6 mmol) was added to a solution of tert-butyl (4-azido-3-hydroxybutan-2-yl)carbamate (1.60 g, 6.96 mmol) in THF (1 mL) at 0° C. The mixture was stirred at 30° C. for 16 hours under N$_2$ atmosphere. After cooled to 20° C., the mixture was diluted with cooled water (1 mL) and extracted with EtOAc (50 mL×3). The combined organic layers were dried over anhydrous sodium sulfate, filtered, and concentrated under reduced pressure. The residue was purified by column chromatography on silica (petroleum ether/ethyl acetate) to afford 5-(azidomethyl)-4-methyloxazolidin-2-one as colorless oil. $^1$HNMR (400 MHz, CDCl$_3$) δ 5.82 (s, 1H), 4.72-4.67 (m, 1H), 4.09-4.05 (m, 1H), 3.68-3.64 (m, 1H), 3.51-3.47 (m, 1H), 1.25 (d, J=6.8 Hz, 3H).

Preparative Example 40

5-(azidomethyl)-5-methyloxazolidin-2-one

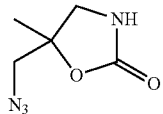

Step 1:

To a mixture of potassium cyanate (1.52 g, 18.8 mmol) in water (72 mL) was slowly added 2-(chloromethyl)-2-methyloxirane (1.00 g, 9.39 mmol). Upon completion of addition the mixture was heated to reflux overnight. The reaction mixture was cooled to 40° C. and extracted while warm with ethyl acetate (35 mL×5). The combined organic layers were dried over anhydrous sodium sulfate and concentrated under reduced pressure to give the desired compound 5-(chloromethyl)-5-methyloxazolidin-2-one as colorless oil. $^1$H NMR (300 MHz, CDCl$_3$) δ 5.66 (brs, 1H), 3.73-3.64 (m, 2H), 3.59-3.52 (m, 1H), 3.34 (d, J=2.0 Hz, 1H), 1.59 (s, 3H).

Step 2:

A solution of 5-(chloromethyl)-5-methyloxazolidin-2-one (800 mg, 5.35 mmol) and sodium azide (1.04 g, 16.0 mmol) in DMF (8 mL) was stirred at 80° C. for 12 hours. The reaction was cooled to room temperature and water (50 mL) was added. The mixture was extracted with EtOAc (50 mL×3), dried over anhydrous sodium sulfate and concentrated under reduced pressure to give the crude compound 5-(azidomethyl)-5-methyloxazolidin-2-one as a colorless oil which was used as is in the next step.

Preparative Example 41

5-(azidomethyl)-2-(benzyloxy)pyridine

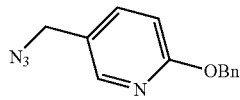 [SMILES: [N-]=[N+]=NCc1ccc(OCc2ccccc2)nc1]

A mixture of 2-(benzyloxy)-5-(bromomethyl)pyridine (400 mg, 1.44 mmol) and NaN$_3$ (188 mg, 2.88 mmol) in DMF (3 mL) was stirred at 80° C. under N$_2$ for 12 hours. The mixture was diluted with H$_2$O (20 mL) and extracted with EtOAc (30 mL×3). The EtOAc layer was washed with brine and dried over anhydrous sodium sulfate and concentrated under reduced pressure to give 5-(azidomethyl)-2-(benzyloxy)pyridine as a yellow solid. MS ESI calc'd. for C$_{13}$H$_{13}$N$_4$O [M+H]$^+$ 241. found 241.

Preparative Example 42

7-(azidomethyl)-6-oxa-4-azaspiro[2.4]heptan-5-one

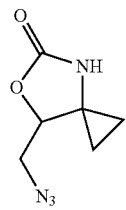

Step 1:

To a solution of tert-butyl (1-(1,2-dihydroxyethyl)cyclopropyl)carbamate (6.90 g, 31.8 mmol) in THF (150 mL) under a nitrogen atmosphere was added sodium hydride (13.6 g, 0.340 mol) at room temperature. The mixture was stirred for 16 hours at 30° C., cooled to 20° C., and the mixture was diluted with water (1 mL). The mixture was dried over anhydrous sodium sulfate, concentrated under reduced pressure and the residue was purified by column chromatography on silica (10:1 dichloromethane/methanol, Rf=0.4) to give 7-(hydroxymethyl)-6-oxa-4-azaspiro[2.4]heptan-5-one as a yellow solid. MS ESI calcd. for C$_6$H$_{10}$NO$_3$ [M+H]$^+$ 144. found 144.

Step 2:

To a solution of 7-(hydroxymethyl)-6-oxa-4-azaspiro[2.4]heptan-5-one (1.00 g, 6.94 mmol) in DCM (36 mL) was added methanesulfonyl chloride (0.950 g, 8.33 mmol) and TEA (1.93 mL, 13.9 mmol) at 0° C. The mixture was stirred at room temperature for 3 hours. The mixture was poured into water (20 mL) and extracted with ethyl acetate (50 mL×3). The combined organic layers were dried over anhydrous sodium sulfate and concentrated under reduced pressure. The residue was purified by column chromatography on silica (100% EtOAc, Rf=0.6) to afford (5-oxo-6-oxa-4-azaspiro[2.4]heptan-7-yl)methyl methanesulfonate as yellow oil. MS ESI calcd. for C$_7$H$_{12}$NO$_5$S [M+H]$^+$ 222. found 222.

Step 3:

To a solution of (5-oxo-6-oxa-4-azaspiro[2.4]heptan-7-yl)methyl methanesulfonate (1.50 g, 6.80 mmol) in DMSO (15 mL) was added sodium azide (0.878 g, 13.5 mmol) and sodium iodide (1.02 g, 6.80 mmol). The mixture was stirred at 100° C. for 5 hours. The mixture was poured into water (20 mL) and extracted with EtOAc (20 mL×3). The combined organic layers were dried over anhydrous sodium sulfate and concentrated under reduced pressure. The residue was purified by column chromatography on silica (100% EtOAc, Rf=0.6) to give 7-(azidomethyl)-6-oxa-4-azaspiro[2.4]heptan-5-one as yellow oil. $^1$H NMR (400 MHz, CDCl$_3$) δ 5.42 (brs, 1H), 4.58 (t, T=4.8 Hz, 1H), 3.55-3.42 (m, 2H), 1.04-0.98 (m, 3H), 0.82-0.70 (m, 1H).

Preparative Example 43

6-Azido-1-methylcyclohex-1-ene

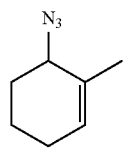

Step 1:

A mixture of 1-methylcyclohex-1-ene (2.66 g, 27.6 mmol), NBS (4.92 g, 27.6 mmol) in acetone (20 mL) and H$_2$O (10 mL) was stirred under N$_2$ at 10° C. for 3 hours. After evaporation of acetone, water was added and the product was extracted with DCM. The organic layer was successively washed with water and brine, dried over anhydrous sodium sulfate and concentrated under reduced pressure to afford crude 2-bromo-1-methylcyclohexanol. MS ESI calc'd. for C$_7$H$_{14}$BrO [M+H]$^+$ 193, 195 found 193, 195.

Step 2:
Boron trifluoride (3.61 mL, 27.6 mmol) was added to a mixture of 2-bromo-1-methylcyclohexanol (5.33 g, 27.6 mmol) in dry DCM (125 mL), and the reaction mixture was refluxed for 1 hour. The reaction was quenched with aqueous NaHCO$_3$ (100 mL) and extracted with 2-methoxy-2-methylpropane. Organic layer was successively washed with water and brine, dried over anhydrous sodium sulfate and concentrated under reduced pressure to afford crude 6-bromo-1-methylcyclohex-1-ene. $^1$H NMR (400 MHz, CDCl$_3$) δ 5.61-5.60 (m, 1H), 4.67 (s, 1H), 2.20-2.16 (m, 2H), 1.97-1.90 (m, 2H), 1.81 (s, 3H), 1.62-1.52 (m, 2H). MS ESI calc'd. for C$_7$H$_{12}$Br [M+H]$^+$ 175, 177 found 175, 177.

Step 3:
A solution of 6-bromo-1-methylcyclohex-1-ene (500 mg, 2.86 mmol) and NaN$_3$ (278 mg, 4.28 mmol) in DMF (5 mL) was stirred at 80° C. for 12 hours. After water (50 mL) was added. Then mixture was extracted with EtOAc (50 mL×3), dried over anhydrous sodium sulfate and concentrated under reduced pressure to give the crude 6-azido-1-methylcyclohex-1-ene.

Preparative Example 44

3-Azido-1-methylcyclohex-1-ene

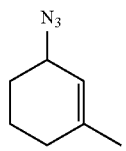

Step 1:
LnCl$_3$ (22.3 g, 0.091 mol) and NaBH$_4$ (3.45 g, 0.0909 mol) were slowly added with string at 0° C. to a solution of 3-methylcycloex-2-enone (10.0 g, 0.091 mol) in methanol (227 mL). The mixture was stirred at 15° C. for 10 minutes. Saturated NH$_4$Cl (200 mL) was added to the mixture and extracted with dichloromethane (300 mL). The organic layer was washed with brine (100 mL), dried over anhydrous sodium sulfate, and concentrated under reduced pressure to afford 3-methylcyclohex-2-enol as a yellow oil, which was used in the next step without further purification. $^1$H NMR: (400 MHz, DMSO-d$_6$) δ 5.39-5.30 (m, 1H), 4.50 (d, J=5.2 Hz, 1H), 3.95 (s, 1H), 1.87-1.72 (m, 2H), 1.71-1.63 (m, 2H), 1.60 (s, 3H), 1.48-1.29 (m, 2H).

Step 2:
Triphenylphosphine (16.4 g, 62.5 mmol) was added to a mixture of 3-methylcyclohex-2-enol (5.00 g, 0.0446 mol) in perchloromethane (60 mL) at 0° C. The mixture was stirred at 70° C. for 16 hours. The mixture was cooled to 0° C. and petroleum ether (80 mL) was added. The suspension was filtered off and washed with petroleum ether. The volatile was removed under reduced pressure. The residue was distilled (38-42° C., 3.0 mmHg) to give 3-chloro-1-methylcyclohex-1-ene as a yellow oil. $^1$H NMR (400 MHz, CDCl$_3$) δ 5.63-5.55 (m, 1H), 4.67 (d, J=2.4 Hz, 1H), 2.06-1.87 (m, 6H), 1.72 (s, 3H).

Step 3:
NaN$_3$ (1.00 g, 15.4 mmol) and NaI (0.116 g, 0.769 mmol) were added to a mixture of 3-chloro-1-methylcyclohex-1-ene (1.00 g, 7.69 mmol) in DMF (20 mL). The mixture was stirred at 70° C. for 16 hours. After cooled to 20° C., the mixture was diluted with saturated brine (50 mL). The mixture was extracted with dichloromethane (100 mL×3), dried over anhydrous sodium sulfate and concentrated under reduced pressure to give 3-azido-1-methylcyclohex-1-ene as a yellow oil, which was used in the next step without further purification.

EXAMPLES

The following Examples presented in the below tables are defined as Formulae Ix or Iy:

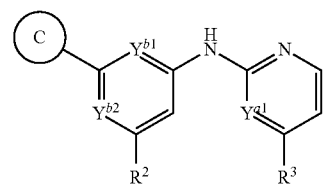

Formula Ix: $Y^{a1}=Y^{b2}=CH$ and $Y^{b1}=N$; or

Formula Iy: $Y^{a1}=N$ and $Y^{b1}=Y^{b2}=CH$;

and ring C:

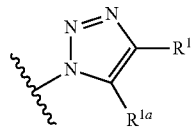
C1

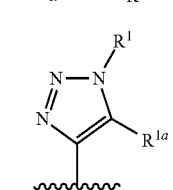
C2

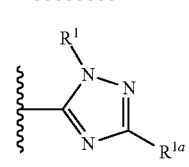
C3

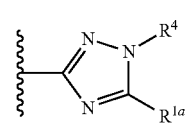
C4

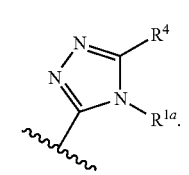
C5

Example 1.1

Methyl N-{(2S)-2-[4-(4-methyl-6-{[4-(trifluoromethyl)pyridin-2-yl]amino}pyridin-2-yl)-1H-1,2,3-triazol-1-yl]propanoyl}glycinate trifluoroacetate

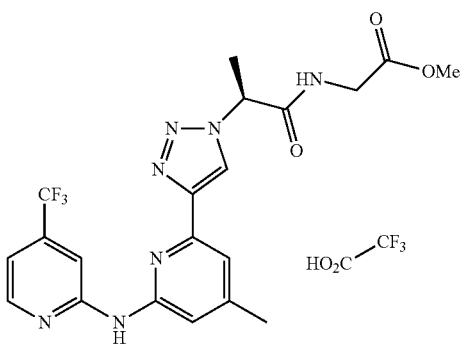 [SMILES: COC(=O)CNC(=O)[C@H](C)n1cc(-c2cc(C)cc(Nc3cc(C(F)(F)F)ccn3)n2)nn1 ; O=C(O)C(F)(F)F]

In a microwave tube, (2S)-2-[4-(4-methyl-6-{[4-(trifluoromethyl)pyridin-2-yl]amino}pyridin-2-yl)-1H-1,2,3-triazol-1-yl]propanoic acid (70 mg, 0.18 mmol), methyl glycinate hydrochloride (44.8 mg, 0.357 mmol), HATU (136 mg, 0.357 mmol), and N-ethyl-N-(propan-2-yl)propan-2-amine (125 µl, 0.714 mmol) were taken up in DMF (1784 µl). The mixture was sealed and stirred at 65° C. overnight. The reaction was diluted with acetonitrile (1 mL) and filtered. The crude product was purified by reverse phase HPLC (ACN/water with 0.1% TFA modifier) to afford methyl N-{(2S)-2-[4-(4-methyl-6-{[4-(trifluoromethyl)pyridin-2-yl]amino}pyridin-2-yl)-1H-1,2,3-triazol-1-yl]propanoyl}glycinate trifluoroacetate as a brown solid. MS ESI calcd. for $C_{20}H_{21}F_3N_7O_3$ [M+H]$^+$ 464. found 464. $^1$H NMR (500 MHz, DMSO-d$_6$) δ 10.55 (s, 1H), 8.95-8.93 (m, 1H), 8.52 (d, J=5.5 Hz, 1H), 8.48 (s, 1H), 8.38 (s, 1H), 7.50 (s, 1H), 7.26 (d, J=5.0 Hz, 1H), 7.25 (s, 1H), 5.59 (q, J=7.0 Hz, 1H), 3.92 (d, J=6.5 Hz, 2H), 3.60 (s, 3H), 2.38 (s, 3H), 1.73 (d, J=7.0 Hz, 3H).

Example 1.2

N-(1,1-Dioxidotetrahydrothiophen-3-yl)-2-[4-(4-methyl-6-{[4-(trifluoromethyl)pyridin-2-yl]amino}pyridin-2-yl)-1H-1,2,3-triazol-1-yl]propanamide (racemic)

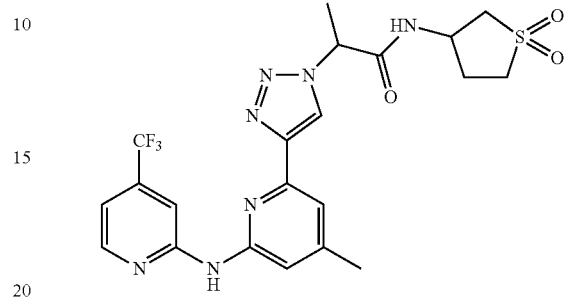

In a microwave tube, 2-[4-(4-methyl-6-{[4-(trifluoromethyl)pyridin-2-yl]amino}pyridin-2-yl)-1H-1,2,3-triazol-1-yl]propanoic acid (100 mg, 0.255 mmol), tetrahydrothiophen-3-amine 1,1-dioxide hydrochloride (65.6 mg, 0.382 mmol), and N-ethyl-N-(propan-2-yl)propan-2-amine (178 µl, 1.02 mmol) were taken up in DMF (1699 µl) at room temperature. T3P (223 µl, 50 wt % in DMF, 0.382 mmol) was added, and the reaction was sealed and stirred overnight. The reaction mixture was diluted with methanol (1 mL) and filtered. The crude product was purified by reverse phase HPLC (ACN/water with 0.1% TFA modifier) to afford N-(1,1-dioxido-tetrahydrothiophen-3-yl)-2-[4-(4-methyl-6-{[4-(trifluoromethyl)pyridin-2-yl]amino}-pyridin-2-yl)-1H-1,2,3-triazol-1-yl]propanamide (racemic) as a yellow solid. MS ESI calcd. for $C_{21}H_{23}F_3N_7O_3S$ [M+H]$^+$ 510. found 510. $^1$H NMR (500 MHz, DMSO-d$_6$) δ 10.21 (s, 1H), 8.99 (s, 1H), 8.58 (d, J=4.0 Hz, 1H), 8.48 (d, J=5.0 Hz, 1H), 8.32 (d, J=2.0 Hz, 1H), 7.44 (s, 1H), 7.25 (d, J=3.0 Hz, 1H), 7.19 (d, J=5.0 Hz, 1H), 5.47-5.44 (m, 1H), 4.48-4.44 (m, 1H), 3.46-3.39 (m, 1H), 3.32-3.25 (m, 1H), 3.19-3.13 (m, 1H), 2.98-2.85 (m, 1H), 2.43-2.37 (m, 1H), 2.34 (s, 3H), 2.11-2.01 (m, 1H), 1.73-1.71 (m, 3H).

The following compounds in Table 1 were prepared according to the method described for Example 1.1 or Example 1.2. $R^{1a}$ is H in the compounds in Table 1.

TABLE 1

| Ex. | C Ring/A & B Rings | $R^1$ | $R^2$ | $R^3$ | Chemical Name | [M + H]+ Calc'd/Observed |
|---|---|---|---|---|---|---|
| 1.3 | C2/Ix | (CH$_2$)$_2$CONH$_2$ | CH$_3$ | CF$_3$ | 3-[4-(4-methyl-6-{[4-(trifluoromethyl)pyridin-2-yl]amino}pyridin-2-yl)-1H-1,2,3-triazol-1-yl]propanamide | 392/392 |
| 1.4 | C2/Ix | ![structure: H2N-C(=O)-cyclohexyl with gem-dimethyl] | CH$_3$ | CF$_3$ | 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxamide | 474/474 |

TABLE 1-continued

| Ex. | C Ring/A & B Rings | R¹ | R² | R³ | Chemical Name | [M + H]+ Calc'd/Observed |
|---|---|---|---|---|---|---|
| 1.5 | C2/Ix | (2,2-dimethylcyclohexanecarboxamide) | CH₃ | CF₃ | 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxamide | 474/474 |
| 1.6 | C2/Ix | (2,2-dimethylcyclohexanecarboxamide) | CH₃ | CF₃ | 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxamide | 474/474 |
| 1.7 | C2/Ix | (cyclohexanecarboxamide) | CH₃ | CF₃ | 4-[4-(3-methyl-5-{[4-(trifluoromethyl)pyrimidin-2-yl]amino}phenyl)-1H-1,2,3-triazol-1-yl]cyclohexanecarboxamide | 446/446 |
| 1.8 | C2/Ix | (2,2-dimethylcyclohexanecarboxamide) | CH₃ | CF₃ | 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxamide | 474/474 |
| 1.9 | C2/Ix TFA salt | (4-carbamoylphenyl-1-hydroxymethylethyl) | CH₃ | CF₃ | 4-{2-hydroxy-1-[4-(4-methyl-6-{[4-(trifluoromethyl)pyridin-2-yl]amino}pyridin-2-yl)-1H-1,2,3-triazol-1-yl]ethyl}benzamide | 484/484 |
| 1.10 | C2/Ix TFA salt | (4-carbamoylphenyl-hydroxyethyl) | CH₃ | CF₃ | 4-{1-hydroxy-2-[4-(4-methyl-6-{[4-(trifluoromethyl)pyridin-2-yl]amino}pyridin-2-yl)-1H-1,2,3-triazol-1-yl]ethyl}benzamide | 484/484 |

TABLE 1-continued

| Ex. | C Ring/A & B Rings | R¹ | R² | R³ | Chemical Name | [M + H]+ Calc'd/Observed |
|---|---|---|---|---|---|---|
| 1.11 | C2/Ix | (1,2,3,4-tetrahydronaphthalene-1-carboxamide group) | CH₃ | CF₃ | 4-[4-(4-methyl-6-{[4-(trifluoromethyl)pyridin-2-yl]amino}pyridin-2-yl)-1H-1,2,3-triazol-1-yl]-1,2,3,4-tetrahydronaphthalene-1-carboxamide | 494/494 |
| 1.12 | C2/Ix | (2-hydroxy-2-methylpropanamide group) | CH₃ | CF₃ | 2-hydroxy-2-methyl-3-[4-(4-methyl-6-{[4-(trifluoromethyl)pyridin-2-yl]amino}pyridin-2-yl)-1H-1,2,3-triazol-1-yl]propanamide | 422/422 |
| 1.13 | C2/Ix | (S)-2-hydroxypropanamide group | CH₃ | CF₃ | (2S)-2-hydroxy-3-[4-(4-methyl-6-{[4-(trifluoromethyl)pyridin-2-yl]amino}pyridin-2-yl)-1H-1,2,3-triazol-1-yl]propanamide | 408/408 |
| 1.14 | C2/Ix | (R)-2-hydroxypropanamide group | CH₃ | CF₃ | (2R)-2-hydroxy-3-[4-(4-methyl-6-{[4-(trifluoromethyl)pyridin-2-yl]amino}pyridin-2-yl)-1H-1,2,3-triazol-1-yl]propanamide | 408/408 |
| 1.15 | C2/Ix | (4-carbamoylphenyl group) | CH₃ | CF₃ | 4-[4-(4-methyl-6-{[4-(trifluoromethyl)pyridin-2-yl]amino}pyridin-2-yl)-1H-1,2,3-triazol-1-yl]benzamide | 440/440 |
| 1.16 | C2/Ix TFA Salt | 1-(4-carbamoylphenyl)ethyl group | CH₃ | CF₃ | 4-{1-[4-(4-methyl-6-{[4-(trifluoromethyl)pyridin-2-yl]amino}pyridin-2-yl)-1H-1,2,3-triazol-1-yl]ethyl}benzamide | 468/468 |

TABLE 1-continued

| Ex. | C Ring/A & B Rings | R¹ | R² | R³ | Chemical Name | [M + H]+ Calc'd/Observed |
|---|---|---|---|---|---|---|
| 1.17 | C2/Ix TFA Salt | 4-fluorophenyl-CH(C(O)NH₂)- | CH₃ | CF₃ | 2-(4-fluorophenyl)-2-[4-(4-methyl-6-{[4-(trifluoromethyl)pyridin-2-yl]amino}pyridin-2-yl)-1H-1,2,3-triazol-1-yl]acetamide | 472/472 |
| 1.18 | C2/Ix TFA Salt | phenyl-CH(C(O)NH₂)- | CH₃ | CF₃ | 2-[4-(4-methyl-6-{[4-(trifluoromethyl)pyridin-2-yl]amino}pyridin-2-yl)-1H-1,2,3-triazol-1-yl]-2-phenylacetamide | 454/454 |
| 1.19 | C2/Ix | R, racemic proline | CH₃ | CF₃ | 1-{(2R)-2-[4-(4-methyl-6-{[4-(trifluoromethyl)pyridin-2-yl]amino}pyridin-2-yl)-1H-1,2,3-triazol-1-yl]propanoyl}prolinamide | 489/489 |
| 1.20 | C2/Ix | S, racemic proline | CH₃ | CF₃ | 1-{(2S)-2-[4-(4-methyl-6-{[4-(trifluoromethyl)pyridin-2-yl]amino}pyridin-2-yl)-1H-1,2,3-triazol-1-yl]propanoyl}prolinamide | 489/489 |
| 1.21 | C2/Ix | R | CH₃ | CF₃ | (2R)-N-(2-amino-2-oxoethyl)-2-[4-(4-methyl-6-{[4-(trifluoromethyl)pyridin-2-yl]amino}pyridin-2-yl)-1H-1,2,3-triazol-1-yl]propanamide | 449/449 |
| 1.22 | C2/Ix | S | CH₃ | CF₃ | (2S)-N-(2-amino-2-oxoethyl)-2-[4-(4-methyl-6-{[4-(trifluoromethyl)pyridin-2-yl]amino}pyridin-2-yl)-1H-1,2,3-triazol-1-yl]propanamide | 449/449 |

TABLE 1-continued

| Ex. | C Ring/A & B Rings | R¹ | R² | R³ | Chemical Name | [M + H]+ Calc'd/Observed |
|---|---|---|---|---|---|---|
| 1.23 | C2/Ix TFA Salt | (structure) R | $CH_3$ | $CF_3$ | (2R)-2-[4-(4-methyl-6-{[4-(trifluoromethyl)pyridin-2-yl]amino}pyridin-2-yl)-1H-1,2,3-triazol-1-yl]propanamide | 392/392 |
| 1.24 | C2/Ix TFA Salt | (structure) S | $CH_3$ | $CF_3$ | (2S)-2-[4-(4-methyl-6-{[4-(trifluoromethyl)pyridin-2-yl]amino}pyridin-2-yl)-1H-1,2,3-triazol-1-yl]propanamide | 392/392 |
| 1.25 | C2/Ix | (structure) racemic | $CH_3$ | $CF_3$ | 2-[4-(4-methyl-6-{[4-(trifluoromethyl)pyridin-2-yl]amino}pyridin-2-yl)-1H-1,2,3-triazol-1-yl]propanamide | 392/392 |
| 1.26 | C2/Ix | (structure) | $CH_3$ | $CF_3$ | (2E)-4-[4-(4-methyl-6-{[4-(trifluoromethyl)pyridin-2-yl]amino}pyridin-2-yl)-1H-1,2,3-triazol-1-yl]but-2-enamide | 404 |
| 1.27 | C2/Ix Formate Salt | (structure) R or S, R | $CH_3$ | $CF_3$ | N-[(1R)-1-benzyl-2-hydroxyethyl]-2-[4-(4-methyl-6-{[4-(trifluoromethyl)pyridin-2-yl]amino}pyridin-2-yl)-1H-1,2,3-triazol-1-yl]propanamide | 526/526 |
| 1.28 | C2/Ix Formate Salt | (structure) racemic | $CH_3$ | $CF_3$ | 6-{1-[2-(3,4-dihydroisoquinolin-2(1H)-yl)-1-methyl-2-oxoethyl]-1H-1,2,3-triazol-4-yl}-4-methyl-N-[4-(trifluoromethyl)pyridin-2-yl]pyridin-2-amine | 508/508 |
| 1.29 | C2/Ix Formate Salt | (structure) racemic | $CH_3$ | $CF_3$ | N-[2-(1H-indol-3-yl)ethyl]-2-[4-(4-methyl-6-{[4-(trifluoromethyl)pyridin-2-yl]amino}pyridin-2-yl)-1H-1,2,3-triazol-1-yl]propanamide | 535/535 |

TABLE 1-continued

| Ex. | C Ring/A & B Rings | R¹ | R² | R³ | Chemical Name | [M + H]+ Calc'd/Observed |
|---|---|---|---|---|---|---|
| 1.30 | C2/Ix Formate Salt | (structure: 2-{[2-(5-(benzyloxy)-1H-indol-3-yl)ethyl]amino}-2-oxo group, racemic) | CH₃ | CF₃ | N-{2-[5-(benzyloxy)-1H-indol-3-yl]ethyl}-2-[4-(4-methyl-6-{[4-(trifluoromethyl)pyridin-2-yl]amino}pyridin-2-yl)-1H-1,2,3-triazol-1-yl]propanamide | 641/641 |
| 1.31 | C2/Ix Formate Salt | (structure: tetrahydro-β-carboline acyl, racemic) | CH₃ | CF₃ | 4-methyl-6-{1-[1-methyl-2-oxo-2-(1,3,4,9-tetrahydro-2H-beta-carbolin-2-yl)ethyl]-1H-1,2,3-triazol-4-yl}-N-[4-(trifluoromethyl)pyridin-2-yl]pyridin-2-amine | 547/547 |
| 1.32 | C2/Ix Formate Salt | (structure: N-(2-(naphthalen-2-yl)ethyl)propanamide, racemic) | CH₃ | CF₃ | 2-[4-(4-methyl-6-{[4-(trifluoromethyl)pyridin-2-yl]amino}pyridin-2-yl)-1H-1,2,3-triazol-1-yl]-N-(2-naphthalen-2-ylethyl)propanamide | 546/546 |

TABLE 1-continued

| Ex. | C Ring/A & B Rings | R¹ | R² | R³ | Chemical Name | [M + H]+ Calc'd/Observed |
|---|---|---|---|---|---|---|
| 1.33 | C2/Ix Formate Salt | (2,1,3-benzothiadiazol-4-ylmethyl)amide group, racemic | CH₃ | CF₃ | N-(2,1,3-benzothiadiazol-4-ylmethyl)-2-[4-(4-methyl-6-{[4-(trifluoromethyl)pyridin-2-yl]amino}pyridin-2-yl)-1H-1,2,3-triazol-1-yl]propanamide | 540/540 |
| 1.34 | C2/Ix Formate Salt | 6,7-dimethoxy-3-methyl-3,4-dihydroisoquinolin-2(1H)-yl acyl group | CH₃ | CF₃ | 6-{1-[2-(6,7-dimethoxy-3-methyl-3,4-dihydroisoquinolin-2(1H)-yl)-1-methyl-2-oxoethyl]-1H-1,2,3-triazol-4-yl}-4-methyl-N-[4-(trifluoromethyl)pyridin-2-yl]pyridin-2-amine | 582/582 |
| 1.35 | C2/Ix Formate Salt | 1-[1-(2-fluorophenyl)-1H-pyrazol-4-yl]ethylamide group | CH₃ | CF₃ | N-{1-[1-(2-fluorophenyl)-1H-pyrazol-4-yl]ethyl}-2-[4-(4-methyl-6-{[4-(trifluoromethyl)pyridin-2-yl]amino}pyridin-2-yl)-1H-1,2,3-triazol-1-yl]propanamide | 580/580 |
| 1.36 | C2/Ix Formate Salt | 2-(3-phenoxyphenyl)ethylamide group | CH₃ | CF₃ | 2-[4-(4-methyl-6-{[4-(trifluoromethyl)pyridin-2-yl]amino}pyridin-2-yl)-1H-1,2,3-triazol-1-yl]-N-[2-(3-phenoxyphenyl)ethyl]propanamide | 588/588 |

TABLE 1-continued

| Ex. | C Ring/A & B Rings | R¹ | R² | R³ | Chemical Name | [M + H]+ Calc'd/Observed |
|---|---|---|---|---|---|---|
| 1.37 | C2/Ix Formate Salt | (structure: methyl group with NH-CH2- linked to isoxazole bearing furan-2-yl) | CH₃ | CF₃ | N-[(5-furan-2-ylisoxazol-3-yl)methyl]-2-[4-(4-methyl-6-{[4-(trifluoromethyl)pyridin-2-yl]amino}pyridin-2-yl)-1H-1,2,3-triazol-1-yl]propanamide | 539/539 |
| 1.38 | C2/Ix Formate Salt | (structure: 2,5-dimethoxyphenyl with hydroxy and methyl substituents on amide) | CH₃ | CF₃ | N-[2-(2,5-dimethoxyphenyl)-2-hydroxy-1-methylethyl]-2-[4-(4-methyl-6-{[4-(trifluoromethyl)pyridin-2-yl]amino}pyridin-2-yl)-1H-1,2,3-triazol-1-yl]propanamide | 586/586 |
| 1.39 | C2/Ix Formate Salt | (structure: 3-(4-fluorophenyl)-6,7-dihydroisoxazolo[4,5-c]pyridin-5(4H)-yl; racemic) | CH₃ | CF₃ | 6-(1-{2-[3-(4-fluorophenyl)-6,7-dihydroisoxazolo[4,5-c]pyridin-5(4H)-yl]-1-methyl-2-oxoethyl}-1H-1,2,3-triazol-4-yl)-4-methyl-N-[4-(trifluoromethyl)pyridin-2-yl]pyridin-2-amine | 593/593 |
| 1.40 | C2/Ix Formate Salt | (structure: (1S,2R)-2-phenylcyclopropyl amide; R or S, R or S) | CH₃ | CF₃ | 2-[4-(4-methyl-6-{[4-(trifluoromethyl)pyridin-2-yl]amino}pyridin-2-yl)-1H-1,2,3-triazol-1-yl]-N-[(1S,2R)-2-phenylcyclopropyl]propanamide | 508/508 |

TABLE 1-continued

| Ex. | C Ring/A & B Rings | R¹ | R² | R³ | Chemical Name | [M + H]+ Calc'd/Observed |
|---|---|---|---|---|---|---|
| 1.41 | C2/Ix Formate Salt | (structure: 6-chloro-1,3,4,5-tetrahydro-2H-pyrido[4,3-b]indol-2-yl acyl group, racemic) | CH₃ | CF₃ | 6-{1-[2-(6-chloro-1,3,4,5-tetrahydro-2H-pyrido[4,3-b]indol-2-yl)-1-methyl-2-oxoethyl]-1H-1,2,3-triazol-4-yl}-4-methyl-N-[4-(trifluoromethyl)pyridin-2-yl]pyridin-2-amine | 581/581 |
| 1.42 | C2/Ix Formate Salt | (structure: 2-phenoxyphenyl ethyl amide, racemic) | CH₃ | CF₃ | 2-[4-(4-methyl-6-{[4-(trifluoromethyl)pyridin-2-yl]amino}pyridin-2-yl)-1H-1,2,3-triazol-1-yl]-N-[2-(2-phenoxyphenyl)ethyl]propanamide | 588/588 |
| 1.43 | C2/Ix Formate Salt | (structure: (7-fluoro-2-oxo-1,2-dihydroquinolin-3-yl)methyl amide, racemic) | CH₃ | CF₃ | N-[(7-fluoro-2-oxo-1,2-dihydroquinolin-3-yl)methyl]-2-[4-(4-methyl-6-{[4-(trifluoromethyl)pyridin-2-yl]amino}pyridin-2-yl)-1H-1,2,3-triazol-1-yl]propanamide | 567/567 |

TABLE 1-continued

| Ex. | C Ring/A & B Rings | R¹ | R² | R³ | Chemical Name | [M + H]+ Calc'd/Observed |
|---|---|---|---|---|---|---|
| 1.44 | C2/Ix Formate Salt | (structure, racemic) | CH₃ | CF₃ | 2-[4-(4-methyl-6-{[4-(trifluoromethyl)pyridin-2-yl]amino}pyridin-2-yl)-1H-1,2,3-triazol-1-yl]-N-(2-naphthalen-1-ylethyl)propanamide | 546/546 |
| 1.45 | C2/Ix Formate Salt | (structure, R or S, R or S) | CH₃ | CF₃ | 6-(1-{2-[2-(4-methoxyphenyl)thiomorpholin-4-yl]-1-methyl-2-oxoethyl}-1H-1,2,3-triazol-4-yl)-4-methyl-N-[4-(trifluoromethyl)pyridin-2-yl]pyridin-2-amine | 584/584 |
| 1.46 | C2/Ix Formate Salt | (structure, racemic) | CH₃ | CF₃ | 2-[4-(4-methyl-6-{[4-(trifluoromethyl)pyridin-2-yl]amino}pyridin-2-yl)-1H-1,2,3-triazol-1-yl]-N-[2-(4-phenoxyphenyl)ethyl]propanamide | 588/588 |
| 1.47 | C2/Ix Formate Salt | (structure, racemic) | CH₃ | CF₃ | N-[(5-methyl-3-phenylisoxazol-4-yl)methyl]-2-[4-(4-methyl-6-{[4-(trifluoromethyl)pyridin-2-yl]amino}pyridin-2-yl)-1H-1,2,3-triazol-1-yl]propanamide | 563/563 |

TABLE 1-continued

| Ex. | C Ring/A & B Rings | R¹ | R² | R³ | Chemical Name | [M + H]+ Calc'd/Observed |
|---|---|---|---|---|---|---|
| 1.48 | C2/Ix Formate Salt | (6-methoxy-tetrahydro-β-carboline acyl group) racemic | $CH_3$ | $CF_3$ | 6-{1-[2-(6-methoxy-1,3,4,9-tetrahydro-2H-beta-carbolin-2-yl)-1-methyl-2-oxoethyl]-1H-1,2,3-triazol-4-yl}-4-methyl-N-1.[4-(trifluoromethyl)pyridin-2-yl]pyridin-2-amine | 577/577 |
| 1.49 | C2/Ix Formate Salt | (4-(4-fluorophenyl)tetrahydropyran-4-yl)methylamide | $CH_3$ | $CF_3$ | N-{[4-(4-fluorophenyl)tetrahydro-2H-pyran-4-yl]methyl}-2-[4-(4-methyl-6-{[4-(trifluoromethyl)pyridin-2-yl]amino}pyridin-2-yl)-1H-1,2,3-triazol-1-yl]propanamide | 584/584 |
| 1.50 | C2/Ix Formate Salt | (4-benzyl-3-phenylpiperazinyl acyl) R or S, R or S | $CH_3$ | $CF_3$ | 6-{1-[2-(4-benzyl-3-phenylpiperazin-1-yl)-1-methyl-2-oxoethyl]-1H-1,2,3-triazol-4-yl}-4-methyl-N-[4-(trifluoromethyl)pyridin-2-yl]pyridin-2-amine | 627/627 |
| 1.51 | C2/Ix Formate Salt | (2-(1-methylindol-3-yl)ethyl)amide | $CH_3$ | $CF_3$ | N-[2-(1-methyl-1H-indol-3-yl)ethyl]-2-[4-(4-methyl-6-{[4-(trifluoromethyl)pyridin-2-yl]amino}pyridin-2-yl)-1H-1,2,3-triazol-1-yl]propanamide | 549/549 |

TABLE 1-continued

| Ex. | C Ring/A & B Rings | R¹ | R² | R³ | Chemical Name | [M + H]+ Calc'd/Observed |
|---|---|---|---|---|---|---|
| 1.52 | C2/Ix Formate Salt | (structure with morpholine, CF₃-phenyl, amide) | CH₃ | CF₃ | 2-[4-(4-methyl-6-{[4-(trifluoromethyl)pyridin-2-yl]amino}pyridin-2-yl)-1H-1,2,3-triazol-1-yl]-N-{2-morpholin-4-yl-2-[4-(trifluoromethyl)phenyl]ethyl}propanamide | 649/649 |
| 1.53 | C2/Ix Formate Salt | (structure with pyrrolidine, pyridine) R or S, R or S | CH₃ | CF₃ | 4-methyl-6-{1-[1-methyl-2-oxo-2-(3-pyridin-4-ylpyrrolidin-1-yl)ethyl]-1H-1,2,3-triazol-4-yl}-N-[4-(trifluoromethyl)pyridin-2-yl]pyridin-2-amine | 523/523 |
| 1.54 | C2/Ix Formate Salt | (structure with benzazepine diol, phenyl) R or S, R or S | CH₃ | CF₃ | 3-{2-[4-(4-methyl-6-{[4-(trifluoromethyl)pyridin-2-yl]amino}pyridin-2-yl)-1H-1,2,3-triazol-1-yl]propanoyl}-1-phenyl-2,3,4,5-tetrahydro-1H-3-benzazepine-7,8-diol | 630 |
| 1.55 | C2/Ix TFA salt | (methyl prolinate structure) R, racemic proline | CH₃ | CF₃ | methyl 1-{(2R)-2-[4-(4-methyl-6-{[4-(trifluoromethyl)pyridin-2-yl]amino}pyridin-2-yl)-1H-1,2,3-triazol-1-yl]propanoyl}prolinate | 504/504 |
| 1.56 | C2/Ix TFA salt | (methyl prolinate structure) S, racemic proline | CH₃ | CF₃ | methyl 1-{(2S)-2-[4-(4-methyl-6-{[4-(trifluoromethyl)pyridin-2-yl]amino}pyridin-2-yl)-1H-1,2,3-triazol-1-yl]propanoyl}prolinate | 504/504 |

TABLE 1-continued

| Ex. | C Ring/A & B Rings | R¹ | R² | R³ | Chemical Name | [M + H]+ Calc'd/Observed |
|---|---|---|---|---|---|---|
| 1.57 | C2/Ix TFA salt | (structure: HN-C(=O)-CH(CH₃)- with glycinate methyl ester) R | $CH_3$ | $CF_3$ | methyl N-{(2R)-2-[4-(4-methyl-6-{[4-(trifluoromethyl)pyridin-2-yl]amino}pyridin-2-yl)-1H-1,2,3-triazol-1-yl]propanoyl}glycinate | 464/464 |
| 1.58 | C2/Iy | (structure: HO-, 2,2-dimethyl cyclohexane with C(=O)NH₂) syn, racemic | $CH_3$ | $CF_3$ | 4-hydroxy-2,2-dimethyl-4-[1-(3-methyl-5-{[4-(trifluoromethyl)pyrimidin-2-yl]amino}phenyl)-1H-1,2,3-triazol-4-yl]cyclohexanecarboxamide | [M + H]+ 490/490, observed [[M + H]+ —H₂O] 472/472 |

Example 2.1

4-(1-(4-(3-((4-Ethylpyridin-2-yl)amino)-5-methylphenyl)-1H-1,2,3-triazol-1-yl)ethyl)benzoic acid

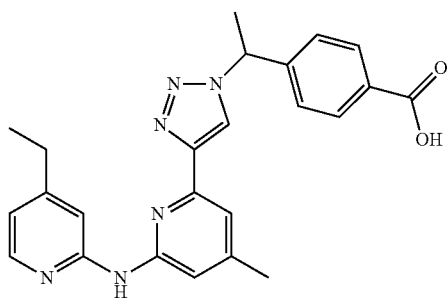 [SMILES: CCc1ccnc(Nc2cc(C)cc(-c3cn(C(C)c4ccc(C(=O)O)cc4)nn3)n2)c1]

A tube was charged with 2-bromo-4-ethylpyridine (37.2 mg, 0.2 mmol), $Pd_2(dba)_3$ (0.018 g, 0.020 mmol), XANT-PHOS (0.015 g, 0.025 mmol), and potassium carbonate (0.042 g, 0.303 mmol). The tube was sealed, evacuated and backfilled with argon. Methyl 4-(1-(4-(3-amino-5-methylphenyl)-1H-1,2,3-triazol-1-yl)ethyl)benzoate (0.034 g, 0.101 mmol) was taken up in fully degassed dioxane (1.010 ml) under argon and then added to the reaction mixture, which was resealed and stirred at 100° C. overnight. The reaction was cooled to room temperature and diluted with dioxane (1 mL). Aqueous potassium hydroxide (0.14 mL, 1.01 mmol) was added, and the mixture was stirred at room temperature for 6 hours. The reaction was concentrated under reduced pressure then dissolved in DMSO (3 mL), filtered, and purified by reverse phase HPLC (ACN/water with 0.1% TFA modifier) to afford 4-(1-(4-(3-((4-ethylpyridin-2-yl)amino)-5-methylphenyl)-1H-1,2,3-triazol-1-yl)ethyl)benzoic acid as the formic acid salt. MS ESI calcd. For $C_{25}H_{26}N_5O_2$ $[M+H]^+$ 429. found 429.

The following compounds in Table 2 were prepared according to the method described for Example 2.1. Carboxylic acids were optionally prepared by hydrolysis of the ester according to the method described in Example 4.1, Step 3. $R^{1a}$ is H for compounds 2.2-2.14 in Table 2.

TABLE 2

| Ex. | C Ring/A & B Rings | R¹ | R² | R³ | Chemical Name | [M + H]+ Calc'd/Observed |
|---|---|---|---|---|---|---|
| 2.2 | C2/Ix Formate Salt | (4-carboxyphenyl-CH(CH₃)- racemic) | $CH_3$ | F | 4-[1-(4-{6-[(4-fluoropyridin-2-yl)amino]-4-methylpyridin-2-yl}-1H-1,2,3-triazol-1-yl)ethyl]benzoic acid | 419/419 |
| 2.3 | C2/Ix Formate Salt | (4-carboxyphenyl-CH(CH₃)- racemic) | $CH_3$ | $CH(OH)CH_3$ | 4-{1-[4-(6-{[4-(1-hydroxyethyl)pyridin-2-yl]amino}-4-methylpyridin-2-yl)-1H-1,2,3-triazol-1-yl]ethyl}benzoic acid | 445/445 |

TABLE 2-continued

| Ex. | C Ring/A & B Rings | R¹ | R² | R³ | Chemical Name | [M + H]+ Calc'd/Observed |
|---|---|---|---|---|---|---|
| 2.4 | C2/Ix Formate Salt | 4-carboxyphenyl (racemic, with CH(CH₃)) | CH₃ | OCH₂CH₂OH | 4-{1-[4-(6-{[4-(2-hydroxyethoxy)pyridin-2-yl]amino}-4-methylpyridin-2-yl)-1H-1,2,3-triazol-1-yl]ethyl}benzoic acid | 461/461 |
| 2.5 | C2/Ix Formate Salt | 4-carboxyphenyl (racemic) | CH₃ | tetrahydrofuran-3-yloxy | 4-{1-[4-(4-methyl-6-{[4-(tetrahydrofuran-3-yloxy)pyridin-2-yl]amino}pyridin-2-yl)-1H-1,2,3-triazol-1-yl]ethyl}benzoic acid | 487/487 |
| 2.6 | C2/Ix Formate Salt | 4-carboxyphenyl (racemic) | CH₃ | cyclohexyloxy | 4-{1-[4-(6-{[4-(cyclohexyloxy)pyridin-2-yl]amino}-4-methylpyridin-2-yl)-1H-1,2,3-triazol-1-yl]ethyl}benzoic acid | 499/499 |
| 2.7 | C2/Ix Formate Salt | 4-carboxyphenyl (racemic) | CH₃ | cyclopentyloxy | 4-{1-[4-(6-{[4-(cyclohexyloxy)pyridin-2-yl]amino}-4-methylpyridin-2-yl)-1H-1,2,3-triazol-1-yl]ethyl}benzoic acid | 485/485 |
| 2.8 | C2/Ix Formate Salt | 4-carboxyphenyl (racemic) | CH₃ | cyclobutyloxy | 4-{1-[4-(6-{[4-(cyclobutyloxy)pyridin-2-yl]amino}-4-methylpyridin-2-yl)-1H-1,2,3-triazol-1-yl]ethyl}benzoic acid | 471/471 |
| 2.9 | C2/Ix Formate Salt | 4-carboxyphenyl (racemic) | CH₃ | OCH₂CH₃ | 4-[1-(4-{6-[(4-ethoxypyridin-2-yl)amino]-4-methylpyridin-2-yl}-1H-1,2,3-triazol-1-yl)ethyl]benzoic acid | 445/445 |
| 2.10 | C2/Ix Formate Salt | 4-carboxyphenyl (racemic) | CH₃ | cyclobutyl | 4-[1-(4-{6-[(4-cyclobutylpyridin-2-yl)amino]-4-methylpyridin-2-yl}-1H-1,2,3-triazol-1-yl)ethyl]benzoic acid | 455/455 |
| 2.11 | C2/Ix Formate Salt | 4-carboxyphenyl (racemic) | CH₃ | c-propyl | 4-[1-(4-{6-[(4-cyclopropylpyridin-2-yl)amino]-4-methylpyridin-2-yl}-1H-1,2,3-triazol-1-yl)ethyl]benzoic acid | 441/441 |
| 2.12 | C2/Ix | 4-carboxyphenyl (racemic) | CH₃ | t-butyl | 4-[1-(4-{6-[(4-tert-butylpyridin-2-yl)amino]-4-methylpyridin-2-yl}-1H-1,2,3-triazol-1-yl)ethyl]benzoic acid | 457/457 |

TABLE 2-continued

| Ex. | C Ring/A & B Rings | R¹ | R² | R³ | Chemical Name | [M + H]+ Calc'd/Observed |
|---|---|---|---|---|---|---|
| 2.13 | C2/Ix | 4-carboxyphenyl-CH(CH₃)- (racemic) | CH₃ | i-propyl | 4-{1-[4-(4-methyl-6-{[4-(1-methylethyl)pyridin-2-yl]amino}pyridin-2-yl)-1H-1,2,3-triazol-1-yl]ethyl}benzoic acid | 443/443 |
| 2.14 | C5/Iy | H | CH₃ | CF₃ | N-[3-methyl-5-(1H-1,2,4-triazol-3-yl)phenyl]-4-(trifluoromethyl)pyrimidin-2-amine | 321/321 |
| 2.15 | C5/Iy | R¹ = H; & R¹ᵃ = (S)-HOCH₂CH(OH)CH₂- | CH₃ | CF₃ | (2S)-3-[5-(3-methyl-5-{[4-(trifluoromethyl)pyrimidin-2-yl]amino}phenyl)-1H-1,2,4-triazol-1-yl]propane-1,2-diol | 395/395 |

Example 3

The following compounds in Table 3 were prepared according to the method described for Example 4.1 Step 3. R¹ᵃ is H for the compounds in Table 3.

TABLE 3

| Ex. | C Ring/A & B Rings | R¹ | R² | R³ | Chemical Name | [M + H]+ Calc'd/Observed |
|---|---|---|---|---|---|---|
| 3.1 | C2/Ix | 4-hydroxy-2,2-dimethyl-4-carboxycyclohexyl-CH₂- (first eluting enantiomer syn) | CH₃ | CF₃ | (R or S) 4-hydroxy-2,2-dimethyl-4-{[4-(4-methyl-6-{[4-(trifluoromethyl)pyridin-2-yl]amino}pyridin-2-yl)-1H-1,2,3-triazol-1-yl]methyl}cyclohexanecarboxylic acid | 505/505 |
| 3.2 | C2/Iy | 4-hydroxy-2,2-dimethyl-4-carboxycyclohexyl-CH₂- (second eluting enantiomer syn) | CH₃ | CF₃ | (R or S) 4-hydroxy-2,2-dimethyl-4-{[4-(3-methyl-5-{[4-(trifluoromethyl)pyrimidin-2-yl]amino}phenyl)-1H-1,2,3-triazol-1-yl]methyl}cyclohexanecarboxylic acid | 505/505 |
| 3.3 | C2/Iy | 4-hydroxy-2,2-dimethyl-4-carboxycyclohexyl-CH₂- (first eluting enantiomer syn) | CH₃ | CF₃ | (R or S) 4-hydroxy-2,2-dimethyl-4-{[4-(3-methyl-5-{4-(trifluoromethyl)pyrimidin-2-yl]amino}phenyl)-1H-1,2,3-triazol-1-yl]methyl}cyclohexanecarboxylic acid | 505/505 |

TABLE 3-continued

| Ex. | C Ring/A & B Rings | R¹ | R² | R³ | Chemical Name | [M + H]+ Calc'd/Observed |
|---|---|---|---|---|---|---|
| 3.4 | C2/Iy | (4-hydroxy-2,2-dimethylcyclohexanecarboxylic acid, syn racemic) | CH₃ | CF₃ | 4-hydroxy-2,2-dimethyl-4-{[4-(3-methyl-5-{[4-(trifluoromethyl)pyrimidin-2-yl]amino}phenyl)-1H-1,2,3-triazol-1-yl]methyl}cyclohexanecarboxylic acid | 505/505 |
| 3.5 | C2/Ix | (4-hydroxy-2,2-dimethylcyclohexanecarboxylic acid, syn racemic) | CH₃ | CF₃ | 4-hydroxy-2,2-dimethyl-4-{[4-(4-methyl-6-{[4-(trifluoromethyl)pyridin-2-yl]amino}pyridin-2-yl)-1H-1,2,3-triazol-1-yl]methyl}cyclohexanecarboxylic acid | 505/505 |
| 3.6 | C2/Ix TFA salt | (2,2-dimethylcyclohexanecarboxylic acid, chiral) | CH₃ | CF₃ | (R or S) 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylic acid | 475/475 |
| 3.7 | C2/Ix TFA salt | (2,2-dimethylcyclohexanecarboxylic acid, chiral) | CH₃ | CF₃ | (R or S) 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylic acid | 475/475 |
| 3.8 | C2/Ix TFA salt | (2,2-dimethylcyclohexanecarboxylic acid, racemic) | CH₃ | CF₃ | 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylic acid | 475/475 |
| 3.9 | C2/Ix | (2,2-dimethylcyclohexanecarboxylic acid, racemic) | CH₃ | CF₃ | 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylic acid | 475/475 |

TABLE 3-continued

| Ex. | C Ring/A & B Rings | R¹ | R² | R³ | Chemical Name | [M + H]+ Calc'd/Observed |
|---|---|---|---|---|---|---|
| 3.10 | C2/Ix TFA salt | 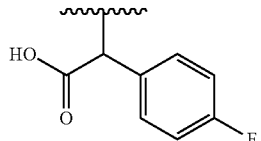<br>racemic | $CH_3$ | $CF_3$ | (4-fluorophenyl)[4-(4-methyl-6-{[4-(trifluoromethyl)pyridin-2-yl]amino}pyridin-2-yl)-1H-1,2,3-triazol-1-yl]acetic acid | 473/473 |
| 3.11 | C2/Ix TFA salt | 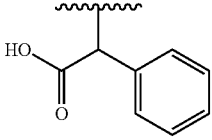<br>racemic | $CH_3$ | $CF_3$ | [4-(4-methyl-6-{[4-(trifluoromethyl)pyridin-2-yl]amino}pyridin-2-yl)-1H-1,2,3-triazol-1-yl](phenyl)acetic acid | 455/455 |
| 3.12 | C2/Ix TFA Salt | 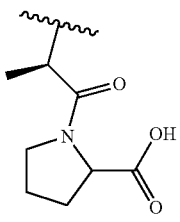<br>R, racemic proline | $CH_3$ | $CF_3$ | 1-{(2R)-2-[4-(4-methyl-6-{[4-(trifluoromethyl)pyridin-2-yl]amino}pyridin-2-yl)-1H-1,2,3-triazol-1-yl]propanoyl}proline | 490/490 |
| 3.13 | C2/Ix TFA Salt | 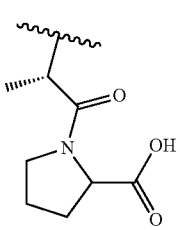<br>S, racemic proline | $CH_3$ | $CF_3$ | 1-{(2S)-2-[4-(4-methyl-6-{[4-(trifluoromethyl)pyridin-2-yl]amino}pyridin-2-yl)-1H-1,2,3-triazol-1-yl]propanoyl}proline | 490/490 |
| 3.14 | C2/Ix TFA Salt | 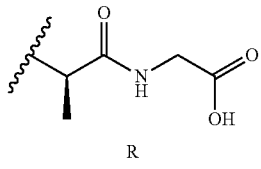<br>R | $CH_3$ | $CF_3$ | N-{(2R)-2-[4-(4-methyl-6-{[4-(trifluoromethyl)pyridin-2-yl]amino}pyridin-2-yl)-1H-1,2,3-triazol-1-yl]propanoyl}glycine | 450/450 |
| 3.15 | C2/Ix TFA Salt | 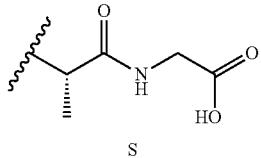<br>S | $CH_3$ | $CF_3$ | N-{(2S)-2-[4-(4-methyl-6-{[4-(trifluoromethyl)pyridin-2-yl]amino}pyridin-2-yl)-1H-1,2,3-triazol-1-yl]propanoyl}glycine | 450/450 |
| 3.16 | C2/Iy | 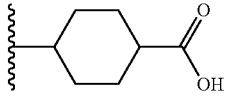<br>mixture of isomers | $CH_3$ | $CF_3$ | 4-[4-(3-methyl-5-{[4-(trifluoromethyl)pyrimidin-2-yl]amino}phenyl)-1H-1,2,3-triazol-1-yl]cyclohexanecarboxylic acid | 447/447 |

TABLE 3-continued

| Ex. | C Ring/A & B Rings | R¹ | R² | R³ | Chemical Name | [M + H]+ Calc'd/Observed |
|---|---|---|---|---|---|---|
| 3.17 | C2/Ix TFA Salt | *structure: 4-(1-hydroxymethyl-ethyl)benzoic acid, racemic* | CH₃ | CF₃ | 4-{2-hydroxy-1-[4-(4-methyl-6-{[4-(trifluoromethyl)pyridin-2-yl]amino}pyridin-2-yl)-1H-1,2,3-triazol-1-yl]ethyl}benzoic acid | 485/485 |
| 3.18 | C2/Ix TFA Salt | *structure: 4-(2-hydroxyethyl)benzoic acid derivative, racemic* | CH₃ | CF₃ | 4-{1-hydroxy-2-[4-(4-methyl-6-{[4-(trifluoromethyl)pyridin-2-yl]amino}pyridin-2-yl)-1H-1,2,3-triazol-1-yl]ethyl}benzoic acid | 485/485 |
| 3.19 | C2/Ix | *structure: 1,2,3,4-tetrahydronaphthalene-1-carboxylic acid, racemic* | CH₃ | CF₃ | 4-[4-(4-methyl-6-{[4-(trifluoromethyl)pyridin-2-yl]amino}pyridin-2-yl)-1H-1,2,3-triazol-1-yl]-1,2,3,4-tetrahydronaphthalene-1-carboxylic acid | 495/495 |

Example 4.1

Racemic syn-4-Hydroxy-2,2-dimethyl-4-((4-(3-methyl-5-((4-(trifluoromethyl)pyrimidin-2-yl)amino)phenyl)-1H-1,2,3-triazol-1-yl)methyl)cyclohexane carboxylic acid

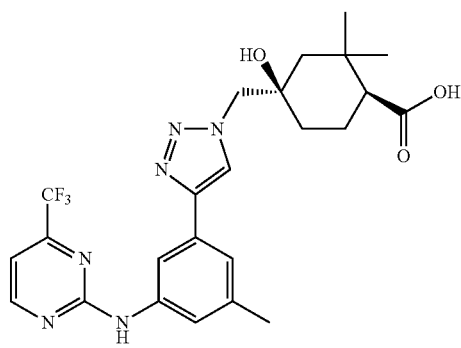 [SMILES: Cc1cc(Nc2nccc(C(F)(F)F)n2)cc(-c2cn(C[C@@]3(O)CC[C@H](C(=O)O)C(C)(C)C3)nn2)c1]

Step 1:

Racemic syn-methyl 5,5-dimethyl-1-oxaspiro[2.5]octane-6-carboxylate (300 mg, 1.51 mmol) was dissolved in methanol (2.2 mL) and water (0.28 mL) and treated with sodium azide (492 mg, 7.57 mmol) and ammonium chloride (178 mg, 3.33 mmol). The reaction stirred at 80° C. overnight. The crude reaction mixture was diluted with ethyl acetate and washed with water. The aqueous layer was extracted with ethyl acetate and the combined organic layers were washed with brine, dried over anhydrous sodium sulfate, filtered, silica gel was added, and the slurry was concentrated under reduced pressure. The residue was purified by column chromatography on silica gel (5 to 40% EtOAc/isohexane) to afford racemic syn-methyl 4-(azidomethyl)-4-hydroxy-2,2-dimethylcyclohexanecarboxylate (275 mg, 1.14 mmol) as a colorless liquid. ¹H NMR (500 MHz, CDCl₃) δ 3.67 (s, 3H), 3.20 (s, 2H), 2.12-2.10 (m, 2H), 1.76-1.75 (m, 1H), 1.67-1.58 (m, 1H), 1.53-1.49 (m, 1H), 1.32-1.20 (m, 2H), 1.12 (s, 3H), 1.01 (s, 3H).

Step 2:

Racemic syn N-(3-ethynyl-5-methylphenyl)-4-(trifluoromethyl)pyrimidin-2-amine (75 mg, 0.271 mmol), methyl 4-(azidomethyl)-4-hydroxy-2,2-dimethylcyclohexanecarboxylate (65.3 mg, 0.27 mmol), copper(II) sulfate pentahydrate (6.75 mg, 0.03 mmol), and sodium ascorbate (21.44 mg, 0.11 mmol) were dissolved in t-butanol (0.75 mL) and water (0.75 mL). The reaction was heated to 65° C. and stirred for 1.5 hours. The crude reaction mixture was diluted with ethyl acetate and washed with saturated ammonium chloride. The organic layer was dried over anhydrous sodium sulfate, filtered, silica gel was added, and the slurry was concentrated under reduced pressure. The residue was purified by column chromatography (10 to 100% EtOAc/isohexane) to afford racemic syn methyl 4-hydroxy-2,2-dimethyl-4-((4-(3-methyl-5-((4-(trifluoromethyl)pyrimidin-2-yl)amino)phenyl)-1H-1,2,3-triazol-1-yl)methyl) cyclohexanecarboxylate (101.9 mg, 0.197 mmol) as a white solid. MS ESI calcd. for $C_{25}H_{30}F_3N_6O_3$ [M+H]$^+$ 519. found 519.

Step 3:

In a vial, racemic syn methyl 4-hydroxy-2,2-dimethyl-4-((4-(3-methyl-5-((4-(trifluoromethyl)pyrimidin-2-yl)amino)phenyl)-1H-1,2,3-triazol-1-yl)methyl)cyclohexanecarboxylate (88.4 mg, 0.170 mmol) was dissolved in methanol (0.88 mL). Sodium hydroxide (1M in water, 1.02 mL, 1.02 mmol) was added and heated to 110° C. for 10 min in the microwave. The reaction was diluted with HCl (1 N) until the pH was adjusted to 3. The crude reaction mixture was diluted with IPA/CHCl$_3$ (3:1) and washed with saturated sodium bicarbonate. The aqueous layer was extracted with IPA/CHCl$_3$ (3:1, 3×) and the combined organic layers were dried over anhydrous sodium sulfate, filtered, and concentrated under reduced pressure to afford racemic syn 4-hydroxy-2,2-dimethyl-4-((4-(3-methyl-5-((4-(trifluoromethyl)pyrimidin-2-yl)amino)phenyl)-1H-1,2,3-triazol-1-yl)methyl)cyclohexanecarboxylic acid (63.9 mg, 0.127 mmol) as a tan solid. MS ESI calcd. For $C_{24}H_{28}F_3N_6O_2$ [M+H]$^+$ 505. found 505. $^1$H NMR (500 MHz, DMSO-d$_6$) δ 11.90 (s, 1H), 10.2 (s, 1H), 8.80 (d, J=4.8 Hz, 1H), 8.20 (s, 1H), 8.06 (s, 1H), 7.49 (s, 1H), 7.30 (s, 1H), 7.23 (d, J=4.9 Hz, 1H), 4.56 (s, 1H), 4.31 (d, J=4.2 Hz, 1H), 4.21 (s, 2H), 3.73 (d, J=4.1 Hz, 1H), 2.31 (s, 3H), 1.98 (s, 1H), 1.83 (d, J=9.9 Hz, 2H), 1.40 (d, J=13.0 Hz, 2H), 0.98 (s, 3H), 0.92 (s, 3H).

The following compounds in Table 4 were prepared according to the method described for Example 4.1. $R^{1a}$ is H in the compounds in Table 4.

TABLE 4

| Ex. | C Ring/A & B Rings | R$^1$ | R$^2$ | R$^3$ | Chemical Name | [M + H]+ Calc'd/Observed |
|---|---|---|---|---|---|---|
| 4.2 | C2/Ix | (structure with OH, CN) second eluting enantiomer | CH$_3$ | CF$_3$ | 3-hydroxy-4-[4-(4-methyl-6-{[4-(trifluoromethyl)pyridin-2-yl]amino}pyridin-2-yl)-1H-1,2,3-triazol-1-yl]pentanenitrile | 418/418 |
| 4.3 | C2/Ix | (structure with OH, CN) second eluting enantiomer | CH$_3$ | CF$_3$ | 3-hydroxy-4-[4-(4-methyl-6-{[4-(trifluoromethyl)pyridin-2-yl]amino}pyridin-2-yl)-1H-1,2,3-triazol-1-yl]pentanenitrile | 418/418 |
| 4.4 | C2/Iy | (tetrahydrofuran structure with HO) anti, second eluting enantiomer | CH$_3$ | CF$_3$ | 4-[4-(3-methyl-5-{[4-(trifluoromethyl)pyrimidin-2-yl]amino}phenyl)-1H-1,2,3-triazol-1-yl]tetrahydrofuran-3-ol | 407/407 |
| 4.5 | C2/Iy | (tetrahydrofuran structure with HO) anti, first eluting enantiomer | CH$_3$ | CF$_3$ | 4-[4-(3-methyl-5-{[4-(trifluoromethyl)pyrimidin-2-yl]amino}phenyl)-1H-1,2,3-triazol-1-yl]tetrahydrofuran-3-ol | 407/407 |
| 4.6 | C2/Iy | (tetrahydrofuran structure with HO) anti, first eluting enantiomer | CH$_3$ | CF$_3$ | 3-hydroxy-4-[4-(3-methyl-5-{[4-(trifluoromethyl)pyrimidin-2-yl]amino}phenyl)-1H-1,2,3-triazol-1-yl]pentanenitrile | 418/418 |
| 4.7 | C2/Iy | (structure with OH, CN) syn, first eluting enantiomer | CH$_3$ | CF$_3$ | 3-hydroxy-4-[4-(3-methyl-5-{[4-(trifluoromethyl)pyrimidin-2-yl]amino}phenyl)-1H-1,2,3-triazol-1-yl]pentanenitrile | 418/418 |

TABLE 4-continued

| Ex. | C Ring/A & B Rings | R¹ | R² | R³ | Chemical Name | [M + H]+ Calc'd/Observed |
|---|---|---|---|---|---|---|
| 4.8 | C2/Iy | 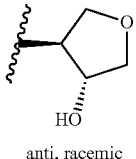<br>anti, racemic | CH₃ | CF₃ | 4-[4-(3-methyl-5-{[4-(trifluoromethyl)pyrimidin-2-yl]amino}phenyl)-1H-1,2,3-triazol-1-yl]tetrahydrofuran-3-ol | 407/407 |
| 4.9 | C2/Iy | 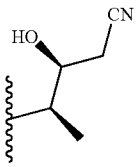<br>syn, racemic | CH₃ | CF₃ | 3-hydroxy-4-[4-(3-methyl-5-{[4-(trifluoromethyl)pyrimidin-2-yl]amino}phenyl)-1H-1,2,3-triazol-1-yl]pentanenitrile | 418/418 |
| 4.10 | C2/Ix | 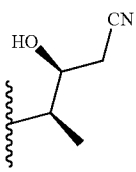<br>syn, racemic | CH₃ | CF₃ | 3-hydroxy-4-[4-(4-methyl-6-{[4-(trifluoromethyl)pyridin-2-yl]amino}pyridin-2-yl)-1H-1,2,3-triazol-1-yl]pentanenitrile | 418/418 |
| 4.11 | C2/Iy | 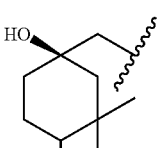<br>syn, racemic | CH₃ | CF₃ | methyl 4-hydroxy-2,2-dimethyl-4-{[4-(3-methyl-5-{[4-(trifluoromethyl)pyrimidin-2-yl]amino}phenyl)-1H-1,2,3-triazol-1-yl]methyl}cyclohexanecarboxylate | 519/519 |
| 4.12 | C2/Ix | 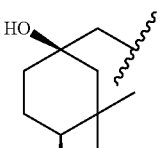<br>syn, racemic | CH₃ | CF₃ | methyl 4-hydroxy-2,2-dimethyl-4-{[4-(4-methyl-6-{[4-(trifluoromethyl)pyridin-2-yl]amino}pyridin-2-yl)-1H-1,2,3-triazol-1-yl]methyl}cyclohexanecarboxylate | 519/519 |
| 4.13 | C2/Ix | 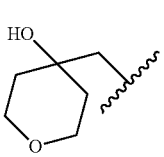 [SMILES: *CC1(O)CCOCC1] | CH₃ | CF₃ | 4-{[4-(4-methyl-6-{[4-(trifluoromethyl)pyridin-2-yl]amino}pyridin-2-yl)-1H-1,2,3-triazol-1-yl]methyl}tetrahydro-2H-pyran-4-ol | 435/435 |
| 4.14 | C2/Iy | 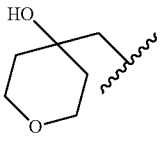 [SMILES: *CC1(O)CCOCC1] | CH₃ | CF₃ | 4-{[4-(3-methyl-5-{[4-(trifluoromethyl)pyrimidin-2-yl]amino}phenyl)-1H-1,2,3-triazol-1-yl]methyl}tetrahydro-2H-pyran-4-ol | 435/435 |

TABLE 4-continued

| Ex. | C Ring/A & B Rings | R¹ | R² | R³ | Chemical Name | [M + H]+ Calc'd/Observed |
|---|---|---|---|---|---|---|
| 4.15 | C2/Ix | 3-hydroxypyrrolidin-4-yl (racemic) | CH₃ | CF₃ | 4-[4-(4-methyl-6-{[4-(trifluoromethyl)pyridin-2-yl]amino}pyridin-2-yl)-1H-1,2,3-triazol-1-yl]pyrrolidin-3-ol | 406/406 |
| 4.16 | C2/Ix TFA Salt | 1-(4-methoxycarbonylphenyl)-2-hydroxyethyl (racemic) | CH₃ | CF₃ | methyl 4-{2-hydroxy-1-[4-(4-methyl-6-{[4-(trifluoromethyl)pyridin-2-yl]amino}pyridin-2-yl)-1H-1,2,3-triazol-1-yl]ethyl}benzoate | 499/499 |
| 4.17 | C2/Ix TFA Salt | 2-(4-methoxycarbonylphenyl)-2-hydroxyethyl (racemic) | CH₃ | CF₃ | methyl 4-{1-hydroxy-2-[4-(4-methyl-6-{[4-(trifluoromethyl)pyridin-2-yl]amino}pyridin-2-yl)-1H-1,2,3-triazol-1-yl]ethyl}benzoate | 499/499 |
| 4.18 | C2/Ix | 2-carboxy-2-hydroxypropyl (racemic) | CH₃ | CF₃ | 2-hydroxy-2-methyl-3-[4-(4-methyl-6-{[4-(trifluoromethyl)pyridin-2-yl]amino}pyridin-2-yl)-1H-1,2,3-triazol-1-yl]propanoic acid | 423/423 |
| 4.19 | C2/Ix | (S)-2-hydroxy-2-carboxyethyl | CH₃ | CF₃ | (2S)-2-hydroxy-3-[4-(4-methyl-6-{[4-(trifluoromethyl)pyridin-2-yl]amino}pyridin-2-yl)-1H-1,2,3-triazol-1-yl]propanoic acid | 409/409 |
| 4.20 | C2/Ix | (R)-2-hydroxy-2-carboxyethyl | CH₃ | CF₃ | (2R)-2-hydroxy-3-[4-(4-methyl-6-{[4-(trifluoromethyl)pyridin-2-yl]amino}pyridin-2-yl)-1H-1,2,3-triazol-1-yl]propanoic acid | 409/409 |
| 4.21 | C2/Iy TFA Salt | (R)-2-hydroxy-2-carboxyethyl | CH₃ | CF₃ | (2R)-2-hydroxy-3-[3-(3-methyl-5-{[4-(trifluoromethyl)pyrimidin-2-yl]amino}phenyl)-1H-1,2,4-triazol-1-yl]propanoic acid | 409/409 |

TABLE 4-continued

| Ex. | C Ring/A & B Rings | R¹ | R² | R³ | Chemical Name | [M + H]+ Calc'd/Observed |
|---|---|---|---|---|---|---|
| 4.22 | C2/Ix | 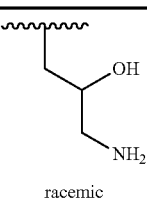 racemic | CH₃ | CF₃ | 1-amino-3-[4-(4-methyl-6-{[4-(trifluoromethyl)pyridin-2-yl]amino}pyridin-2-yl)-1H-1,2,3-triazol-1-yl]propan-2-ol | 394/394 |
| 4.23 | C2/Ix | 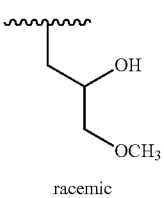 racemic | CH₃ | CF₃ | 1-methoxy-3-[4-(4-methyl-6-{[4-(trifluoromethyl)pyridin-2-yl]amino}pyridin-2-yl)-1H-1,2,3-triazol-1-yl]propan-2-ol | 409/409 |
| 4.24 | C2/Ix | 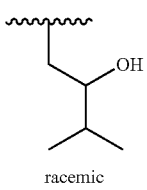 racemic | CH₃ | CF₃ | 3-methyl-1-[4-(4-methyl-6-{[4-(trifluoromethyl)pyridin-2-yl]amino}pyridin-2-yl)-1H-1,2,3-triazol-1-yl]butan-2-ol | 407/407 |
| 4.25 | C2/Ix | 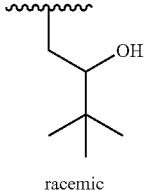 [SMILES: *CC(O)C(C)(C)C] racemic | CH₃ | CF₃ | 3,3-dimethyl-1-[4-(4-methyl-6-{[4-(trifluoromethyl)pyridin-2-yl]amino}pyridin-2-yl)-1H-1,2,3-triazol-1-yl]butan-2-ol | 421/421 |
| 4.26 | C2/Ix | 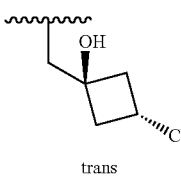 trans | CH₃ | CF₃ | trans-3-hydroxy-3-{[4-(4-methyl-6-{[4-(trifluoromethyl)pyridin-2-yl]amino}pyridin-2-yl)-1H-1,2,3-triazol-1-yl]methyl}cyclobutanecarbonitrile | 430/430 |
| 4.27 | C2/Ix | 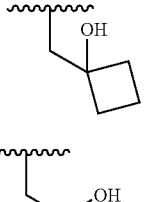 | CH₃ | CF₃ | 1-{[4-(4-methyl-6-{[4-(trifluoromethyl)pyridin-2-yl]amino}pyridin-2-yl)-1H-1,2,3-triazol-1-yl]methyl}cyclobutanol | 405/405 |
| 4.28 | C2/Ix | 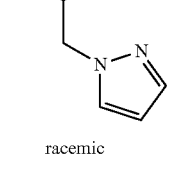 racemic | CH₃ | CF₃ | 1-[4-(4-methyl-6-{[4-(trifluoromethyl)pyridin-2-yl]amino}pyridin-2-yl)-1H-1,2,3-triazol-1-yl]-3-(1H-pyrazol-1-yl)propan-2-ol | 445/445 |
| 4.29 | C2/Ix | 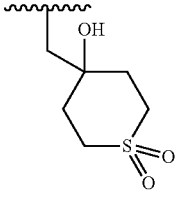 [SMILES: *CC1(O)CCS(=O)(=O)CC1] | CH₃ | CF₃ | 4-{[4-(4-methyl-6-{[4-(trifluoromethyl)pyridin-2-yl]amino}pyridin-2-yl)-1H-1,2,3-triazol-1-yl]methyl}tetrahydro-2H-thiopyran-4-ol 1,1-dioxide | 483/483 |

TABLE 4-continued

| Ex. | C Ring/A & B Rings | R¹ | R² | R³ | Chemical Name | [M + H]+ Calc'd/Observed |
|---|---|---|---|---|---|---|
| 4.30 | C2/Ix | 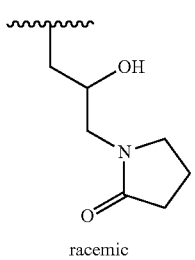 [SMILES: *CC(O)CN1CCCC1=O] racemic | CH₃ | CF₃ | 1-{2-hydroxy-3-[4-(4-methyl-6-{[4-(trifluoromethyl)pyridin-2-yl]amino}pyridin-2-yl)-1H-1,2,3-triazol-1-yl]propyl}pyrrolidin-2-one | 462/462 |
| 4.31 | C2/Ix | 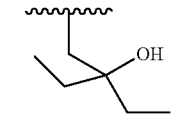 [SMILES: *CC(O)(CC)CC] | CH₃ | CF₃ | 3-{[4-(4-methyl-6-{[4-(trifluoromethyl)pyridin-2-yl]amino}pyridin-2-yl)-1H-1,2,3-triazol-1-yl]methyl}pentan-3-ol | 421/421 |
| 4.32 | C2/Ix | 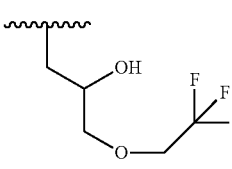 racemic | CH₃ | CF₃ | 1-[4-(4 methyl-6-{[4-(trifluoromethyl)pyridin-2-yl]amino}pyridin-2-yl)-1H-1,2,3-triazol-1-yl]-3-(2,2,2-trifluoroethoxy)propan-2-ol | 477/477 |
| 4.33 | C2/Ix | 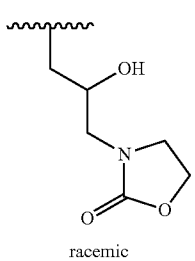 [SMILES: *CC(O)CN1CCOC1=O] racemic | CH₃ | CF₃ | 3-{2-hydroxy-3-[4-(4-methyl-6-{[4-(trifluoromethyl)pyridin-2-yl]amino}pyridin-2-yl)-1H-1,2,3-triazol-1-yl]propyl}-1,3-oxazolidin-2-one | 464/464 |
| 4.34 | C2/Iy | 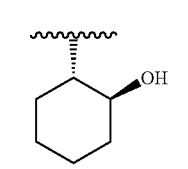 single isomer, early eluting | CH₃ | C(H)F₂ | (2-[4-(3-{[4-(difluoromethyl)pyrimidin-2-yl]amino}-5-methylphenyl)-1H-1,2,3-triazol-1-yl]cyclohexanol | 401/401 |
| 4.35 | C2/Iy | 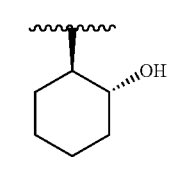 single isomer, late eluting | CH₃ | C(H)F₂ | 2-[4-(3-{[4-(difluoromethyl)pyrimidin-2-yl]amino}-5-methylphenyl)-1H-1,2,3-triazol-1-yl]cyclohexanol | 401/401 |

Example 5.1

2-(4-(3-Methyl-5-((4-(trifluoromethyl)pyrimidin-2-yl)amino)phenyl)-1H-1,2,3-triazol-1-yl)ethanol

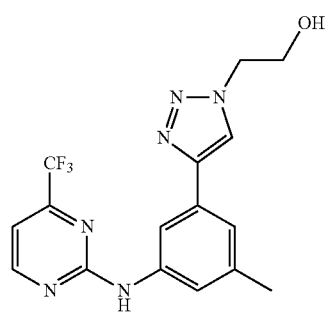 [SMILES: Cc1cc(Nc2nccc(C(F)(F)F)n2)cc(-c2cn(CCO)nn2)c1]

N-(3-Ethynyl-5-methylphenyl)-4-(trifluoromethyl)pyrimidin-2-amine (0.020 g, 0.072 mmol), 2-bromoethanol (0.009 g, 0.072 mmol), sodium azide (0.005 g, 0.076 mmol), copper sulfate (1M, 0.015 mL, 0.014 mmol), copper (0.0040, 0.058 g), t-butanol (0.12 mL) and water (0.12 mL) were added to a vial. The reaction tube was sealed and irradiated in a microwave at 125° C. for 10 minutes. DMSO (1.0 mL) was added to the reaction mixture, passed through a syringe filter and then purified by reverse phase preparative HPLC (0 to 95% ACN/water with 0.1% formic acid modifier) to afford 2-(4-(3-methyl-5-((4-(trifluoromethyl)pyrimidin-2-yl)amino)phenyl)-1H-1,2,3-triazol-1-yl)ethanol. MS ESI calc. for $C_{16}H_{16}F_3N_6O$ $[M+H]^+$ 365. found 365. $^1H$ NMR (600 MHz, DMSO-$d_6$) δ 10.19 (s, 1H), 8.80 (d, J=4.9, 1H), 8.36 (s, 1H), 8.05 (s, 1H), 7.48 (s, 1H), 7.29 (s, 1H), 7.23 (d, J=4.9, 1H), 5.06 (s, 1H), 4.41 (t, J=5.4, 2H), 3.79 (s, 2H), 2.30 (s, 3H).

The following compounds in Table 5A were prepared according to the method described for Example 5.1. $R^{1a}$ is H in the compounds in Table 5.

TABLE 5A

| Ex. No. | C Ring/A & B Rings | $R^1$ | $R^2$ | $R^3$ | Chemical Name | $[M + H]^+$ Calc'd/Observed |
|---|---|---|---|---|---|---|
| 5.2 | C2/Iy Ammonium Salt | *(structure: 4-methylenephenylacetic acid)* | $CH_3$ | $CF_3$ | (4-{[4-(3-methyl-5-{[4-(trifluoromethyl)pyrimidin-2-yl]amino}phenyl)-1H-1,2,3-triazol-1-yl]methyl}phenyl)acetic acid | 469/469 |
| 5.3 | C2/Ix | *(structure: (R)-pyrrolidin-2-one-5-ylmethyl)* | $CH_3$ | $CF_3$ | (5R)-5-{[4-(4-methyl-6-{[4-(trifluoromethyl)pyridin-2-yl]amino}pyridin-2-yl)-1H-1,2,3-triazol-1-yl]methyl}pyrrolidin-2-one | 418/418 |
| 5.4 | C2/Ix | *(structure: tetrahydro-2H-pyran-2-ylmethyl, racemic)* | $CH_3$ | $CF_3$ | 4-methyl-6-[1-(tetrahydro-2H-pyran-2-ylmethyl)-1H-1,2,3-triazol-4-yl]-N-[4-(trifluoromethyl)pyridin-2-yl]pyridin-2-amine | 419/419 |
| 5.5 | C2/Ix | *(structure: 2-hydroxybutyl, racemic)* | $CH_3$ | $CF_3$ | 1-[4-(4-methyl-6-{[4-(trifluoromethyl)pyridin-2-yl]amino}pyridin-2-yl)-1H-1,2,3-triazol-1-yl]butan-2-ol | 393/393 |

TABLE 5A-continued

| Ex. No. | C Ring/A & B Rings | R¹ | R² | R³ | Chemical Name | [M + H]+ Calc'd/Observed |
|---|---|---|---|---|---|---|
| 5.6 | C2/Iy Ammonium Salt | (CH₂CH₂-phenyl-CO₂H group) | CH₃ | CF₃ | 4-{2-[4-(4-methyl-6-{[4-(trifluoromethyl) pyridin-2-yl]amino}pyridin-2-yl)-1H-1,2,3-triazol-1-yl]ethyl}benzoic acid | 469/469 |
| 5.7 | C2/Ix Free base, Formate Salt | (2S)-CH₂CH(OH)CH₂OH group, S | CH₃ | CF₃ | (2S)-3-[4-(4-methyl-6-{[4-(trifluoromethyl) pyridin-2-yl]amino}pyridin-2-yl)-1H-1,2,3-triazol-1-yl]propane-1,2-diol | 395/395 |
| 5.8 | C2/Iy | (2S)-CH₂CH(OH)CH₂OH group, S | CH₃ | OCH₂CH₂OH | (2S)-3-[4-(3-{[4-(2-hydroxyethoxy) pyrimidin-2-yl] amino}-5-methylphenyl)-1H-1,2,3-triazol-1-yl]propane-1,2-diol | 387/387 |
| 5.9 | C2/Ix | (CH₂)CO₂H | CH₃ | CF₃ | 3-[4-(4-methyl-6-{[4-(trifluoromethyl) pyridin-2-yl]amino}pyridin-2-yl)-1H-1,2,3-triazol-1-yl]propanoic acid | 393/393 |
| 5.10 | C2/Ix | (CH₂)₂CO₂CH₃ | CH₃ | CF₃ | methyl 3-[4-(4-methyl-6-{[4-(trifluoromethyl) pyridin-2-yl]amino}pyridin-2-yl)-1H-1,2,3-triazol-1-yl]propanoate | 407/407 |
| 5.11 | C2/Ix | (tetrahydrofuran-3-ol-CH₂- group) second eluting enantiomer | CH₃ | CF₃ | 3-{[4-(4-methyl-6-{[4-(trifluoromethyl) pyridin-2-yl]amino}pyridin-2-yl)-1H-1,2,3-triazol-1-yl]methyl} tetrahydrofuran-3-ol | 421/421 |
| 5.12 | C2/Ix | (tetrahydrofuran-3-ol-CH₂- group) first eluting enantiomer | CH₃ | CF₃ | 3-{[4-(4-methyl-6-{[4-(trifluoromethyl) pyridin-2-yl]amino}pyridin-2-yl)-1H-1,2,3-triazol-1-yl]methyl} tetrahydrofuran-3-ol | 421/421 |
| 5.13 | C2/Ix | (tetrahydrofuran-3-ol-CH₂- group) racemic | CH₃ | CF₃ | 3-{[4-(4-methyl-6-{[4-(trifluoromethyl) pyridin-2-yl]amino}pyridin-2-yl)-1H-1,2,3-triazol-1-yl]methyl} tetrahydrofuran-3-ol | 421/421 |

TABLE 5A-continued

| Ex. No. | C Ring/A & B Rings | R¹ | R² | R³ | Chemical Name | [M + H]+ Calc'd/Observed |
|---|---|---|---|---|---|---|
| 5.14 | C2/Ix Formate Salt | CH₂-CH(OH)-CH₂-CN (R) | CH₃ | CH₃ | (3R)-3-hydroxy-4-(4-{4-methyl-6-[(4-methylpyridin-2-yl)amino]pyridin-2-yl}-1H-1,2,3-triazol-1-yl)butanenitrile | 350/350 |
| 5.15 | C2/Ix Formate Salt | CH₂-CH(CH₃)-CH₂OH (R) | CH₃ | CH₃ | (2R)-2-methyl-3-(4-{4-methyl-6-[(4-methylpyridin-2-yl)amino]pyridin-2-yl}-1H-1,2,3-triazol-1-yl)propan-1-ol | 339/339 |
| 5.16 | C2/Ix Formate Salt | CH₂-CH(CH₃)-CH₂OH (S) | CH₃ | CH₃ | (2S)-2-methyl-3-(4-{4-methyl-6-[(4-methylpyridin-2-yl)amino]pyridin-2-yl}-1H-1,2,3-triazol-1-yl)propan-1-ol | 339/339 |
| 5.17 | C2/Ix Formate Salt | CH₂-CH(OH)-CF₃ racemic | CH₃ | CH₃ | 1,1,1-trifluoro-3-(4-{4-methyl-6-[(4-methylpyridin-2-yl)amino]pyridin-2-yl}-1H-1,2,3-triazol-1-yl)propan-2-ol | 379/379 |
| 5.18 | C2/Ix Formate Salt | (CH₂)₂OH | CH₃ | CH₃ | 2-(4-{4-methyl-6-[(4-methylpyridin-2-yl)amino]pyridin-2-yl}-1H-1,2,3-triazol-1-yl)ethanol | 311/311 |
| 5.19 | C2/Ix Formate Salt | HOCH₂-CH(OH)-CH₂- (R) | CH₃ | CF₃ | (2R)-3-[4-(4-methyl-6-{[4-(trifluoromethyl)pyridin-2-yl]amino}pyridin-2-yl)-1H-1,2,3-triazol-1-yl]propane-1,2-diol | 395/395 |
| 5.20 | C2/Ix | CH(CH₃)-CO₂CH₃ racemic | CH₃ | CF₃ | methyl 2-[4-(4-methyl-6-{[4-(trifluoromethyl)pyridin-2-yl]amino}pyridin-2-yl)-1H-1,2,3-thiazol-1-yl]propanoate | 407/407 |
| 5.21 | C2/Iy | CH₂-C₆H₄-COOH | CH₃ | CF₃ | 4-{[4-(3-methyl-5-{[4-(trifluoromethyl)pyrimidin-2-yl]amino}phenyl)-1H-1,2,3-triazol-1-yl]methyl}benzoic acid | 455/455 |
| 5.22 | C2/Ix | 3-hydroxypyrrolidin-4-yl racemic | CH₃ | CF₃ | 4-[4-(4-methyl-6-{[4-(trifluoromethyl)pyridin-2-yl]amino}pyridin-2-yl)-1H-1,2,3-triazol-1-yl]pyrrolidin-3-ol | 406/406 |

TABLE 5A-continued

| Ex. No. | C Ring/A & B Rings | R¹ | R² | R³ | Chemical Name | [M + H]+ Calc'd/Observed |
|---|---|---|---|---|---|---|
| 5.23 | C2/Iy | (structure with OH, HO, S; 2S configuration) | CH$_2$OCH$_3$ | CF$_3$ | (2S)-3-{4-[3-(methoxymethyl)-5-{[4-(trifluoromethyl)pyrimidin-2-yl]amino}phenyl]-1H-1,2,3-triazol-1-yl}propane-1,2-diol | 425/425 |
| 5.24 | C2/Iy | (structure with OH, OH, S) | CH$_3$ | CF$_3$ | (2S)-3-[4-(3-methyl-5-{[4-(trifluoromethyl)pyrimidin-2-yl]amino}phenyl)-1H-1,2,3-triazol-1-yl]propane-1,2-diol | 395/395 |
| 5.25 | C2/Ix TFA salt | (tetrahydronaphthalene with CO$_2$CH$_3$; racemic) | CH$_3$ | CF$_3$ | methyl 4-[4-(4-methyl-6-{[4-(trifluoromethyl)pyridin-2-yl]amino}pyridin-2-yl)-1H-1,2,3-triazol-1-yl]-1,2,3,4-tetrahydronaphthalene-1-carboxylate | 509/509 |
| 5.26 | C2/Ix | (4-fluorophenyl methyl ester; racemic) | CH$_3$ | CF$_3$ | methyl (4-fluorophenyl)[4-(4-methyl-6-{[4-(trifluoromethyl)pyridin-2-yl]amino}pyridin-2-yl)-1H-1,2,3-triazol-1-yl]acetate | 487/487 |
| 5.27 | C2/Ix | (ethyl ester with propyl, EtO; racemic) | CH$_3$ | CF$_3$ | ethyl 2-[4-(4-methyl-6-{[4-(trifluoromethyl)pyridin-2-yl]amino}pyridin-2-yl)-1H-1,2,3-triazol-1-yl]pentanoate | 449/449 |
| 5.28 | C2/Ix | (ethyl ester with ethyl, OEt; racemic) | CH$_3$ | CF$_3$ | ethyl 2-[4-(4-methyl-6-{[4-(trifluoromethyl)pyridin-2-yl]amino}pyridin-2-yl)-1H-1,2,3-triazol-1-yl]butanoate | 435/435 |
| 5.29 | C2/Ix | (methyl, OH, O; R) | CH$_3$ | CF$_3$ | (2R)-2-[4-(4-methyl-6-{[4-(trifluoromethyl)pyridin-2-yl]amino}pyridin-2-yl)-1H-1,2,3-triazol-1-yl]propanoic acid | 393/393 |
| 5.30 | C2/Ix | (methyl, OH, O; S) | CH$_3$ | CF$_3$ | (2S)-2-[4-(4-methyl-6-{[4-(trifluoromethyl)pyridin-2-yl]amino}pyridin-2-yl)-1H-1,2,3-triazol-1-yl]propanoic acid | 393/393 |

TABLE 5A-continued

| Ex. No. | C Ring/A & B Rings | R¹ | R² | R³ | Chemical Name | [M + H]+ Calc'd/Observed |
|---|---|---|---|---|---|---|
| 5.31 | C2/Ix | (pent-2-en-1-yl) | CH₃ | CF₃ | 4-methyl-6-{1-[(2E)-pent-2-en-1-yl]-1H-1,2,3-triazol-4-yl}-N-[4-(trifluoromethyl)pyridin-2-yl]pyridin-2-amine | 389/389 |
| 5.32 | C2/Ix | (2-chlorophenoxy)but-2-en-1-yl | CH₃ | CF₃ | 6-{1-[(2E)-4-(2-chlorophenoxy)but-2-en-1-yl]-1H-1,2,3-triazol-4-yl}-4-methyl-N-[4-(trifluoromethyl)pyridin-2-yl]pyridin-2-amine | 501/501 |
| 5.33 | C2/Ix | 3-pyridin-4-ylprop-2-en-1-yl | CH₃ | CF₃ | 4-methyl-6-{1-[(2E)-3-pyridin-4-ylprop-2-en-1-yl]-1H-1,2,3-triazol-4-yl}-N-[4-(trifluoromethyl)pyridin-2-yl]pyridin-2-amine | 438/438 |
| 5.34 | C2/Ix | CO₂Et-but-2-enoate | CH₃ | CF₃ | ethyl (2E)-4-[4-(4-methyl-6-{[4-(trifluoromethyl)pyridin-2-yl]amino}pyridin-2-yl)-1H-1,2,3-triazol-1-yl]but-2-enoate | 433/433 |
| 5.35 | C2/Ix | 3-phenylprop-2-en-1-yl | CH₃ | CF₃ | 4-methyl-6-{1-[(2E)-3-phenylprop-2-en-1-yl]-1H-1,2,3-triazol-4-yl}-N-[4-(trifluoromethyl)pyridin-2-yl]pyridin-2-amine | 437/437 |
| 5.36 | C2/Ix | cyclohex-2-en-1-yl | CH₃ | CF₃ | 6-(1-cyclohex-2-en-1-yl-1H-1,2,3-triazol-4-yl)-4-methyl-N-[4-(trifluoromethyl)pyridin-2-yl]pyridin-2-amine | 401/401 |
| 5.37 | C2/Ix | 3-methylbut-2-en-1-yl | CH₃ | CF₃ | 4-methyl-6-[1-(3-methylbut-2-en-1-yl)-1H-1,2,3-triazol-4-yl]-N-[4-(trifluoromethyl)pyridin-2-yl]pyridin-2-amine | 389/389 |

TABLE 5A-continued

| Ex. No. | C Ring/A & B Rings | R¹ | R² | R³ | Chemical Name | [M + H]+ Calc'd/Observed |
|---|---|---|---|---|---|---|
| 5.38 | C2/Ix | (but-2-en-1-yl group) | CH₃ | CF₃ | 6-{1-[(2E)-but-2-en-1-yl]-1H-1,2,3-triazol-4-yl}-4-methyl-N-[4-(trifluoromethyl)pyridin-2-yl]pyridin-2-amine | 375/375 |
| 5.39 | C2/Ix | HO₂C-CH(OH)-CH₂- racemic | CH₃ | CF₃ | 2-hydroxy-3-[4-(4-methyl-6-{[4-(trifluoromethyl)pyridin-2-yl]amino}pyridin-2-yl)-1H-1,2,3-triazol-1-yl]propanoic acid | 409/409 |
| 5.40 | C2/Ix | (2-methylprop-2-en-1-yl) | CH₃ | CF₃ | 4-methyl-6-[1-(2-methylprop-2-en-1-yl)-1H-1,2,3-triazol-4-yl]-N-[4-(trifluoromethyl)pyridin-2-yl]pyridin-2-amine | 375/375 |
| 5.41 | C2/Ix Na salt | 1-(4-carboxyphenyl)ethyl racemic | CH₃ | CF₃ | 4-{1-[4-(4-methyl-6-{[4-(trifluoromethyl)pyridin-2-yl]amino}pyridin-2-yl)-1H-1,2,3-triazol-1-yl]ethyl}benzoic acid | 469/469 |
| 5.42 | C2/Ix Na salt | 4-(carboxyphenyl)methyl | CH₃ | CF₃ | 4-{[4-(4-methyl-6-{[4-(trifluoromethyl)pyridin-2-yl]amino}pyridin-2-yl)-1H-1,2,3-triazol-1-yl]methyl}benzoic acid | 455/455 |
| 5.43 | C2/Ix Free Base, Formate Salt | CH(CH₃)CO₂H racemic | CH₃ | CF₃ | 2-[4-(4-methyl-6-{[4-(trifluoromethyl)pyridin-2-yl]amino}pyridin-2-yl)-1H-1,2,3-triazol-1-yl]propanoic acid | 393/393 |
| 5.44 | C2/Ix Free Base, Formate Salt | CH₂-CH(OH)-CH₂-CN R | CH₃ | CF₃ | (3R)-3-hydroxy-4-[4-(4-methyl-6-{[4-(trifluoromethyl)pyridin-2-yl]amino}pyridin-2-yl)-1H-1,2,3-thiazol-1-yl]butanenitrile | 404/404 |
| 5.45 | C2/Ix | CH₂-CH=CH-CO₂H | CH₃ | CF₃ | (2E)-4-[4-(4-methyl-6-{[4-(trifluoromethyl)pyridin-2-yl]amino}pyridin-2-yl)-1H-1,2,3-triazol-1-yl]but-2-enoic acid | 405/405 |

TABLE 5A-continued

| Ex. No. | C Ring/A & B Rings | R¹ | R² | R³ | Chemical Name | [M + H]+ Calc'd/Observed |
|---|---|---|---|---|---|---|
| 5.46 | C2/Ix | cyclohexane with CO₂H (mixture of isomers) | CH₃ | CF₃ | 4-[4-(4-methyl-6-{[4-(trifluoromethyl)pyridin-2-yl]amino}pyridin-2-yl)-1H-1,2,3-triazol-1-yl]cyclohexane-carboxylic acid | 447/447 |
| 5.47 | C2/Iy Formate Salt | trans-3,5-dimethylmorpholine-4-yl-2-oxoethyl | CH₃ | CF₃ | N-[3-(1-{2-[trans-3,5-dimethylmorpholin-4-yl]-2-oxoethyl}-1H-1,2,3-triazol-4-yl)-5-methylphenyl]-4-(trifluoromethyl)pyrimidin-2-amine | 476/476 |
| 5.48 | C2/Iy Formate Salt | (CH₂)₃NH₂ | CH₃ | CF₃ | N-{3-[1-(3-aminopropyl)-1H-1,2,3-triazol-4-yl]-5-methylphenyl}-4-(trifluoromethyl)pyrimidin-2-amine | 378/378 |
| 5.49 | C2/Iy Formate Salt | -CH₂CH₂-O-CH₂CH₂-OH | CH₃ | CF₃ | 2-{2-[4-(3-methyl-5-{[4-(trifluoromethyl)pyrimidin-2-yl]amino}phenyl)-1H-1,2,3-triazol-1-yl]ethoxy}ethanol | 409/409 |
| 5.50 | C2/Iy Formate Salt | oxetan-2-ylmethyl (racemic) | CH₃ | CF₃ | N-{3-methyl-5-[1-(oxetan-2-ylmethyl)-1H-1,2,3-triazol-4-yl]phenyl}-4-(trifluoromethyl)pyrimidin-2-amine | 391/391 |
| 5.51 | C2/Iy Formate Salt | 3-morpholin-4-ylpropyl | CH₃ | CF₃ | N-{3-methyl-5-[1-(3-morpholin-4-ylpropyl)-1H-1,2,3-triazol-4-yl]phenyl}-4-(trifluoromethyl)pyrimidin-2-amine | 448/448 |
| 5.52 | C2/Iy Formate Salt | 3-fluoro-2-hydroxypropyl (racemic) | CH₃ | CF₃ | 1-fluoro-3-[4-(3-methyl-5-{[4-(trifluoromethyl)pyrimidin-2-yl]amino}phenyl)-1H-1,2,3-triazol-1-yl]propan-2-ol | 397/397 |

TABLE 5A-continued

| Ex. No. | C Ring/A & B Rings | R¹ | R² | R³ | Chemical Name | [M + H]+ Calc'd/Observed |
|---|---|---|---|---|---|---|
| 5.53 | C2/Iy Formate Salt | 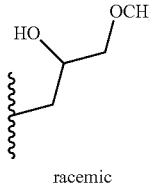 racemic | CH₃ | CF₃ | 1-methoxy-3-[4-(3-methyl-5-{[4-(trifluoromethyl) pyrimidin-2-yl]amino}phenyl)-1H-1,2,3-triazol-1-yl]propan-2-ol | 409/409 |
| 5.54 | C2/Iy Formate Salt | 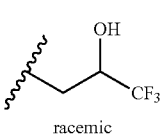 racemic | CH₃ | CF₃ | 1,1,1-trifluoro-3-[4-(3-methyl-5-{[4-(trifluoromethyl) pyrimidin-2-yl]amino}phenyl)-1H-1,2,3-triazol-1-yl]propan-2-ol | 433/433 |
| 5.55 | C2/Iy Formate Salt | 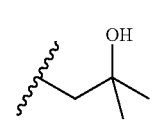 [SMILES: *CC(C)(C)O] | CH₃ | CF₃ | 2-methyl-1-[4-(3-methyl-5-{[4-(trifluoromethyl) pyrimidin-2-yl]amino}phenyl)-1H-1,2,3-triazol-1-yl]propan-2-ol | 393/393 |
| 5.56 | C2/Iy Formate Salt | 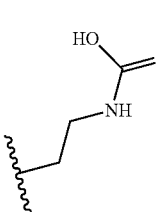 | CH₃ | CF₃ | 1-{2-[4-(3-methyl-5-{[4-(trifluoromethyl) pyrimidin-2-yl]amino}phenyl)-1H-1,2,3-triazol-1-yl]ethyl}urea | 407/407 |
| 5.57 | C2/Iy Formate Salt | 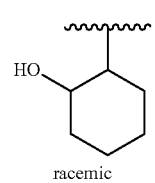 racemic | CH₃ | CF₃ | 2-[4-(3-methyl-5-{[4-(trifluoromethyl) pyrimidin-2-yl]amino}phenyl)-1H-1,2,3-triazol-1-yl]cyclohexanol | 419/419 |
| 5.58 | C2/Iy Formate Salt | CH₂CO₂H | CH₃ | CF₃ | [4-(3-methyl-5-{[4-(trifluoromethyl) pyrimidin-2-yl]amino}phenyl)-1H-1,2,3-triazol-1-yl]acetic acid | 379/379 |
| 5.59 | C2/Iy Formate Salt | 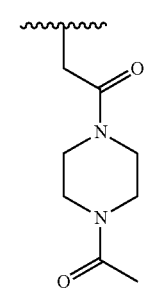 | CH₃ | CF₃ | N-(3-{1-[2-(4-acetylpiperazin-1-yl)-2-oxoethyl]-1H-1,2,3-triazol-4-yl}-5-methylphenyl)-4-(trifluoromethyl) pyrimidin-2-amine | 489/489 |
| 5.60 | C2/Iy Formate Salt | CH₂CH₂CO₂H | CH₃ | CF₃ | 3-[4-(3-methyl-5-{[4-(trifluoromethyl) pyrimidin-2-yl]amino}phenyl)-1H-1,2,3-triazol-1-yl]propanoic acid | 393/393 |

TABLE 5A-continued

| Ex. No. | C Ring/A & B Rings | R¹ | R² | R³ | Chemical Name | [M + H]+ Calc'd/Observed |
|---|---|---|---|---|---|---|
| 5.61 | C2/Iy Formate Salt | 2-hydroxy-CH(OH)-CH2-C(O)OH (racemic) | CH₃ | CF₃ | 2-hydroxy-3-[4-(3-methyl-5-{[4-(trifluoromethyl)pyrimidin-2-yl]amino}phenyl)-1H-1,2,3-triazol-1-yl]propanoic acid | 409/409 |
| 5.62 | C2/Iy Formate Salt | (CH₂)₂SO₂CH₃ | CH₃ | CF₃ | N-(3-methyl-5-{1-[2-(methylsulfonyl)ethyl]-1H-1,2,3-triazol-4-yl}phenyl)-4-(trifluoromethyl)pyrimidin-2-amine | 427/427 |
| 5.63 | C2/Iy Formate Salt | 4-hydroxytetrahydrothiophene-3-yl 1,1-dioxide | CH₃ | CF₃ | 4-[4-(3-methyl-5-{[4-(trifluoromethyl)pyrimidin-2-yl]amino}phenyl)-1H-1,2,3-triazol-1-yl]tetrahydrothiophene-3-ol 1,1-dioxide | 455/455 |
| 5.64 | C2/Iy Formate Salt | CH(CH₃)C(O)OH (racemic) | CH₃ | CF₃ | 2-[4-(3-methyl-5-{[4-(trifluoromethyl)pyrimidin-2-yl]amino}phenyl)-1H-1,2,3-triazol-1-yl]propanoic acid | 393/393 |
| 5.65 | C2/Iy Formate Salt | CH₂-C(O)-(cis-3,5-dimethylmorpholin-4-yl) | CH₃ | CF₃ | N-[3-(1-{2-[(cis)-3,5-dimethylmorpholin-4-yl]-2-oxoethyl}-1H-1,2,3-triazol-4-yl)-5-methylphenyl]-4-(trifluoromethyl)pyrimidin-2-amine | 476/476 |
| 5.66 | C2/Iy Formate Salt | CH₂-C(O)-(3,3-dimethylmorpholin-4-yl) | CH₃ | CF₃ | N-(3-{1-[2-(3,3-dimethylmorpholin-4-yl)-2-oxoethyl]-1H-1,2,3-triazol-4-yl}-5-methylphenyl)-4-(trifluoromethyl)pyrimidin-2-amine | 476/476 |
| 5.67 | C2/Iy Formate Salt | CH₂-C(O)-NH-C(CH₃)₂-CH₂-OCH₃ | CH₃ | CF₃ | N-(2-methoxy-1,1-dimethylethyl)-2-[4-(3-methyl-5-{[4-(trifluoromethyl)pyrimidin-2-yl]amino}phenyl)-1H-1,2,3-triazol-1-yl]acetamide | 464/464 |
| 5.68 | C2/Iy Formate Salt | CH₂-C(O)-(4,4-dimethyl-1,3-oxazolidin-3-yl) | CH₃ | CF₃ | N-(3-{1-[2-(4,4-dimethyl-1,3-oxazolidin-3-yl)-2-oxoethyl]-1H-1,2,3-triazol-4-yl}-5-methylphenyl)-4-(trifluoromethyl)pyrimidin-2-amine | 462/462 |

TABLE 5A-continued

| Ex. No. | C Ring/A & B Rings | R¹ | R² | R³ | Chemical Name | [M + H]+ Calc'd/Observed |
|---|---|---|---|---|---|---|
| 5.69 | C2/Iy Formate Salt | 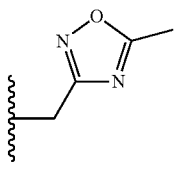 [SMILES: *Cc1noc(C)n1] | CH₃ | CF₃ | N-(3-methyl-5-{1-[(5-methyl-1,2,4-oxadiazol-3-yl)methyl]-1H-1,2,3-triazol-4-yl}phenyl)-4-(trifluoromethyl)pyrimidin-2-amine | 417/417 |
| 5.70 | C2/Iy Formate Salt | 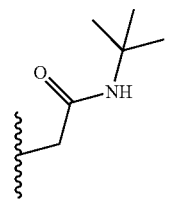 [SMILES: *CC(=O)NC(C)(C)C] | CH₃ | CF₃ | N-tert-butyl-2-[4-(3-methyl-5-{[4-(trifluoromethyl)pyrimidin-2-yl]amino}phenyl)-1H-1,2,3-triazol-1-yl]acetamide | 434/434 |
| 5.71 | C2/Iy Formate Salt | 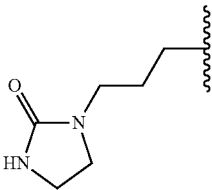 [SMILES: *CCCN1CCNC1=O] | CH₃ | CF₃ | 1-{3-[4-(3-methyl-5-{[4-(trifluoromethyl)pyrimidin-2-yl]amino}phenyl)-1H-1,2,3-triazol-1-yl]propyl}imidazolidin-2-one | 447/447 |
| 5.72 | C2/Iy Formate Salt | 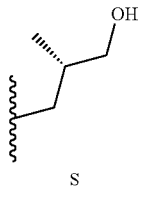 | CH₃ | CF₃ | (2S)-2-methyl-3-[4-(3-methyl-5-{[4-(trifluoromethyl)pyrimidin-2-yl]amino}phenyl)-1H-1,2,3-triazol-1-yl]propan-1-ol | 393/393 |
| 5.73 | C2/Iy Formate Salt | 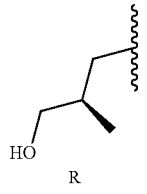 | CH₃ | CF₃ | (2R)-2-methyl-3-[4-(3-methyl-5-{[4-(trifluoromethyl)pyrimidin-2-yl]amino}phenyl)-1H-1,2,3-triazol-1-yl]propan-1-ol | 393/393 |
| 5.74 | C2/Iy Formate Salt | (CH₂)₂NH₂ | CH₃ | CF₃ | N-{3-[1-(2-aminoethyl)-1H-1,2,3-triazol-4-yl]-5-methylphenyl}-4-(trifluoromethyl)pyrimidin-2-amine | 364/364 |
| 5.75 | C2/Iy Formate Salt | (CH₂)₂CONH₂ | CH₃ | CF₃ | 3-[4-(3-methyl-5-{[4-(trifluoromethyl)pyrimidin-2-yl]amino}phenyl)-1H-1,2,3-triazol-1-yl]propanamide | 392/392 |
| 5.76 | C2/Iy Formate Salt | 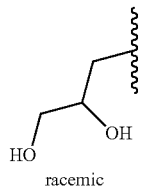 | CH₃ | CF₃ | 3-[4-(3-methyl-5-{[4-(trifluoromethyl)pyrimidin-2-yl]amino}phenyl)-1H-1,2,3-triazol-1-yl]propane-1,2-diol | 395/395 |
| 5.77 | C2/Iy Formate Salt | (CH₂)₃OH | CH₃ | CF₃ | 3-[4-(3-methyl-5-{[4-(trifluoromethyl)pyrimidin-2-yl]amino}phenyl)-1H-1,2,3-triazol-1-yl]propan-1-ol | 379/379 |

TABLE 5A-continued

| Ex. No. | C Ring/A & B Rings | R¹ | R² | R³ | Chemical Name | [M + H]+ Calc'd/Observed |
|---|---|---|---|---|---|---|
| 5.78 | C2/Iy Formate Salt | CH$_2$CN | CH$_3$ | CF$_3$ | [4-(3-methyl-5-{[4-(trifluoromethyl)pyrimidin-2-yl]amino}phenyl)-1H-1,2,3-triazol-1-yl]acetonitrile | 360/360 |
| 5.79 | C2/Iy Formate Salt | CH$_2$CONH$_2$ | CH$_3$ | CF$_3$ | 2-[4-(3-methyl-5-{[4-(trifluoromethyl)pyrimidin-2-yl]amino}phenyl)-1H-1,2,3-triazol-1-yl]acetamide | 378/378 |
| 5.80 | C2/Ix Formate Salt | (piperidine-4-carboxylic acid N-acetyl, racemic) | CH$_3$ | CF$_3$ | 1-{[4-(4-methyl-6-{[4-(trifluoromethyl)pyridin-2-yl]amino}pyridin-2-yl)-1H-1,2,3-triazol-1-yl]acetyl}piperidine-4-carboxylic acid | 490/490 |
| 5.81 | C2/Ix Formate Salt | (2R)-3-hydroxy-2-methylpropyl, R | CH$_3$ | CF$_3$ | (2R)-2-methyl-3-[4-(4-methyl-6-{[4-(trifluoromethyl)pyridin-2-yl]amino}pyridin-2-yl)-1H-1,2,3-triazol-1-yl]propan-1-ol | 393/393 |
| 5.82 | C2/Ix Formate Salt | (2S)-3-hydroxy-2-methylpropyl, S | CH$_3$ | CF$_3$ | (2S)-2-methyl-3-[4-(4-methyl-6-{[4-(trifluoromethyl)pyridin-2-yl]amino}pyridin-2-yl)-1H-1,2,3-triazol-1-yl]propan-1-ol | 393/393 |
| 5.83 | C2/Ix Formate Salt | 4,4,4-trifluoro-3-hydroxybutyl, racemic | CH$_3$ | CF$_3$ | 1,1,1-trifluoro-3-[4-(4-methyl-6-{[4-(trifluoromethyl)pyridin-2-yl]amino}pyridin-2-yl)-1H-1,2,3-triazol-1-yl]propan-2-ol | 433/433 |
| 5.84 | C2/Ix Formate Salt | (2-oxo-1,3-oxazolidin-5-yl)methyl, racemic | CH$_3$ | CF$_3$ | 5-{[4-(4-methyl-6-{[4-(trifluoromethyl)pyridin-2-yl]amino}pyridin-2-yl)-1H-1,2,3-triazol-1-yl]methyl}-1,3-oxazolidin-2-one | 420/420 |

TABLE 5A-continued

| Ex. No. | C Ring/A & B Rings | R¹ | R² | R³ | Chemical Name | [M + H]+ Calc'd/Observed |
|---|---|---|---|---|---|---|
| 5.85 | C2/Ix Formate Salt | (methyl butanoate group, racemic) | $CH_3$ | $CF_3$ | methyl 2-methyl-4-[4-(4-methyl-6-{[4-(trifluoromethyl)pyridin-2-yl]amino}pyridin-2-yl)-1H-1,2,3-triazol-1-yl]butanoate | 435/435 |
| 5.86 | C2/Ix Formate Salt | (methyl propanoate group, S) | $CH_3$ | $CF_3$ | methyl (2S)-2-methyl-3-[4-(4-methyl-6-{[4-(trifluoromethyl)pyridin-2-yl]amino}pyridin-2-yl)-1H-1,2,3-triazol-1-yl]propanoate | 421/421 |
| 5.87 | C2/Ix Formate Salt | (2-oxo-2-pyrrolidin-1-ylethyl) | $CH_3$ | $CF_3$ | 4-methyl-6-[1-(2-oxo-2-pyrrolidin-1-ylethyl)-1H-1,2,3-triazol-4-yl]-N-[4-(trifluoromethyl)pyridin-2-yl]pyridin-2-amine | 432/432 |
| 5.88 | C2/Ix Formate Salt | $CH_2CO_2H$ | $CH_3$ | $CF_3$ | [4-(4-methyl-6-{[4-(trifluoromethyl)pyridin-2-yl]amino}pyridin-2-yl)-1H-1,2,3-triazol-1-yl]acetic acid | 379/379 |
| 5.89 | C2/Ix Formate Salt | (2-hydroxycyclohexyl, racemic) | $CH_3$ | $CF_3$ | 2-[4-(4-methyl-6-{[4-(trifluoromethyl)pyridin-2-yl]amino}pyridin-2-yl)-1H-1,2,3-triazol-1-yl]cyclohexanol | 419/419 |
| 5.90 | C2/Ix Formate Salt | (3-hydroxy tetrahydrothiophene 1,1-dioxide, R,S) | $CH_3$ | $CF_3$ | 4-[4-(4-methyl-6-{[4-(trifluoromethyl)pyridin-2-yl]amino}pyridin-2-yl)-1H-1,2,3-triazol-1-yl]tetrahydrothiophene-3-ol 1,1-dioxide | 455/455 |
| 5.91 | C2/Ix Formate Salt | $CH_2CH_2OH$ | $CH_3$ | $CF_3$ | 2-[4-(4-methyl-6-{[4-(trifluoromethyl)pyridin-2-yl]amino}pyridin-2-yl)-1H-1,2,3-triazol-1-yl]ethanol | 365/365 |
| 5.92 | C2/Ix Formate Salt | $CH_2CN$ | $CH_3$ | $CF_3$ | [4-(4-methyl-6-{[4-(trifluoromethyl)pyridin-2-yl]amino}pyridin-2-yl)-1H-1,2,3-triazol-1-yl]acetonitrile | 360/360 |
| 5.93 | C2/Ix Formate Salt | (1-fluoro-2-hydroxypropyl, racemic) | $CH_3$ | $CF_3$ | 1-fluoro-3-[4-(4-methyl-6-{[4-(trifluoromethyl)pyridin-2-yl]amino}pyridin-2-yl)-1H-1,2,3-triazol-1-yl]propan-2-ol | 397/397 |

TABLE 5A-continued

| Ex. No. | C Ring/A & B Rings | R¹ | R² | R³ | Chemical Name | [M + H]+ Calc'd/Observed |
|---|---|---|---|---|---|---|
| 5.94 | C2/Ix Formate Salt | (CH₂)₃OH | CH₃ | CF₃ | 3-[4-(4-methyl-6-{[4-(trifluoromethyl) pyridin-2-yl]amino}pyridin-2-yl)-1H-1,2,3-triazol-1-yl]propan-1-ol | 379/379 |
| 5.95 | C2/Ix Formate Salt | 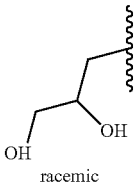 racemic | CH₃ | CF₃ | 3-[4-(4-methyl-6-{[4-(trifluoromethyl) pyridin-2-yl]amino}pyridin-2-yl)-1H-1,2,3-triazol-1-yl]propane-1,2-diol | 395/395 |
| 5.96 | C2/Ix Formate Salt | (CH₂)₂SO₂CH₃ | CH₃ | CF₃ | 4-methyl-6-{1-[2-(methylsulfonyl) ethyl]-1H-1,2,3-triazol-4-yl}-N-[4-(trifluoromethyl) pyridin-2-yl]pyridin-2-amine | 427/427 |
| 5.97 | C2/Ix Formate Salt | 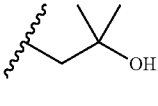 [SMILES: *CC(C)(C)O] | CH₃ | CF₃ | 2-methyl-1-[4-(4-methyl-6-{[4-(trifluoromethyl) pyridin-2-yl]amino}pyridin-2-yl)-1H-1,2,3-triazol-1-yl]propan-2-ol | 393/393 |
| 5.98 | C2/Iy Formate Salt | 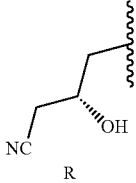 R | CH₃ | CF₃ | (3R)-3-hydroxy-4-[4-(3-methyl-5-{[4-(trifluoromethyl) pyrimidin-2-yl]amino}phenyl)-1H-1,2,3-triazol-1-yl]butanenitrile | 404/404 |
| 5.99 | C2/Iy | 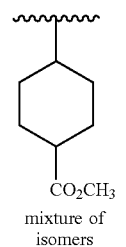 mixture of isomers | CH₃ | CF₃ | methyl 4-[4-(3-methyl-5-{[4-(trifluoromethyl) pyrimidin-2-yl]amino}phenyl)-1H-1,2,3-triazol-1-yl]cyclohexane-carboxylate | 461/461 |
| 5.100 | C2/Ix | CH₂CO₂C₂CH₅ | CH₃ | CF₃ | ethyl [4-(4-methyl-6-{[4-(trifluoromethyl) pyridin-2-yl]amino}pyridin-2-yl)-1H-1,2,3-triazol-1-yl]acetate | 407/407 |
| 5.101 | C2/Ix | H | CH₃ | CF₃ | 4-methyl-6-(1H-1,2,3-triazol-4-yl)-N-[4-(trifluoromethyl) pyridin-2-yl]pyridin-2-amine | 321/321 |

Examples 5.102-5.115 in Table 5B below had the following general structural formula, wherein R$^1$ is as specified in the table below.

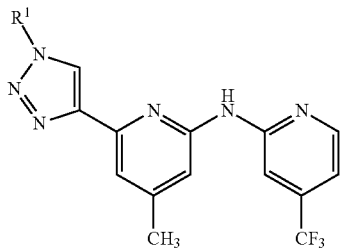

TABLE 5B

| Ex. No. | R$^1$ | Chemical Name | [M + H]+ Calc'd/Observed |
|---|---|---|---|
| 5.102 | | (5R)-5-{[4-(4-methyl-6-{[4-(trifluoromethyl)pyridin-2-yl]amino}pyridin-2-yl)-1H-1,2,3-triazol-1-yl]methyl}-1,3-oxazolidin-2-one | 420/420 |
| 5.103 | | (5S)-5-{[4-(4-methyl-6-{[4-(trifluoromethyl)pyridin-2-yl]amino}pyridin-2-yl)-1H-1,2,3-triazol-1-yl]methyl}-1,3-oxazolidin-2-one | 420/420 |
| 5.104 | | 4-methyl-6-{1-[(2-methyl-1H-imidazol-5-yl)methyl]-1H-1,2,3-triazol-4-yl}-N-[4-(trifluoromethyl)pyridin-2-yl]pyridin-2-amine | 415/415 |
| 5.105 | | 4-methyl-6-{1-[2-(1H-pyrazol-4-yl)ethyl]-1H-1,2,3-triazol-4-yl}-N-[4-(trifluoromethyl)pyridin-2-yl]pyridin-2-amine | 415/415 |
| 5.106 | | 4-methyl-6-{1-[(4-methyl-1H-imidazol-5-yl)methyl]-1H-1,2,3-triazol-4-yl}-N-[4-(trifluoromethyl)pyridin-2-yl]pyridin-2-amine | 415/415 |
| 5.107 | | 1-[4-(4-methyl-6-{[4-(trifluoromethyl)pyridin-2-yl]amino}pyridin-2-yl)-1H-1,2,3-triazol-1-yl]methanesulfonamide | 414/414 |

TABLE 5B-continued

| Ex. No. | R¹ | Chemical Name | [M + H]+ Calc'd/Observed |
|---|---|---|---|
| 5.108 | (CH2-imidazole) | 6-[1-(1H-imidazol-4-ylmethyl)-1H-1,2,3-triazol-4-yl]-4-methyl-N-[4-(trifluoromethyl)pyridin-2-yl]pyridin-2-amine | 401/401 |
| 5.109 | (CH2-tetrazole) | 4-methyl-6-[1-(1H-tetrazol-5-ylmethyl)-1H-1,2,3-triazol-4-yl]-N-[4-(trifluoromethyl)pyridin-2-yl]pyridin-2-amine | 403/403 |
| 5.110 | (CH2CH2-O-C(O)NH2) | 2-[4-(4-methyl-6-{[4-(trifluoromethyl)pyridin-2-yl]amino}pyridin-2-yl)-1H-1,2,3-triazol-1-yl]ethyl carbamate | 408/408 |
| 5.111 | (CH2-pyrazole) | 4-methyl-6-[1-(1H-pyrazol-3-ylmethyl)-1H-1,2,3-triazol-4-yl]-N-[4-(trifluoromethyl)pyridin-2-yl]pyridin-2-amine | 401/401 |
| 5.112 | (CH2-aminocyclopropyl) | 6-{1-[(1-aminocyclopropyl)methyl]-1H-1,2,3-triazol-4-yl}-4-methyl-N-[4-(trifluoromethyl)pyridin-2-yl]pyridin-2-amine | 390/390 |

Example 6.1

6-(1-(3-Chloropyridin-2-yl)-1H-1,2,3-triazol-4-yl)-4-methyl-N-(4-(trifluoromethyl)pyridin-2-yl)pyridin-2-amine

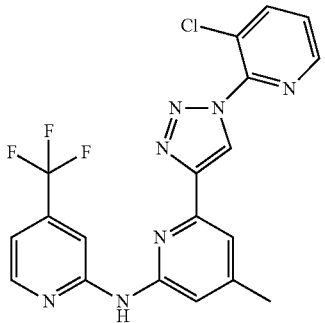 [SMILES: Cc1cc(Nc2cc(C(F)(F)F)ccn2)nc(-c2cn(-c3ncccc3Cl)nn2)c1]

6-Ethynyl-4-methyl-N-(4-(trifluoromethyl)pyridin-2-yl)pyridin-2-amine (0.20 g, 0.72 mmol), 8-chlorotetrazolo[1,5-a]pyridine (0.12 g, 0.79 mmol), copper trifluoromethanesulfonate (0.052 g, 0.14 mmol), dioxane (2.6 mL) and benzene (0.26 mL) were added to a vial. The reaction tube was sealed and heated to 110° C. for 12 hours. The reaction mixture was concentrated under reduced pressure. The residue was taken up in DMSO and purified by reverse phase preparative HPLC (0 to 95% ACN/water) to afford 6-(1-(3-chloropyridin-2-yl)-1H-1,2,3-triazol-4-yl)-4-methyl-N-(4-(trifluoromethyl)pyridin-2-yl)pyridin-2-amine. MS ESI calc. for $C_{19}H_{14}ClF_3N_7$ [M+H]⁺ 432. found 432. ¹H NMR (500 MHz, DMSO-$d_6$) δ 10.23 (s, 1H), 8.81 (s, 1H), 8.67 (d, J=3.3, 1H), 8.54-8.44 (m, 2H), 8.38 (d, J=8.1, 1H), 7.74 (dd, J=4.6, 8.1, 1H), 7.55 (s, 1H), 7.37 (s, 1H), 7.19 (d, 1H), 2.38 (s, 3H).

The following compound in Table 6 was prepared according to the method described for Example 6.1. $R^{1a}$ is H in the compound in Table 6

TABLE 6

| Ex. | C Rings/A & B Rings | R¹ | R² | R³ | Chemical Name | [M + H]+ Calc'd/Observed |
|---|---|---|---|---|---|---|
| 6.2 | C2/Ix | (5-bromopyridin-2-yl) | CH₃ | CF₃ | 6-[1-(5-bromopyridin-2-yl)-1H-1,2,3-triazol-4-yl]-4-methyl-N-[4-(trifluoromethyl)pyridin-2-yl]pyridin-2-amine | 476/476 |

Example 7.1

4-(4-(4-Methyl-6-((4-(trifluoromethyl)pyridin-2-yl)amino)pyridin-2-yl)-1H-1,2,3-triazol-1-yl)benzoic acid

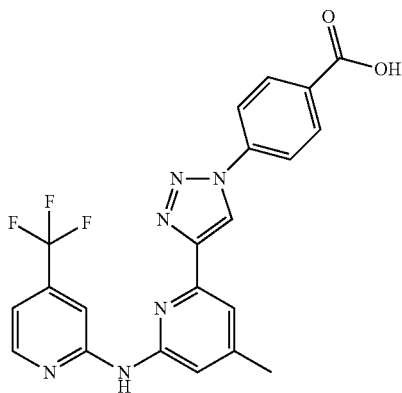 [SMILES: Cc1cc(Nc2cc(C(F)(F)F)ccn2)nc(-c2cn(-c3ccc(C(=O)O)cc3)nn2)c1]

6-Ethynyl-4-methyl-N-(4-(trifluoromethyl)pyridin-2-yl)pyridin-2-amine (0.20 g, 0.72 mmol), 4-azidobenzoic acid (0.13 g, 0.79 mmol), copper sulfate pentahydrate (0.018 g, 0.072 mmol), sodium ascorbate (0.057 g, 0.29 mmol), t-butanol (1.8 mL) and water (1.8 mL) were added to a vial. The reaction tube was sealed and heated to 50° C. for 3 hours then, diluted with water and the pH was adjusted to 3. The precipitate was collected via filtration, washed sequentially with water and ether and dried in vacuo to afford 4-(4-(4-methyl-6-((4-(trifluoromethyl)pyridin-2-yl)amino)pyridin-2-yl)-1H-1,2,3-triazol-1-yl)benzoic acid. MS ESI calc. for $C_{21}H_{16}F_3N_6O_2$ [M+H]+ 441. found 441. $^1$H NMR (600 MHz, DMSO-$d_6$) δ 10.20 (s, 1H), 9.01 (s, 1H), 8.53 (s, 1H), 8.47 (d, J=5.1, 1H), 8.29-7.95 (m, 4H), 7.48 (s, 1H), 7.36 (s, 1H), 7.17 (d, J=4.8, 1H), 2.35 (s, 3H).

Example 7.2 and 7.3

5-(1-(4-(3-((4-(Difluoromethyl)pyrimidin-2-yl)amino)-5-methylphenyl)-1H-1,2,3-triazol-1-yl)ethyl)oxazolidin-2-one (Isomer 1, first eluting) and 5-(1-(4-(3-((4-(difluoromethyl)pyrimidin-2-yl)amino)-5-methylphenyl)-1H-1,2,3-triazol-1-yl)ethyl)oxazolidin-2-one (Isomer 2, second eluting)

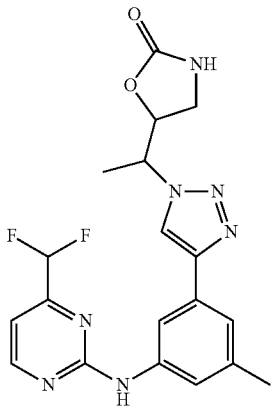 [SMILES: Cc1cc(Nc2nccc(C(F)F)n2)cc(-c2cn(C(C)C3CNC(=O)O3)nn2)c1]

A mixture of 4-(difluoromethyl)-N-(3-ethynyl-5-methylphenyl)pyrimidin-2-amine (111 mg, 0.430 mmol), 5-(1-azidoethyl)oxazolidin-2-one (100 mg, 0.640 mmol) CuSO$_4$.5H$_2$O (11.0 mg, 0.0430 mmol) and sodium ascorbate (34.0 mg, 0.170 mmol) in t-BuOH (1 mL) and H$_2$O (1 mL) was heated to 65° C. for 12 hours. The mixture was quenched with H$_2$O (20 mL) and then extracted with EtOAc (50 mL×3). The combined organic layers were dried over anhydrous sodium sulfate, filtered and concentrated under reduced pressure. The residue was purified by prep-TLC (1:10 MeOH/EtOAc, R$_f$=0.4) to afford 5-(1-(4-(3-((4-(difluoromethyl)pyrimidin-2-yl)amino)-5-methylphenyl)-1H-1,2,3-triazol-1-yl)ethyl)oxazolidin-2-one as a yellow solid. The resulting solid was purified by chiral SFC (Column: Chiralpak AD-3 50*4.6 mm I.D., 3 um Mobile phase: methanol (0.05% DEA) in CO$_2$ from 5% to 40% Flow rate: 4 mL/minute) to afford two isomers of 5-(1-(4-(3-((4-(difluoromethyl)pyrimidin-2-yl)amino)-5-methylphenyl)-1H-1,2,3-triazol-1-yl)ethyl)oxazolidin-2-one.

Example No. 7.2

Isomer 1, first eluting: MS ESI calc'd. for $C_{19}H_{20}F_2N_7O_2$ [M+H]+ 416. found 416. $^1$H NMR (400 MHz, DMSO-$d_6$) δ 10.02 (s, 1H), 8.73 (d, J=4.8 Hz, 1H), 8.55 (s, 1H), 8.13 (s, 1H), 7.57 (s, 1H), 7.52 (s, 1H), 7.30 (s, 1H), 7.08 (d, J=4.8 Hz, 1H), 6.87 (t, J=54.4 Hz, 1H), 5.00-4.92 (m, 2H), 3.66-3.62 (m, 1H), 3.31 (s, 1H), 2.34 (s, 3H), 1.58 (d, J=6.8 Hz, 3H).

Example No. 7.3

Isomer 2, second eluting: MS ESI calc'd. for $C_{19}H_{20}F_2N_7O_2$ [M+H]+ 416. found 416. $^1$H NMR (400 MHz, DMSO-$d_6$) δ 10.02 (s, 1H), 8.73 (d, J=4.8 Hz, 1H), 8.55 (s, 1H), 8.13 (s, 1H), 7.58-7.54 (m, 2H), 7.30 (s, 1H), 7.08 (d, J=4.8 Hz, 1H), 6.87 (t, J=54.4 Hz, 1H), 5.00-4.92 (m, 2H), 3.66-3.62 (m, 1H), 3.31 (s, 1H), 2.34 (s, 3H), 1.58 (d, J=6.8 Hz, 3H).

The following compounds in Table 7 were prepared according to the method described for Example 7.1 or Examples 7.2/7.3. The compounds in Table 7 had one of the following general formulas:

Formula C2(a)/Ix(a)

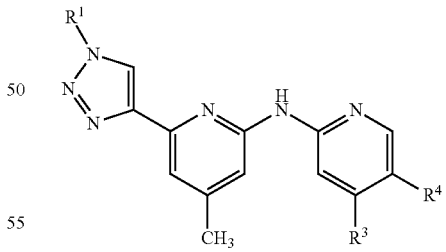

Formula C2(a)/Iy(a)

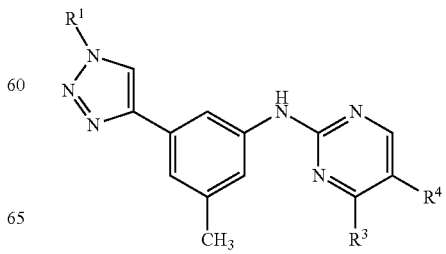

TABLE 7

| Ex. No. | C-Rings/A & B Rings | | R³ | R⁴ | Chemical Name | [M + H]+ Calc'd/Observed |
|---|---|---|---|---|---|---|
| 7.4 | C2(a)/Iy(a) | Single isomer, early eluting | C(H)F₂ | H | 5-((4-(3-((4-(difluoromethyl)pyrimidin-2-yl)amino)-5-methylphenyl)-1H-1,2,3-triazol-1-yl)methyl)oxazolidin-2-one | 402/402 |
| 7.5 | C2(a)/Iy(a) | Single isomer, late eluting | C(H)F₂ | H | 5-((4-(3-((4-(difluoromethyl)pyrimidin-2-yl)amino)-5-methylphenyl)-1H-1,2,3-triazol-1-yl)methyl)oxazolidin-2-one | 402/402 |
| 7.6 | C2(a)/Iy(a) | Single isomer, early eluting | C(H)F₂ | H | 5-((4-(3-((4-(difluoromethyl)pyrimidin-2-yl)amino)-5-methylphenyl)-1H-1,2,3-triazol-1-yl)methyl)-4-methyloxazolidin-2-one | 416/416 |
| 7.7 | C2(a)/Iy(a) | Single isomer, late eluting | C(H)F₂ | H | 5-((4-(3-((4-(difluoromethyl)pyrimidin-2-yl)amino)-5-methylphenyl)-1H-1,2,3-triazol-1-yl)methyl)-4-methyloxazolidin-2-one | 416/416 |
| 7.8 | C2(a)/Ix(a) | Single isomer, early eluting | C(H)F₂ | H | 5-((4-(6-((4-(difluoromethyl)pyridin-2-yl)amino)-4-methylpyridin-2-yl)1H-1,2,3-triazol-1-yl)methyl)-5-methyloxazolidin-2-one | 416/416 |
| 7.9 | C2(a)/Ix(a) | Single isomer, late eluting | C(H)F₂ | H | 5-((4-(6-((4-(difluoromethyl)pyridin-2-yl)amino)-4-methylpyridin-2-yl)-1H-1,2,3-triazol-1-yl)methyl)-5-methyloxazolidin-2-one | 416/416 |

TABLE 7-continued

| Ex. No. | C-Rings/A & B Rings | | R³ | R⁴ | Chemical Name | [M + H]+ Calc'd/Observed |
|---|---|---|---|---|---|---|
| 7.10 | C2(a)/Ix(a) | [isopropyl-oxazolidin-2-one structure] Single isomer, early eluting | C(H)F₂ | H | 5-(1-(4-(6-((4-(difluoromethyl)pyridin-2-yl)amino)-4-methylpyridin-2-yl)-1H-1,2,3-triazol-1-yl)ethyl)oxazolidin-2-one | 416/416 |
| 7.11 | C2(a)/Ix(a) | [isopropyl-oxazolidin-2-one structure] Single isomer, late eluting | C(H)F₂ | H | 5-(1-(4-(6-((4-(difluoromethyl)pyridin-2-yl)amino)-4-methylpyridin-2-yl)-1H-1,2,3-triazol-1-yl)ethyl)oxazolidin-2-one | 416/416 |
| 7.12 | C2(a)/Ix(a) | [methyl-oxazolidin-2-one structure] Single isomer, early eluting | C(H)F₂ | H | 5-((4-(6-((4-(difluoromethyl)pyridin-2-yl)amino)-4-methylpyridin-2-yl)-1H-1,2,3-triazol-1-yl)methyl)oxazolidin-2-one | 402/402 |
| 7.13 | C2(a)/Ix(a) | [methyl-oxazolidin-2-one structure] Single isomer, late eluting | C(H)F₂ | H | 5-((4-(6-((4-(difluoromethyl)pyridin-2-yl)amino)-4-methylpyridin-2-yl)-1H-1,2,3-triazol-1-yl)methyl)oxazolidin-2-one | 402/402 |
| 7.14 | C2(a)/Ix(a) | [4-methyl-oxazolidin-2-one structure] Single isomer, early eluting | C(H)F₂ | H | 5-((4-(6-((4-(difluoromethyl)pyridin-2-yl)amino)-4-methylpyridin-2-yl)-1H-1,2,3-triazol-1-yl)methyl)-4-methyloxazolidin-2-one | 416/416 |
| 7.15 | C2(a)/Ix(a) | [4-methyl-oxazolidin-2-one structure] Single isomer, late eluting | C(H)F₂ | H | 5-((4-(6-((4-(difluoromethyl)pyridin-2-yl)amino)-4-methylpyridin-2-yl)-1H-1,2,3-triazol-1-yl)methyl)-4-methyloxazolidin-2-one | 416/416 |
| 7.16 | C2(a)/Iy(a) | [pyridin-2(1H)-one structure] | C(H)F₂ | H | 5-((4-(3-((4-(difluoromethyl)pyrimidin-2-yl)amino)-5-methylphenyl)-1H-1,2,3-triazol-1-yl)methyl)pyridin-2(3H)-one | 410/410 |

TABLE 7-continued

| Ex. No. | C-Rings/A & B Rings | | R³ | R⁴ | Chemical Name | [M + H]+ Calc'd/Observed |
|---|---|---|---|---|---|---|
| 7.17 | C2(a)/Iy(a) | Single isomer, early eluting | C(H)F₂ | H | 7-((4-(3-((4-(difluoromethyl)pyrimidin-2-yl)amino)-5-methylphenyl)-1H-1,2,3-triazol-1-yl)methyl)-6-oxa-4-azaspiro[2.4]heptan-5-one | 428/428 |
| 7.18 | C2(a)/Iy(a) | Single isomer, late eluting | C(H)F₂ | H | 7-((4-(3-((4-(difluoromethyl)pyrimidin-2-yl)amino)-5-methylphenyl)-1H-1,2,3-triazol-1-yl)methyl)-6-oxa-4-azaspiro[2.4]heptan-5-one | 428/428 |
| 7.19 | C2(a)/Iy(a) | Single isomer, early eluting | C(H)F₂ | H | 2-[4-(3-{[4-(difluoromethyl)pyrimidin-2-yl]amino}-5-methylphenyl)-1H-1,2,3-triazol-1-yl]-1-methylcyclohexanol | 415/415 |
| 7.20 | C2(a)/Iy(a) | Single isomer, late eluting | C(H)F₂ | H | 2-[4-(3-{[4-(difluoromethyl)pyrimidin-2-yl]amino}-5-methylphenyl)-1H-1,2,3-triazol-1-yl]-1-methylcyclohexanol | 415/415 |
| 7.21 | C2(a)/Iy(a) | Single isomer, early eluting | CH₃ | H | 2-(4-{3-methyl-5-[(4-methylpyrimidin-2-yl)amino]phenyl}-1H-1,2,3-triazol-1-yl)cyclohexanol | 365/365 |
| 7.22 | C2(a)/Iy(a) | Single isomer, late eluting | CH₃ | H | 2-(4-{3-methyl-5-[(4-methylpyrimidin-2-yl)amino]phenyl}-1H-1,2,3-triazol-1-yl)cyclohexanol | 365/365 |
| 7.23 | C2(a)/Ix(a) | Single isomer, early eluting | C(H)F₂ | H | 2-[4-(6-{[4-(difluoromethyl)pyridin-2-yl]amino}-4-methylpyridin-2-yl)-1H-1,2,3-triazol-1-yl]cyclohexanol | 401/401 |

TABLE 7-continued

| Ex. No. | C-Rings/A & B Rings | | R³ | R⁴ | Chemical Name | [M + H]+ Calc'd/Observed |
|---|---|---|---|---|---|---|
| 7.24 | C2(a)/Ix(a) | Single isomer, late eluting | C(H)F₂ | H | 2-[4-(6-{[4-(difluoromethyl)pyridin-2-yl]amino}-4-methylpyridin-2-yl)-1H-1,2,3-triazol-1-yl]cyclohexanol | 401/401 |
| 7.25 | C2(a)/Iy(a) | Single isomer, early eluting | C(H)F₂ | H | 2-[4-(3-{[4-(difluoromethyl)-5-fluoropyrimidin-2-yl]amino}-5-methylphenyl)-1H-1,2,3-triazol-1-yl]-1-methylcyclohexanol | 433/433 |
| 7.26 | C2(a)/Iy(a) | Single isomer, late eluting | C(H)F₂ | H | 2-[4-(3-{[4-(difluoromethyl)-5-fluoropyrimidin-2-yl]amino}-5-methylphenyl)-1H-1,2,3-triazol-1-yl]-1-methylcyclohexanol | 433/433 |
| 7.27 | C2(a)/Iy(a) | Single isomer, early eluting | CH₃ | H | 1-methyl-2-(4-{3-methyl-5-[(4-methylpyrimidin-2-yl)amino]phenyl}-1H-1,2,3-triazol-1-yl)cyclohexanol | 379/379 |
| 7.28 | C2(a)/Iy(a) | Single isomer, late eluting | CH₃ | H | 1-methyl-2-(4-{3-methyl-5-[(4-methylpyrimidin-2-yl)amino]phenyl}-1H-1,2,3-triazol-1-yl)cyclohexanol | 379/379 |
| 7.29 | C2(a)/Iy(a) | Single isomer, early eluting | C(H)F₂ | H | 2-[4-(3-{[4-(difluoromethyl)-5-fluoropyrimidin-2-yl]amino}-5-methylphenyl)-1H-1,2,3-triazol-1-yl]cyclohexanol | 419/419 |
| 7.30 | C2(a)/Iy(a) | Single isomer, late eluting | C(H)F₂ | H | 2-[4-(3-{[4-(difluoromethyl)-5-fluoropyrimidin-2-yl]amino}-5-methylphenyl)-1H-1,2,3-triazol-1-yl]cyclohexanol | 419/419 |
| 7.31 | C2(a)/Iy(a) | Single isomer, second eluting | C(H)F₂ | H | 5-{[4-(3-{[4-(difluoromethyl)pyrimidin-2-yl]amino}-5-methylphenyl)-1H-1,2,3-triazol-1-yl]methyl}-5-methyl-1,3-oxazolidin-2-one | 416/416 |

TABLE 7-continued

| Ex. No. | C-Rings/A & B Rings | | R³ | R⁴ | Chemical Name | [M + H]+ Calc'd/Observed |
|---|---|---|---|---|---|---|
| 7.32 | C2(a)/Iy(a) | Single isomer, early eluting | C(H)F₂ | H | 5-{[4-(3-{[4-(difluoromethyl)pyrimidin-2-yl]amino}-5-methylphenyl)-1H-1,2,3-triazol-1-yl]methyl}-5-methyl-1,3-oxazolidin-2-one | 416/416 |
| 7.33 | C2(a)/Iy(a) | Single isomer, late eluting | C(H)F₂ | F | 7-{[4-(3-{[4-(difluoromethyl)-5-fluoropyrimidin-2-yl]amino}-5-methylphenyl)-1H-1,2,3-triazol-1-yl]methyl}-6-oxa-4-azaspiro[2.4]heptan-5-one | 446/446 |
| 7.34 | C2(a)/Iy(a) | Single isomer, early eluting | C(H)F₂ | F | 7-{[4-(3-{[4-(difluoromethyl)-5-fluoropyrimidin-2-yl]amino}-5-methylphenyl)-1H-1,2,3-triazol-1-yl]methyl}-6-oxa-4-azaspiro[2.4]heptan-5-one | 446/446 |
| 7.35 | C2(a)/Iy(a) | Single isomer, late eluting | C(H)F₂ | F | 5-{[4-(3-{[4-(difluoromethyl)-5-fluoropyrimidin-2-yl]amino}-5-methylphenyl)-1H-1,2,3-triazol-1-yl]methyl}-1,3-oxazolidin-2-one | 420/420 |
| 7.36 | C2(a)/Iy(a) | | C(H)F₂ | F | 5-{[4-(3-{[4-(difluoromethyl)-5-fluoropyrimidin-2-yl]amino}-5-methylphenyl)-1H-1,2,3-triazol-1-yl]methyl}-1,3-oxazolidin-2-one | 420/420 |
| 7.37 | C2(a)/Iy(a) | Single isomer, first eluting | C(H)F₂ | F | 5-{[4-(3-{[4-(difluoromethyl)-5-fluoropyrimidin-2-yl]amino}-5-methylphenyl)-1H-1,2,3-triazol-1-yl]methyl}-4-methyl-1,3-oxazolidin-2-one | 434/434 |
| 7.38 | C2(a)/Iy(a) | Single isomer, second eluting | C(H)F₂ | F | 5-{[4-(3-{[4-(difluoromethyl)-5-fluoropyrimidin-2-yl]amino}-5-methylphenyl)-1H-1,2,3-triazol-1-yl]methyl}-4-methyl-1,3-oxazolidin-2-one | 434/434 |

TABLE 7-continued

| Ex. No. | C-Rings/A & B Rings | | R³ | R⁴ | Chemical Name | [M + H]+ Calc'd/Observed |
|---|---|---|---|---|---|---|
| 7.39 | C2(a)/Iy(a) | Single isomer, third eluting | C(H)F₂ | F | 5-{[4-(3-{[4-(difluoromethyl)-5-fluoropyrimidin-2-yl]amino}-5-methylphenyl)-1H-1,2,3-triazol-1-yl]methyl}-4-methyl-1,3-oxazolidin-2-one | 434/434 |
| 7.40 | C2(a)/Iy(a) | Single isomer, fourth eluting | C(H)F₂ | F | 5-{[4-(3-{[4-(difluoromethyl)-5-fluoropyrimidin-2-yl]amino}-5-methylphenyl)-1H-1,2,3-triazol-1-yl]methyl}-4-methyl-1,3-oxazolidin-2-one | 434/434 |
| 7.41 | C2(a)/Iy(a) | using chiral azide SM (Isomer 2, second eluting) | C(H)F₂ | H | 5-{[4-(3-{[4-(difluoromethyl)pyrimidin-2-yl]amino}-5-methylphenyl)-1H-1,2,3-triazol-1-yl]methyl}-4-methyl-1,3-oxazolidin-2-one | 416/416 |
| 7.42 | C2(a)/Iy(a) | using chiral azide SM (Isomer 1, first eluting) | C(H)F₂ | H | 5-{[4-(3-{[4-(difluoromethyl)pyrimidin-2-yl]amino}-5-methylphenyl)-1H-1,2,3-triazol-1-yl]methyl}-4-methyl-1,3-oxazolidin-2-one | 416/ |
| 7.43 | C2(a)/Ix(a) | using chiral azide SM (Isomer 2, second eluting) | C(H)F₂ | H | 5-{[4-(6-{[4-(difluoromethyl)pyridin-2-yl]amino}-4-methylpyridin-2-yl)-1H-1,2,3-triazol-1-yl]methyl}-4-methyl-1,3-oxazolidin-2-one | 416/416 |
| 7.44 | C2(a)/Ix(a) | using chiral azide SM (Isomer 2, second eluting) | C(H)F₂ | H | 5-{[4-(6-{[4-(difluoromethyl)pyridin-2-yl]amino}-4-methylpyridin-2-yl)-1H-1,2,3-triazol-1-yl]methyl}-4-methyl-1,3-oxazolidin-2-one | 416/416 |

Example Method 8.1

Methyl 1-[4-(4-methyl-6-{[4-(trifluoromethyl)pyridin-2-yl]amino}pyridin-2-yl)-1H-1,2,3-triazol-1-yl]cyclopropanecarboxylate

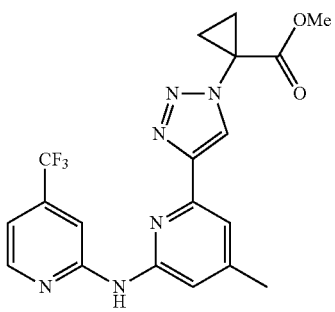 [SMILES: COC(=O)C1(n2cc(-c3cc(C)cc(Nc4cc(C(F)(F)F)ccn4)n3)nn2)CC1]

Step 1:
Sodium azide (211 mg, 3.25 mmol) was dissolved in dichloromethane (1.8 mL). The mixture was cooled to 0° C. and trifluoromethanesulfonic anhydride (0.55 mL, 3.3 mmol) was added. The mixture was stirred for 1 hour at 0° C. and the resulting trifluoromethanesulfonyl azide was used as is in the next step.

Step 2:
Water (0.90 mL) and tert-butanol (0.90 mL) were added at room temperature to a vial under an argon gas atmosphere containing methyl 1-aminocyclopropane carboxylate hydrochloride (246 mg, 1.62 mmol), copper(II) sulfate pentahydrate (40.5 mg, 0.16 mmol), and N,N-diisopropylethylamine (0.43 mL, 2.4 mmol). A solution of trifluoromethanesulfonyl azide (1.65 M in dichloromethane, 1.8 mL, 3.0 mmol) was added and the reaction mixture was stirred at room temperature for 18 hours. 6-Ethynyl-4-methyl-N-[4-(trifluoromethyl)pyridin-2-yl]pyridin-2-amine (150 mg, 0.54 mmol) and sodium ascorbate (129 mg, 0.65 mmol) were then added. The mixture was stirred at 50° C. for 5 hours and then cooled to room temperature and concentrated under reduced pressure. The residue was purified by reverse phase HPLC (0 to 95% ACN/water with 0.1% trifluoroacetic acid modifier) to afford methyl 1-[4-(4-methyl-6-{[4-(trifluoromethyl)pyridin-2-yl]amino}pyridin-2-yl)-1H-1,2,3-triazol-1-yl]cyclopropanecarboxylate. MS ESI calcd. for $C_{19}H_{18}F_3N_6O_2$ [M+H]$^+$ 419. found 419. $^1$H NMR (500 MHz, DMSO-d$_6$) δ 10.19 (s, 1H), 8.51 (s, 1H), 8.48 (d, J=5.1, 1H), 8.42 (s, 1H), 7.44 (s, 1H), 7.30 (s, 1H), 7.19 (d, J=5.2, 1H), 3.31 (s, 2H), 3.15 (s, 1H), 2.35 (s, 3H), 1.91-1.81 (m, 4H).

The following compound in Table 8 was prepared according to the method described for Example 8.1. $R^{1a}$ is H in the compound in Table 8.

Example 9.1

(R or S) 2,2-Dimethyl-4-[4-(4-methyl-6-{[4-(trifluoromethyl)pyridin-2-yl]amino}pyridin-2-yl)-1 H-1,2,3-triazol-1-yl]cyclohexanecarboxylic acid

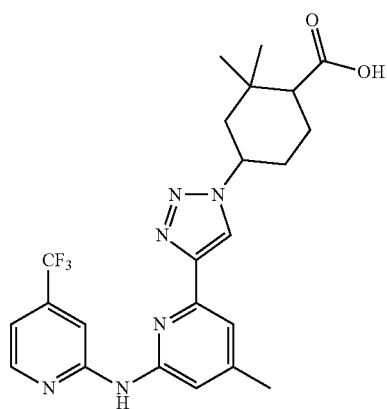 [SMILES: Cc1cc(Nc2cc(C(F)(F)F)ccn2)nc(-c2cn(C3CCC(C(=O)O)C(C)(C)C3)nn2)c1]

Step 1:
Sodium borohydride (1.85 g, 48.9 mmol) was added to a flask containing methyl 2,2-dimethyl-4-oxocyclohexanecarboxylate (3.0 g, 16.3 mmol) dissolved in ethanol (65 mL) at −20° C. The mixture was stirred at −20° C. for 2 h. Hydrochloric acid (1M) was added drop wise and the mixture was extracted with dichloromethane (3×). The combined organic layers were dried over anhydrous sodium sulfate, filtered, and concentrated under reduced pressure to afford methyl 4-hydroxy-2,2-dimethylcyclohexanecarboxylate as a 3:1 mixture of diastereomers. $^1$H NMR (500 MHz, DMSO-d$_6$) δ 4.45 (d, J=4.6, 1H), 4.37 (d, J=4.0, 1H'), 3.69-3.59 (m, 1H), 3.57-3.52 (m, 3H), 2.15-2.05 (m, 1H), 1.75-1.46 (m, 5H), 1.09-0.97 (m, 1H), 0.96-0.88 (m, 6H).

Step 2:
Methanesulfonyl chloride (1.69 mL, 21.7 mmol) was added to a flask containing methyl 4-hydroxy-2,2-dimethylcyclohexanecarboxylate (3.11 g, 16.69 mmol) and triethylamine (4.65 mL, 33.4 mmol) dissolved in dichloromethane (66.8 mL) at −20° C. The reaction was stirred at −20° C. for 3 hours then the mixture was diluted with saturated sodium bicarbonate and extracted with dichloromethane (3×). The combined organic layers were washed with brine, dried over anhydrous sodium sulfate, filtered, and concentrated to afford methyl 2,2-dimethyl-4-[(methylsulfonyl)oxy]cyclohexane carboxylate as a 3:1 mixture of diastereomers. $^1$H NMR (500 MHz, CDCl$_3$) δ 4.89-4.73 (m, 1H), 4.80-4.72 (m, 1H'), 4.29 (q, J=7.1, 1H), 4.13-4.07 (m, 1H$^1$), 3.65 (s, 3H), 2.99 (s, 3H), 2.27-2.14 (m, 1H), 2.13-1.99 (m, 1H), 1.97-1.88 (m, 1H), 1.88-1.68 (m, 2H), 1.52-1.35 (m, 1H), 1.07-0.96 (m, 6H).

TABLE 8

| Ex. | C Rings/A & B Rings | $R^1$ | $R^2$ | $R^3$ | Chemical Name | [M + H]+ Calc'd/Observed |
|---|---|---|---|---|---|---|
| 8.2 | C2/Ix | ◇ CO₂Et | CH₃ | CF₃ | ethyl 1-[4-(4-methyl-6-{[4-(trifluoromethyl)-pyridin-2-yl]amino}-pyridin-2-yl)-1H-1,2,3-triazol-1-yl]cyclobutane-carboxylate | 447/447 |

Step 3:

Sodium azide (0.37 g, 5.67 mmol) was added to a flask containing methyl 2,2-dimethyl-4-[(methylsulfonyl)oxy]cyclohexane carboxylate (1.0 g, 3.8 mmol) dissolved in DMF (7.6 mL) at room temperature. The reaction was stirred at 90° C. for 19 hours. The mixture was then cooled to room temperature, diluted with ethyl acetate, and washed with water and brine. The organic layer was dried over anhydrous sodium sulfate, filtered, and concentrated under reduced pressure. The residue was purified by column chromatography on silica gel (0 to 15% methanol/dichloromethane) to afford methyl 4-azido-2,2-dimethylcyclohexanecarboxylate as a 3:1 mixture of diastereomers. $^1$H NMR (500 MHz, CDCl$_3$) δ 3.65 (s, 3H), 3.56-3.49 (m, 1H), 3.47-3.41 (m, 1H$^1$), 2.27-2.12 (m, 1H), 2.10-2.02 (m, 1H), 1.91-1.68 (m, 4H), 1.30-1.18 (m, 1H), 1.04-0.96 (m, 6H).

Step 4:

tert-Butanol (2.0 mL) and water (2.0 mL) were added to an oven-dried flask containing 6-ethynyl-4-methyl-N-[4-(trifluoromethyl)pyridin-2-yl]pyridin-2-amine (280 mg, 1.01 mmol), methyl 4-azido-2,2-dimethylcyclohexanecarboxylate (320 mg, 1.52 mmol), copper(II) sulfate pentahydrate (25.2 mg, 0.10 mmol), and sodium ascorbate (80 mg, 0.40 mmol). The reaction was stirred at 65° C. for 17 hours. The mixture was then cooled to room temperature, diluted with water, and extracted with ethyl acetate (2×). The combined organic layers were dried over anhydrous sodium sulfate, filtered, and concentrated under reduced pressure. The residue was purified by column chromatography on silica gel (0 to 70% ethyl acetate/hexanes) to afford methyl 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylate. MS ESI calcd. for C$_{24}$H$_{28}$F$_3$N$_6$O$_2$ [M+H]$^+$ 489. found 489.

Step 5:

Sodium hydroxide (1.0M in water, 1.23 mL, 1.23 mmol) was added to a flask containing methyl 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylate (200 mg, 0.41 mmol) dissolved in THF (1.36 mL), water (0.34 mL) and methanol (0.34 mL). The reaction was heated to 65° C. for 48 hours. The mixture was then cooled to room temperature, diluted with hydrochloric acid (1.0 M, 1.2 mL), and filtered. The solid was dried in vacuo to afford 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylic acid. MS ESI calcd. for C$_{23}$H$_{26}$F$_3$N$_6$O$_2$ [M+H]$^+$ 475. found 475.

Step 6:

2,2-Dimethyl-4-[4-(4-methyl-6-{[4-(trifluoromethyl)pyridin-2-yl]amino}pyridin-2-yl)-1H-1,2,3-triazol-1-yl]cyclohexanecarboxylic acid (62 mg, 0.13 mmol) was dissolved in methanol (6 mL) with trifluoroacetic acid buffer and subjected to purification by chiral supercritical fluid chromatography (OJ 21×250 mm, 10 μm column, 15 to 85% methanol with 0.25% trifluoroacetic acid buffer/CO$_2$ with a flow rate of 70 mL/min and a 6 minute run time) to afford (R or S) 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylic acid as the second of three peaks. MS ESI calcd. for C$_{23}$H$_{26}$F$_3$N$_6$O$_2$ [M+H]$^+$ 475. found 475. $^1$H NMR (500 MHz, DMSO-d$_6$) δ 10.22 (s, 1H), 8.53 (s, 1H), 8.49 (d, J=5.1, 1H), 8.33 (s, 1H), 7.41 (s, 1H), 7.23 (s, 1H), 7.20 (d, J=5.2, 1H), 7.17 (s, 1H), 7.07 (s, 1H), 6.96 (s, 1H), 2.34 (s, 3H), 2.22-2.19 (m, 2H), 1.95-1.67 (m, 4H), 1.06 (d, J=9.5, 6H).

The following compounds in Table 9 were prepared according to the method described for Example 9.1. R$^{1a}$ is H in the compounds in Table 9. Compounds were prepared with commercially available mesylates where appropriate.

TABLE 9

| Ex. | C Ring/A & B Rings | R$^1$ | R$^2$ | R$^3$ | Chemical Name | [M + H]+ Calc'd/Observed |
|---|---|---|---|---|---|---|
| 9.2 | C2/Ix | cyclohept-2-en-1-yl (racemic) | CH$_3$ | CF$_3$ | 6-(1-cyclohept-2-en-1-yl-1H-1,2,3-triazol-4-yl)-4-methyl-N-[4-(trifluoromethyl)-pyridin-2-yl]pyridin-2-amine | 415/415 |
| 9.3 | C2/Ix | 2,2-dimethylcyclohexyl-CO$_2$CH$_3$ (racemic) | CH$_3$ | CF$_3$ | methyl 2,2-dimethyl-4-[4-(4-methyl-6-{[4-(trifluoromethyl)pyridin-2-yl]amino}pyridin-2-yl)-1H-1,2,3-triazol-1-yl]cyclohexanecarboxylate | 489/489 |
| 9.4 | C2/Iy | 2,2-dimethylcyclohexyl-CO$_2$t-butyl (mixture of isomers) | CH$_3$ | CF$_3$ | tert-butyl 4-[4-(3-methyl-5-{[4-(trifluoromethyl)-pyrimidin-2-yl]amino}-phenyl)-1H-1,2,3-triazol-1-yl]cyclohexanecarboxylate | 503/503 |

TABLE 9-continued

| Ex. | C Ring/A & B Rings | R¹ | R² | R³ | Chemical Name | [M + H]+ Calc'd/Observed |
|---|---|---|---|---|---|---|
| 9.5 | C2/Ix | (structure: 4-CO₂H-phenyl with (R)-CH(CH₃)- linker) | CH₃ | CF₃ | 4-{(1R)-1-[4-(4-methyl-6-{[4-(trifluoromethyl)-pyridin-2-yl]amino}pyridin-2-yl)-1H-1,2,3-triazol-1-yl]ethyl}benzoic acid | 469/469 |
| 9.6 | C2/Ix | (structure: cyclohex-1-en-1-ylmethyl) | CH₃ | CF₃ | 6-[1-(cyclohex-1-en-1-ylmethyl)-1H-1,2,3-triazol-4-yl]-4-methyl-N-[4-(trifluoromethyl)pyridin-2-yl]pyridin-2-amine | 415/415 |
| 9.7 | C2/Ix | (structure: 4-CO₂H-phenyl with (S)-CH(CH₃)- linker) S | CH₃ | CF₃ | 4-{(1S)-1-[4-(4-methyl-6-{[4-(trifluoromethyl)pyridin-2-yl]amino}pyridin-2-yl)-1H-1,2,3-triazol-1-yl]ethyl}benzoic acid | 469/469 |

Example 10.1

3-(4-(4-Methyl-6-((4-(trifluoromethyl)pyridin-2-yl)amino)pyridin-2-yl)-1H-1,2,3-triazol-1-yl)-1-phenyl-propane-1,2-diol

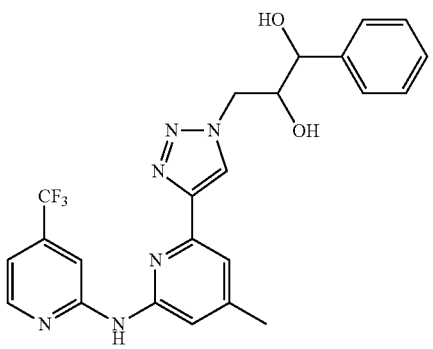 [SMILES: Cc1cc(Nc2cc(C(F)(F)F)ccn2)nc(-c2cn(CC(O)C(O)c3ccccc3)nn2)c1]

Step 1:

Cinnamyl chloride (181 μl, 1.30 mmol) followed by tert-butanol (0.9 mL) and water (0.9 mL) was added to a reaction vial which was evacuated and purged with argon. Sodium azide (73.9 mg, 1.14 mmol) was added, and the resulting mixture was stirred at 70° C. for approximately 17 hours. 6-ethynyl-4-methyl-N-(4-(trifluoromethyl)pyridin-2-yl)pyridin-2-amine (150 mg, 0.541 mmol) was then added, followed by copper(II) sulfate pentahydrate (13.5 mg, 0.054 mmol), and sodium ascorbate (42.9 mg, 0.216 mmol). The resulting mixture was sealed and stirred at 65° C. for 3 hours. The reaction mixture was diluted with water, and the resulting precipitate was collected via filtration. The solids were washed with water and ether, and then dried in vacuo overnight. The filtrate was extracted with ethyl acetate (3×). The filtered solids from the previous step were taken-up in ethyl acetate and added to the organic mixture. The combined organic fractions were dried over anhydrous magnesium sulfate, filtered, and concentrated under reduced pressure. The residue was purified by column chromatography on silica gel (0 to 15% methanol/dichloromethane). Further purification by reverse phase HPLC (ACN/water with 0.1% TFA modified) to afforded 6-(1-cinnamyl-1H-1,2,3-triazol-4-yl)-4-methyl-N-(4-(trifluoromethyl)pyridin-2-yl)pyridin-2-amine. MS ESI calcd. for $C_{23}H_{20}F_3N_6$ $[M+H]^+$ 437. found 437. $^1H$ NMR (500 MHz, DMSO-$d_6$) δ 10.19 (br s, 1H), 8.47 (s, 1H), 8.46 (s, 1H), 8.26 (s, 1H), 7.52-7.45 (m, 3H), 7.34 (t, J=7.0 Hz, 2H), 7.29-7.26 (m, 2H), 7.15 (d, J=5.5 Hz, 1H), 6.78 (d, J=16.0 Hz, 1H), 6.57 (dt, J=15.5, 7.0 Hz, 1H), 5.26 (d, J=6.5 Hz, 2H), 2.34 (s, 3H).

Step 2:

6-(1-Cinnamyl-1H-1,2,3-triazol-4-yl)-4-methyl-N-(4-(trifluoromethyl)pyridin-2-yl)pyridin-2-amine (130 mg, 0.298 mmol) and N-methylmorpholine N-oxide (52.3 mg, 0.447 mmol) were added to a vial, followed by THF (2.0 mL) and water (1.0 mL). A solution of osmium tetroxide (4% by weight, 0.58 mL, 0.074 mmol) was added, and the resulting mixture was stirred for approximately 13 hours at ambient temperature. The reaction mixture was diluted with water, and the resulting precipitate was collected via filtration. The solids were washed with water and ether and dried in vacuo overnight to afford 3-(4-(4-methyl-6-((4-(trifluoromethyl)pyridin-2-yl)amino)pyridin-2-yl)-1H-1,2,3-triazol-1-yl)-1-phenylpropane-1,2-diol. MS ESI calcd. for $C_{23}H_{22}F_3N_6O_2$ [M+H]+ 471. found 471. $^1$H NMR (500 MHz, DMSO-d$_6$) δ 10.15 (s, 1H), 8.47 (d, J=5.5 Hz, 1H), 8.41 (s, 1H), 8.20 (s, 1H), 7.43-7.40 (m, 3H), 7.36-7.32 (m, 3H), 7.26 (t, J=7.5 Hz, 1H), 7.17 (d, J=4.0 Hz, 1H), 5.61 (d, J=1H); 5.32 (d, J=6.0 Hz, 1H), 4.57 (t, J=5.0 Hz, 1H), 4.45 (dd, J=14.0, 3.0 Hz, 1H), 4.15 (dd, J=14.0, 9.0 Hz, 1H), 3.98-3.85 (m, 1H), 2.33 (s, 3H).

The following compounds in Table 10 were prepared according to the method described for Example 10.1. $R^{1a}$ is H in the compounds in Table 10.

TABLE 10

| Ex. | C Ring/A & B Rings | R$^1$ | R$^2$ | R$^3$ | Chemical Name | [M + H]+ Calc'd/Observed |
|---|---|---|---|---|---|---|
| 10.2 | C2/Ix | cycloheptane-1,2-diol (R or S; cis diol) | CH$_3$ | CF$_3$ | 3-[4-(4-methyl-6-{[4-(trifluoromethyl)pyridin-2-yl]amino}pyridin-2-yl)-1H-1,2,3-triazol-1-yl]cycloheptane-1,2-diol | 449/449 |
| 10.3 | C2/Ix | cycloheptane-1,2-diol (R or S; cis diol) | CH$_3$ | CF$_3$ | 3-[4-(4-methyl-6-{[4-(trifluoromethyl)pyridin-2-yl]amino}pyridin-2-yl)-1H-1,2,3-triazol-1-yl]cycloheptane-1,2-diol | 449/449 |
| 10.4 | C2/Ix | cycloheptane-1,2-diol (R or S; cis diol) | CH$_3$ | CF$_3$ | 3-[4-(4-methyl-6-{[4-(trifluoromethyl)pyridin-2-yl]amino}pyridin-2-yl)-1H-1,2,3-triazol-1-yl]cycloheptane-1,2-diol | 449/449 |
| 10.5 | C2/Ix | cycloheptane-1,2-diol (R or S; cis diol) | CH$_3$ | CF$_3$ | 3-[4-(4-methyl-6-{[4-(trifluoromethyl)pyridin-2-yl]amino}pyridin-2-yl)-1H-1,2,3-triazol-1-yl]cycloheptane-1,2-diol | 449/449 |
| 10.6 | C2/Ix | cycloheptane-1,2-diol (racemic) | CH$_3$ | CF$_3$ | 3-[4-(4-methyl-6-{[4-(trifluoromethyl)pyridin-2-yl]amino}pyridin-2-yl)-1H-1,2,3-triazol-1-yl]cycloheptane-1,2-diol | 449/449 |
| 10.7 | C2/Ix | pentitol (racemic) | CH$_3$ | CF$_3$ | 1,4,5-trideoxy-1-[4-(4-methyl-6-{[4-(trifluoromethyl)pyridin-2-yl]amino}pyridin-2-yl)-1H-1,2,3-triazol-1-yl]pentitol | 423/423 |

TABLE 10-continued

| Ex. | C Ring/A & B Rings | R¹ | R² | R³ | Chemical Name | [M + H]+ Calc'd/Observed |
|---|---|---|---|---|---|---|
| 10.8 | C2/Ix | 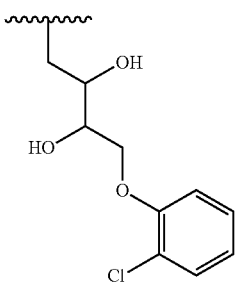 racemic | CH$_3$ | CF$_3$ | 1-(2-chlorophenoxy)-4-[4-(4-methyl-6-{[4-(trifluoromethyl)pyridin-2-yl]amino}pyridin-2-yl)-1H-1,2,3-triazol-1-yl]butane-2,3-diol | 535/535 |
| 10.9 | C2/Ix | 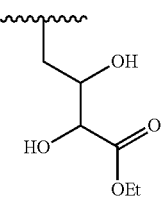 racemic | CH$_3$ | CF$_3$ | ethyl 2,3-dihydroxy-4-[4-(4-methyl-6-{[4-(trifluoromethyl)pyridin-2-yl]amino}pyridin-2-yl)-1H-1,2,3-triazol-1-yl]butanoate | 467/467 |
| 10.10 | C2/Ix | 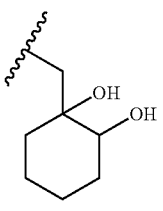 racemic | CH$_3$ | CF$_3$ | 1-{[4-(4-methyl-6-{[4-(trifluoromethyl)pyridin-2-yl]amino}pyridin-2-yl)-1H-1,2,3-triazol-1-yl]methyl}cyclohexane-1,2-diol | 449/449 |
| 10.11 | C2/Ix | 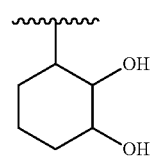 [SMILES: *C1CCCC(O)C1O] | CH$_3$ | CF$_3$ | 3-[4-(4-methyl-6-{[4-(trifluoromethyl)pyridin-2-yl]amino}pyridin-2-yl)-1H-1,2,3-triazol-1-yl]cyclohexane-1,2-diol | 435/435 |
| 10.12 | C2/Ix | 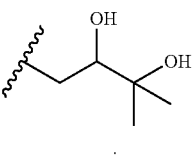 racemic | CH$_3$ | CF$_3$ | 3-methyl-1-[4-(4-methyl-6-{[4-(trifluoromethyl)pyridin-2-yl]amino}pyridin-2-yl)-1H-1,2,3-triazol-1-yl]butane-2,3-diol | 423/423 |
| 10.13 | C2/Ix | 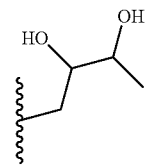 racemic | CH$_3$ | CF$_3$ | 1-[4-(4-methyl-6-{[4-(trifluoromethyl)pyridin-2-yl]amino}pyridin-2-yl)-1H-1,2,3-triazol-1-yl]butane-2,3-diol | 409/409 |

TABLE 10-continued

| Ex. | C Ring/A & B Rings | R¹ | R² | R³ | Chemical Name | [M + H]+ Calc'd/Observed |
|---|---|---|---|---|---|---|
| 10.14 | C2/Ix | CH₂-C(CH₃)(OH)-CH₂OH (R or S) | CH₃ | CF₃ | 2-methyl-3-[4-(4-methyl-6-{[4-(trifluoromethyl)pyridin-2-yl]amino}pyridin-2-yl)-1H-1,2,3-triazol-1-yl]propane-1,2-diol | 409/409 |
| 10.15 | C2/Ix | CH₂-C(CH₃)(OH)-CH₂OH (R or S) | CH₃ | CF₃ | 2-methyl-3-[4-(4-methyl-6-{[4-(trifluoromethyl)pyridin-2-yl]amino}pyridin-2-yl)-1H-1,2,3-triazol-1-yl]propane-1,2-diol | 409/409 |
| 10.16 | C2/Ix | CH₂-C(CH₃)(OH)-CH₂OH (racemic) | CH₃ | CF₃ | 2-methyl-3-[4-(4-methyl-6-{[4-(trifluoromethyl)pyridin-2-yl]amino}pyridin-2-yl)-1H-1,2,3-triazol-1-yl]propane-1,2-diol | 409/409 |

Example 11

5-[4-(4-Methyl-6-{[4-(trifluoromethyl)pyridin-2-yl]amino}pyridin-2-yl)-1H-1,2,3-triazol-1-yl]azepan-2-one (racemic)

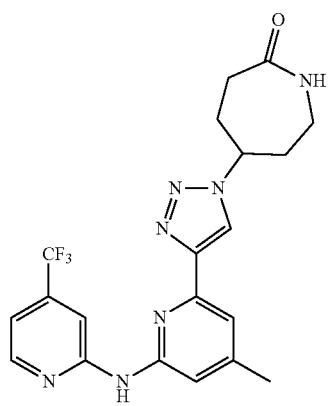 [SMILES: Cc1cc(Nc2cc(C(F)(F)F)ccn2)nc(-c2cn(C3CCNC(=O)CC3)nn2)c1]

Step 1:

In a microwave vial, 1,4-dioxaspiro[4.5]dec-8-yl methanesulfonate (511 mg, 2.16 mmol) was taken up in t-butanol (1200 µl) and water (1200 µl) under argon. Sodium azide (141 mg, 2.164 mmol) was added, and the resulting mixture was stirred at 70° C. overnight. 6-Ethynyl-4-methyl-N-[4-(trifluoromethyl)pyridin-2-yl]pyridin-2-amine (200 mg, 0.721 mmol), copper(II) sulfate pentahydrate (18.01 mg, 0.072 mmol), and sodium ascorbate (57.2 mg, 0.289 mmol) were sequentially added. The resulting mixture was sealed and stirred at 65° C. for 3 hours. The reaction mixture was then cooled, diluted with water, and extracted with ethyl acetate (2×). The organic layers were combined and concentrated under reduced pressure. The residue was purified by reverse phase HPLC (20 to 70% ACN/water with 0.1% TFA modifier). Desired fractions were combined and poured into ethyl acetate and saturated aqueous sodium bicarbonate. The organic layer was separated, dried over anhydrous magnesium sulfate, filtered, and concentrated under reduced pressure to afford 4-[4-(4-methyl-6-{[4-(trifluoromethyl)pyridin-2-yl]amino}pyridin-2-yl)-1H-1,2,3-triazol-1-yl]cyclohexanone as a brown oil. MS ESI calcd. for $C_{20}H_{20}F_3N_6O$ [M+H]⁺ 417. found 417.

Step 2:

Sodium azide (92 mg, 1.42 mmol) was added to a stirring solution of 4-[4-(4-methyl-6-{[4-(trifluoromethyl)pyridin-2-yl]amino}pyridin-2-yl)-1H-1,2,3-triazol-1-yl]cyclohexanone (197 mg, 0.473 mmol) in chloroform (9 mL). Methanesulfonic acid (0.37 mL, 5.7 mmol) was added and the reaction was capped and stirred at 65° C. for 2.5 hours. The reaction mixture was partitioned between EtOAc (2×75 ml) and saturated aqueous sodium bicarbonate (80 mL). The combined organic layers were dried over anhydrous magnesium sulfate and concentrated under reduced pressure. The residue was purified by reverse phase HPLC (ACN/water with 0.1% TFA modifier). The desired fractions were freebased by partitioning between EtOAc (50 ml) and saturated aqueous sodium bicarbonate (50 ml). The organic layer was concentrated under reduced pressure and the resulting residue was purified by column chromatography on silica gel (0 to 15% methanol/EtOAc) to afford 5-[4-(4-methyl-6-{[4-(trifluoromethyl)pyridin-2-yl]amino}pyridin-2-yl)-1H-1,2,3-triazol-1-yl]azepan-2-one as a pale yellow solid. MS ESI calcd. for $C_{20}H_{21}F_3N_7O$ [M+H]⁺ 432. found 432. ¹H NMR (500 MHz, DMSO-d₆) δ 10.16 (s, 1H), 8.55 (s, 1H), 8.47 (d, J=5.0 Hz, 1H), 8.34 (s, 1H), 7.70-7.60 (m, 1H), 7.40 (s, 1H), 7.25 (s, 1H), 7.18 (d, J=4.0 Hz, 1H), 4.92-4.85 (m, 1H), 3.73-3.29 (m, 1H), 3.19-3.12 (m, 1H), 2.72-2.66 (m, 1H), 2.34 (s, 3H), 2.30-2.18 (m, 3H), 2.00-1.88 (m, 2H).

The following compounds in Table 11 were prepared according to the method described for Example 11.1. $R^{1a}$ is H in the compounds in Table 11.

TABLE 11

| Ex. | C Ring/A & B Rings | R¹ | R² | R³ | Chemical Name | [M+ H]+ Calc'd/Observed |
|---|---|---|---|---|---|---|
| 11.2 | C2/Ix | azepan-2-one (R or S) | $CH_3$ | $CF_3$ | 5-[4-(4-methyl-6-{[4-(trifluoromethyl)pyridin-2-yl]amino}pyridin-2-yl)-1H-1,2,3-triazol-1-yl]azepan-2-one | 432/432 |
| 11.3 | C2/Ix | azepan-2-one Single isomer (R or S), early eluting | $CH_3$ | $CF_3$ | 5-[4-(4-methyl-6-{[4-(trifluoromethyl)pyridin-2-yl]amino}pyridin-2-yl)-1H-1,2,3-triazol-1-yl]azepan-2-one | 432/432 |
| 11.4 | C2/Iy | 4-hydroxy-azepan-2-one racemic | $CH_3$ | $CF_3$ | 5-hydroxy-5-[1-(3-methyl-5-{[4-(trifluoromethyl)pyrimidin-2-yl]amino}phenyl)-1H-1,2,3-triazol-4-yl]azepan-2-one | 448/448 |

Example 12.1

((R)-3-Hydroxy-4-(4-(4-methyl-6-((4-(trifluoromethyl)pyridin-2-yl)amino)pyridin-2-yl)-1H-1,2,3-triazol-1-yl)butanamide

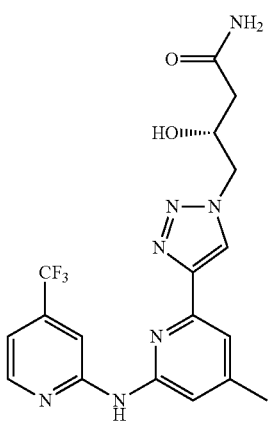 [SMILES: Cc1cc(Nc2cc(C(F)(F)F)ccn2)nc(-c2cn(C[C@H](O)CC(N)=O)nn2)c1]

Step 1:

(R)-4-Chloro-3-hydroxybutyronitrile (103 mg, 0.866 mmol) and sodium azide (49.2 mg, 0.757 mmol) followed by t-butyl alcohol (1.20 mL) and water (1.20 mL) were added to a dry vial. The reaction was heated at 70° C. for 16 hours and then charged with 6-ethynyl-4-methyl-N-(4-(trifluoromethyl)pyridin-2-yl)pyridin-2-amine (200 mg, 0.72 mmol), copper(II)sulfate pentahydrate (36.0 mg, 0.144 mmol) and sodium ascorbate (114 mg, 0.578 mmol). The vial was sealed and heated to 125° C. for 30 minutes. After cooling, DMSO (2 mL) was added and the reaction mixture was filtered and purified by reverse phase HPLC (10 to 100% ACN/water with 0.1% TFA modifier) to afford (R)-3-hydroxy-4-(4-(4-methyl-6-((4-(trifluoromethyl)pyridin-2-yl)amino)pyridin-2-yl)-1H-1,2,3-triazol-1-yl)butanenitrile (83.5 mg, 0.207 mmol).

Step 2:

(R)-3-Hydroxy-4-(4-(4-methyl-6-((4-(trifluoromethyl)pyridin-2-yl)amino)pyridin-2-yl)-1H-1,2,3-triazol-1-yl)butanenitrile was added to a vial (70.0 mg, 0.174 mmol) along with potassium carbonate (132 mg, 0.954 mmol). Hydrogen peroxide (30% aqueous, 0.18 mL, 1.74 mmol) and dimethylsulfoxide (1.4 mL) were added. The vial was sealed, heated to 70° C. for 3 hours and then cooled to room temperature. Acetonitrile (2 mL) was added, the mixture was filtered and then purified by reverse phase HPLC (10 to 100% ACN/water with 0.1% TFA modifier) to afford (R)-3-hydroxy-4-(4-(4-methyl-6-((4-(trifluoromethyl)pyridin-2-yl)amino)pyridin-2-yl)-1H-1,2,3-triazol-1-yl)butanamide as a white powder. MS ESI calc'd for $C_{18}H_{19}F_3N_7O_2$ [M+H]⁺ 422. found 422. ¹H NMR (500 MHz, DMSO-$d_6$) δ 10.16 (s, 1H), 8.47 (d, J=5.2, 1H), 8.39 (s, 1H), 8.23 (s, 1H), 7.45 (s, 1H), 7.36 (s, 2H), 7.17 (dd, J=0.9, 5.2, 1H), 6.89 (s, 1H), 5.34 (d, J=5.3, 1H), 4.59-4.46 (m, 1H), 4.40 (ddd, J=5.3, 10.2, 21.0, 1H), 4.29-4.16 (m, 1H), 2.34 (s, 3H), 2.26-2.11 (m, 2H).

Example Method 13.1

(+/−)-2-Bydroxy-1-((3R,4R)-3-hydroxy-4-(4-(4-methyl-6-((4-(trifluoromethyl)pyridin-2-yl)amino)pyridin-2-yl)-1H-1,2,3-triazol-1-yl)pyrrolidin-1-yl)ethanone

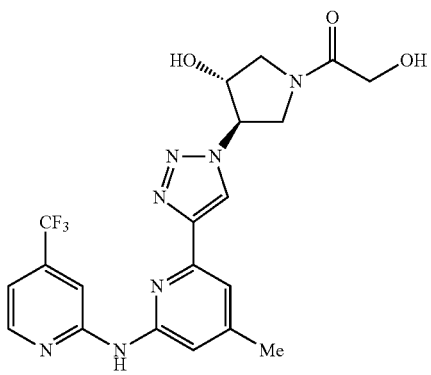 [SMILES: Cc1cc(Nc2cc(C(F)(F)F)ccn2)nc(-c2cn([C@@H]3CN(C(=O)CO)C[C@H]3O)nn2)c1]

Hydroxyacetic acid (13.0 mg, 0.17 mmol), and Hunig's base (106 uL, 0.60 mmol) were added to (3R,4R)-4-(4-(4-methyl-6-((4-(trifluoromethyl)pyridin-2-yl)amino)pyridin-2-yl)-1H-1,2,3-triazol-1-yl)pyrrolidin-3-ol (35 mg, 0.09 mmol) in DMF (2 mL). A solution of HATU (49.2 mg, 0.13 mmol) in DMF (1 mL) was added and the reaction was stirred for 66 hours at room temperature. The reaction was diluted with ethyl acetate (25 mL) and sodium bicarbonate (10 mL). The organic phase was separated, dried over anhydrous magnesium sulfate, filtered and concentrated under reduced pressure. The residue was purified by reverse phase HPLC (10 to 100% ACN/water with 0.1% TFA modifier) to afford (+/−)-2-hydroxy-1-((3R,4R)-3-hydroxy-4-(4-(4-methyl-6-((4-(trifluoromethyl)pyridin-2-yl)amino)pyridin-2-yl)-1H-1,2,3-triazol-1-yl)pyrrolidin-1-yl)ethanone (10.0 mg, 0.022 mmol) as a white powder. MS ESI calc'd for $C_{20}H_{21}F_3N_7O_3$ [M+H]$^+$ 464. found 464. $^1$H NMR (500 MHz, CD$_3$OD) δ 8.93 (d, J=7.2, 1H), 8.78 (s, 1H), 7.67 (s, 1H), 7.55 (d, J=4.8, 1H), 7.49 (s, 1H), 7.18 (d, J=15.2, 1H), 5.25-5.18 (m, 2H), 4.74-4.66 (m, 2H), 4.34-4.09 (m, 4H), 4.00-3.86 (m, 1H), 3.57 (dd, J=12.0, 27.6, 1H), 2.61 (s, 3H).

The following compounds in Table 13 were prepared according to the method described for Example 13.1. R$^{1a}$ is H in the compounds in Table 13.

TABLE 13

| Ex. | C Ring/A & B Rings | R$^1$ | R$^2$ | R$^3$ | Chemical Name | [M + H]+ Calc'd/Observed |
|---|---|---|---|---|---|---|
| 13.2 | C2/Ix | R,R,S or S,S,S | CH$_3$ | CF$_3$ | 1-[2-hydroxypropanoyl]-4-[4-(4-methyl-6-{[4-(trifluoromethyl)pyridin-2-yl]amino}pyridin-2-yl)-1H-1,2,3-triazol-1-yl]pyrrolidin-3-ol | 478/478 |
| 13.3 | C2/Ix | R,R,S or S,S,S | CH$_3$ | CF$_3$ | 1-[2-hydroxypropanoyl]-4-[4-(4-methyl-6-{[4-(trifluoromethyl)pyridin-2-yl]amino}pyridin-2-yl)-1H-1,2,3-triazol-1-yl]pyrrolidin-3-ol | 478/478 |
| 13.4 | C2/Ix | R,R,S or S,S,S | CH$_3$ | CF$_3$ | 1-[2-hydroxypropanoyl]-4-[4-(4-methyl-6-{[4-(trifluoromethyl)pyridin-2-yl]amino}pyridin-2-yl)-1H-1,2,3-triazol-1-yl]pyrrolidin-3-ol | 478/478 |

TABLE 13-continued

| Ex. | C Ring/A & B Rings | R¹ | R² | R³ | Chemical Name | [M + H]+ Calc'd/Observed |
|---|---|---|---|---|---|---|
| 13.5 | C2/Ix | 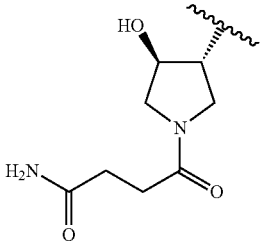 racemic | CH₃ | CF₃ | 4-{-3-hydroxy-4-[4-(4-methyl-6-{[4-(trifluoromethyl)pyridin-2-yl]amino}pyridin-2-yl)-1H-1,2,3-triazol-1-yl]pyrrolidin-1-yl}-4-oxobutanamide | 505/505 |
| 13.6 | C2/Ix | 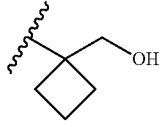 [SMILES: *C1(CO)CCC1] | CH₃ | CF₃ | {1-[4-(4-methyl-6-{[4-(trifluoromethyl)pyridin-2-yl]amino}pyridin-2-yl)-1H-1,2,3-triazol-1-yl]cyclobutyl}methanol | 405/405 |
| 13.7 | C2/Ix | 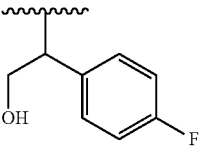 racemic | CH₃ | CF₃ | 2-(4-fluorophenyl)-2-[4-(4-methyl-6-{[4-(trifluoromethyl)pyridin-2-yl]amino}pyridin-2-yl)-1H-1,2,3-triazol-1-yl]ethanol | 459/459 |
| 13.8 | C2/Ix | 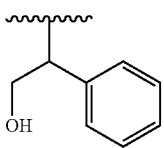 racemic | CH₃ | CF₃ | 2-[4-(4-methyl-6-{[4-(trifluoromethyl)pyridin-2-yl]amino}pyridin-2-yl)-1H-1,2,3-triazol-1-yl]-2-phenylethanol | 441/441 |
| 13.9 | C2/Ix | 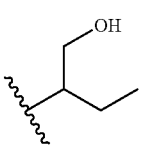 racemic | CH₃ | CF₃ | 2-[4-(4-methyl-6-{[4-(trifluoromethyl)pyridin-2-yl]amino}pyridin-2-yl)-1H-1,2,3-triazol-1-yl]butan-1-ol | 393/393 |
| 13.10 | C2/Ix | 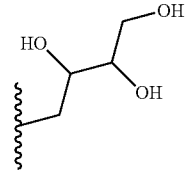 racemic | CH₃ | CF₃ | 4-[4-(4-methyl-6-{[4-(trifluoromethyl)pyridin-2-yl]amino}pyridin-2-yl)-1H-1,2,3-triazol-1-yl]butane-1,2,3-triol | 425/425 |

Example 14

2-Hydroxy-3-(4-(4-methyl-6-((4-(trifluoromethyl)pyridin-2-yl)amino)pyridin-2-yl)-1H-1,2,3-triazol-1-yl)propanoic acid

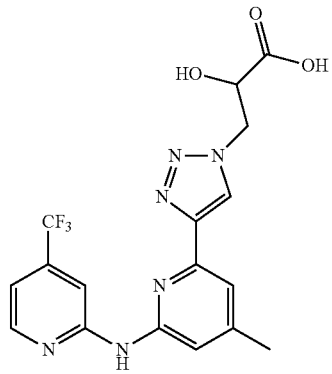 [SMILES: Cc1cc(Nc2cc(C(F)(F)F)ccn2)nc(-c2cn(CC(O)C(=O)O)nn2)c1]

t-Butyl alcohol (1.2 mL) and water (1.2 mL) were added to a vial containing 6-ethynyl-4-methyl-N-(4-(trifluoromethyl)pyridin-2-yl)pyridin-2-amine (200 mg, 0.72 mmol), beta-chlorolactic acid (180 mg, 1.44 mmol), sodium azide (98.0 mg, 1.52 mmol), copper(II)sulfate pentahydrate (18.0 mg, 0.072 mmol) and sodium ascorbate (57.2 mg, 0.289 mmol). The reaction mixture was heated at 65° C. for 6 hours and then diluted with cold water and the resulting precipitate was collected by filtration. The solid was dried overnight in vacuo to yield 2-hydroxy-3-(4-(4-methyl-6-((4-(trifluoromethyl)pyridin-2-yl)amino)pyridin-2-yl)-1H-1,2,3-triazol-1-yl)propanoic acid as a brown solid. MS ESI calc'd for $C_{17}H_{16}F_3N_6O_3$ [M+H]$^+$ 409. found 409. $^1$H NMR (500 MHz, DMSO-d$_6$) δ 10.16 (s, 1H), 8.47 (d, J=5.4, 1H), 8.34 (s, 1H), 8.24 (s, 1H), 7.51-7.32 (m, 2H), 7.17 (d, J=5.1, 1H), 6.05-5.83 (m, 1H), 4.72 (dd, J=3.5, 14.6, 1H), 4.61 (dd, J=7.2, 14.4, 1H), 4.45-4.35 (m, 1H), 2.33 (s, 3H).

Example 15

8-[1-(3-Methyl-5-{[4-(trifluoromethyl)pyrimidin-2-yl]amino}phenyl)-1H-1,2,3-triazol-4-yl]-1,4-dioxaspiro[4.5]decan-8-ol

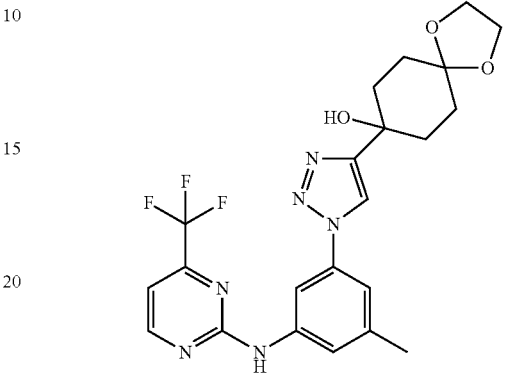

N-(3-Azido-5-methylphenyl)-4-(trifluoromethyl)pyrimidin-2-amine (150 mg, 0.510 mmol), 8-ethynyl-1,4-dioxaspiro[4.5]decan-8-ol (93 mg, 0.510 mmol), sodium ascorbate (40.4 mg, 0.204 mmol), and copper(II) sulfate pentahydrate (12.73 mg, 0.051 mmol) were combined in a vial and taken up in DMF (2.10 ml) and water (0.700 ml). The reaction was vigorously stirred at room temperature overnight then, diluted with water. The resulting precipitate was collected by filtration. The collected solids were washed with diethyl ether and dried in vacuo to afford 8-[1-(3-methyl-5-{[4-(trifluoromethyl)pyrimidin-2-yl]amino}phenyl)-1H-1,2,3-triazol-4-yl]-1,4-dioxaspiro[4.5]decan-8-ol as a white solid. MS ESI calcd. for $C_{22}H_{24}F_3N_6O_3$ [M+H]$^+$ 477. found 477. $^1$H NMR (500 MHz, DMSO-d$_6$) δ 10.43 (s, 1H), 8.60 (d, J=5.0 Hz, 1H), 8.48 (s, 1H), 8.24 (s, 1H), 7.58 (s, 1H), 7.35 (s, 1H), 7.32 (d, J=5.0 Hz, 1H), 5.18 (s, 1H), 3.87 (s, 4H), 2.37 (s, 3H), 2.11-2.06 (m, 2H), 1.89-1.84 (m, 4H), 1.55-1.53 (m, 2H).

The following compounds in Table 15 were prepared according to the method described for Example 15. R$^{1a}$ is H in the compounds in Table 15. Carboxylic acids were optionally prepared by hydrolysis of the ester according to the method described in Example 4.1, Step 3.

TABLE 15

| Ex. | C Ring/A & B Rings | R$^1$ | R$^2$ | R$^3$ | Chemical Name | [M + H]+ Calc'd/Observed |
|---|---|---|---|---|---|---|
| 15.1 | C1/Iy | 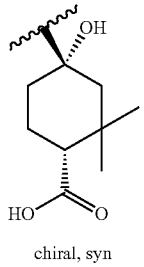<br>chiral, syn | CH$_3$ | CF$_3$ | 4-hydroxy-2,2-dimethyl-4-[1-(3-methyl-5-{[4-(trifluoromethyl)pyrimidin-2-yl]amino}phenyl)-1H-1,2,3-triazol-4-yl]cyclohexanecarboxylic acid | 491/491 |

TABLE 15-continued

| Ex. | C Ring/A & B Rings | R¹ | R² | R³ | Chemical Name | [M + H]+ Calc'd/Observed |
|---|---|---|---|---|---|---|
| 15.2 | C1/Iy | (cyclohexane with OH, two methyls, COOH) chiral, syn | CH₃ | CF₃ | (4-hydroxy-2,2-dimethyl-4-[1-(3-methyl-5-{[4-(trifluoromethyl)pyrimidin-2-yl]amino}phenyl)-1H-1,2,3-triazol-4-yl]cyclohexanecarboxylic acid | 491/491 |
| 15.3 | C1/Iy | (cyclohexane with OH, methyl, COOH) anti | CH₃ | CF₃ | trans-4-hydroxy-4-[1-(3-methyl-5-{[4-(trifluoromethyl)pyrimidin-2-yl]amino}phenyl)-1H-1,2,3-triazol-4-yl]cyclohexanecarboxylic acid | 463/463 |
| 15.4 | C1/Iy | (cyclohexane with OH, methyl, COOH) syn | CH₃ | CF₃ | cis-4-hydroxy-4-[1-(3-methyl-5-{[4-(trifluoromethyl)pyrimidin-2-yl]amino}phenyl)-1H-1,2,3-triazol-4-yl]cyclohexanecarboxylic acid | 463/463 |
| 15.5 | C1/Iy | (cyclohexane with OH, methyl, t-butyl ester) anti | CH₃ | CF₃ | tert-butyl trans-4-hydroxy-4-[1-(3-methyl-5-{[4-(trifluoromethyl)pyrimidin-2-yl]amino}phenyl)-1H-1,2,3-triazol-4-yl]cyclohexanecarboxylate | 519/519 |
| 15.6 | C1/Iy | (cyclohexane with OH, methyl, t-butyl ester) syn | CH₃ | CF₃ | tert-butyl cis-4-hydroxy-4-[1-(3-methyl-5-{[4-(trifluoromethyl)pyrimidin-2-yl]amino}phenyl)-1H-1,2,3-triazol-4-yl]cyclohexanecarboxylate | 519/519 |

TABLE 15-continued

| Ex. | C Ring/A & B Rings | R¹ | R² | R³ | Chemical Name | [M + H]+ Calc'd/Observed |
|---|---|---|---|---|---|---|
| 15.7 | C1/Iy | (CH₂CH(OH)CH₂OH), racemic | CH₃ | CF₃ | 3-[1-(3-methyl-5-{[4-(trifluoromethyl)pyrimidin-2-yl]amino}phenyl)-1H-1,2,3-triazol-4-yl]propane-1,2-diol | 395/395 |
| 15.8 | C1/Iy | (1,4-dioxaspiro[4.5]decan-8-ol-8-yl), racemic | CH₃ | CF₃ | 8-[1-(3-methyl-5-{[4-(trifluoromethyl)pyrimidin-2-yl]amino}phenyl)-1H-1,2,3-triazol-4-yl]-1,4-dioxaspiro[4.5]decan-8-ol | 477/477 |
| 15.9 | C1/Iy | (1S,4R)-4-hydroxy-2,2-dimethylcyclohexanecarboxylic acid, syn, racemic | CH₃ | CF₃ | (1S,4R)-4-hydroxy-2,2-dimethyl-4-[1-(3-methyl-5-{[4-(trifluoromethyl)pyrimidin-2-yl]amino}phenyl)-1H-1,2,3-triazol-4-yl]cyclohexanecarboxylic acid | 491/491 |
| 15.10 | C1/Iy | methyl (1S,4R)-4-hydroxy-2,2-dimethylcyclohexanecarboxylate, syn, racemic | CH₃ | CF₃ | methyl (1S,4R)-4-hydroxy-2,2-dimethyl-4-[1-(3-methyl-5-{[4-(trifluoromethyl)pyrimidin-2-yl]amino}phenyl)-1H-1,2,3-triazol-4-yl]cyclohexanecarboxylate | 505/505 |
| 15.11 | C1/Iy | H | CH₃ | CF₃ | N-[3-methyl-5-(1H-1,2,3-triazol-1-yl)phenyl]-4-(trifluoromethyl)pyrimidin-2-amine | 321/321 |
| 15.12 | C1/Iy | (CH₃)₃Si | CH₃ | CF₃ | N-{3-methyl-5-[4-(trimethylsilyl)-1H-1,2,3-triazol-1-yl]phenyl}-4-(trifluoromethyl)pyrimidin-2-amine | 393/393 |
| 15.13 | C1/Iy | (CH₂C(CH₃)₂CO₂H) | CH₃ | CF₃ | 2,2-dimethyl-3-[1-(3-methyl-5-{[4-(trifluoromethyl)pyrimidin-2-yl]amino}phenyl)-1H-1,2,3-triazol-4-yl]propanoic acid | 421/421 |
| 15.14 | C1/Iy | (CH₂CH₂CO₂H) | CH₃ | CF₃ | 3-[1-(3-methyl-5-{[4-(trifluoromethyl)pyrimidin-2-yl]amino}phenyl)-1H-1,2,3-triazol-4-yl]propanoic acid | 393/393 |

TABLE 15-continued

| Ex. | C Ring/A & B Rings | R¹ | R² | R³ | Chemical Name | [M + H]+ Calc'd/Observed |
|---|---|---|---|---|---|---|
| 15.15 | C1/Iy | (ethyl 2,2-dimethylpropanoate group, EtO-C(=O)-C(CH₃)₂-CH₂-) | CH₃ | CF₃ | ethyl 2,2-dimethyl-3-[1-(3-methyl-5-{[4-(trifluoromethyl)pyrimidin-2-yl]amino}phenyl)-1H-1,2,3-triazol-4-yl]propanoate | 449/449 |
| 15.16 | C1/Iy | trans-1,4-dihydroxycyclohexyl (anti) | CH₃ | CF₃ | trans-1-[1-(3-methyl-5-{[4-(trifluoromethyl)pyrimidin-2-yl]amino}phenyl)-1H-1,2,3-triazol-4-yl]cyclohexane-1,4-diol | 435/435 |
| 15.17 | C1/Iy | cis-1,4-dihydroxycyclohexyl (syn) | CH₃ | CF₃ | cis-1-[1-(3-methyl-5-{[4-(trifluoromethyl)pyrimidin-2-yl]amino}phenyl)-1H-1,2,3-triazol-4-yl]cyclohexane-1,4-diol | 435/435 |

Example 16.1

6-(4,5-dimethyl-4H-1,2,4-triazol-3-yl)-4-methyl-N-[4-(trifluoromethyl)pyridin-2-yl]pyridin-2-amine

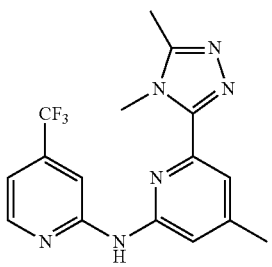 [SMILES: Cc1cc(Nc2cc(C(F)(F)F)ccn2)nc(-c2nnc(C)n2C)c1]

4-Methyl-6-{[4-(trifluoromethyl)pyridin-2-yl]amino}pyridine-2-carbohydrazide (250 mg, 0.651 mmol) was taken up in N-methylacetamide (2.0 mL, 26.0 mmol). The vial was sealed and heated overnight at 165° C. The reaction was diluted with acetonitrile (2 mL) and filtered. The resulting mixture was purified by reverse phase HPLC (ACN/water with 0.1% TFA modified) to afford 6-(4,5-dimethyl-4H-1,2,4-triazol-3-yl)-4-methyl-N-[4-(trifluoromethyl)pyridin-2-yl]pyridin-2-amine as a light brown solid. MS ESI calcd. for $C_{16}H_{16}F_3N_6$ [M+H]⁺ 349 found 349. ¹H NMR (500 MHz, DMSO-d₆) δ 10.14 (s, 1H), 8.50 (d, J=5.3, 1H), 7.94 (s, 1H), 7.64 (s, 1H), 7.49 (s, 1H), 7.19 (d, J=5.1, 1H), 3.89 (s, 3H), 2.41 (s, 3H), 2.36 (s, 3H).

The following compounds in Table 16 were prepared according to the method described for Example 16.1.

TABLE 16

| Ex. | C Ring/A & B Rings | R¹/R¹ᵃ | R² | R³ | Chemical Name | [M + H]+ Calc'd/Observed |
|---|---|---|---|---|---|---|
| 16.2 | C5/Ix | H/H | CH₃ | CF₃ | 4-methyl-6-(4H-1,2,4-triazol-3-yl)-N-[4-(trifluoromethyl)pyridin-2-yl]pyridin-2-amine | 321/321 |
| 16.3 | C5/Ix | H/CH₃ | CH₃ | CF₃ | 4-methyl-6-(4-methyl-4H-1,2,4-triazol-3-yl)-N-[4-(trifluoromethyl)pyridin-2-yl]pyridin-2-amine | 335/335 |

Example 17.1

Racemic cis-3-(4-(3-methyl-5-((4-(trifluoromethyl)pyrimidin-2-yl)amino)phenyl)-1H-1,2,3-triazol-1-yl)cyclohexanol

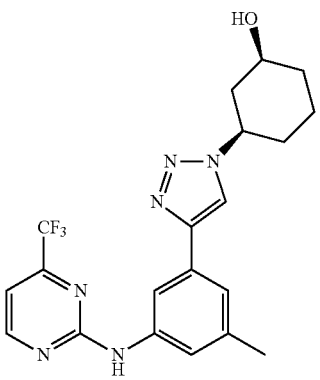 [SMILES: Cc1cc(Nc2nccc(C(F)(F)F)n2)cc(-c2cn([C@@H]3CCC[C@H](O)C3)nn2)c1]

Step 1:

N-(3-Ethynyl-5-methylphenyl)-4-(trifluoromethyl)pyrimidin-2-amine (Intermediate 1.2; 50.0 mg, 0.180 mmol), 3-azidocyclohexanone (prepared as described in Guerin, D. J, Horstmann, T. E., Miller, S. J. Org. Lett. 19991, 1107; 50.2 mg, 0.361 mmol), copper(II) sulfate pentahydrate (4.5 mg, 0.018 mmol), and sodium ascorbate (14.3 mg, 0.0720 mmol) were added to a vial. tert-Butanol (0.5 ml) and water (0.5 mL) were then added, and the resulting suspension was stirred at 65° C. for 2 hours. The reaction mixture cooled to room temperature then was partitioned between ethyl acetate and 5% aqueous ammonium chloride. The aqueous layer was extracted with additional ethyl acetate. The combined organic layers were dried over anhydrous sodium sulfate, filtered, silica gel added, and the slurry was concentrated under reduced pressure. The residue was purified by column chromatography on silica gel to afford 3-(4-(3-methyl-5-((4-(trifluoromethyl)pyrimidin-2-yl)amino)phenyl)-1H-1,2,3-triazol-1-yl)cyclohexanone (racemic). MS ESI calcd. for $C_{20}H_{20}F_3N_6O$ $[M+H]^+$ 417. found 417. $^1$H NMR (500 MHz, DMSO-$d_6$) δ 10.22 (s, 1H), 8.81 (d, J=5.0 Hz, 1H), 8.52 (s, 1H), 8.08 (s, 1H), 7.51 (s, 1H), 7.27 (s, 1H), 7.25 (d, J=5.0 Hz, 1H), 5.03 (m, 1H), 3.28 (m, 1H; overlapping with water peak), 2.99 (dd, J=14.0, 10.0 Hz, 1H), 2.46 (dd, J=14.0, 5.0 Hz, 1H), 2.50-2.38 (m, 1H), 2.36-2.22 (m, 1H), 2.31 (s, 3H), 2.22-2.12 (m, 1H), 1.92-1.86 (m, 1H), 1.80-1.71 (m, 1H).

Step 2:

3-(4-(3-Methyl-5-((4-(trifluoromethyl)pyrimidin-2-yl)amino)phenyl)-1H-1,2,3-triazol-1-yl)cyclohexanone (racemic, 50.0 mg, 0.12 mmol), followed by methanol (1.0 mL) were added to a vial. The resulting suspension was cooled to 0° C., then sodium borohydride (9.1 mg, 0.24 mmol) was added (caution: gas evolution). The cooling bath was removed, and the reaction mixture was allowed to warm to ambient and stirred for approximately 1 hour. The reaction mixture was diluted with EtOAc, and silica gel was added. The mixture was concentrated under reduced pressure. The residue was purified by column chromatography on silica gel, eluting with (0 to 5% gradient) to afford cis-3-(4-(3-methyl-5-((4-(trifluoromethyl)pyrimidin-2-yl)amino)phenyl)-1H-1,2,3-triazol-1-yl)cyclohexanol (racemic). MS ESI calcd. for $C_{20}H_{22}F_3N_6O$ $[M+H]^+$ 419. found 419. $^1$H NMR (500 MHz, DMSO-$d_6$) δ 10.20 (s, 1H), 8.81 (d, J=4.5 Hz, 1H), 8.52 (s, 1H), 8.08 (s, 1H), 7.48 (s, 1H), 7.24 (d, J=4.5 Hz, 1H), 4.87 (d, J=4.5 Hz, 1H), 4.54 (t, J=12.0 Hz, 1H), 3.64-3.54 (m, 1H), 3.28 (m, 1H; overlapping with water peak), 2.34-2.24 (m, 1H), 2.31 (s, 3H), 2.06-1.99 (m, 1H), 1.90-1.84 (m, 1H), 1.84-1.76 (m, 1H), 1.72-1.68 (m, 2H), 1.46-1.35 (m, 1H), 1.21-1.12 (m, 1H).

Example 18.1

2-[4-(4-Methyl-6-{[4-(trifluoromethyl)pyridin-2-yl]amino}pyridin-2-yl)-1H-1,2,3-triazol-1-yl]propan-1-ol

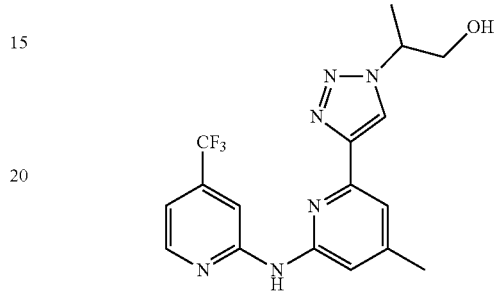

Step 1:

In a microwave vial, methyl 2-bromopropanoate (452 mg, 2.71 mmol) was taken up in tert-butanol (1500 μl) and water (1500 μl) under argon. Sodium azide (176 mg, 2.71 mmol) was added, and the resulting mixture was stirred at 70° C. overnight. 6-Ethynyl-4-methyl-N-[4-(trifluoromethyl)pyridin-2-yl]pyridin-2-amine (250 mg, 0.902 mmol), copper(II) sulfate pentahydrate (22.5 mg, 0.09 mmol), and sodium ascorbate (71.5 mg, 0.361 mmol) were sequentially added. The reaction was sealed and stirred at 65° C. for 4 hours. The resulting mixture was diluted with water and saturated aqueous ammonium chloride and extracted with ethyl acetate (3×). The organic layers were combined, dried over anhydrous magnesium sulfate and concentrated under reduced pressure. The residue was purified by column chromatography on silica gel (0 to 100% ethyl acetate/hexanes) to afford methyl 2-[4-(4-methyl-6-{[4-(trifluoromethyl)pyridin-2-yl]amino}pyridin-2-yl)-1H-1,2,3-triazol-1-yl]propanoate as a white solid. MS ESI calcd. for $C_{18}H_{18}F_3N_6O_2$ $[M+H]^+$ 407. found 407.

Step 2:

Dibal-H (2.4 mL, 1.0M in hexanes, 2.4 mmol) was added drop wise to a 0° C. solution of methyl 2-[4-(4-methyl-6-{[4-(trifluoromethyl)pyridin-2-yl]amino}pyridin-2-yl)-1H-1,2,3-triazol-1-yl]propanoate (240 mg, 0.591 mmol) in THF (4 mL). The mixture was stirred for one hour and then warmed to room temperature for one hour. The mixture was then diluted with aqueous sodium potassium tartrate and vigorously stirred until the emulsion broke (overnight). The layers were separated and the aqueous layer was extracted with ethyl acetate (2×). The combined organics were dried over anhydrous magnesium sulfate, filtered, and concentrated under reduced pressure. The residue was purified by column chromatography on silica gel (0 to 10% methanol/ethyl acetate) to afford 2-[4-(4-methyl-6-{[4-(trifluoromethyl)pyridin-2-yl]amino}pyridin-2-yl)-1H-1,2,3-triazol-1-yl]propan-1-ol as a white solid. MS ESI calcd. for $C_{17}H_{18}F_3N_6O$ $[M+H]^+$ 379. found 379. $^1$H NMR (500 MHz, DMSO-$d_6$) δ 10.18 (s, 1H), 8.56 (s, 1H), 8.48 (d, J=5.5 Hz, 1H), 8.26 (s, 1H), 7.43 (s, 1H), 7.25 (s, 1H), 7.19 (d, J=4.5 Hz, 1H), 5.15 (t, J=5.0 Hz, 1H), 4.78-4.76 (m, 1H), 3.74-3.68 (m, 2H), 2.34 (s, 3H), 1.50 (d, J=7.0 Hz, 3H).

Example 19.1

(+/−)-(3S,4R)-4-(4-(4-Methyl-6-((4-(trifluoromethyl)pyridin-2-yl)amino)pyridin-2-yl)-1H-1,2,3-triazol-1-yl)pyrrolidin-3-ol

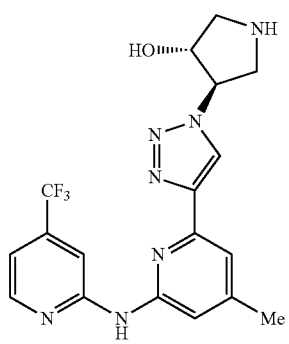 [SMILES: Cc1cc(Nc2cc(C(F)(F)F)ccn2)nc(-c2cn([C@@H]3CNC[C@H]3O)nn2)c1]

Step 1:

6-Ethynyl-4-methyl-N-(4-(trifluoromethyl)pyridin-2-yl)pyridin-2-amine (1.23 g, 4.42 mmol), (+/−)-(3S,4S)-benzyl 3-azido-4-hydroxypyrrolidine-1-carboxylate (1.16 g, 4.42 mmol), copper(II)sulfate pentahydrate (110 mg, 0.44 mmol) and sodium ascorbate (350 mg, 1.77 mmol) were added to a microwave vial. tert-Butyl alcohol (5.5 mL) and water (5.5 mL) were added and the reaction was sealed and warmed to 70° C. for 16 hours. After cooling, the reaction was diluted with ethyl acetate and 10% aqueous ammonium hydroxide. The organic phase was separated, washed with saturated sodium chloride. The combined organics were dried over anhydrous magnesium sulfate, filtered and concentrated under reduced pressure. The residue was purified by column chromatography on silica gel (50 to 100%, EtOAc/hexanes) to afford (+/−)-(3R,4R)-benzyl 3-hydroxy-4-(4-(4-methyl-6-((4-(trifluoromethyl)pyridin-2-yl)amino)pyridin-2-yl)-1H-1,2,3-triazol-1-yl)pyrrolidine-1-carboxylate. MS ESI calc'd for $C_{26}H_{25}F_3N_7O_3$ [M+H]$^+$ 540. found 540. $^1$H NMR (500 MHz, DMSO-d$_6$) δ 10.16 (s, 1H), 8.30-8.04 (m, 3H), 7.99-7.85 (m, 4H), 7.60-7.43 (m, 1H), 7.38 (d, J=7.2, 2H), 6.85 (d, J=8.4, 1H), 6.77 (t, J=8.9, 1H), 5.11 (s, 2H), 3.85-3.81 (m, 3H), 2.91-2.80 (m, 2H), 2.76-2.65 (m, 1H), 2.01 (s, 3H).

Step 2:

(3S,4R)-Benzyl 3-hydroxy-4-(4-(4-methyl-6-((4-(trifluoromethyl)pyridin-2-yl)amino)pyridin-2-yl)-1H-1,2,3-triazol-1-yl)pyrrolidine-1-carboxylate (500 mg, 0.93 mmol) was treated with acetic acid (0.50 mL) and hydrobromic acid (48%, 0.11 mL). The reaction was heated to 60° C. for a period of 3 hours and then allowed to cool to ambient temperature. The reaction was concentrated under reduced pressure and the residual solid was dissolved in acetonitrile, filtered and purified by reverse phase HPLC (10 to 100% ACN/water with 0.1% TFA modifier) to afford (+/−)-(3S,4R)-4-(4-(4-methyl-6-((4-(trifluoromethyl)pyridin-2-yl)amino)pyridin-2-yl)-1H-1,2,3-triazol-1-yl)pyrrolidin-3-ol as a white powder. MS ESI calc'd for $C_{18}H_{19}F_3N_7O$ [M+H]$^+$ 406. found 406. $^1$H NMR (500 MHz, DMSO-d$_6$) δ 10.17 (s, 1H), 8.47 (d, J=5.2, 1H), 8.44 (d, J=3.4, 1H), 8.34 (d, J=2.0, 1H), 7.53-7.23 (m, 2H), 7.18 (d, J=4.2, 1H), 6.25 (s, broad, 1H) 5.90 (s, 1H), 5.25-4.95 (m, 3H), 4.58-4.42 (m, 1H), 3.91-3.79 (m, 1H), 3.69 (ddd, J=5.7, 11.6, 26.5, 1H), 2.34 (s, 3H).

Example 20.1

3-(5-(3-Methyl-5-((4-(trifluoromethyl)pyrimidin-2-yl)amino)phenyl)-4H-1,2,4-triazol-3-yl)propanoic acid

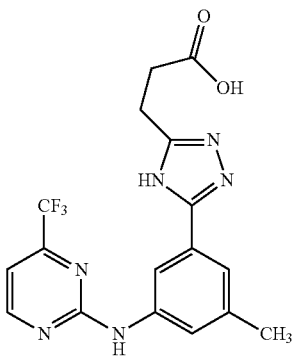 [SMILES: Cc1cc(Nc2nccc(C(F)(F)F)n2)cc(-c2nnc(CCC(=O)O)[nH]2)c1]

Step 1:

N-(3-bromo-5-methylphenyl)-4-(trifluoromethyl)pyrimidin-2-amine (3.0 g, 9.0 mmol), zinc cyanide (0.80 g, 6.8 mmol), Pd(Ph$_3$P)$_4$ (1.04 g, 0.90 mmol) and DMF (12.0 ml) were added to a vial and the mixture was stirred for 2 minutes, then sealed. The reaction was heated in a microwave at 150° C. for 1 hour. The reaction mixture was partitioned between water and EtOAc and the layers were separated. The aqueous layer was extracted with EtOAc. The combined organic layers were washed with water, then brine, dried over anhydrous magnesium sulfate, filtered, and concentrated under reduced pressure. The reaction was purified by column chromatography on silica gel (0 to 50% EtOAc/hexanes) to afford 3-methyl-5-((4-(trifluoromethyl)pyrimidin-2-yl)amino)benzonitrile (as a white powder. MS ESI calc'd for $C_{13}H10F_3N_4$ [M+H]$^+$ 279. found 279.

Step 2:

N-Methyl pyrrolidine (0.83 mL) and hydrazine monohydrate (0.79 mL, 16.5 mmol) were added to a flask containing 3-methyl-5-((4-(trifluoromethyl)pyrimidin-2-yl)amino)benzonitrile (230 mg, 0.827 mmol) and sodium hydride (60% by weight, 83.0 mg, 16.5 mmol). Once gas evolution ceased, the reaction was sealed and heated to 140° C. for a period of 90 minutes. The reaction mixture was filtered and purified by reverse phase HPLC (10 to 100% ACN/water with 0.1% TFA modifier) to afford the crude product an off-white solid which was used immediately in the next step.

Step 3:

4-Methoxy-4-oxobutanoic acid (61.3 mg, 0.464 mmol), EDC (89 mg, 0.46 mmol), HOBT (71 mg, 0.46 mmol), triethylamine (0.14 mL, 0.97 mmol) and DMF (3.9 mL) were added to a flask containing the material prepared above in Step 1. The reaction was stirred for 2 hours where anhydrous magnesium sulfate was then added and the reaction was heated to 100° C. for a period of 3 hours. The reaction mixture was diluted ethyl acetate (25 mL) and sodium bicarbonate (10% aqueous, 25 mL). The organic phase was separated, dried over anhydrous sodium sulfate, filtered and concentrated under reduced pressure. The residue was purified by reverse phase HPLC (10 to 100% ACN/water with 0.1% TFA modifier) and the desired fractions were concentrated under reduced pressure. The resulting oil was dissolved in KOH (40% aqueous, 0.5 mL) and ethanol (1 mL) and stirred for 3 days at 0° C. The mixture was then neutralized with TFA, filtered and purified by reverse phase HPLC (10 to 100% ACN/water with 0.1% TFA modifier) to afford 3-(5-(3-methyl-5-((4-(trifluoromethyl)pyrimidin-2-yl)amino)phenyl)-4H-1,2,4-triazol-3-yl) propanoic acid as a white solid (3.1 mg, 0.08 mmol). MS ESI calc'd for $C_{17}H_{16}F_3N_6O_2$ [M+H]$^+$ 393. found 393. $^1$H NMR (500 MHz, $CD_3OD$) δ 8.73 (d, J=4.8, 1H), 8.13 (s, 1H), 7.75 (s, 1H), 7.47 (s, 1H), 7.14 (d, J=4.9, 1H), 3.15 (t, J=7.3, 2H), 2.88 (t, J=7.3, 2H), 2.43 (s, 3H).

Example 21.1 and 21.2

2-Methyl-3-(4-(3-methyl-5-((4-methylpyrimidin-2-yl)amino)phenyl)-1H-1,2,3-triazol-1-yl)propane-1,2-diol (Isomer 1, first eluting) and 2-methyl-3-(4-(3-methyl-5-((4-methylpyrimidin-2-yl)amino)phenyl)-1H-1,2,3-triazol-1-yl)propane-1,2-diol (Isomer 2, second eluting)

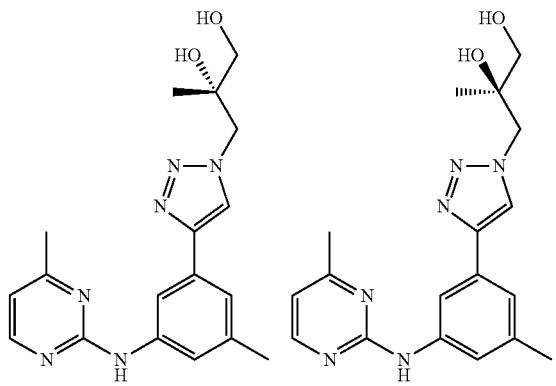

Step 1:
Sodium azide (8.6 mg, 0.13 mmol) was added to a heterogeneous solution of 3-bromo-2-methylprop-1-ene (13 μL, 0.13 mmol), 4-methyl-N-(3-methyl-5-((trimethylsilyl)ethynyl)phenyl)pyrimidin-2-amine (37 mg, 0.13 mmol), copper(II) sulfate pentahydrate (6.3 mg, 0.03 mmol) and copper (6.4 mg, 0.10 mmol) in water (0.2 mL) and t-BuOH (0.2 mL). The vial was sealed and placed under argon through 3 cycles of evacuation and argon flushing. The reaction mixture was stirred at 85° C. for 4 hours. The reaction mixture was diluted with EtOAc, washed with aqueous sodium bicarbonate, then brine, dried over anhydrous sodium sulfate, filtered and concentrated under reduced pressure to afford crude 4-methyl-N-(3-methyl-5-(1-(2-methylallyl)-1H-1,2,3-triazol-4-yl)phenyl)pyrimidin-2-amine as a yellow oil. MS ESI calcd. for $C_{18}H_{20}N_6$[M+H]$^+$ 321. found 321.

Step 2:
Osmium tetroxide (0.2 mL, 0.03 mmol) was added to a flask containing 4-methyl-N-(3-methyl-5-(1-(2-methylallyl)-1H-1,2,3-triazol-4-yl)phenyl)pyrimidin-2-amine (34 mg, 0.11 mmol), 4-methylmorpholine 4-oxide (18.65 mg, 0.159 mmol), THF (0.7 mL) and water (0.35 mL). The reaction mixture was stirred at room temperature for 2 hrs. Silica was added and the mixture was concentrated under reduced pressure to dryness. The residue was purified by column chromatography on silica (0-20% MeOH/DCM) and concentrated under reduced pressure to afford racemic product. The racemic mixture was purified by chiral SFC (Chiralpak AS-H, 15% methanol+0.25% dimethyl ethyl amine/ $CO_2$) to afford 2-methyl-3-(4-(3-methyl-5-((4-methylpyrimidin-2-yl)amino)phenyl)-1H-1,2,3-triazol-1-yl) propane-1,2-diol (Isomer 1, first eluting): MS ESI calcd. for $C_{18}H_{23}N_6O_2$ [M+H]$^+$ 355. found 355, $^1$H NMR (500 MHz, DMSO-$d_6$): 9.55 (1H, s), 8.34-8.36 (1H, m), 8.24 (1H, s), 8.13 (1H, s), 7.55 (1H, d, J=2.29 Hz), 7.22 (1H, s), 6.72-6.74 (1H, m), 4.98 (1H, dd, J=5.40, 5.25 Hz), 4.88 (1H, s), 4.34-4.36 (2H, m), 2.37 (3H, s), 2.32 (3H, s), 0.97 (3H, s), and 2-methyl-3-(4-(3-methyl-5-((4-methylpyrimidin-2-yl)amino)phenyl)-1H-1,2,3-triazol-1-yl)propane-1,2-diol (Isomer 2, second eluting): MS ESI calcd. for $C_{18}H_{23}N_6O_2$ [M+H]$^+$ 355. found 355, $^1$H NMR (500 MHz, DMSO-$d_6$): 9.55 (1H, s), 8.34-8.36 (1H, m), 8.24 (1H, s), 8.13 (1H, s), 7.55 (1H, d, J=2.29 Hz), 7.22 (1H, s), 6.72-6.74 (1H, m), 4.98 (1H, dd, J=5.40, 5.25 Hz), 4.88 (1H, s), 4.34-4.36 (2H, m), 2.37 (3H, s), 2.32 (3H, s), 0.97 (3H, s), as white powders.

The following compounds in Table 21 were prepared according to the method described for Examples 21.1 and 21.2. The compounds in Table 21 had one of the following general formulas:

Formula C2(a)/Ix(b)

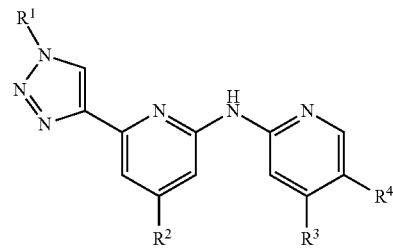

Formula C2(a)/Iy(b)

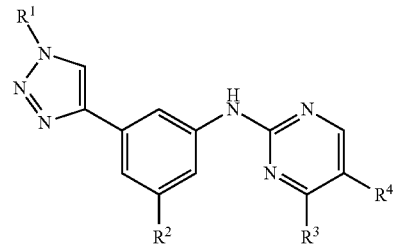

TABLE 21

| Ex. No | C Ring/A & B Rings | R$^1$ | R$^2$ | R$^3$ | R$^4$ | Chemical Name | [M + H]+ Calc'd/Observed |
|---|---|---|---|---|---|---|---|
| 21.3 | C2(a)/Iy(b) | HO⟋⟍OH Single isomer, late eluting | CH$_3$ | CF$_3$ | H | 2-methyl-3-[4-(3-methyl-5-{[4-(trifluoromethyl)pyrimidin-2-yl]amino}phenyl)-1H-1,2,3-triazol-1-yl]propane-1,2-diol | 409/409 |

TABLE 21-continued

| Ex. No | C Ring/A & B Rings | R$^1$ | R$^2$ | R$^3$ | R$^4$ | Chemical Name | [M + H]+ Calc'd/Observed |
|---|---|---|---|---|---|---|---|
| 21.4 | C2(a)/Iy(b) | (structure: OH, OH; Single isomer, early eluting) | CH$_3$ | CF$_3$ | H | 2-methyl-3-[4-(3-methyl-5-{[4-(trifluoromethyl)pyrimidin-2-yl]amino}phenyl)-1H-1,2,3-triazol-1-yl]propane-1,2-diol | 409/409 |
| 21.5 | C2(a)/Iy(b) | (structure: OH, OH; Single isomer, early eluting) | H | CF$_3$ | H | 2-methyl-3-[4-(3-{[4-(trifluoromethyl)pyrimidin-2-yl]amino}phenyl)-1H-1,2,3-triazol-1-yl]propane-1,2-diol | 395/395 |
| 21.6 | C2(a)/Iy(b) | (structure: HO, OH; Single isomer, late eluting) | H | CF$_3$ | H | 2-methyl-3-[4-(3-{[4-(trifluoromethyl)pyrimidin-2-yl]amino}phenyl)-1H-1,2,3-triazol-1-yl]propane-1,2-diol | 395/395 |
| 21.7 | C2(a)/Iy(b) | (structure: OH, OH; R or S, early eluting) | CH$_3$ | C(H)F$_2$ | H | 3-[4-(3-{[4-(difluoromethyl)pyrimidin-2-yl]amino}-5-methylphenyl)-1H-1,2,3-triazol-1-yl]-2-methylpropane-1,2-diol | 391/391 |
| 21.8 | C2(a)/Iy(b) | (structure: HO, OH; Single isomer, late eluting) | CH$_3$ | C(H)F$_2$ | H | 3-[4-(3-{[4-(difluoromethyl)pyrimidin-2-yl]amino}-5-methylphenyl)-1H-1,2,3-triazol-1-yl]-2-methylpropane-1,2-diol | 391/391 |
| 21.9 | C2(a)/Ix(b) | (structure: OH, OH; Single isomer, late eluting) | CH$_3$ | C(H)F$_2$ | H | 1-[4-(6-{[4-(difluoromethyl)pyridin-2-yl]amino}-4-methylpyridin-2-yl)-1H-1,2,3-triazol-1-yl]-2,3-dimethylbutane-2,3-diol | 419/419 |
| 21.10 | C2(a)/Ix(b) | (structure: OH, OH; Single isomer, late eluting) | CH$_3$ | CH$_3$ | Cl | 1-(4-{6-[(5-chloro-4-methylpyridin-2-yl)amino]-4-methylpyridin-2-yl}-1H-1,2,3-triazol-1-yl)-2,3-dimethylbutane-2,3-diol | 417/417 |
| 21.11 | C2(a)/Iy(b) | (structure: OH, OH; Single isomer, late eluting) | CH$_3$ | CH$_3$ | Cl | 1-(4-{3-[(5-chloro-4-methylpyrimidin-2-yl)amino]-5-methylphenyl}-1H-1,2,3-triazol-1-yl)-2,3-dimethylbutane-2,3-diol | 417/417 |

TABLE 21-continued

| Ex. No | C Ring/A & B Rings | R¹ | R² | R³ | R⁴ | Chemical Name | [M + H]+ Calc'd/Observed |
|---|---|---|---|---|---|---|---|
| 21.12 | C2(a)/Iy(b) | (CH₂)C(OH)(CH₃)C(OH)(CH₃)₂, Single isomer, late eluting | CH₃ | OCH₃ | H | 1-(4-{3-[(4-methoxypyrimidin-2-yl)amino]-5-methylphenyl}-1H-1,2,3-triazol-1-yl)-2,3-dimethylbutane-2,3-diol | 399/399 |
| 21.13 | C2(a)/Iy(b) | (CH₂)C(OH)(CH₃)C(OH)(CH₃)₂, Single isomer, late eluting | CH₃ | OC(H)CH₃ | H | 2,3-dimethyl-1-[4-(3-methyl-5-{[4-(1-methylethoxy)pyrimidin-2-yl]amino}phenyl)-1H-1,2,3-triazol-1-yl]butane-2,3-diol | 427/427 |
| 21.14 | C2(a)/Iy(b) | (CH₂)C(OH)(CH₃)C(OH)(CH₃)₂, Single isomer, late eluting | CH₃ | cPr | H | 1-(4-{3-[(4-cyclopropylpyrimidin-2-yl)amino]-5-methylphenyl}-1H-1,2,3-triazol-1-yl)-2,3-dimethylbutane-2,3-diol | 409/409 |
| 21.15 | C2(a)/Iy(b) | (CH₂)C(OH)(CH₃)C(OH)(CH₃)₂, Single isomer, late eluting | CH₃ | C(H)F₂ | F | 1-[4-(3-{[4-(difluoromethyl)-5-fluoropyrimidin-2-yl]amino}-5-methylphenyl)-1H-1,2,3-triazol-1-yl]-2,3-dimethylbutane-2,3-diol | 437/437 |
| 21.16 | C2(a)/Iy(b) | (CH₂)C(OH)(CH₃)C(OH)(CH₃)₂, Single isomer, late eluting | CH₃ | OCH₃ | Cl | 1-(4-{3-[(5-chloro-4-methoxypyrimidin-2-yl)amino]-5-methylphenyl}-1H-1,2,3-triazol-1-yl)-2,3-dimethylbutane-2,3-diol | 433/433 |
| 21.17 | C2(a)/Ix(b) | (CH₂)C(OH)(CH₃)C(OH)(CH₃)₂, Single isomer, late eluting | CH₃ | C(H)(F)CH₃ | H | 1-[4-(6-{[4-(1-fluoroethyl)pyridin-2-yl]amino}-4-methylpyridin-2-yl)-1H-1,2,3-triazol-1-yl]-2,3-dimethylbutane-2,3-diol | 415/415 |
| 21.18 | C2(a)/Iy(b) | (CH₂)C(OH)(CH₃)C(OH)(CH₃)₂, Single isomer, late eluting | CH₃ | C(H)F₂ | H | 1-[4-(3-{[4-(difluoromethyl)pyrimidin-2-yl]amino}-5-methylphenyl)-1H-1,2,3-triazol-1-yl]-2,3-dimethylbutane-2,3-diol | 419/419 |

TABLE 21-continued

| Ex. No | C Ring/A & B Rings | R¹ | R² | R³ | R⁴ | Chemical Name | [M + H]+ Calc'd/Observed |
|---|---|---|---|---|---|---|---|
| 21.19 | C2(a)/Iy(b) | 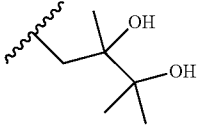 Single isomer, late eluting | $CH_3$ | $CF_3$ | H | 2,3-dimethyl-1-[4-(3-methyl-5-{[4-(trifluoromethyl)pyrimidin-2-yl]amino}phenyl)-1H-1,2,3-triazol-1-yl]butane-2,3-diol | 437/437 |
| 21.20 | C2(a)/Iy(b) | 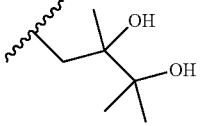 [SMILES: *CC(C)(O)C(C)(C)O] Single isomer, late eluting | $CH_3$ | $OCH_3$ | F | 1-(4-{3-[(5-fluoro-4-methoxypyrimidin-2-yl)amino]-5-methylphenyl}-1H-1,2,3-triazol-1-yl)-2,3-dimethylbutane-2,3-diol | 417/417 |
| 21.21 | C2(a)/Iy(b) | 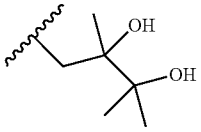 Single isomer, late eluting | $CH_3$ | $CH_3$ | H | 2,3-dimethyl-1-(4-{3-methyl-5-[(4-methylpyrimidin-2-yl)amino]phenyl}-1H-1,2,3-triazol-1-yl)butane-2,3-diol | 383/383 |
| 21.22 | C2(a)/Ix(b) | 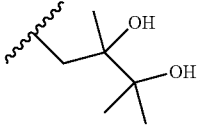 Single isomer, late eluting | $CH_3$ | $CH_3$ | F | 1-(4-{6-[(5-fluoro-4-methylpyridin-2-yl)amino]-4-methylpyridin-2-yl}-1H-1,2,3-triazol-1-yl)-2,3-dimethylbutane-2,3-diol | 401/401 |
| 21.23 | C2(a)/Iy(b) | 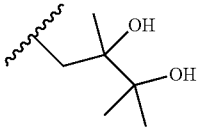 Single isomer, early eluting | $CH_3$ | $OCH_3$ | H | 1-(4-{3-[(4-methoxypyrimidin-2-yl)amino]-5-methylphenyl}-1H-1,2,3-triazol-1-yl)-2,3-dimethylbutane-2,3-diol | 399/399 |
| 21.24 | C2(a)/Ix(b) | 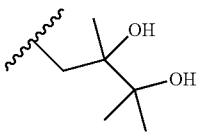 Single isomer, early eluting | $CH_3$ | $CH_3$ | Cl | 1-(4-{6-[(5-chloro-4-methylpyridin-2-yl)amino]-4-methylpyridin-2-yl}-1H-1,2,3-triazol-1-yl)-2,3-dimethylbutane-2,3-diol | 417/417 |
| 21.25 | C2(a)/Iy(b) | 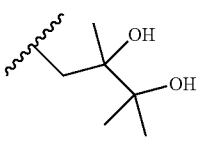 Single isomer, early eluting | $CH_3$ | $C(H)F_2$ | H | 1-[4-(3-{[4-(difluoromethyl)pyrimidin-2-yl]amino}-5-methylphenyl)-1H-1,2,3-triazol-1-yl]-2,3-dimethylbutane-2,3-diol | 419/419 |

TABLE 21-continued

| Ex. No | C Ring/A & B Rings | R¹ | R² | R³ | R⁴ | Chemical Name | [M + H]+ Calc'd/Observed |
|---|---|---|---|---|---|---|---|
| 21.26 | C2(a)/Iy(b) | (CH₂-C(CH₃)(OH)-C(CH₃)₂-OH) Single isomer, early eluting | CH₃ | cPr | H | 1-(4-{3-[(4-cyclopropylpyrimidin-2-yl)amino]-5-methylphenyl}-1H-1,2,3-triazol-1-yl)-2,3-dimethylbutane-2,3-diol | 409/409 |
| 21.27 | C2(a)/Iy(b) | (CH₂-C(CH₃)(OH)-C(CH₃)₂-OH) Single isomer, early eluting | CH₃ | OCH₃ | Cl | 1-(4-{3-[(5-chloro-4-methoxypyrimidin-2-yl)amino]-5-methylphenyl}-1H-1,2,3-triazol-1-yl)-2,3-dimethylbutane-2,3-diol | 433/433 |
| 21.28 | C2(a)/Iy(b) | (CH₂-C(CH₃)(OH)-C(CH₃)₂-OH) Single isomer, early eluting | CH₃ | CF₃ | H | 2,3-dimethyl-1-[4-(3-methyl-5-{[4-(trifluoromethyl)pyrimidin-2-yl]amino}phenyl)-1H-1,2,3-triazol-1-yl]butane-2,3-diol | 437/437 |
| 21.29 | C2(a)/Ix(b) | (CH₂-C(CH₃)(OH)-C(CH₃)₂-OH) Single isomer, early eluting | CH₃ | CH₃ | F | 1-(4-{6-[(5-fluoro-4-methylpyridin-2-yl)amino]-4-methylpyridin-2-yl}-1H-1,2,3-triazol-1-yl)-2,3-dimethylbutane-2,3-diol | 401/401 |
| 21.30 | C2(a)/Iy(b) | (CH₂-C(CH₃)(OH)-C(CH₃)₂-OH) | CH₃ | CH₃ | Cl | 1-(4-{3-[(5-chloro-4-methylpyrimidin-2-yl)amino]-5-methylphenyl}-1H-1,2,3-triazol-1-yl)-2,3-dimethylbutane-2,3-diol | 417/417 |
| 21.31 | C2(a)/Iy(b) | (CH₂-C(CH₃)(OH)-C(CH₃)₂-OH) Single isomer, early eluting | CH₃ | OC(H)(CH₃)₂ | H | 2,3-dimethyl-1-[4-(3-methyl-5-{[4-(1-methylethoxy)pyrimidin-2-yl]amino}phenyl)-1H-1,2,3-triazol-1-yl]butane-2,3-diol | 427/427 |
| 21.32 | C2(a)/Ix(b) | (CH₂-C(CH₃)(OH)-C(CH₃)₂-OH) Single isomer, early eluting | CH₃ | C(H)(F)CH₃ | H | 1-[4-(6-{[4-(1-fluoroethyl)pyridin-2-yl]amino}-4-methylpyridin-2-yl)-1H-1,2,3-triazol-1-yl]-2,3-dimethylbutane-2,3-diol | 415/415 |

TABLE 21-continued

| Ex. No | C Ring/A & B Rings | R¹ | R² | R³ | R⁴ | Chemical Name | [M + H]+ Calc'd/Observed |
|---|---|---|---|---|---|---|---|
| 21.33 | C2(a)/Iy(b) | (2,3-dihydroxy-2,3-dimethylbutyl) Single isomer, early eluting | $CH_3$ | $OCH_3$ | F | 1-(4-{3-[(5-fluoro-4-methoxypyrimidin-2-yl)amino]-5-methylphenyl}-1H-1,2,3-triazol-1-yl)-2,3-dimethylbutane-2,3-diol | 417/417 |
| 21.34 | C2(a)/Iy(b) | (2,3-dihydroxy-2,3-dimethylbutyl) Single isomer, early eluting | $CH_3$ | $C(H)F_2$ | F | 1-[4-(3-{[4-(difluoromethyl)-5-fluoropyrimidin-2-yl]amino}-5-methylphenyl)-1H-1,2,3-triazol-1-yl]-2,3-dimethylbutane-2,3-diol | 437/437 |
| 21.35 | C2(a)/Iy(b) | (2,3-dihydroxy-2,3-dimethylbutyl) Single isomer, early eluting | $CH_3$ | $CH_3$ | H | 2,3-dimethyl-1-(4-{3-methyl-5-[(4-methylpyrimidin-2-yl)amino]phenyl}-1H-1,2,3-triazol-1-yl)butane-2,3-diol | 383/383 |
| 21.36 | C2(a)/Ix(b) | (2,3-dihydroxy-2,3-dimethylbutyl) Single isomer, early eluting | $CH_3$ | $C(H)F_2$ | H | 1-[4-(6-{[4-(difluoromethyl)pyridin-2-yl]amino}-4-methylpyridin-2-yl)-1H-1,2,3-triazol-1-yl]-2,3-dimethylbutane-2,3-diol | 419/419 |
| 21.37 | C2(a)/Ix(b) | (2,3-dihydroxycyclohexyl) Single isomer, early eluting | $CH_3$ | $C(H)F_2$ | H | 3-(4-(6-((4-(difluoromethyl)pyridin-2-yl)amino)-4-methylpyridin-2-yl)-1H-1,2,3-triazol-1-yl)cyclohexane-1,2-diol | 417/417 |
| 21.38 | C2(a)/Ix(b) | (2,3-dihydroxycyclohexyl) Single isomer, late eluting | $CH_3$ | $C(H)F_2$ | H | 3-(4-(6-((4-(difluoromethyl)pyridin-2-yl)amino)-4-methylpyridin-2-yl)-1H-1,2,3-triazol-1-yl)cyclohexane-1,2-diol | 417/417 |
| 21.39 | C2(a)/Ix(b) | (2,3-dihydroxy-2-methylpropyl) Single isomer, early eluting | $CH_3$ | $C(H)F_2$ | H | 3-(4-(6-((4-(difluoromethyl)pyridin-2-yl)amino)-4-methylpyridin-2-yl)-1H-1,2,3-triazol-1-yl)-2-methylpropane-1,2-diol | 391/391 |

TABLE 21-continued

| Ex. No | C Ring/A & B Rings | R¹ | R² | R³ | R⁴ | Chemical Name | [M + H]+ Calc'd/Observed |
|---|---|---|---|---|---|---|---|
| 21.40 | C2(a)/Ix(b) | <br>Single isomer, late eluting | CH₃ | C(H)F₂ | H | 3-(4-(6-((4-(difluoromethyl)pyridin-2-yl)amino)-4-methylpyridin-2-yl)-1H-1,2,3-triazol-1-yl)-2-methylpropane-1,2-diol | 391/391 |

Example 22.1 and 22.2

4-(Difluoromethyl)-N-(3-methyl-5-(1-(morpholin-2-ylmethyl)-1H-1,2,3-triazol-4-yl)phenyl) pyrimidin-2-amine (Isomer 1, first eluting) and 4-(difluoromethyl)-N-(3-methyl-5-(1-(morpholin-2-ylmethyl)-1H-1,2,3-triazol-4-yl)phenyl) pyrimidin-2-amine (Isomer 2, second eluting)

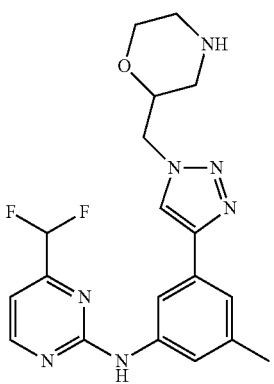 [SMILES: Cc1cc(Nc2nccc(C(F)F)n2)cc(-c2cn(CC3CNCCO3)nn2)c1]

Step 1:

To a solution of tert-butyl 2-(hydroxymethyl)morpholine-4-carboxylate (1.00 g, 4.60 mmol) in DCM (20 mL) was added MsCl (1.58 g, 13.8 mmol) and TEA (1.39 mg, 13.8 mmol) at 0° C. The mixture was stirred at 25° C. for 3 hours. The mixture was diluted with H₂O (20 mL) and extracted with EtOAc (50 mL×3). The combined organic layers was dried over anhydrous sodium sulfate, filtered and concentrated under reduced pressure. The residue was purified by column chromatography on silica (2:1 petroleum ether/ethyl acetate) to afford tert-butyl-2-(((methylsulfonyl)oxy)methyl)morpholine-4-carboxylate as a yellow oil. ¹H NMR (400 MHz, DMSO-d₆) δ 4.21-4.17 (m, 2H), 3.86-3.83 (m, 2H), 3.63-3.60 (m, 2H), 3.42-3.39 (m, 1H), 3.35 (s, 3H), 2.78-3.66 (m, 2H), 1.41 (s, 9H). MS ESI calcd. for C₁₁H₂₂NO₆S [M+H]⁺ 296. found 296.

Step 2:

NaN₃ (859 mg, 13.2 mmol) and NaI (66.0 mg, 0.44 mmol) were added to a solution of tert-butyl 2-(((methylsulfonyl)oxy)methyl)morpholine-4-carboxylate (1.30 g, 4.40 mmol) in DMF (20 mL). The reaction mixture was stirred at 80° C. under N₂ for 12 hours. The mixture was diluted with H₂O (20 mL) and extracted with EtOAc (50 mL×3). The combined layers were washed with brine, dried over anhydrous sodium sulfate, filtered and concentrated under reduced pressure to afford tert-butyl 2-(azidomethyl)morpholine-4-carboxylate as a yellow oil. MS ESI calcd. for C₁₀H₁₉N₄O₃ [M+H]⁺ 243. found 243.

Step 3:

tert-Butyl 2-(azidomethyl)morpholine-4-carboxylate (325 mg, 1.34 mmol), CuSO₄.5H₂O (28.0 mg, 0.11 mmol) and sodium ascorbate (89.0 mg, 0.45 mmol) were added to a solution of 4-(difluoromethyl)-N-(3-ethynyl-5-methylphenyl)pyrimidin-2-amine (300 mg, 1.12 mmol) in t-BuOH (2 mL) and H₂O (2 mL). The reaction mixture was stirred at 70° C. for 12 hours. The mixture was diluted with water (20 mL) and extracted with EtOAc (50 mL×3). The combined organic layers were dried over anhydrous sodium sulfate, filtered and concentrated under reduced pressure. The residue was purified by prep-TLC (1:1 petroleum ether/ethyl acetate) to afford tert-butyl-2-((4-(3-((4-(difluoromethyl)pyrimidin-2-yl)amino)-5-methylphenyl)-1H-1,2,3-triazol-1-yl)methyl)morpholine-4-carboxylate as a yellow solid. ¹H NMR (400 MHz, DMSO-d₆) δ 10.02 (s, 1H), 8.72 (d, J=4.8 Hz, 1H), 8.42 (s, 1H), 8.10 (s, 1H), 7.55 (s, 1H), 7.30 (s, 1H), 7.08 (d, J=4.8 Hz, 1H), 6.87 (t, J=54.4 Hz, 1H), 4.63-4.49 (m, 2H), 3.90-3.81 (m, 4H), 3.40-3.33 (m, 1H), 2.86-2.72 (m, 2H), 2.34 (s, 3H), 1.41 (s, 9H). MS ESI calcd. for C₂₄H₃₀F₂N₇O₃ [M+H]⁺ 502. found 502.

Step 4:

TFA (2 mL) was added to a solution of tert-butyl 2-((4-(3-((4-(difluoromethyl)pyrimidin-2-yl)amino)-5-methylphenyl)-1H-1,2,3-triazol-1-yl)methyl)morpholine-4-carboxylate (500 mg, 0.998 mmol) in DCM (5 mL). The mixture was stirred at 25° C. for 1 hour. The mixture was diluted with saturated NaHCO₃ solution (30 mL) and extracted with DCM (50 mL×3). The combined organic layers were dried over anhydrous sodium sulfate, filtered and concentrated under reduced pressure to afford 4-(difluoromethyl)-N-(3-methyl-5-(1-(morpholin-2-ylmethyl)-1H-1,2,3-triazol-4-yl)phenyl)pyrimidin-2-amine as a yellow solid. MS ESI calcd. for C₁₉H₂₂F₂N₇O [M+H]⁺ 402. found 402. The racemic mixture was purified by chiral SFC (Column: Chiralcel OD-3 50*4.6 mm I.D, 3 um, ethanol (0.05% DEA) in CO₂ from 5% to 40%) to afford Ex. No. 22.1, 4-(difluoromethyl)-N-(3-methyl-5-(1-(morpholin-2-ylmethyl)-1H-1,2,3-triazol-4-yl)phenyl) pyrimidin-2-amine (Isomer 1, first eluting). ¹H NMR (400 MHz, DMSO-d₆) δ 10.00 (s, 1H), 8.71 (d, J=4.8 Hz, 1H), 8.38 (s, 1H), 8.10 (s, 1H), 7.54 (s, 1H), 7.30 (s, 1H), 7.08 (d, J=4.8 Hz, 1H), 6.87 (t, J=54.4 Hz, 1H), 4.46-4.41 (m, 2H), 3.79-3.75 (m, 2H), 3.40-3.38 (m, 1H), 2.92-2.89 (m, 1H), 2.65-2.53 (m, 2H), 2.41-2.40 (m, 1H), 2.34 (s, 3H). MS ESI calcd. For C₁₉H₂₂F₂N₇O [M+H]⁺ 402. found 402 and Ex. No. 22.2, 4-(difluoromethyl)-N-(3-methyl-5-(1-(morpholin-2-ylmethyl)-1H-1,2,3-triazol-4-yl)phenyl) pyrimidin-2-amine (Isomer 2, second eluting). $^1$H NMR (400 MHz, DMSO-d$_6$) δ 9.99 (s, 1H), 8.70 (d, J=5.0 Hz, 1H), 8.36 (s, 1H), 8.08 (s, 1H), 7.52 (s, 1H), 7.28 (s, 1H), 7.06 (d, J=5.0 Hz, 1H), 6.85 (t, J=54.4 Hz, 1H), 4.46-4.41 (m, 2H), 3.80-3.75 (m, 2H), 3.42-3.38 (m, 1H), 2.90-2.87 (m, 1H), 2.69-2.54 (m, 2H), 2.46-2.43 (m, 1H), 2.32 (s, 3H). MS ESI calcd. For $C_{19}H_{22}F_2N_7O$ [M+H]$^+$ 402. found 402.

Example 23.1 and 23.2

4-(4-(6-((4-(Difluoromethyl)pyridin-2-yl)amino)-4-methylpyridin-2-yl)-1H-1,2,3-triazol-1-yl)-3-hydroxy-3-methylbutanenitrile (Isomer 1, first eluting) and 4-(4-(6-((4-(difluoromethyl)pyridin-2-yl)amino)-4-methylpyridin-2-yl)-1H-1,2,3-triazol-1-yl)-3-hydroxy-3-methylbutanenitrile (Isomer 2, second eluting)

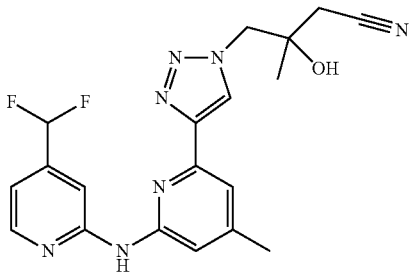 [SMILES: Cc1cc(Nc2cc(C(F)F)ccn2)nc(-c2cn(CC(C)(O)CC#N)nn2)c1]

Step 1:
Acetic acid (8.65 mL, 82.0 mmol) was added to a solution of sodium azide (3.20 g, 49.0 mmol) and 2-(chloromethyl)-2-methyloxirane (1.00 g, 9.00 mmol) in water (15 mL), and the reaction mixture was stirred at 30° C. for 5 hours. The reaction mixture was diluted with brine (50 mL) and extracted with ethyl acetate (3×50 mL). The organic layers were combined, dried over anhydrous sodium sulfate, filtered, and concentrated under reduced pressure to afford 1-azido-3-chloro-2-methylpropan-2-ol as yellow oil. $^1$H NMR (400 MHz, DMSO-d$_6$) δ 5.35 (s, 1H), 3.58-3.46 (m, 2H), 3.26 (s, 2H), 1.18 (s, 3H).
Step 2:
A solution of 1-azido-3-chloro-2-methylpropan-2-ol (173 mg, 1.16 mmol), N-(4-(difluoromethyl)pyridin-2-yl)-6-ethynyl-4-methylpyridin-2-amine (200 mg, 0.770 mmol), copper (II) sulfate pentahydrate (19.0 mg, 0.0800 mmol), and sodium ascorbate (61.0 mg, 0.310 mmol) in tert-butanol (1.7 mL) and water (1.7 mL) was heated to 65° C. overnight. The reaction mixture was diluted with brine (30 mL) and extracted with ethyl acetate (3×50 mL). The organic layers were combined and then concentrated under reduced pressure to afford the crude product residue. The crude product residue was purified by column chromatography on silica (1:1 petroleum ether/ethyl acetate) to afford 1-chloro-3-(4-(6-((4-(difluoromethyl)pyridin-2-yl)amino)-4-methylpyridin-2-yl)-1H-1,2,3-triazol-1-yl)-2-methylpropan-2-ol as a white solid. MS ESI calc'd. for $C_{18}H_{20}ClF_2N_6O$ [M+H]$^+$ 409. found 409.
Step 3:
Potassium cyanide (250 mg, 3.65 mmol) was added to a mixture of 1-chloro-3-(4-(6-((4-(difluoromethyl)pyridin-2-yl)amino)-4-methylpyridin-2-yl)-1H-1,2,3-triazol-1-yl)-2-methylpropan-2-ol (300 mg, 0.730 mmol) and sodium iodide (110 mg, 0.730 mmol) in DMF (3 mL). The mixture was stirred at 70° C. for 2 hours. The suspension was diluted with water (50 mL) and extracted with ethyl acetate (3×50 mL). The organic layers were combined, dried over anhydrous sodium sulfate, filtered, and concentrated under reduced pressure to afford the crude product residue. The crude product residue was purified by prep-TLC (100% ethyl acetate) to afford 4-(4-(6-((4-(difluoromethyl)pyridin-2-yl)amino)-4-methylpyridin-2-yl)-1H-1,2,3-triazol-1-yl)-3-hydroxy-3-methylbutanenitrile as a yellow solid. MS ESI calc'd. for $C_{19}H_{20}F_2N_7O$ [M+H]$^+$ 400. found 400.
Step 4:
4-(4-(6-((4-(Difluoromethyl)pyridin-2-yl)amino)-4-methylpyridin-2-yl)-1H-1,2,3-triazol-1-yl)-3-hydroxy-3-methylbutanenitrile was separated by chiral SFC (Chiralpak AS-H 150*4.6 mm I.D column, 5-40% ethanol (0.05% DEA) in CO$_2$) to afford Ex. No. 23.1, 4-(4-(6-((4-(difluoromethyl)pyridin-2-yl)amino)-4-methylpyridin-2-yl)-1H-1,2,3-triazol-1-yl)-3-hydroxy-3-methylbutanenitrile (Isomer 1, first eluting): MS ESI calc'd. for $C_{19}H_{20}F_2N_7O$ [M+H]$^+$ 400. found 400. $^1$H NMR (400 MHz, DMSO-d$_6$) δ 9.99 (s, 1H), 8.39 (d, J=5.2 Hz, 1H), 8.30 (s, 1H), 8.19 (s, 1H), 7.46 (s, 1H), 7.39 (s, 1H), 7.06 (t, J=54.4 Hz, 1H), 7.03 (d, J=5.2 Hz, 1H), 5.74 (s, 1H), 4.54-4.45 (m, 2H), 2.81-2.67 (m, 2H), 2.35 (s, 3H), 1.22 (s, 3H), and Ex. No. 23.2, 4-(4-(6-((4-(difluoromethyl)pyridin-2-yl)amino)-4-methylpyridin-2-yl)-1H-1,2,3-triazol-1-yl)-3-hydroxy-3-methylbutanenitrile (Isomer 2, second eluting): MS ESI calc'd. for $C_{19}H_{20}F_2N_7O$ [M+H]$^+$ 400. found 400. $^1$H NMR (400 MHz, DMSO-d$_6$) δ 9.99 (s, 1H), 8.39 (d, J=5.2 Hz, 1H), 8.30 (s, 1H), 8.19 (s, 1H), 7.46 (s, 1H), 7.39 (s, 1H), 7.06 (t, J=54.4 Hz, 1H), 7.03 (d, J=5.2 Hz, 1H), 5.74 (s, 1H), 4.54-4.45 (m, 2H), 2.81-2.67 (m, 2H), 2.35 (s, 3H), 1.22 (s, 3H).

Example 24.1 and 24.2

4-((4-(6-((4-(Difluoromethyl)pyridin-2-yl)amino)-4-methylpyridin-2-yl)-1H-1,2,3-triazol-1-yl)methyl) pyrrolidin-2-one (Isomer 1, first eluting) and 4-((4-(6-((4-(difluoromethyl)pyridin-2-yl)amino)-4-methylpyridin-2-yl)-1H-1,2,3-triazol-1-yl)methyl) pyrrolidin-2-one (Isomer 2, second eluting)

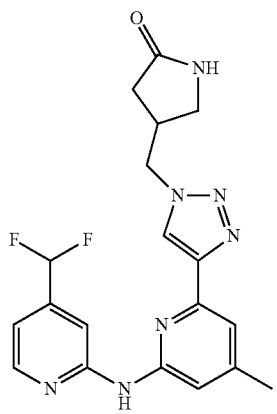 [SMILES: Cc1cc(Nc2cc(C(F)F)ccn2)nc(-c2cn(CC3CNC(=O)C3)nn2)c1]

Step 1:
A mixture of (1-(2,4-dimethoxybenzyl)-5-oxopyrrolidin-3-yl)methyl methanesulfonate (343 mg, 1.00 mmol), sodium azide (130 mg, 2.00 mmol) and sodium iodide (15.0 mg, 0.100 mmol) in DMF (5 mL) was stirred at 100° C. under a nitrogen atmosphere for 4 hours. The mixture was diluted with water (20 mL) and extracted with ethyl acetate (3×50 mL). The organic layers were combined, dried over anhydrous sodium sulfate, filtered, and concentrated under reduced pressure to afford 4-(azidomethyl)-1-(2,4-dimethoxybenzyl)pyrrolidin-2-one as a yellow oil. The material was used in the next step without further purification. MS ESI calc'd. for $C_{14}H_{19}N_4O_3$ [M+H]$^+$ 291. found 291.

Step 2:

A mixture of 4-(azidomethyl)-1-(2,4-dimethoxybenzyl)pyrrolidin-2-one (200 mg, 0.690 mmol), N-(4-(difluoromethyl)pyridin-2-yl)-6-ethynyl-4-methylpyridin-2-amine (178 mg, 0.690 mmol), copper (II) sulfate pentahydrate (18.0 mg, 0.0700 mmol), and sodium ascorbate (0.210 mmol, 410 mg) in tert-butanol (2 mL) and water (2 mL) was stirred at 65° C. for 3 hours. The reaction mixture was quenched with water (20 mL) and extracted with ethyl acetate (3×50 mL). The organic layers were combined, dried over anhydrous sodium sulfate, filtered, and concentrated under reduced pressure to afford the crude product residue. The crude product residue was purified by prep-TLC (1:1 petroleum ether/ethyl acetate) to afford 4-((4-(6-((4-(difluoromethyl)pyridin-2-yl)amino)-4-methylpyridin-2-yl)-1H-1,2,3-triazol-1-yl)methyl)-1-(2,4-dimethoxybenzyl)pyrrolidin-2-one as a white solid. MS ESI calc'd. for $C_{28}H_{30}F_2N_7O_3$ [M+H]$^+$ 550. found 550.

Step 3:

A solution of 4-((4-(6-((4-(difluoromethyl)pyridin-2-yl)amino)-4-methylpyridin-2-yl)-1H-1,2,3-triazol-1-yl)methyl)-1-(2,4-dimethoxybenzyl)pyrrolidin-2-one (250 mg, 0.450 mmol) in TFA (3 mL) was stirred at 60° C. for 12 hours. The mixture was then diluted with water (20 mL) and extracted with ethyl acetate (3×50 mL). The organic layers were combined, dried over anhydrous sodium sulfate, filtered, and concentrated under reduced pressure to give 4-((4-(6-((4-(difluoromethyl)pyridin-2-yl)amino)-4-methylpyridin-2-yl)-1H-1,2,3-triazol-1-yl)methyl)pyrrolidin-2-one as a yellow solid. MS ESI calc'd. for $C_{19}H_{20}N_7F_2O$ [M+H]$^+$ 400. found 400.

Step 4:

4-((4-(6-((4-(Difluoromethyl)pyridin-2-yl)amino)-4-methylpyridin-2-yl)-1H-1,2,3-triazol-1-yl)methyl)pyrrolidin-2-one was separated by chiral SFC (Chiralpak AD-3 50*4.6*4.6 mm I.D. column, 60% ethanol (0.05% DEA) in $CO_2$) to afford Ex. No. 24.1, 4-((4-(6-((4-(difluoromethyl)pyridin-2-yl)amino)-4-methylpyridin-2-yl)-1H-1,2,3-triazol-1-yl)methyl)pyrrolidin-2-one (Isomer 1, first eluting): MS ESI calc'd. for $C_{19}H_{20}N_7F_2O$ [M+H]$^+$ 400. found 400. $^1$H NMR (400 MHz, DMSO-d$_6$) δ 10.49 (s, 1H), 8.55 (s, 1H), 8.46 (d, J=5.6 Hz, 1H), 8.09 (s, 1H), 7.63 (s, 1H), 7.51 (s, 1H), 7.29 (s, 1H), 7.14 (d, J=5.6 Hz, 1H), 7.12 (t, J=54.4 Hz, 1H), 4.56 (d, J=7.2 Hz, 2H), 3.38-3.35 (m, 1H), 3.08-2.77 (m, 2H), 2.40 (s, 3H), 2.30-2.28 (m, 1H), 2.10-2.08 (m, 1H, and Ex. 24.2, 4-((4-(6-((4-(difluoromethyl)pyridin-2-yl)amino)-4-methylpyridin-2-yl)-1H-1,2,3-triazol-1-yl)methyl)pyrrolidin-2-one (Isomer 2, second eluting): MS ESI calc'd. for $C_{19}H_{20}N_7F_2O$ [M+H]$^+$ 400. found 400. $^1$H NMR (400 MHz, DMSO-d$_6$) δ 10.60 (s, 1H), 8.59 (s, 1H), 8.47 (d, J=5.6 Hz, 1H), 8.05 (s, 1H), 7.63 (s, 1H), 7.52 (s, 1H), 7.28 (s, 1H), 7.16 (d, J=5.6 Hz, 1H), 7.15 (t, J=54.4 Hz, 1H), 4.57 (d, J=7.2 Hz, 2H), 3.38-3.33 (m, 1H), 3.12-3.08 (m, 2H), 2.40 (s, 3H), 2.30-2.28 (m, 1H), 2.10-2.08 (m, 1H).

Example 25.1 and 25.2

3-(4-(3-((4-(Difluoromethyl)pyrimidin-2-yl)amino)-5-methylphenyl)-1H-1,2,3-triazol-1-yl)cyclohexane-1,2-diol (Isomer 1, first eluting) and 3-(4-(3-((4-(difluoromethyl)pyrimidin-2-yl)amino)-5-methylphenyl)-1H-1,2,3-triazol-1-yl)cyclohexane-1,2-diol (Isomer 2, second eluting)

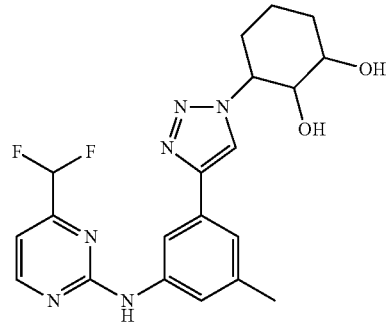 [SMILES: Cc1cc(Nc2nccc(C(F)F)n2)cc(-c2cn(C3CCCC(O)C3O)nn2)c1]

Step 1:

A mixture of 3-bromocyclohex-1-ene (1.00 g, 6.20 mmol) and NaN$_3$ (807 mg, 12.4 mmol) in DMF (10 mL) was heated to 70° C. under a N$_2$ atmosphere for 12 hours. Upon cooling to room temperature, the mixture was diluted with H$_2$O (20 mL) and extracted with EtOAc (50 mL×3). The combined organic layers were washed with brine (20 mL), dried over anhydrous sodium sulfate, filtered and concentrated under reduced pressure to afford 3-azidocyclohex-1-ene as yellow oil. MS ESI calc'd. for $C_6H_{10}N_3$ [M+H]$^+$ 124. found 124.

Step 2:

A mixture of 3-azidocyclohex-1-ene (380 mg, 3.09 mmol), 4-(difluoromethyl)-N-(3-ethynyl-5-methylphenyl)pyrimidin-2-amine (400 mg, 1.54 mmol), CuSO$_4$.5H$_2$O (39.0 mg, 0.150 mmol) and sodium ascorbate (122 mg, 0.620 mmol) in t-BuOH (2 mL) and H$_2$O (2 mL) was heated to 65° C. for 12 hours. Upon cooling to room temperature, the mixture was diluted with water (20 mL) and extracted with EtOAc (50 mL×3). The combined organic layers were dried over anhydrous sodium sulfate, filtered and concentrated under reduced pressure. The residue was purified by column chromatography on silica (3:1 petroleum ether/ethyl acetate, R$_f$=0.4) to afford N-(3-(1-(cyclohex-2-en-1-yl)-1H-1,2,3-triazol-4-yl)-5-methylphenyl)-4-(difluoromethyl)pyrimidin-2-amine as a yellow solid. MS ESI calc'd. for $C_{20}H_{21}F_2N_6$ [M+H]$^+$ 383. found 383. $^1$H NMR (400 MHz, DMSO-d$_6$) δ 9.97 (s, 1H), 8.70 (d, J=4.8 Hz, 1H), 8.39 (s, 1H), 8.10 (s, 1H), 7.52 (s, 1H), 7.30 (s, 1H), 7.05 (d, J=4.8 Hz, 1H), 6.84 (t, J=54.4 Hz, 1H), 6.10-6.07 (m, 1H), 5.83-5.80 (m, 1H), 5.28-5.26 (m, 1H), 2.31 (s, 3H), 2.14-2.11 (m, 3H), 2.09-1.98 (m, 1H), 1.71-1.69 (m, 2H).

Step 3:

A mixture of N-(3-(1-(cyclohex-2-en-1-yl)-1H-1,2,3-triazol-4-yl)-5-methylphenyl)-4-(difluoromethyl)pyrimidin-2-amine (550 mg, 1.44 mmol), NMO (672 mg, 5.74 mmol), OsO$_4$ (37.0 mg, 0.144 mmol) in THF (1 mL) and H$_2$O (1 mL) was stirred at 25° C. under a N$_2$ atmosphere for 12 hours. The mixture was diluted with saturated aqueous NaHSO$_3$ solution (30 mL) and extracted with EtOAc (50 mL×3). The combined organic layers were dried over anhydrous sodium sulfate, filtered and concentrated under reduced pressure to afford 3-(4-(3-((4-(difluoromethyl)pyrimidin-2-yl)amino)-5-methylphenyl)-1H-1,2,3-triazol-1-yl)cyclohexane-1,2-diol as light yellow solid. The resulting solid was purified by chiral SFC (Column: Chiralcel OJ 250*30 mm I.D., 5 um, Mobile phase: Supercritical CO$_2$/EtOH (0.1%) NH$_3$.H$_2$O=60/40 at 50 mL/minute) to afford two isomers of 3-(4-(3-((4-(Difluoromethyl)pyrimidin-2-yl)amino)-5-methylphenyl)-1H-1,2,3-triazol-1-yl)cyclohexane-1,2-diol.

Example No. 25.1

Isomer 1, first eluting: MS ESI calc'd. for $C_{20}H_{23}F_2N_6O_2$ [M+H]$^+$ 417. found 417. $^1$H NMR (400 MHz, DMSO-d$_6$) δ 10.00 (s, 1H), 8.72 (d, J=4.8 Hz, 1H), 8.45 (s, 1H), 8.09 (s, 1H), 7.53 (s, 1H), 7.27 (s, 1H), 7.08 (d, J=4.8 Hz, 1H), 6.87 (t, J=54.4 Hz, 1H), 4.62-4.57 (m, 1H), 3.96-3.89 (m, 2H), 3.82-3.79 (m, 2H), 2.34 (s, 3H), 1.98-1.90 (m, 2H), 1.81-1.78 (m, 2H), 1.53-1.51 (m, 2H).

Example No. 25.2

Isomer 2, second eluting: MS ESI calc'd. for $C_{20}H_{23}F_2N_6O_2$ [M+H]$^+$ 417. found 417. $^1$H NMR (400 MHz, DMSO-d$_6$) δ 10.00 (s, 1H), 8.72 (d, J=4.8 Hz, 1H), 8.45 (s, 1H), 8.09 (s, 1H), 7.53 (s, 1H), 7.27 (s, 1H), 7.08 (d, J=4.8 Hz, 1H), 6.87 (t, J=54.4 Hz, 1H), 4.62-4.57 (m, 1H), 3.96-3.88 (m, 2H), 3.82-3.79 (m, 2H), 2.34 (s, 3H), 1.98-1.90 (m, 2H), 1.78-1.75 (m, 2H), 1.53-1.51 (m, 2H).

Example 26.1 and 26.2

N-(4-(Difluoromethyl)pyridin-2-yl)-4-methyl-6-(1-(morpholin-2-ylmethyl)-1H-1,2,3-triazol-4-yl)pyridin-2-amine (Isomer 1, isomer eluting) and N-(4-(difluoromethyl)pyridin-2-yl)-4-methyl-6-(1-(morpholin-2-ylmethyl)-1H-1,2,3-triazol-4-yl)pyridin-2-amine (Isomer 2, second eluting)

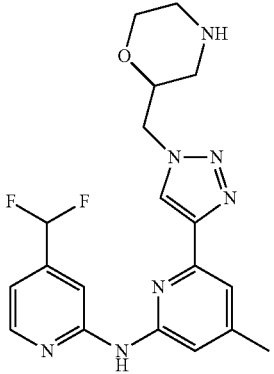 [SMILES: Cc1cc(Nc2cc(C(F)F)ccn2)nc(-c2cn(CC3CNCCO3)nn2)c1]

Step 1:

A mixture of tert-butyl 2-(azidomethyl)morpholine-4-carboxylate (325 mg, 1.34 mmol), N-(4-(difluoromethyl)pyridin-2-yl)-6-ethynyl-4-methylpyridin-2-amine (300 mg, 1.12 mmol), copper(II) sulfate pentahydrate (28.0 mg, 0.110 mmol), and sodium ascorbate (89.0 mg, 0.450 mmol) in tert-butanol (2 mL) and water (2 mL) was stirred at 70° C. for 12 hours. Water (20 mL) was then added and the mixture was extracted with ethyl acetate (50 mL×3). The combined organic layers were dried over anhydrous sodium sulfate and concentrated under reduced pressure. The residue was purified by prep-TLC (1:1 petroleum ether/ethyl acetate) to give the compound tert-butyl 2-((4-(6-((4-(difluoromethyl)pyridin-2-yl)amino)-4-methylpyridin-2-yl)-1H-1,2,3-triazol-1-yl)methyl)morpholine-4-carboxylate. MS ESI calc'd. for $C_{24}H_{30}F_2N_7O_3$ [M+H]$^+$ 502. found 502. $^1$H NMR (400 MHz, DMSO-d$_6$): δ 9.98 (s, 1H), 8.39-8.29 (m, 3H), 7.45 (s, 1H), 7.31 (s, 1H), 7.10 (t, J=54.4 Hz, 1H), 7.04 (d, J=5.2 Hz, 1H), 4.69-4.65 (m, 1H), 4.57-4.55 (m, 1H), 3.92-3.81 (m, 4H), 3.41-3.40 (m, 1H), 2.91-2.72 (m, 2H), 2.35 (s, 3H), 1.40 (s, 9H).

Step 2:

To a mixture of tert-butyl 2-((4-(6-((4-(difluoromethyl)pyridine-2-yl)amino)-4-methyl pyrimidin-2-yl)-1H-1,2,3-triazol-1-yl)methyl)morpholine-4-carboxylate (550 mg, 1.09 mmol) in DCM (5 mL) was added TFA (2 mL). The mixture was stirred at 25° C. for 1 hour. The mixture was diluted with saturated NaHCO$_3$ (20 mL) solution and extracted with DCM (50 mL×3). The combined organic layers were dried over anhydrous sodium sulfate and concentrated under reduced pressure to give N-(4-(difluoromethyl)pyridine-2-yl)-4-methyl-6-(1-(morpholin-2-ylmethyl)-1H-1,2,3-triazol-4-yl)pyridin-2-amine. MS ESI calc'd. for $C_{19}H_{22}F_2N_7O$ [M+H]$^+$ 402. found 402.

Step 3:

N-(4-(difluoromethyl)pyridin-2-yl)-4-methyl-6-(1-(morpholin-2-ylmethyl)-1H-1,2,3-triazol-4-yl)pyridin-2-amine was separated by chiral preparative SFC (Chiralcel OJ 250*30 mm I.D., 60/40% CO$_2$/EtOH (0.1% NH$_3$H$_2$O)) to afford Ex. No. 26.1, N-(4-(difluoromethyl)pyridin-2-yl)-4-methyl-6-(1-(morpholin-2-ylmethyl)-1H-1,2,3-triazol-4-yl)pyridin-2-amine (Isomer 1, first eluting). MS ESI calc'd. for $C_{19}H_{22}F_2N_7O$ [M+H]$^+$ 402. found 402. $^1$H NMR (400 MHz, DMSO-d$_6$) δ 9.95 (s, 1H), 8.37 (d, J=5.0 Hz, 1H), 8.27-8.26 (m, 2H), 7.42 (s, 1H), 7.30 (s, 1H), 7.08 (t, J=54.4 Hz, 1H), 7.02 (d, J=5.0 Hz, 1H), 4.50-4.44 (m, 2H), 3.73-3.70 (m, 2H), 3.40-3.34 (m, 1H), 2.86-2.82 (m, 1H), 2.62-2.53 (m, 2H), 2.37-2.34 (m, 1H), 2.33 (s, 3H); and Ex. No. 26.2, N-(4-(difluoromethyl)pyridin-2-yl)-4-methyl-6-(1-(morpholin-2-ylmethyl)-1H-1,2,3-triazol-4-yl)pyridin-2-amine (Isomer 2, second eluting). MS ESI calc'd. for $C_{19}H_{22}F_2N_7O$ [M+H]$^+$ 402. found 402. $^1$H NMR (400 MHz, DMSO-d$_6$): δ 9.96 (s, 1H), 8.36 (d, J=5.2 Hz, 1H), 8.26-8.25 (m, 2H), 7.42 (s, 1H), 7.30 (s, 1H), 7.08 (t, J=54.4 Hz, 1H), 7.02 (d, J=5.2 Hz, 1H), 4.50-4.44 (m, 2H), 3.73-3.70 (m, 2H), 3.40-3.31 (m, 1H), 2.85-2.82 (m, 1H), 2.62-2.52 (m, 2H), 2.37-2.34 (m, 1H), 2.32 (s, 3H).

Example 27.1 and 27.2

4-(4-(3-((4-(Difluoromethyl)pyrimidin-2-yl)amino)-5-methylphenyl)-1H-1,2,3-triazol-1-yl)-3-hydroxy-3-methylbutanenitrile (Isomer 1, first eluting) and 4-(4-(3-((4-(difluoromethyl)pyrimidin-2-yl)amino)-5-methylphenyl)-1H-1,2,3-triazol-1-yl)-3-hydroxy-3-methylbutanenitrile (Isomer 2, second eluting)

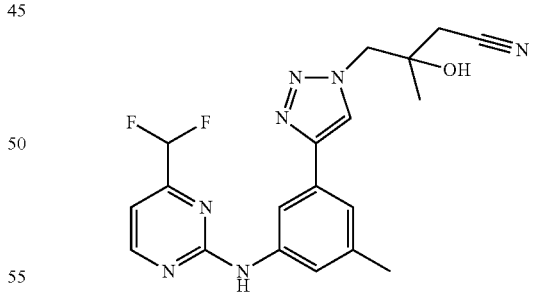

Step 1:

A solution of 1-azido-3-chloro-2-methylpropan-2-ol (173 mg, 1.16 mmol), 4-(difluoromethyl)-N-(3-ethynyl-5-methylphenyl)pyrimidin-2-amine (200 mg, 0.77 mmol), CuSO$_4$.5H$_2$O (19.2 mg, 0.077 mmol) and sodium ascorbate (61.0 mg, 0.310 mmol) in t-BuOH (1.7 mL) and water (1.7 mL) was heated to 65° C. overnight. The mixture was poured into brine (30 mL) and extracted with EtOAc (20 mL×3). The combined organic layer was concentrated under reduced pressure. The residue was purified by column chromatography on silica (1:1 petroleum ether/ethyl acetate)

to afford 1-chloro-3-(4-(3-((4-(difluoromethyl)pyrimidin-2-yl)amino)-5-methylphenyl)-1H-1,2,3-triazol-1-yl)-2-methylpropan-2-ol as a yellow solid. MS ESI calc'd. for $C_{18}H_{20}ClF_2N_6O$ [M+H]$^+$ 409. found 409.

Step 2:

KCN (310 mg, 4.77 mmol) was added to a mixture of 1-chloro-3-(4-(3-((4-(difluoromethyl)pyrimidin-2-yl)amino)-5-methylphenyl)-1H-1,2,3-triazol-1-yl)-2-methylpropan-2-ol (390 mg, 0.95 mmol) and NaI (143 mg, 0.95 mmol) in DMF (3.9 mL). The mixture was stirred at 70° C. for 2 hours. The suspension was poured into water (20 mL) and extracted with EtOAc (20 mL×3). The organic layer was dried over anhydrous sodium sulfate and concentrated under reduced pressure. The residue was purified by prep-TLC (1:1 petroleum ether/ethyl acetate) to afford 4-(4-(3-((4-(difluoromethyl)pyrimidin-2-yl)amino)-5-methylphenyl)-1H-1,2,3triazol-1-yl)-3-hydroxy-3-methylbutanenitrile as a yellow solid. MS ESI calc'd. for $C_{19}H_{20}F_2N_7O$ [M+H]$^+$ 400. found 400.

Step 3:

Racemic 4-(4-(3-((4-(difluoromethyl)pyrimidin-2-yl)amino)-5-methylphenyl)-1H-1,2,3-triazol-1-yl)-3-hydroxy-3-methylbutanenitrile was purified by chiral SFC (Chiralpak AD-3 50*4.6 mm I.D, 40% ethanol (0.05% DEA) in $CO_2$) to afford Ex. No. 27.1, 4-(4-(3-((4-(difluoromethyl)pyrimidin-2-yl)amino)-5-methylphenyl)-1H-1,2,3-triazol-1-yl)-3-hydroxy-3-methylbutanenitrile (Isomer 1, first eluting). $^1$H NMR (400 MHz, DMSO-d$_6$) δ 10.01 (s, 1H), 8.71 (d, J=5.0 Hz, 1H), 8.34 (s, 1H), 8.11 (s, 1H), 7.56 (s, 1H), 7.32 (s, 1H), 7.07 (d, J=5.0 Hz, 1H), 6.87 (t, J=54.4, 1H), 5.80 (s, 1H), 4.50-4.42 (m, 2H), 2.80-2.66 (m, 2H), 2.34 (s, 3H), 1.22 (s, 3H). MS ESI calc'd. for $C_{19}H_{20}F_2N_7O$ [M+H]$^+$ 400. found 400; and Ex. No. 27.2, 4-(4-(3-((4-(Difluoromethyl)pyrimidin-2-yl)amino)-5-methylphenyl)-1H-1,2,3-triazol-1-yl)-3-hydroxy-3-methylbutanenitrile (Isomer 2, second eluting). $^1$H NMR (400 MHz, DMSO-d$_6$) δ 10.01 (s, 1H), 8.71 (d, J=5.0 Hz, 1H), 8.34 (s, 1H), 8.11 (s, 1H), 7.56 (s, 1H), 7.32 (s, 1H), 7.07 (d, J=5.0 Hz, 1H), 6.86 (t, J=54.4, 1H), 5.80 (s, 1H), 4.50-4.42 (m, 2H), 2.80-2.66 (m, 2H), 2.34 (s, 3H), 1.22 (s, 3H). MS ESI calc'd. for $C_{19}H_{20}F_2N_7O$ [M+H]$^+$ 400. found 400.

Example 28.1 and 28.2

4-((4-(3-((4-(Difluoromethyl)pyrimidin-2-yl)amino)-5-methylphenyl)-1H-1,2,3-triazol-1-yl)methyl)pyrrolidin-2-one (Isomer 1, first eluting) and 4-((4-(3-((4-(difluoromethyl)pyrimidin-2-yl)amino)-5-methylphenyl)-1H-1,2,3-triazol-1-yl)methyl)pyrrolidin-2-one (Isomer 2, second eluting)

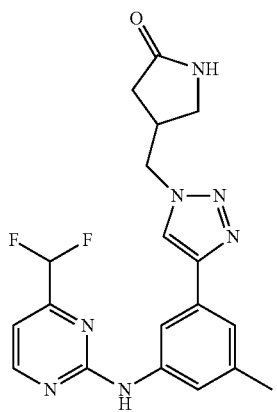 [SMILES: Cc1cc(Nc2nccc(C(F)F)n2)cc(-c2cn(CC3CNC(=O)C3)nn2)c1]

Step 1:

A mixture of 4-(azidomethyl)-1-(2,4-dimethoxybenzyl)pyrrolidin-2-one (290 mg, 1.00 mmol), 4-(difluoromethyl)-N-(3-ethynyl-5-methylphenyl)pyrimidin-2-amine (259 mg, 1.00 mmol), CuSO$_4$.5H$_2$O (25.0 mg, 0.10 mmol), sodium ascorbate (60.0 mg, 0.30 mmol) in t-BuOH (2 mL) and H$_2$O (2 mL) was stirred at 65° C. for 3 hours. Then the reaction was quenched by water (20 mL) and extracted with EtOAc (20 mL×3). The EtOAc layer was dried over anhydrous sodium sulfate and concentrated under reduced pressure. The residue was purified by prep-TLC (1:1 petroleum ether/ethyl acetate) to give 4-((4-(3-((4-(difluoromethyl)pyrimidin-2-yl)amino)-5-methylphenyl)-1H-1,2,3-triazol-1-yl)methyl)-1-(2,4-dimethoxybenzyl)pyrrolidin-2-one as a yellow solid. $^1$H NMR (400 MHz, DMSO-d$_6$) δ 10.0 (s, 1H), 8.72 (d, J=4.8 Hz, 1H), 8.45 (s, 1H), 8.10 (s, 1H), 7.55 (s, 1H), 7.27 (s, 1H), 7.08 (d, J=4.8 Hz, 1H), 6.99 (d, J=8.4 Hz, 1H), 6.87 (t, J=54.4 Hz, 1H), 6.56 (s, 1H), 6.47 (d, J=8.4 Hz, 1H), 4.47 (d, J=7.2 Hz, 2H), 4.26 (s, 2H), 3.78 (s, 3H), 3.33 (s, 3H), 3.26-3.10 (m, 1H), 3.08-3.05 (m, 1H), 2.89-2.73 (m, 1H), 2.53-2.46 (m, 1H), 2.34 (s, 3H), 2.26-2.08 (m, 1H). MS ESI calc'd. for $C_{28}H_{30}F_2N_7O_3$ [M+H]$^+$ 550. found 550.

Step 2:

To a solution of 4-((4-(3-((4-(difluoromethyl)pyrimidin-2-yl)amino)-5-methylphenyl)-1H-1,2,3-triazol-1-yl)methyl)-1-(2,4-dimethoxybenzyl)pyrrolidin-2-one (350 mg, 0.63 mmol) in TFA (3 mL) was stirred at 60° C. for 12 hours. Then the mixture was diluted with water (20 mL) and extracted with EtOAc (20 mL×3). The EtOAc layer was dried over anhydrous sodium sulfate and concentrated under reduced pressure to give 4-((4-(3-((4-(difluoromethyl)pyrimidin-2-yl)amino)-5-methylphenyl)-1H-1,2,3-triazol-1-yl)methyl)pyrrolidin-2-one as a yellow solid. MS ESI calc'd. for $C_{19}H_{20}N_7F_2O$ [M+H]$^+$ 400. found 400.

Step 3:

Racemic 4-((4-(3-((4-(difluoromethyl)pyrimidin-2-yl)amino)-5-methylphenyl)-1H-1,2,3-triazol-1-yl)methyl)pyrrolidin-2-one was purified by chiral SFC (Chiralpak AD-3 50*4.6 mm I.D., 60% ethanol (0.05% DEA) in $CO_2$) to afford Ex. No. 28.1, 4-((4-(3-((4-(difluoromethyl)pyrimidin-2-yl)amino)-5-methylphenyl)-1H-1,2,3-triazol-1-yl)methyl)pyrrolidin-2-one (Isomer 1, first eluting). $^1$H NMR (400 MHz, DMSO-d$_6$) δ 10.00 (s, 1H), 8.70 (d, J=5.0 Hz, 1H), 8.50 (s, 1H), 8.09 (s, 1H), 7.60 (s, 1H), 7.53 (s, 1H), 7.27 (s, 1H), 7.06 (d, J=5.0 Hz, 1H), 6.85 (t, J=54.4 Hz, 1H), 4.46 (d, J=7.2 Hz, 2H), 3.33-3.29 (m, 1H), 3.06-2.96 (m, 2H), 2.32 (s, 3H), 2.31-2.27 (m, 1H), 2.06-2.04 (m, 1H). MS ESI calc'd. for $C_{19}H_{20}N_7F_2O$ [M+H]$^+$ 400. found 400; and Ex. No. 28.2, 4-((4-(3-((4-(difluoromethyl)pyrimidin-2-yl)amino)-5-methylphenyl)-1H-1,2,3-triazol-1-yl)methyl)pyrrolidin-2-one (Isomer 2, second eluting). $^1$H NMR (400 MHz, DMSO-d$_6$) δ 10.00 (s, 1H), 8.70 (d, J=5.0 Hz, 1H), 8.50 (s, 1H), 8.09 (s, 1H), 7.60 (s, 1H), 7.53 (s, 1H), 7.27 (s, 1H), 7.06 (d, J=5.0 Hz, 1H), 6.85 (t, J=54.4 Hz, 1H), 4.46 (d, J=7.2 Hz, 2H), 3.31-3.08 (m, 1H), 3.06-2.96 (m, 2H), 2.32 (s, 3H), 2.31-2.27 (m, 1H), 2.24-2.06 (m, 1H). MS ESI calc'd. for $C_{19}H_{20}N_7F_2O$ [M+H]$^+$ 400. found 400.

Example 29.1-29.3

3-(4-(3-((4-(difluoromethyl)pyrimidin-2-yl)amino)-5-methylphenyl)-1H-1,2,3-triazol-1-yl)-1-methylcyclohexane-1,2-diol (Isomer 1, first eluting) and 3-(4-(3-((4-(difluoromethyl)pyrimidin-2-yl)amino)-5-methylphenyl)-1H-1,2,3-triazol-1-yl)-1-methylcyclohexane-1,2-diol (Isomer 1, second eluting) and 3-(4-(3-((4-(difluoromethyl)pyrimidin-2-yl)amino)-5-methylphenyl)-1H-1,2,3-triazol-1-yl)-1-methylcyclohexane-1,2-diol (Isomer 3, fourth eluting)

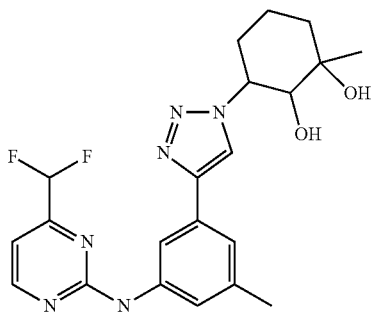 [SMILES: Cc1cc(Nc2nccc(C(F)F)n2)cc(-c2cn(C3CCCC(C)(O)C3O)nn2)c1]

Step 1:

A solution of 3-azido-1-methylcyclohex-1-ene (312 mg, 1.54 mmol), and 4-(difluoromethyl)-N-(3-ethynyl-5-methylphenyl)pyrimidin-2-amine (200 mg, 0.77 mmol), $CuSO_4 \cdot 5H_2O$ (19.0 mg, 0.08 mmol) and sodium ascorbate (61.0 mg, 0.31 mmol) in t-BuOH (8 mL) and water (8 mL) was heated to 70° C. overnight. After cooled to 20° C., the mixture was diluted with saturated brine (50 mL). The mixture was extracted with EtOAc (50 mL×3), dried over anhydrous sodium sulfate and concentrated under reduced pressure. The residue was purified by column chromatography on silica (2:1 petroleum ether/ethyl acetate) to give 4-(difluoromethyl)-N-(3-methyl-5-(1-(3-methylcyclohex-2-en-1-yl)-1H-1,2,3-triazol-4-yl)phenyl)pyrimidin-2-amine as a yellow solid. $^1$H NMR (400 MHz, $CD_3OD$) δ 8.61 (d, J=5.0 Hz, 1H), 8.18 (s, 1H), 8.01 (s, 1H), 7.52 (s, 1H), 7.33 (s, 1H), 7.01 (d, J=5.0 Hz, 1H), 6.58 (t, J=54.4 Hz, 1H), 5.61 (d, J=1.2 Hz, 1H), 5.27 (s, 1H), 2.39 (s, 3H), 2.25-2.06 (m, 3H), 2.03-1.95 (m, 1H), 1.84 (s, 3H), 1.81-1.71 (m, 2H).

Step 2:

NMO (414 mg, 3.54 mmol) and $OsO_4$ (22.8 mg, 0.0882 mmol) were added at 0° C. to a mixture of 4-(difluoromethyl)-N-(3-methyl-5-(1-(3-methylcyclohex-2-en-1-yl)-1H-1,2,3-triazol-4-yl)phenyl)pyrimidin-2-amine (350 mg, 0.88 mmol) in THF (5 mL) and water (5 mL). The mixture was stirred 15° C. for 16 hours. Water (20 mL) was added to the mixture and extracted with ethyl acetate (30 mL×2). The combined organic layer was washed with brine, dried over anhydrous sodium sulfate and concentrated under reduced pressure. The residue was purified by column chromatography on silica (1:1 petroleum ether/ethyl acetate) to give 3-(4-(3-((4-(difluoromethyl)pyrimidin-2-yl)amino)-5-methylphenyl)-1H-1,2,3-triazol-1-yl)-1-methylcyclohexane-1,2-diol as a yellow solid.

Step 3:

3-(4-(3-((4-(difluoromethyl)pyrimidin-2-yl)amino)-5-methylphenyl)-1H-1,2,3-triazol-1-yl)-1-methylcyclohexane-1,2-diol was separated by prep chiral SFC group (Chiralcel OJ-3, 5-40% methanol (0.05% DEA) in $CO_2$) to afford three isomers.

Example No. 29.1

3-(4-(3-((4-(Difluoromethyl)pyrimidin-2-yl)amino)-5-methylphenyl)-1H-1,2,3-triazol-1-yl)-1-methylcyclohexane-1,2-diol (Isomer 1, first eluting). $^1$H NMR (400 MHz, DMSO-$d_6$) δ 10.02-9.95 (m, 1H), 8.71 (d, J=4.8 Hz, 1H), 8.40 (s, 1H), 8.12-8.04 (m, 1H), 7.53 (s, 1H), 7.32 (s, 1H), 7.07 (d, J=4.8 Hz, 1H), 6.86 (t, J=54.4 Hz, 1H), 5.02 (d, J=4.0 Hz, 1H), 4.81-4.70 (m, 1H), 4.39 (s, 1H), 3.62-3.55 (m, 1H), 2.33 (s, 3H), 2.19-1.98 (m, 1H), 1.77-1.68 (m, 2H), 1.53-1.44 (m, 1H), 1.39-1.32 (m, 1H), 1.25 (s, 3H), 0.96-0.87 (m, 1H).

Example No. 29.2

3-(4-(3-((4-(Difluoromethyl)pyrimidin-2-yl)amino)-5-methylphenyl)-1H-1,2,3-triazol-1-yl)-1-methylcyclohexane-1,2-diol (Isomer 2, second eluting). $^1$H NMR (400 MHz, DMSO-$d_6$) δ 10.00 (s, 1H), 8.71 (d, J=4.8 Hz, 1H), 8.44 (s, 1H), 8.08 (s, 1H), 7.52 (s, 1H), 7.27 (s, 1H), 7.07 (d, J=4.8 Hz, 1H), 6.87 (t, J=54.4 Hz, 1H), 4.78 (d, J=8.0 Hz, 1H), 4.61-4.48 (m, 1H), 4.30 (s, 1H), 3.63-3.54 (m, 1H), 2.33 (s, 3H), 2.01-1.85 (m, 2H), 1.79-1.64 (m, 2H), 1.54-1.40 (m, 2H), 1.19 (s, 3H).

Example No. 29.3

3-(4-(3-((4-(Difluoromethyl)pyrimidin-2-yl)amino)-5-methylphenyl)-1H-1,2,3-triazol-1-yl)-1-methylcyclohexane-1,2-diol (Isomer 3, fourth eluting). $^1$H NMR (400 MHz, DMSO-$d_6$) δ 10.00 (s, 1H), 8.71 (d, J=4.8 Hz, 1H), 8.44 (s, 1H), 8.08 (s, 1H), 7.52 (s, 1H), 7.27 (s, 1H), 7.07 (d, J=4.8 Hz, 1H), 6.87 (t, J=54.4 Hz, 1H), 4.78 (d, J=7.6 Hz, 1H), 4.61-4.48 (m, 1H), 4.30 (s, 1H), 3.64-3.52 (m, 1H), 2.33 (s, 3H), 2.02-1.84 (m, 2H), 1.82-1.65 (m, 2H), 1.54-1.40 (m, 2H) 1.19 (s, 3H).

The following compounds in Table 29 were prepared according to the method described for Example 29.1-29.3, and have the general formula below:

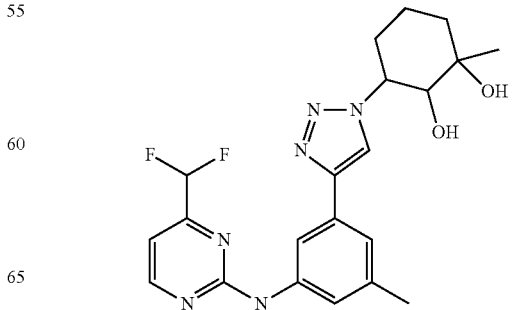

TABLE 29

| Ex. No. | Isomer Order of Elution | Chemical Name | Calc'd/Observed [M + H]+ |
|---|---|---|---|
| 29.4 | Single isomer, first eluting | 6-[4-(3-{[4-(difluoromethyl)pyrimidin-2-yl]amino}-5-methylphenyl)-1H-1,2,3-triazol-1-yl]-1-methylcyclohexane-1,2-diol | 431/431 |
| 29.5 | Single isomer, second eluting | 6-[4-(3-{[4-(difluoromethyl)pyrimidin-2-yl]amino}-5-methylphenyl)-1H-1,2,3-triazol-1-yl]-1-methylcyclohexane-1,2-diol | 431/431 |
| 29.6 | Single isomer, third eluting | 6-[4-(3-{[4-(difluoromethyl)pyrimidin-2-yl]amino}-5-methylphenyl)-1H-1,2,3-triazol-1-yl]-1-methylcyclohexane-1,2-diol | 431/431 |
| 29.7 | Single isomer, fourth eluting | 6-[4-(3-{[4-(difluoromethyl)pyrimidin-2-yl]amino}-5-methylphenyl)-1H-1,2,3-triazol-1-yl]-1-methylcyclohexane-1,2-diol | 431/431 |

Examples 30.1-30.4

3-(4-(3-((4-(Difluoromethyl)pyrimidin-2-yl)amino)-5-methylphenyl)-1H-1,2,3-triazol-1-yl)-2-methylbutane-1,2-diol (Isomer 1, first eluting), 3-(4-(3-((4-(Difluoromethyl)pyrimidin-2-yl)amino)-5-methylphenyl)-1H-1,2,3-triazol-1-yl)-2-methylbutane-1,2-diol (Isomer 2, second eluting), 3-(4-(3-((4-(Difluoromethyl)pyrimidin-2-yl)amino)-5-methylphenyl)-1H-1,2,3-triazol-1-yl)-2-methylbutane-1,2-diol (Isomer 3, third eluting), 3-(4-(3-((4-(Difluoromethyl)pyrimidin-2-yl)amino)-5-methylphenyl)-1H-1,2,3-triazol-1-yl)-2-methylbutane-1,2-diol (Isomer 4, fourth eluting)

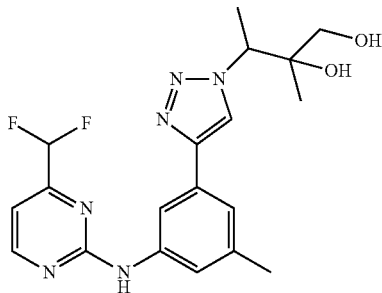 [SMILES: Cc1cc(Nc2nccc(C(F)F)n2)cc(-c2cn(C(C)C(C)(O)CO)nn2)c1]

Step 1:

A mixture of 4-(difluoromethyl)-N-(3-ethynyl-5-methylphenyl)pyrimidin-2-amine (500 mg, 1.93 mmol), 3-chlorobutan-2-one (409 mg, 3.86 mmol), NaN$_3$ (251 mg, 3.86 mmol) and CuI (73.3 mg, 0.386 mmol) in dioxane (10 mL) and H$_2$O (2 mL) was stirred at 100° C. under N$_2$ for 12 hours. The mixture was cooled to room temperature, diluted with H$_2$O (50 mL) and extracted with EtOAc (100 mL×3). The EtOAc layer was washed with saturated brine (50 mL×3), dried over anhydrous sodium sulfate and concentrated under reduced pressure. The residue was purified by column chromatography on silica (1:1 petroleum ether/ethyl acetate,) to give 3-(4-(6-((4-(difluoromethyl)pyridin-2-yl)amino)-4-methylpyridin-2-yl)-1H-1,2,3-triazol-1-yl)butan-2-one as a white solid. $^1$H NMR (400 MHz, CD$_3$OD) δ 8.59 (d, J=4.8 Hz, 1H), 8.34 (s, 1H), 7.99 (s, 1H), 7.52 (s, 1H), 7.31 (s, 1H), 6.98 (d, J=4.8 Hz, 1H), 6.56 (t, J=54.8 Hz, 1H), 5.80 (q, J=7.2 Hz, 1H), 2.36 (s, 3H), 2.19 (s, 3H), 1.82 (d, J=7.2 Hz, 3H). MS ESI calc'd. for C$_{18}$H$_{19}$F$_2$N$_6$O [M+H]$^+$ 373. found 373.

Step 2:

Methyllithium (1.6 M in Et$_2$O, 37.7 mL, 60.3 mmol) was added drop wise over 20 min at −15° C. to a suspension of titanocene dichloride (6.00 g, 24.1 mmol) in toluene (50 mL). The resulting orange slurry was stirred for 1 hour at −5° C., warmed to 0° C. and quenched carefully with cold aqueous NH$_4$Cl (15 mL) and diluted with toluene (60 mL). The organic phase was washed with water (15 mL) and brine (15 mL) and dried over anhydrous sodium sulfate. The red solution was concentrated under reduced pressure to 75 mL. The concentration was determined to be 7 wt % in toluene. (7 wt % in toluene, 7.5 mL, 2.17 mmol) was added to a stirred solution of 3-(4-(6-((4-(difluoromethyl)pyridin-2-yl)amino)-4-methylpyridin-2-yl)-1H-1,2,3-triazol-1-yl)butan-2-one (500 mg, 1.34 mmol) and pyridine (42 mg, 0.54 mmol) in toluene (20 mL) and the resulting orange mixture was heated to 105° C. for 24 hours. After cooled to room temperature the solvent was diluted by EtOAc, filtered, and concentrated under reduced pressure. The residue was purified by column chromatography on silica (1:1 petroleum ether/ethyl acetate) to give 4-(difluoromethyl)-N-(3-methyl-5-(1-(3-methylbut-3-en-2-yl)-1H-1,2,3-triazol-4-yl)phenyl)pyrimidin-2-amine as a white solid. $^1$H NMR (400 MHz, CD$_3$OD) δ 8.67 (d, J=5.2 Hz, 1H), 8.31 (s, 1H), 8.06 (s, 1H), 7.58 (s, 1H), 7.36 (s, 1H), 7.05 (d, J=5.2 Hz, 1H), 6.65 (t, J=55.2 Hz, 1H), 5.34 (q, J=6.8 Hz, 1H), 5.08 (s, 1H), 5.06 (s, 1H), 2.41 (s, 3H), 1.82 (d, J=6.8 Hz, 3H), 1.73 (s, 3H). MS ESI calc'd. for C$_{19}$H$_{21}$F$_2$N$_6$ [M+H]$^+$ 371. found 371.

Step 3:

NMO (189 mg, 1.62 mmol) and OsO$_4$ (10.5 mg, 0.0405 mmol) at 0° C. were added to a mixture of 4-(difluoromethyl)-N-(3-methyl-5-(1-(3-methylbut-3-en-2-yl)-1H-1,2,3-triazol-4-yl)phenyl)pyrimidin-2-amine (150 mg, 0.405 mmol) in THF/H$_2$O (10 mL/10 mL). The mixture was stirred at room temperature for 5 hours. The mixture was diluted with saturated aqueous of Na$_2$SO$_3$ (20 mL), extracted with EtOAc (20 mL×5), dried over anhydrous sodium sulfate and concentrated under reduced pressure. The residue was purified by prep-TLC (100% ethyl acetate) to give 3-(4-(3-((4-(difluoromethyl)pyrimidin-2-yl)amino)-5-methylphenyl)-1H-1,2,3-triazol-1-yl)-2-methylbutane-1,2-diol as a white solid. MS ESI calc'd. for C$_{19}$H$_{23}$F$_2$N$_6$O$_2$ [M+H]$^+$ 405. found 405.

Step 4:

3-(4-(3-((4-(4-(Difluoromethyl)pyrimidin-2-yl)amino)-5-methylphenyl)-1H-1,2,3-triazol-1-yl)-2-methylbutane-1,2-diol (Isomer 1&2, Isomer 3&4) was separated by prep chiral SFC (AD 250×30 mm, 40% IPA (0.1% NH$_3$H$_2$O)/supercritical CO$_2$).

3-(4-(3-((4-(4-(Difluoromethyl)pyrimidin-2-yl)amino)-5-methylphenyl)-1H-1,2,3-triazol-1-yl)-2-methylbutane-1,2-diol (Isomer 1 and Isomer 2) were separated by prep chiral SFC (OD, 250×30 mm, 25% MeOH (0.1% NH$_3$H$_2$O)/supercritical CO$_2$).

Example No. 30.1

3-(4-(3-((4-(4-(Difluoromethyl)pyrimidin-2-yl)amino)-5-methylphenyl)-1H-1,2,3-triazol-1-yl)-2-methylbutane-1,2-diol (Isomer 1, first eluting) as a white solid. $^1$H NMR (400 MHz, DMSO-d$_6$) δ 9.97 (s, 1H), 8.71 (d, J=4.8 Hz, 1H), 8.31 (s, 1H), 8.15 (s, 1H), 7.54 (s, 1H), 7.32 (s, 1H), 7.07 (d, J=4.8 Hz, 1H), 6.85 (t, J=54.4 Hz, 1H), 4.80 (q, J=7.2 Hz, 1H), 3.41 (d, J=10.8 Hz, 1H), 3.21 (d, J=10.8 Hz, 1H), 2.33 (s, 3H), 1.50 (d, J=7.2 Hz, 3H), 0.86 (s, 3H). MS ESI calc'd. for $C_{19}H_{23}F_2N_6O_2$ [M+H]$^+$ 405. found 405.

Example No. 30.2

3-(4-(3-((4-(Difluoromethyl)pyrimidin-2-yl)amino)-5-methylphenyl)-1H-1,2,3-triazol-1-yl)-2-methylbutane-1,2-diol (Isomer 2, second eluting) as a white solid. $^1$H NMR (400 MHz, DMSO-d$_6$) δ 9.97 (s, 1H), 8.72 (d, J=4.8 Hz, 1H), 8.32 (s, 1H), 8.11 (s, 1H), 7.54 (s, 1H), 7.32 (s, 1H), 7.07 (d, J=4.8 Hz, 1H), 6.86 (t, J=54.4 Hz, 1H), 4.80 (q, J=6.8 Hz, 1H), 3.41 (d, J=10.8 Hz, 1H), 3.21 (d, J=10.8 Hz, 1H), 2.33 (s, 3H), 1.50 (d, J=7.2 Hz, 3H), 0.86 (s, 3H). MS ESI calc'd. for $C_{19}H_{23}F_2N_6O_2$ [M+H]$^+$ 405. found 405.

3-(4-(3-((4-(Difluoromethyl)pyrimidin-2-yl)amino)-5-methylphenyl)-1H-1,2,3-triazol-1-yl)-2-methylbutane-1,2-diol (Isomer 3 and Isomer 4) were separated by prep chiral SFC (OD, 250×30 mm, 25% MeOH (0.1% NH$_3$H$_2$O)/supercritical CO$_2$).

Example No. 30.3

3-(4-(3-((4-(Difluoromethyl)pyrimidin-2-yl)amino)-5-methylphenyl)-1H-1,2,3-triazol-1-yl)-2-methylbutane-1,2-diol (Isomer 3, third eluting) as a white solid. $^1$H NMR (400 MHz, DMSO-d$_6$) δ 9.97 (s, 1H), 8.71 (d, J=4.8 Hz, 1H), 8.29 (s, 1H), 8.09 (s, 1H), 7.54 (s, 1H), 7.30 (s, 1H), 7.07 (d, J=4.8 Hz, 1H), 6.85 (t, J=54.4 Hz, 1H), 4.81-4.76 (m, 3H), 3.15 (d, J=10.8 Hz, 1H), 3.09 (d, J=10.8 Hz, 1H), 2.33 (s, 3H), 1.53 (d, J=6.8 Hz, 3H), 1.12 (s, 3H). MS ESI calc'd. for $C_{19}H_{23}F_2N_6O_2$ [M+H]$^+$ 405. found 405.

Example No. 30.4

3-(4-(3-((4-(Difluoromethyl)pyrimidin-2-yl)amino)-5-methylphenyl)-1H-1,2,3-triazol-1-yl)-2-methylbutane-1,2-diol (Isomer 4, fourth eluting) as a white solid. $^1$H NMR (400 MHz, DMSO-d$_6$) δ 9.96 (s, 1H), 8.71 (d, J=5.2 Hz, 1H), 8.29 (s, 1H), 8.09 (s, 1H), 7.53 (s, 1H), 7.29 (s, 1H), 7.07 (d, J=5.2 Hz, 1H), 6.85 (t, J=54.5 Hz, 1H), 4.83-4.75 (m, 3H), 3.14-3.05 (m, 2H), 2.33 (s, 3H), 1.53 (d, J=7.2 Hz, 3H), 1.08 (s, 3H). MS ESI calc'd. for $C_{19}H_{23}F_2N_6O_2$ [M+H]$^+$ 405. found 405.

The following compounds in Table 30 were prepared according to the method described for Example 30.1-30.4 and had the following structure:

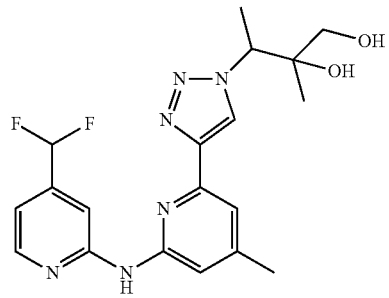

TABLE 30

| Ex. No. | Isomer Order of Elution | Chemical Name | [M + H]+ Calc'd/Observed |
|---|---|---|---|
| 30.5 | Single isomer, first eluting | 3-[4-(6-{[4-(difluoromethyl)pyridin-2-yl]amino}-4-methylpyridin-2-yl)-1H-1,2,3-triazol-1-yl]-2-methylbutane-1,2-diol | 405/405 |
| 30.6 | Single isomer, second eluting | 3-[4-(6-{[4-(difluoromethyl)pyridin-2-yl]amino}-4-methylpyridin-2-yl)-1H-1,2,3-triazol-1-yl]-2-methylbutane-1,2-diol | 405/405 |
| 30.7 | Single isomer, third eluting | 3-[4-(6-{[4-(difluoromethyl)pyridin-2-yl]amino}-4-methylpyridin-2-yl)-1H-1,2,3-triazol-1-yl]-2-methylbutane-1,2-diol | 405/405 |
| 30.8 | Single isomer, fourth eluting | 3-[4-(6-{[4-(difluoromethyl)pyridin-2-yl]amino}-4-methylpyridin-2-yl)-1H-1,2,3-triazol-1-yl]-2-methylbutane-1,2-diol | 405/405 |

Example 31.1 and 31.2

4-((4-(3-((4-(Difluoromethyl)pyrimidin-2-yl)amino)-5-methylphenyl)-1H-1,2,3-triazol-1-yl)methyl)-4-hydroxypyrrolidin-2-one (Isomer 1, first eluting) and 4-((4-(3-((4-(Difluoromethyl)pyrimidin-2-yl)amino)-5-methylphenyl)-1H-1,2,3-triazol-1-yl)methyl)-4-hydroxypyrrolidin-2-one (Isomer 2. second eluting)

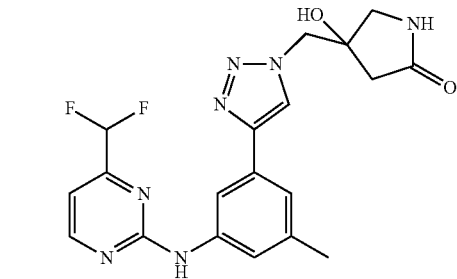 [SMILES: Cc1cc(Nc2nccc(C(F)F)n2)cc(-c2cn(CC3(O)CNC(=O)C3)nn2)c1]

Step 1:

NaN$_3$ (1.98 g, 30.4 mmol) was added under N$_2$ to a mixture of ethyl 4-chloro-3-oxobutanoate (5.00 g, 30.4 mmol) and NaI (4.60 g 30.4 mmol) in DMSO (60 mL). The mixture was stirred at 70° C. for 3 hours. The mixture was diluted with H$_2$O (100 mL), extracted with EtOAc (20 mL×5). The EtOAc layer was dried over anhydrous sodium sulfate and concentrated under reduced pressure to give crude ethyl 4-azido-3-oxobutanoate as a yellow oil.

Step 2:

A solution of ethyl 4-azido-3-oxobutanoate (790 mg, 4.64 mmol), 4-(difluoromethyl)-N-(3-ethynyl-5-methylphenyl)pyrimidin-2-amine (600 mg, 2.32 mmol), sodium ascorbate (184 mg, 0.930 mmol) and $CuSO_4 \cdot 5H_2O$ (580 mg, 2.32 mmol) in $t\text{-BuOH}/H_2O$ (10 mL/10 mL) was stirred at 65° C. for 3 hours. The mixture was diluted with $H_2O$ (50 mL) and extracted with EtOAc (20 mL×5). The organic layer was dried over anhydrous sodium sulfate and concentrated under reduced pressure. The residue was purified by column chromatography on silica (4:1 petroleum ether/ethyl acetate) to give ethyl 4-(4-(3-((4-(difluoromethyl)pyrimidin-2-yl)amino)-5-methylphenyl)-1H-1,2,3-triazol-1-yl)-3-oxobutanoate as a yellow oil. MS ESI calc'd. for $C_{20}H_{21}F_2N_6O_3$ $[M+H]^+$ 431. found 431.

Step 3:

TMSCN (24.0 g, 242 mmol) was added at 0° C. under $N_2$ to a mixture of ethyl 4-(4-(3-((4-(difluoromethyl)pyrimidin-2-yl)amino)-5-methylphenyl)-1H-1,2,3-triazol-1-yl)-3-oxobutanoate (780 mg, 1.80 mmol), $PPh_3$ (3.00 g 12.0 mmol) and methyl acrylate (18.0 mL, 199 mmol) in $CHCl_3$ (10 mL). The mixture was stirred at room temperature for 3 hours. The mixture was diluted with $H_2O$ (50 mL), extracted with EtOAc (20 mL×5). The EtOAc layer was dried over anhydrous sodium sulfate and concentrated under reduced pressure. The residue was purified by column chromatography on silica (2:1 petroleum ether/ethyl acetate) to give ethyl 3-cyano-4-(4-(3-((4-(difluoromethyl)pyrimidin-2-yl)amino)-5-methylphenyl)-1H-1,2,3-triazol-1-yl)-3-((trimethylsilyl)oxy)butanoate as a yellow oil. $^1$H NMR (400 MHz, DMSO-$d_6$) δ 10.01 (s, 1H), 8.70 (d, J=4.0 Hz, 1H), 8.37 (s, 1H), 8.11 (s, 1H), 7.54 (s, 1H), 7.33 (s, 1H), 7.07 (d, J=4.0 Hz, 1H), 6.84 (t, J=56.0 Hz, 1H), 5.40-4.98 (m, 1H), 4.92-4.85 (m, 1H), 4.12-4.18 (m, 2H), 3.13-2.98 (m, 2H), 2.34 (s, 3H), 1.23 (t, J=8.0 Hz, 3H), 0.08 (s, 9H). MS ESI calc'd. for $C_{24}H_{30}F_2N_7O_3Si$ $[M+H]^+$ 530. found 530.

Step 4:

$NaBH_4$ (18.0 g, 492 mmol) was slowly added at −20° C. over 40 minutes to a solution of ethyl 3-cyano-4-(4-(3-((4-(difluoromethyl)pyrimidin-2-yl)amino)-5-methyl phenyl)-1H-1,2,3-triazol-1-yl)-3-((trimethylsilyl)oxy)butanoate (310 g, 0.585 mmol) and $CoCl_2 \cdot 6H_2O$ (555 g, 2.34 mmol). The mixture was diluted with saturated aqueous $NH_4Cl$ solution (100 mL) and extracted with EtOAc (20 mL×5). The organic layers were combined, dried over anhydrous sodium sulfate, and concentrated under reduced pressure to give crude ethyl 4-amino-3-((4-(3-((4-(difluoromethyl)pyrimidin-2-yl)amino)-5-methylphenyl)-1H-1,2,3-triazol-1-yl)methyl)-3-((trimethylsilyl)oxy)butanoate as yellow solid. MS ESI calc'd. for $C_{24}H_{34}F_2N_7O_3Si$ $[M+H]^+$ 534. found 534.

Step 5:

A mixture of ethyl 4-amino-3-((4-(3-((4-(difluoromethyl)pyrimidin-2-yl)amino)-5-methyl phenyl)-1H-1,2,3-triazol-1-yl)methyl)-3-((trimethylsilyl)oxy)butanoate (312 mg, 0.585 mmol) and NaOH (47.0 mg, 1.17 mmol) in MeOH (10 mL) was stirred at room temperature for 40 minutes. The mixture was diluted with $H_2O$ (50 mL), extracted with EtOAc, dried over anhydrous sodium sulfate and concentrated under reduced pressure. The residue was purified by column chromatography on silica (100% ethyl acetate) to give 4-((4-(3-((4-(difluoromethyl)pyrimidin-2-yl)amino)-5-methylphenyl)-1H-1,2,3-triazol-1-yl)methyl)-4-hydroxypyrrolidin-2-one as a yellow solid. MS ESI calc'd. for $C_{19}H_{20}F_2N_7O_2$ $[M+H]^+$ 416. found 416.

Step 6:

4-((4-(3-((4-(Difluoromethyl)pyrimidin-2-yl)amino)-5-methylphenyl)-1H-1,2,3-triazol-1-yl)methyl)-4-hydroxypyrrolidin-2-one (100 mg, 0.241 mmol) was separated by prep chiral SFC (AD 250 mm×20 mm, 55% MeOH (0.05% $NH_3H_2O$)/supercritical $CO_2$).

Example No. 31.1

4-((4-(3-((4-(Difluoromethyl)pyrimidin-2-yl)amino)-5-methylphenyl)-1H-1,2,3-triazol-1-yl)methyl)-4-hydroxypyrrolidin-2-one (Isomer 1, first eluting). $^1$H NMR (400 MHz, DMSO-$d_6$) δ 10.00 (s, 1H), 8.71 (d, J=4.0 Hz, 1H), 8.35 (s, 1H), 8.10 (s, 1H), 7.66 (s, 1H), 7.55 (s, 1H), 7.32 (s, 1H), 7.07 (d, J=4.0 Hz, 1H), 6.86 (t, J=56.0 Hz, 1H), 4.56 (s, 2H), 3.47-3.44 (m, 2H), 3.04 (d, J=10.0 Hz, 1H), 2.56 (s, 1H), 2.34 (s, 3H), 2.06 (d, J=16.4 Hz, 1H). MS ESI calc'd. for $C_{19}H_{20}F_2N_7O_2$ $[M+H]^+$ 416. found 416.

Example No. 31.2

4-((4-(3-((4-(Difluoromethyl)pyrimidin-2-yl)amino)-5-methylphenyl)-1H-1,2,3-triazol-1-yl)methyl)-4-hydroxypyrrolidin-2-one (Isomer 2, second eluting). $^1$H NMR (400 MHz, DMSO-$d_6$) δ 9.99 (s, 1H), 8.71 (d, J=4.0 Hz, 1H), 8.35 (s, 1H), 8.10 (s, 1H), 7.65 (s, 1H), 7.55 (s, 1H), 7.31 (s, 1H), 7.07 (d, J=4.0 Hz, 1H), 6.86 (t, J=56.0 Hz, 1H), 4.55 (s, 2H), 3.47-3.44 (m, 2H), 3.03 (d, J=10.0 Hz, 1H), 2.55 (s, 1H), 2.34 (s, 3H), 2.06 (d, T=16.8 Hz, 1H). MS ESI calc'd. for $C_{19}H_{20}F_2N_7O_2$ $[M+H]^+$ 416. found 416.

Example 32

5-((4-(4-(3-((4-(Difluoromethyl)-5-fluoropyrimidin-2-yl)amino)-5-methylphenyl)-1H-1,2,3-triazol-1-yl)methyl)pyridin-2-ol

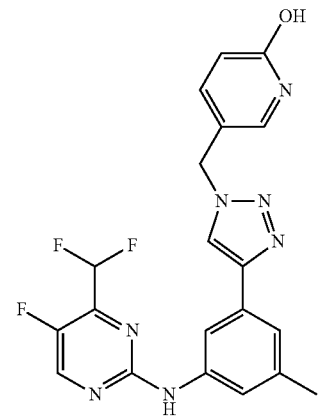 [SMILES: Cc1cc(Nc2ncc(F)c(C(F)F)n2)cc(-c2cn(Cc3ccc(O)nc3)nn2)c1]

Step 1:

A mixture of 5-(azidomethyl)-2-(benzyloxy)pyridine (142 mg, 0.596 mmol), 4-(difluoromethyl)-N-(3-ethynyl-5-methylphenyl)-5-fluoropyrimidin-2-amine (150 mg, 0.541 mmol), $CuSO_4 \cdot 5H_2O$ (13.0 mg, 0.0540 mmol), sodium ascorbate (42.0 mg, 0.220 mmol) in t-BuOH (2 mL) and $H_2O$ (2 mL) was stirred at 70° C. for 12 hours. Water (20 mL) was added to the mixture and then extracted with ethyl acetate (20 mL×5). The ethyl acetate layer was dried over anhydrous sodium sulfate and concentrated under reduced pressure. The residue was purified by prep-TLC (1:1 petroleum ether/ethyl acetate, Rf=0.3) to give N-(3-(1-((6-(benzyloxy)pyridin-3-yl)methyl)-1H-1,2,3-triazol-4-yl)-5-methylphenyl)-4-(difluoromethyl)-5-fluoropyrimidin-2-amine as a yellow solid. MS ESI calc'd. for $C_{27}H_{23}F_3N_7O$ [M+H]$^+$ 518. found 518.

Step 2:

Pd(OH)$_2$ (20 mg) was added at 25° C. under H$_2$ to a mixture of N-(3-(1-((6-(benzyloxy)pyridin-3-yl)methyl)-1H-1,2,3-triazol-4-yl)-5-methylphenyl)-4-(difluoromethyl)-5-fluoropyrimidin-2-amine (200 mg, 0.390 mmol) in MeOH (10 mL) and stirred for 12 hours. The mixture was filtered, concentrated under reduced pressure and the residue was purified by prep-HPLC to give the 5-((4-(3-((4-(difluoromethyl)-5-fluoropyrimidin-2-yl)amino)-5-methylphenyl)-1H-1,2,3-triazol-1-yl)methyl)pyridin-2-ol. $^1$H NMR (400 MHz, DMSO-d$_6$) δ 10.06 (s, 1H), 8.79 (s, 1H), 8.46 (s, 1H), 8.04 (s, 1H), 7.59 (s, 1H), 7.58 (s, 1H), 7.47 (d, J=9.0 Hz, 1H), 7.28 (s, 1H), 7.11 (t, T=54.4 Hz, 1H), 6.34 (d, T=9.0 Hz, 1H), 5.38 (s, 2H), 2.33 (s, 3H). MS ESI calc'd. for $C_{20}H_{17}F_3N_7O$ [M+H]$^+$ 428. found 428.

Example 33

5-((4-(3-((4-(Difluoromethyl)pyrimidin-2-yl)amino)-5-methylphenyl)-1H-1,2,3-triazol-1-yl)methyl)pyridin-2(3H)-one

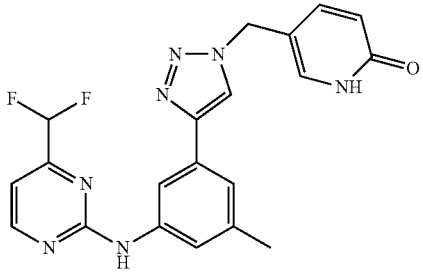 [SMILES: Cc1cc(Nc2nccc(C(F)F)n2)cc(-c2cn(Cc3ccc(=O)[nH]c3)nn2)c1]

Step 1:

A mixture of 5-(azidomethyl)-2-(benzyloxy)pyridine (111 mg, 0.46 mmol), (difluoromethyl)-N-(3-ethynyl-5-methylphenyl)pyrimidin-2-amine (100 mg, 0.39 mmol), CuSO$_4$.5H$_2$O (10.0 mg, 0.04 mmol) and sodium ascorbate (31.0 mg, 0.150 mmol) in t-BuOH (2 mL) and H$_2$O (2 mL) was stirred at 70° C. for 12 hours. Water was added to the mixture and then extracted with ethyl acetate. The ethyl acetate layer was dried over anhydrous sodium sulfate and concentrated under reduced pressure. The residue was purified by prep-TLC (1:1 petroleum ether/ethyl acetate, Rf=0.3) to give the compound N-(3-(1-((6-(benzyloxy)pyridin-3-yl)methyl)-1H-1,2,3-triazol-4-yl)-5-methylphenyl)-4-(difluoromethyl)pyrimidin-2-amine as a yellow solid. MS ESI calc'd. for $C_{27}H_{24}F_2N_7O$ [M+H]$^+$ 500. found 500.

Step 2:

Pd(OH)$_2$/C (8.00 mg) was added to a mixture of N-(3-(1-((6-(benzyloxy)pyridin-3-yl)methyl)-1H-1,2,3-triazol-4-yl)-5-methyl phenyl)-4-(difluoromethyl)pyrimidin-2-amine (80.0 mg, 0.160 mmol) in methanol (10 mL) and the resultant mixture was stirred at 25° C. with H$_2$ balloon for 12 hours. The mixture was filtered, concentrated under reduced pressure and the residue was purified by reverse phase HPLC to give the 5-((4-(3-((4-(difluoromethyl)pyrimidin-2-yl)amino)-5-methylphenyl)-1H-1,2,3-triazol-1-yl)methyl)pyridin-2(3H)-one as a yellow solid. $^1$H NMR (400 MHz, DMSO-d$_6$) δ 9.99 (s, 1H), 8.72 (d, J=4.8 Hz, 1H), 8.46 (s, 1H), 8.08 (s, 1H), 7.60 (s, 1H), 7.55 (s, 1H), 7.47-7.44 (m, 1H), 7.28 (s, 1H), 7.08 (d, J=4.8 Hz, 1H), 6.86 (t, J=54.4 Hz, 1H), 6.33 (d, J=9.2 Hz, 1H), 5.37 (s, 2H), 2.33 (s, 3H). MS ESI calc'd. for $C_{20}H_{18}F_2N_7O$ [M+H]$^+$ 410. found 410.

Example 34

Compounds of Formula (I) Using the General Methods Illustrated in Scheme 13

The description provided in Example 34 is a prophetic example.

Procedure A

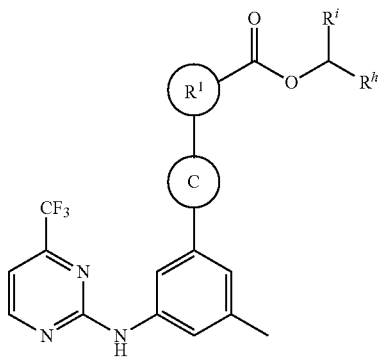

This general procedure describes the procedure for conversion of (A1) to (A) as shown in Scheme 13. To a mixture of compound of formula (A1) (1 mmol), 1° or 2° alcohol (5 mmol), and triphenylphosphine (resin-bound, 1.6 mmol/g loading, 2 mmol) in tetrahydrofuran is added di-tert-butyl azodicarboxylate (2 mmol) at 20° C. The reaction mixture is stirred at 20° C. for 16 hours. The reaction mixture is diluted with TFA (1 mL) and water (1 drop). The mixture is stirred for 30 minutes. The mixture is then filtered through CELITE, washing with dichloromethane (3x). The filtrate is concentrated under reduced pressure to afford the crude residue TFA salt. The residue is diluted carefully with saturated aqueous sodium bicarbonate solution and ethyl acetate. The organic layer is separated, washed with brine, dried over magnesium sulfate, filtered, and concentrated under reduced pressure to afford the crude residue free base. The residue is purified by silica gel chromatography to afford the product residue. The residue is lyophilized from acetonitrile and water to afford a compound of structural subtype (A).

The following compounds could be prepared according to procedures which are analogous to those described in Example 34, Procedure A.

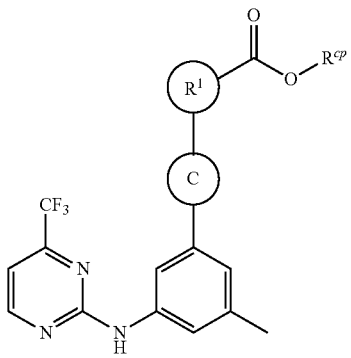

| Ex. No. | R^cp |
|---|---|
| 34.1 | benzyl |
| 34.2 | n-propyl |
| 34.3 | isobutyl |
| 34.4 | n-butyl |
| 34.5 | sec-butyl |
| 34.6 | isopentyl |
| 34.7 | n-pentyl |
| 34.8 | neopentyl |
| 34.9 | n-hexyl |
| 34.10 | n-heptyl |
| 34.11 | cyclohexyl |
| 34.12 | tetrahydropyran-4-yl |
| 34.13 | cyclohexylmethyl |
| 34.14 | -CH2CH2OCH3 |
| 34.15 | -CH2CH2OCH2CH2OCH2CH3 |
| 34.16 | -CH2C(O)OCH3 |
| 34.17 | -CH2C(O)N(CH3)2 |
| 34.18 | -CH2CH2CH2-morpholinyl |
| 34.19 | -CH2CH2CH2N(CH3)2 |
| 34.20 | (5-methyl-2-oxo-1,3-dioxol-4-yl)methyl |

Procedure B

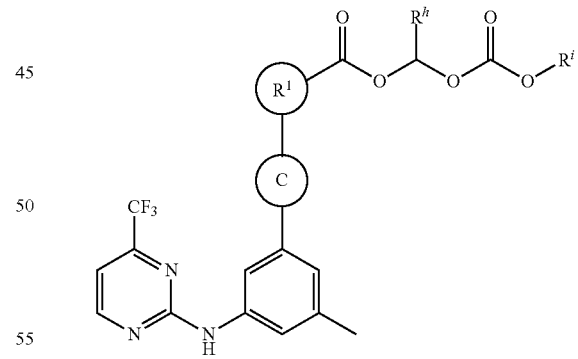

This general procedure describes the procedure for conversion of (A1) to (C) as shown in Scheme 13. A mixture of compound of formula (A1) (1.0 mmol), potassium carbonate (2.0 mmol), and sodium iodide (0.50 mmol) in DMF is stirred at 20° C. After 30 minutes, alkyl halide of formula (C1) (0.95 mmol) is added and the reaction mixture is stirred at 20° C. After 16 hours, the reaction mixture is diluted with ethyl acetate and washed with water (4×). The organic layer is separated, washed with brine, dried over magnesium sulfate, filtered, and concentrated under reduced pressure to afford the crude residue. The residue is purified by silica gel chromatography (ethyl acetate/hexanes, linear gradient) to afford the product residue. The residue is lyophilized from acetonitrile and water to afford a compound of formula (C).

The following compounds could be prepared according to procedures which are analogous to those described in Example 34, Procedure B.

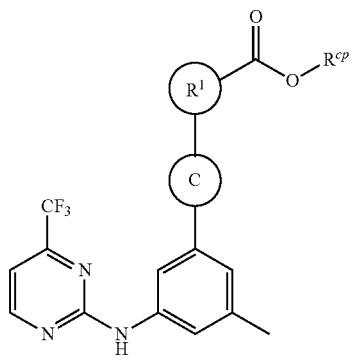

| Ex. No. | $R^{cp}$ |
|---|---|
| 34.21 | |
| 34.22 | |
| 34.23 | |
| 34.24 | |

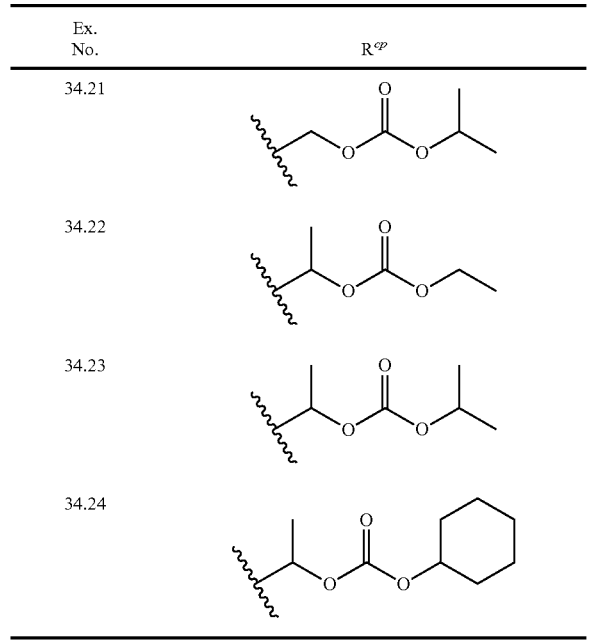

Procedure C

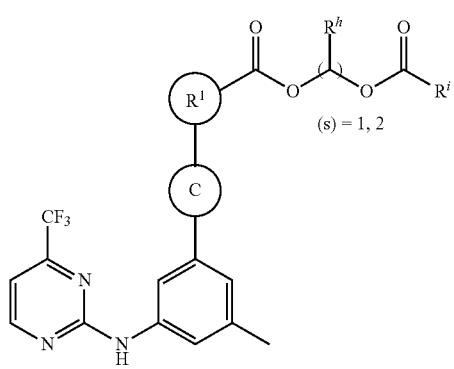

This general procedure describes the procedure for conversion of (A1) to (B) as shown in Scheme 13. To a solution of compound of formula (A1) (1.0 mmol) in DMF is added potassium carbonate (2.0 mmol) and sodium iodide (0.20 mmol). After 75 minutes, alkyl halide of formula (B1) (1.0 mmol) is added and the reaction mixture is stirred for an additional 4 hours. The reaction mixture is then partitioned between ethyl acetate and aqueous saturated sodium bicarbonate. The layers are separated, and then the organic layer is washed with water (3×) and brine, dried over sodium sulfate, filtered, and concentrated under reduced pressure. The resulting residue is purified by silica gel chromatography (ethyl acetate/hexanes, linear gradient) to afford the product residue. The residue is lyophilized from acetonitrile and water to afford a compound of formula (B).

The following compounds could be prepared according to procedures which were analogous to those described in Example 34, Procedure C.

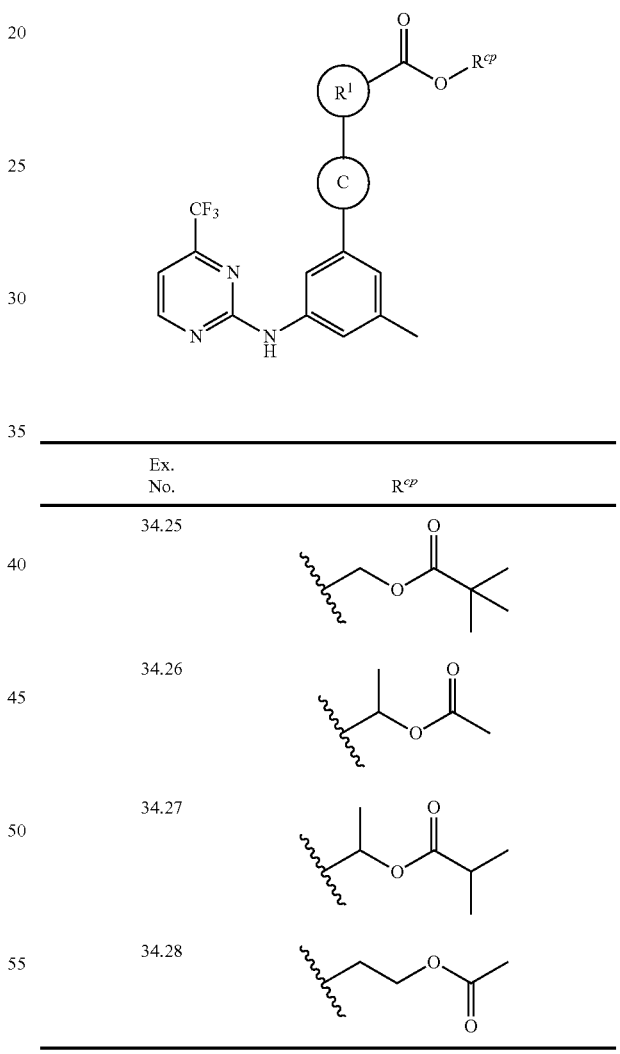

| Ex. No. | $R^{cp}$ |
|---|---|
| 34.25 | |
| 34.26 | |
| 34.27 | |
| 34.28 | |

Example 35

Compounds of Formula (I) Using the General Methods Illustrated in Scheme 14

The description provided in Example 35 is a prophetic example.

Example 35.1

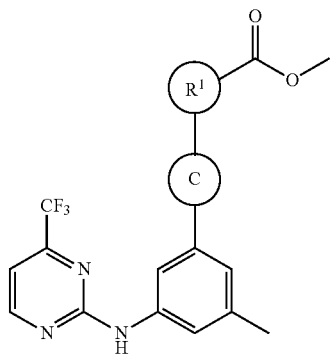

This general procedure describes the procedure for conversion of (A1) to (D) as shown in Scheme 14. To a suspension of compound of formula (A1) (1.0 mmol) in 1:1 methanol:dichloromethane is added trimethylsilyldiazomethane (2.0 M in diethyl ether, 1.0 mmol) at 0° C. The reaction mixture is stirred at 0° C. until all gas evolution ceases. The reaction mixture is allowed to warm to ambient temperature and quenched by the addition of several drops of acetic acid. The reaction mixture is concentrated under reduced pressure and the residue is purified by silica gel chromatography (ethyl acetate/hexanes, linear gradient) to afford the product residue. The residue is lyophilized from acetonitrile and water to afford Example 35.1.

Example 36

Preparation of Hydroxyalkyl Esters

The description provided in Example 36 is a prophetic example.

Example 36.1

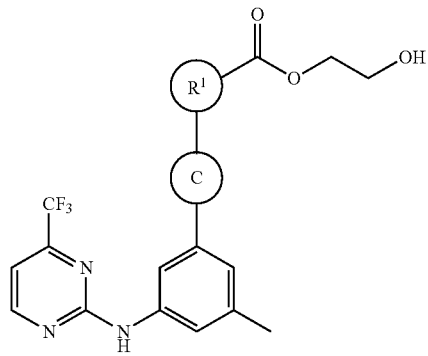

A mixture of compounds of formula (A1) (1.0 mmol), potassium carbonate (6.0 mmol) and sodium iodide (1.0 mmol) in DMF is stirred for 10 minutes at ambient temperature. To this mixture is added 2-chloroethanol (4.0 mmol) and the reaction mixture is heated at 60° C. for 16 hours. After 16 hours, additional 2-chloroethanol (1.0 mmol) is added and the reaction mixture is heated to 65° C. for an additional 2 hours. The reaction mixture is then diluted with ethyl acetate and washed sequentially with water (3×), aqueous sodium carbonate solution (2×), additional water (3×), and brine (2×). The organic layer is dried over magnesium sulfate, filtered, and concentrated under reduced pressure to afford the crude product residue. The residue is purified by silica gel chromatography ([3% (1.0 M ammonia in dioxane) in ethyl acetate]/[3% (1.0M ammonia in dioxane) in dichloromethane], linear gradient) to afford Example 36.1

The invention claimed is:
1. A compound of Formula I:

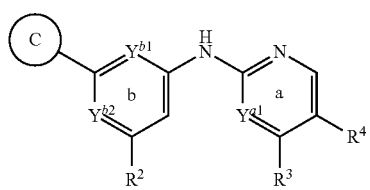

I or a pharmaceutically acceptable salt thereof, wherein:

is:

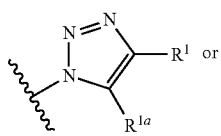

(1)

(2)

ring a is

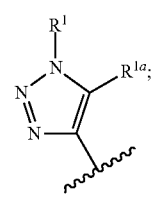

ring b is

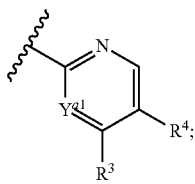

Y$^{a1}$ is CH;
Y$^{b1}$ is N;
Y$^{b2}$ is CH;
R$^{1a}$ is independently: H, halogen, or C$_1$-C$_3$-alkyl;
R$^1$ is
  halogen;
  Si(CH$_3$)$_3$; or
  C$_1$-C$_6$-alkyl or C$_2$-C$_6$-alkenyl, optionally substituted with one to four substituents selected from the group consisting of: CN; OH; oxo; NH$_2$; halogen; CO$_2$R$^c$; CONH$_2$; C$_1$-C$_3$-alkyl; C$_1$-C$_3$-haloalkyl; C$_1$-C$_3$-alkoxyl optionally substituted with OH or fluoro; aryl; Oaryl optionally substituted with halogen; or heterocyclyl;
Heterocyclyl is a 4-, 5-, 6-, or 7-membered monocyclic ring or 8-, 9-, 10-, 11-membered bicyclic ring, or 13- or 14-membered tricyclic ring; the monocyclic, bicyclic or tricyclic ring can be saturated, unsaturated or aromatic, containing 1, 2, 3 or 4 heteroatoms selected from O, N or S, the point of attachment of the heterocyclyl can be on the carbon or nitrogen and the heterocyclyl may optionally be substituted with one to four substituents selected from CN; OH; oxo; NH$_2$; halogen; CO(CH$_2$)$_m$CH$_3$, optionally substituted with one or two substituents selected from OH and CO$_2$R$^c$; C$_1$-C$_3$-alkyl; C$_2$-C$_4$-alkenyl; C$_1$-C$_3$-haloalkyl; C$_1$-C$_3$-alkoxyl optionally substituted with OH; aryl optionally substituted with one or two substituents selected from C$_1$-C$_3$-alkoxyl, halogen, or Oaryl; CH$_2$aryl; OCH$_2$aryl; Oaryl optionally substituted with one or two substituents selected from halogen; (CR$^a$R$^b$)$_n$CO$_2$R$^c$; (CR$^a$R$^b$)$_n$CONR$^d$R$^e$; (CHR$^a$)$_n$NHCONR$^d$R$^e$; (CHR$^a$)$_p$—C(O)-heterocyclyl; and furyl; or alternatively, 2 substituents which are geminally substituted on a common ring carbon atom of said heterocyclyl may together with the common ring carbon atom form a C$_3$-C$_6$ spirocyclic ring;
Aryl is a phenyl or napthyl ring, the aryl may optionally be substituted with one to four substituents selected from halogen, hydroxyl, C$_1$-C$_3$-alkyl, C$_1$-C$_3$-alkoxyl, Oaryl, (CR$^a$R$^b$)$_n$CO$_2$R$^c$; and (CR$^a$R$^b$)$_n$CONR$^d$R$^e$;
R$^2$ is halogen, C$_1$-C$_3$-alkyl, or C$_1$-C$_3$-haloalkyl;
R$^3$ is halogen or C$_1$-C$_3$-fluoroalkyl;
R$^4$ is H, halogen, or C$_1$-C$_3$-alkyl;
R$^a$ and R$^b$ are independently: H, OH, CN, CO$_2$R$^c$, CONH$_2$, NH$_2$, cyclopropyl, C$_1$-C$_3$-haloalkyl, or C$_1$-C$_3$-alkyl optionally substituted with hydroxyl;
R$^c$ is: H; C$_{1-4}$alkyl; -M-R$^{CH}$; —(CH$_2$)$_{1-2}$—R$^f$; —(CH$_2$)$_2$—O—(CH$_2$)$_2$—R$^f$; —(CH$_2$)$_2$—R$^g$; —CHR$^h$OCO$_2$R$^i$, —CHR$^i$R$^h$, or —(CHR$^h$)$_s$OC(O)R$^i$;
R$^d$ and R$^e$ are independently: H, C$_1$-C$_3$-alkoxyl or C$_1$-C$_6$-alkyl, optionally substituted with one, two or three substituents CN; OH; oxo; NH$_2$; halogen; CO$_2$R$^c$; CONH$_2$; C$_1$-C$_3$-alkoxyl, CO$_2$R$^c$; aryl, carbocyclyl, or heterocyclyl; or cyclopropyl optionally substituted with phenyl;
R$^f$ is —OC(O)R$^{f1}$;
R$^{f1}$ is C$_{1-4}$alkyl; and
R$^g$ is OH, C$_{1-4}$alkoxyl, NH$_2$, NH(C$_{1-4}$alkyl) or N(C$_{1-4}$alkyl)$_2$;
R$^h$ is H or C$_{1-4}$alkyl; and
R$^i$ is C$_{1-4}$alkyl, C$_{3-6}$cycloalkyl, or phenyl; and,
M is a bond or —(CH$_2$)$_{1-3}$—;
R$^{CH}$ is (a) aryl or carbocycle optionally substituted with 1-3 groups independently selected from halo, C$_{1-4}$alkyl, or C$_{1-4}$alkoxy; or (b) a 5- to 6-membered monocyclic heterocycle containing 1 or 2 heteroatoms independently selected from the group consisting of N and O, wherein said heterocycle of R$^{CH}$ is optionally substituted with 1 or 2 groups independently selected from the group consisting of oxo and C$_{1-3}$ alkyl;
m is 0, 1, or 2;
n is 0, 1, 2, 3 or 4;
p is 0 or 1; and
s is 1 or 2.

2. The compound of claim 1 or a pharmaceutically acceptable salt thereof, having the Formula Ia:

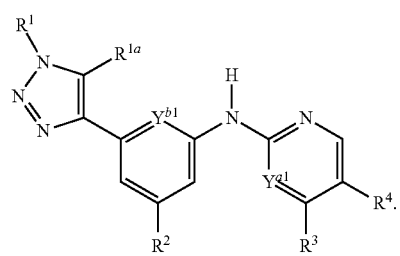

Ia

3. The compound of claim 1 or a pharmaceutically acceptable salt thereof, having the Formula Ib:

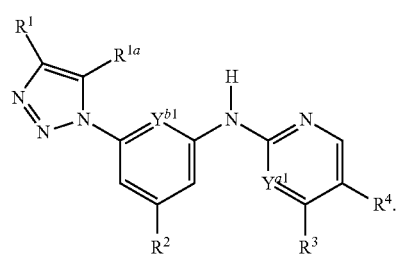

Ib

4. The compound of claim 2 or a pharmaceutically acceptable salt thereof, wherein Formula Ia is:

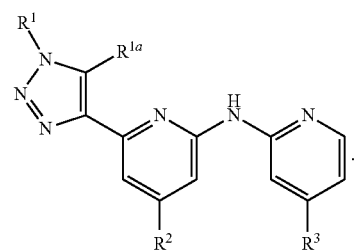

5. The compound of claim 4 or a pharmaceutically acceptable salt thereof, wherein Formula Ia is:

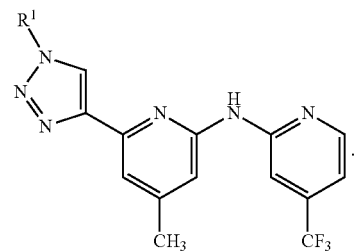

6. The compound of claim 5 or a pharmaceutically acceptable salt thereof, wherein R$^1$ is Si(CH)$_3$ or C$_1$-C$_6$- alkyl, optionally substituted with one to four substituents selected from the group consisting of: CN, OH, oxo, $NH_2$, halogen, $CF_3$, $C_1$-$C_3$-alkyl, and $C_1$-$C_3$-alkoxyl.

7. The compound of claim 6 or a pharmaceutically acceptable salt thereof, wherein $R^1$ is $C_1$-$C_6$-alkyl, optionally substituted with one to four substituents selected from the group consisting of: CN, OH, oxo, $NH_2$, halogen, $CF_3$, $CH_3$ and $OCH_3$.

8. The compound of claim 1, or a pharmaceutically acceptable salt thereof, which is selected from the group consisting of:
   2-methyl-3-[4-(4-methyl-6-{[4-(trifluoromethyl)pyridin-2-yl]amino}pyridin-2-yl)-1H-1,2,3-triazol-1-yl]propane-1,2-diol;
   (3R)-3-hydroxy-4-[4-(4-methyl-6-{[4-(trifluoromethyl)pyridin-2-yl]amino}pyridin-2-yl)-1H-1,2,3-triazol-1-yl]butanenitrile;
   3-[4-(4-methyl-6-{[4-(trifluoromethyl)pyridin-2-yl]amino}pyridin-2-yl)-1H-1,2,3-triazol-1-yl]propane-1,2-diol;
   1-fluoro-3-[4-(4-methyl-6-{[4-(trifluoromethyl)pyridin-2-yl]amino}pyridin-2-yl)-1H-1,2,3-triazol-1-yl]propan-2-ol;
   3-hydroxy-4-[4-(4-methyl-6-{[4-(trifluoromethyl)pyridin-2-yl]amino}pyridin-2-yl)-1H-1,2,3-triazol-1-yl]pentanenitrile;
   (2S)-3-[4-(4-methyl-6-{[4-(trifluoromethyl)pyridin-2-yl]amino}pyridin-2-yl)-1H-1,2,3-triazol-1-yl]propane-1,2-diol;
   1-[4-(4-methyl-6-{[4-(trifluoromethyl)pyridin-2-yl]amino}pyridin-2-yl)-1H-1,2,3-triazol-1-yl]butane-2,3-diol;
   (3R)-3-hydroxy-4-[4-(4-methyl-6-{[4-(trifluoromethyl)pyridin-2-yl]amino}pyridin-2-yl)-1H-1,2,3-triazol-1-yl]butanamide;
   2-[4-(4-methyl-6-{[4-(trifluoromethyl)pyridin-2-yl]amino}pyridin-2-yl)-1H-1,2,3-triazol-1-yl]ethanol;
   2-methyl-1-[4-(4-methyl-6-{[4-(trifluoromethyl)pyridin-2-yl]amino}pyridin-2-yl)-1H-1,2,3-triazol-1-yl]propan-2-ol;
   (2R)-2-[4-(4-methyl-6-{[4-(trifluoromethyl)pyridin-2-yl]amino}pyridin-2-yl)-1H-1,2,3-triazol-1-yl]propanamide.

9. The compound of claim 1, or a pharmaceutically acceptable salt thereof, which is selected from the group consisting of:
   (R)-1-[4-(6-{[4-(difluoromethyl)pyridin-2-yl]amino}-4-methylpyridin-2-yl)-1H-1,2,3-triazol-1-yl]-2,3-dimethylbutane-2,3-diol;
   (S)-1-[4-(6-{[4-(difluoromethyl)pyridin-2-yl]amino}-4-methylpyridin-2-yl)-1H-1,2,3-triazol-1-yl]-2,3-dimethylbutane-2,3-diol;
   (R)-1-(4-{6-[(5-chloro-4-methylpyridin-2-yl)amino]-4-methylpyridin-2-yl}-1H-1,2,3-triazol-1-yl)-2,3-dimethylbutane-2,3-diol;
   (S)-1-(4-{6-[(5-chloro-4-methylpyridin-2-yl)amino]-4-methylpyridin-2-yl}-triazol-1-yl)-2,3-dimethylbutane-2,3-diol;
   (R)-1-[4-(6-{[4-(1-fluoroethyl)pyridin-2-yl]amino}-4-methylpyridin-2-yl)-1H-1,2,3-triazol-1-yl]-2,3-dimethylbutane-2,3-diol;
   (S)-1-[4-(6-{[4-(1-fluoroethyl)pyridin-2-yl]amino}-4-methylpyridin-2-yl)-1H-1,2,3-triazol-1-yl]-2,3-dimethylbutane-2,3-diol;
   (R)-1-(4-{6-[(5-fluoro-4-methylpyridin-2-yl)amino]-4-methylpyridin-2-yl}-triazol-1-yl)-2,3-dimethylbutane-2,3-diol;
   (S)-1-(4-{6-[(5-fluoro-4-methylpyridin-2-yl)amino]-4-methylpyridin-2-yl}-triazol-1-yl)-2,3-dimethylbutane-2,3-diol;
   (R)-3-(4-(6-((4-(difluoromethyl)pyridin-2-yl)amino)-4-methylpyridin-2-yl)-1H-1,2,3-triazol-1-yl)-2-methylpropane-1,2-diol;
   (S)-3-(4-(6-((4-(difluoromethyl)pyridin-2-yl)amino)-4-methylpyridin-2-yl)-1H-1,2,3-triazol-1-yl)-2-methylpropane-1,2-diol;
   (3R)-4-(4-(6-((4-(difluoromethyl)pyridin-2-yl)amino)-4-methylpyridin-2-yl)-1H-1,2,3-triazol-1-yl)-3-hydroxy-3-methylbutanenitrile;
   (3S)-4-(4-(6-((4-(difluoromethyl)pyridin-2-yl)amino)-4-methylpyridin-2-yl)-1H-1,2,3-triazol-1-yl)-3-hydroxy-3-methylbutanenitrile;
   (4R)-4-((4-(6-((4-(difluoromethyl)pyridin-2-yl)amino)-4-methylpyridin-2-yl)-1H-1,2,3-triazol-1-yl)methyl)pyrrolidin-2-one;
   (4S)-4-((4-(6-((4-(difluoromethyl)pyridin-2-yl)amino)-4-methylpyridin-2-yl)-1H-1,2,3-triazol-1-yl)methyl)pyrrolidin-2-one;
   (2R,3R)-3-[4-(6-{[4-(difluoromethyl)pyridin-2-yl]amino}-4-methylpyridin-2-yl)-1H-1,2,3-triazol-1-yl]-2-methylbutane-1,2-diol;
   (2R,3S)-3-[4-(6-{[4-(difluoromethyl)pyridin-2-yl]amino}-4-methylpyridin-2-yl)-1H-1,2,3-triazol-1-yl]-2-methylbutane-1,2-diol;
   (2S,3R)-3-[4-(6-{[4-(difluoromethyl)pyridin-2-yl]amino}-4-methylpyridin-2-yl)-1H-1,2,3-triazol-1-yl]-2-methylbutane-1,2-diol; and
   (2S,3S)-3-[4-(6-{[4-(difluoromethyl)pyridin-2-yl]amino}-4-methylpyridin-2-yl)-1H-1,2,3-triazol-1-yl]-2-methylbutane-1,2-diol.

10. A pharmaceutical composition comprising a therapeutically effective amount of the compound of claim 1 or a pharmaceutically acceptable salt thereof, and a pharmaceutically acceptable carrier.

11. A method for the treatment of asthma or COPD, comprising administering to a patient in need thereof a therapeutically effective amount of the compound of claim 1 or a pharmaceutically acceptable salt thereof.

12. A method for the treatment of NHL B cell lymphomas, comprising administering to a patient in need thereof a therapeutically effective amount of the compound of claim 1 or a pharmaceutically acceptable salt thereof.

13. The compound of claim 1 or a pharmaceutically salt thereof, wherein the compound of the Formula I has the formula Ih Ih wherein
$Y^{a1}$ is CH and $Y^{b1}$ is N;
each $R^q$ is independently H, $C_{1-3}$alkyl, or $C_{1-3}$fluoroalkyl;
$R^r$ is H or $C_{1-3}$alkyl;

$R^s$ is hydroxyl or CN;
$R^2$ is methyl;
$R^3$ is $C_{1-3}$fluoroalkyl; and
$R^4$ is H or fluoro.

14. The compound of claim 13 or a pharmaceutically acceptable salt thereof, wherein
$Y^{a1}$ is CH and $Y^{b1}$ is N;
each $R^q$ is independently H or Me;
$R^r$ is H or Me;
$R^s$ is hydroxyl;
$R^2$ is methyl;
$R^3$ is $C_{1-3}$fluoroalkyl; and
$R^4$ is H or fluoro.

15. The compound of claim 14 or a pharmaceutically acceptable salt thereof, wherein the compound is 3-(4-(6-((4-(difluoromethyl)pyridin-2-yl)amino)-4-methylpyridin-2-yl)-1H-1,2,3-triazol-1-yl)-2-methylpropane-1,2-diol.

* * * * *

UNITED STATES PATENT AND TRADEMARK OFFICE
CERTIFICATE OF CORRECTION

PATENT NO.         : 9,586,931 B2                              Page 1 of 1
APPLICATION NO.    : 14/431895
DATED              : March 7, 2017
INVENTOR(S)        : Michelle R. Machacek et al.

It is certified that error appears in the above-identified patent and that said Letters Patent is hereby corrected as shown below:

On the Title Page

Item (71) Applicants:
Delete "Michelle R. Machacek, Brookline, MA (US); Eric T. Romeo, Allston, MA (US); Solomon D. Kattar, Arlington, MA (US); Matthew Christopher, Brookline, MA (US); Michael D. Altman, Needham, MA (US); Alan B. Northrup, Reading, MA (US); John Michael Ellis, Needham, MA, (US); Brendan O'Boyle, Milpitas, CA (US); Anthony Donofrio, Cambridge, MA (US); Jonathan Grimm, Ashburn, VA (US); Michael H. Reutershan, Brookline, MA (US); Kaleen Konrad Childers, Medfield, MA (US); Ryan D. Otte, Natick, MA (US); Brandon Cash, Framingham, MA (US); Yves Ducharme, Brookline, MA (US); Andrew M. Haidle, Cambridge, MA (US); Kerrie Spencer, Woonsocket, RI (US); Dilrukshi Vitharana, Somerville, MA (US); Lingyun Wu, Shanghai (CN); Li Zhang, Shanghai (CN); Peng Zhang, Shanghai (CN); Christian Beaulieu, Laval (CA); Daniel Guay, Lachine (CA)"

Insert -- Merck Sharp & Dohme Corp. Rahway, NJ (US); Merck Canada Inc., Kirkland, Quebec (CA) --

Signed and Sealed this
Eleventh Day of July, 2017

Joseph Matal
*Performing the Functions and Duties of the
Under Secretary of Commerce for Intellectual Property and
Director of the United States Patent and Trademark Office*